United States Patent
Dow et al.

(10) Patent No.: US 6,699,893 B2
(45) Date of Patent: Mar. 2, 2004

(54) GLUCOCORTICOID RECEPTOR MODULATORS

(75) Inventors: Robert L. Dow, Waterford, CT (US); Kevin K. Liu, East Lyme, CT (US); Bradley P. Morgan, Lyme, CT (US); Andrew G. Swick, East Lyme, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/080,174

(22) Filed: Feb. 19, 2002

(65) Prior Publication Data

US 2002/0147336 A1 Oct. 10, 2002

Related U.S. Application Data

(62) Division of application No. 09/559,384, filed on Apr. 27, 2000, now Pat. No. 6,380,223.
(60) Provisional application No. 60/132,130, filed on Apr. 30, 1999.

(51) Int. Cl.$^7$ .................. C07D 213/02; A61K 31/44
(52) U.S. Cl. .............. 514/357; 514/231.2; 514/247; 514/256; 514/364; 514/396; 514/408; 514/277; 544/106; 544/224; 544/242; 546/329; 546/339; 548/131; 548/335.1; 548/400
(58) Field of Search ................ 546/339, 329; 514/277, 231.2, 247, 256, 357, 364, 396.408; 544/106, 224, 242; 548/131, 335.1, 400

(56) References Cited

U.S. PATENT DOCUMENTS

| | | | |
|---|---|---|---|
| 3,683,091 A | 8/1972 | Nagata et al. | 424/331 |
| 5,696,127 A | 12/1997 | Jones et al. | 514/285 |
| 5,767,113 A | 6/1998 | Cohn et al. | 514/176 |

FOREIGN PATENT DOCUMENTS

| | | |
|---|---|---|
| EP | 0188396 | 7/1986 |
| EP | 0683172 | 11/1995 |
| EP | 0903146 | 3/1999 |
| JP | 4514056 | 5/1970 |
| JP | 4536500 | 11/1970 |
| JP | 6263688 | 9/1994 |
| JP | 9052899 | 2/1997 |
| WO | 9510266 | 4/1995 |
| WO | 9826783 | 6/1998 |
| WO | 9827986 | 7/1998 |
| WO | 9831702 | 7/1998 |

OTHER PUBLICATIONS

Chemical Abstracts, Vol 108, Abstract No. 67,094, 1988.*
Tius et al, Tetrahedron Letters, Vol 27, No. 38, pp. 4541–4544 , 1986.*
Basu, et al, Tetrahedron Letters, Vol 25, No. 11, pp. 1195–1196, 1984.*
Matsumoto et al, Tetrahedron Letters, Vol 9, pp. 1127–1131, 1968.*
Turner et al, J. Am. Chem. Soc, Vol 88, No. 8, pp. 1786–1792, 1966.*
Saha, Synthetic Communications, Vol 23, No 13, pp. 1821–1828, 1993.*
C.F. Bigge et al., J. Med. Chem. 1993, 36, 1977–1995, "Synthesis and Pharmacological Evaluation of 4a–Phenanthrenamine Derivatives Acting at the Phencyclidine Binding Site of the N–Methyl–D–aspartate Receptor Complex".
P. R. Kanjilal et al., J. Org. Chem. 1985, 50, 857–863, "Synthetic Studies toward Complex Diterpenoids. 16.$^1$ A Novel Synthetic Route to the Carbocyclic Skeleta of Stemodin and Stemarin by Acid–Catalyzed Intramolecular C–Alkylation and Rearrangement Reactions".
G. Sinha et al., J. Chem. Soc., Perkin Trans. I (1983), (10), 2519–2528, "Condensed Cyclic and Bridged–ring System. Part 9.$^1$ Stereocontrolled Synthesis and X–Ray Structural Analyses of cis–3,4,4a,9,10,10a–Hexahydro–1, 4a–ethanophenanthrene–2–(1H), 12–dione and trans–3,4, 4a,9,10,10a–Hexahydro–3,4a–ethanophenanthrene–2(1H), 12–dione".
U. R. Ghatak et al., Tetrahedron Letters No. 32, pp. 2929–2931, 1978, Angular Alkylation Through a Novel Intramolecular Cationic Reaction. A Simple Stereospecific Route to Polycyclic Bridged–Ring Intermediates Towards Some Complex Diterpenoid.
P. N. Chakrabortty et al., Indian J. Chem. (1974), 12(9), 948–55, "Synthetic Studies in Resin Acid Series: Part VII*—Synthesis of Iα–Methyl–Iβ,4aβ–dicarboxy–1,2,3,4, 4a,9,10,10aβ–octahydrophenanthrene & 1β,4aβ–Dicarboxyl2,3,4,4a,9,10,10aα–octahydrophenanthrene".

(List continued on next page.)

*Primary Examiner*—Zinna Northington Davis
(74) *Attorney, Agent, or Firm*—Scully, Scott, Murphy & Presser

(57) ABSTRACT

The present invention provides non-steroidal compounds of formula I which are selective modulators (i.e., agonists and antagonists) of a steroid receptor, specifically, the glucocorticoid receptor. The present invention also provides pharmaceutical compositions containing these compounds and methods for using these compounds to treat animals requiring glucocorticoid receptor agonist or antagonist therapy. Glucocorticoid receptor modulators are useful to treat diseases, such as obesity, diabetes, inflammation and others as described below. The present invention also provides intermediates and processes for preparing these compounds.

I

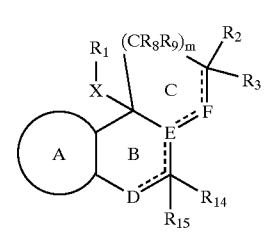

82 Claims, No Drawings

OTHER PUBLICATIONS

E. Fujita et al., J. Chem. Soc., Perkin Trans. 1 (1974), (1), 165–77, "Terpenoids. Part XXVII.[1] Total Synthesis of Enmein[2]".

H. Sdassi et al., Synthetic Communications, 25(17), 2569–2573 (1995), "Enantioselective Synthesis of (R)–(+)–4a–Cyanomethyl–6–Methoxy–3,4,9,10–Tetrahydrophenanthren–2–One".

T. Ibuka et al., Yakugaku Zasshi (1967), 87(8), 1014–17, "Studies on the Alkaloids of Menispermaceous Plants. CCXXXVI.*[3]" (English translation included).

D. Bonnet–Delpon et al., Tetrahedron (1996), 52(1), 59–70, "Trifluoromethylalkenes in Cycloaddition Reactions#".

J. A. Findlay et al., Tetrahedron Letters No. 19, pp. 869–872, 1962, Synthesis in the Diterpene Alkaloid Series—I The Stereo–specific "Synthesis of an Intermediate and Its Identification With a Natural Degradation Product".

Chemical Abstracts, vol. 84, No. 19, May 10, 1976 (May 10, 1976) Columbus, Ohio, US; abstract No. 135496w, Kigasawa K Al; "1,2–Cycloalkanoisoquinolines" & JP 50 111098—(Grelan Pharmaceutical Co., Ltd.,Japan)*.

* cited by examiner

GLUCOCORTICOID RECEPTOR MODULATORS

CROSS REFERENCE TO RELATED APPLICATIONS

This is a divisional application of U.S. Ser. No. 09/559,384, filed Apr. 27, 2000 now U.S. Pat. No. 6,380,223, now allowed, which claims the benefit of U.S. provisional application No. 60/132,130, filed Apr. 30, 1999.

FIELD OF THE INVENTION

The present invention provides non-steroidal compounds which are selective modulators (i.e., agonists and antagonists) of a steroid receptor, specifically, the glucocorticoid receptor. The present invention also provides pharmaceutical compositions containing these compounds and methods for using these compounds to treat animals requiring glucocorticoid receptor agonist and/or antagonist therapy. Glucocorticoid receptor modulators are useful to treat diseases, such as obesity, diabetes, inflammation and others as described below. The present invention also provides intermediates and processes for preparing these compounds.

BACKGROUND OF THE INVENTION

Nuclear receptors are classically defined as a family of ligand dependent transcription factors, that are activated in response to ligand binding (R. M. Evans, 240 Science, 889 (1988)). Members of this family include the following receptors: glucocorticoid, mineralocorticoid, androgen, progesterone and estrogen. Naturally occurring ligands to these receptors are low molecular weight molecules that play an important role in health and in many diseases. Excesses or deficiencies of these ligands can have profound physiological consequences. As an example, glucocorticoid excess results in Cushing's Syndrome, while glucocorticoid insufficiency results in Addison's Disease.

The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NFκ-B. Such interactions result in inhibition of API- and NFκ-B-mediated transcription and are believed to be responsible for some of the anti-inflammatory activity of endogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisilone. By definition, glucocorticoid receptor antagonists bind to the receptor and prevent glucocorticoid receptor agonists from binding and eliciting GR mediated events, including transcription. RU486 is an example of a non-selective glucocorticoid receptor antagonist.

U.S. Pat. No. 3,683,091 discloses phenanthrene compounds, specifically certain di-7-hydroxy or methyl-2,3,4,4a,9,10-hexahydrophenanthren-2-one and 4a-alkyl derivatives, hydrogenated derivatives, functional derivatives and optically active isomers thereof useful as specific antiacne agents.

Japanese Patent Application, Publication No. 45014056, published May 20, 1970, discloses the manufacture of 1,2,3,4,9,10,11α, 12-octahydro-7-methoxy-12β-butylphenanthren-2β-ol and certain of its derivatives useful as antiandrogenic and antianabolic drugs.

Japanese Patent Application, Publication No. 6-263688, published Sep. 20, 1994, discloses certain phenanthrene derivatives which are interleukin-1 (IL-1) inhibitors. It also discloses their preparation and certain intermediates thereto.

International Patent Application Publication No. WO 95/10266, published Apr. 20, 1995, discloses the preparation and formulation of certain phenanthrene derivatives as nitrogen monoxide synthesis inhibitors.

Japanese Patent Application, Publication No. 45-36500, published Nov. 20, 1970, discloses a method of making certain optically active phenanthrene derivatives which are useful as antiandrogenic agents.

European Patent Application, Publication No. 0 188 396, published Jul. 23, 1986, discloses certain substituted steroid compounds, certain processes and intermediates for preparing them, their use and pharmaceutical compositions containing them. These compounds are disclosed to possess antiglucocorticoid activity, and some of them have glucocorticoid activity.

C. F. Bigge et al., J. Med. Chem. 1993, 36, 1977–1995, discloses the synthesis and pharmacolgical evaluation of a series of octahydrophenanthrenamines and certain of their heterocyclic analogues as potential noncompetitive antagonists of the N-methyl-D-aspartate receptor complex.

P. R. Kanjilal et al., J. Org. Chem. 1985, 50, 857–863, discloses synthetic studies toward the preparation of certain complex diterpenoids.

G. Sinha et al., J. Chem. Soc., Perkin Trans. I (1983), (10), 2519–2528, discloses the synthesis of the isomeric bridged diketones cis-3,4,4a,9,10,10a-hexahydro-1,4a-ethanophenanthren-2(1H),12-dione and trans-3,4,4a,9,10,10a-hexahydro-3,4a-ethanophenanthren-2(1H),1,2-dione by highly regioselective intramolecular aldol condensations through the stereochemically defined cis- and trans-2,2-ethylenedioxy-1,2,3,4,4a,9,10,10a-octahydrophenanthren-4a-ylacetaldehydes.

U. R. Ghatak, M. Sarkar and S. K. Patra, Tetrahedron Letters No. 32, pp. 2929–2931, 1978, discloses a simple stereospecific route to certain polycyclic bridged-ring intermediates useful in preparing some complex diterpenoids.

P. N. Chakrabortty et al., Indian J. Chem. (1974), 12(9), 948–55, discloses the synthesis of 1α-methyl-1β,4aβ-dicarboxy-1,2,3,4,4a,9,10,10aβ-octahydro-phenanthrene, an intermediate in the synthesis of certain diterpenoids and diterpene alkaloids, and of 1β,4aβ-dicarboxy-1,2,3,4,4a,9,10,10aβ-octahydrophenanthrene.

E. Fujita et al., J. Chem. Soc., Perkin Trans. I (1974), (1), 165–77, discloses the preparation of enmein from 5-methoxy-2-tetralone via ent-3-β,2-epoxy-3-methoxy-17-norkaurane-6α,16α-diol.

H. Sdassi et al., Synthetic Communications, 25(17), 2569–2573 (1995) discloses the enantioselective synthesis of (R)-(+)-4a-cyanomethyl-6-methoxy-3,4,9,10-tetrahydrophenanthren-2-one, which is a key intermediate in morphinan synthesis.

T. Ibuka et al., Yakugaku Zasshi (1967), 87(8), 1014–17, discloses certain alkaloids of menispermaceous plants.

Japanese Patent 09052899, dated Feb. 25, 1997, discloses certain diterpene or triterpene derivatives which are leukotriene antagonists obtained by extraction from *Tripterygium wilfordii* for therapeutic use.

U.S. Pat. No. 5,696,127 discloses certain nonsteroidal compounds, such as 5H-chromeno[3,4-f]quinolines, which are selective modulators of steroid receptors.

U.S. Pat. No. 5,767,113 discloses certain synthetic steroid compounds useful for concurrently activating glucocorticoid-induced response and reducing multidrug resistance.

Published European Patent Application 0 683 172, published Nov. 11, 1995, discloses certain 11,21-bisphenyl-19-norpregnane derivatives having anti-glucocorticoid activity and which can be used to treat or prevent glucocorticoid dependent diseases.

D. Bonnet-Delpon et al., Tetrahedron (1996), 52(1), 59–70, discloses certain $CF_3$-substituted alkenes as good partners in Diels-Alder reactions with Danishefsky's diene and in 1,3-dipolar cycloadditions with certain nitrones and non-stabilized azomethine ylides.

International Patent Application Publication No. WO 98/26783, published Jun. 25, 1998, discloses the use of certain steroid compounds with anti-glucocorticoid activity, with the exception of mifepristone, for preparing medicaments for the prevention or treatment of psychoses or addictive behavior.

International Patent Application Publication No. WO 98/27986, published Jul. 2, 1998, discloses methods for treating non-insulin dependent Diabetes Mellitus (NIDDM), or Type II Diabetes, by administering a combination of treatment agents exhibiting glucocorticoid receptor type I agonist activity and glucocorticoid receptor type II antagonist activity. Treatment agents such as certain steroid compounds having both glucocorticoid receptor type I agonist activity and glucocorticoid receptor type II antagonist activity are also disclosed.

International Patent Application Publication No. WO 98/31702, published Jul. 23, 1998, discloses certain 16-hydroxy-11-(substituted phenyl)-estra-4,9-diene derivatives useful in the treatment or prophylaxis of glucocorticoid dependent diseases or symptoms.

Published European Patent Application 0 903 146, published Mar. 24, 1999, discloses that the steroid 21-hydroxy-6,19-oxidoprogesterone (21OH-6OP) has been found to be a selective antiglucocorticoid and is used for the treatment of diseases associated with an excess of glucocorticoids in the body, such as the Cushing's syndrome or depression.

All of the above cited patents and published patent applications are hereby incorporated by reference herein in their entirety.

J. A. Findlay et al, Tetrahedron Letters No. 19, pp. 869–872, 1962, discloses certain intermediates in the synthesis of diterpene alkaloids.

Although there are glucocorticoid receptor therapies in the art, there is a continuing need for and a continuing search in this field of art for selective glucocorticoid receptor therapies. Thus, the identification of non-steroidal compounds which have specificity for one or more steroid receptors, but which have reduced or no cross-reactivity for other steroid or intracellular receptors, is of significant value in this field.

SUMMARY OF THE INVENTION

The present invention particularly provides: compounds of formula I

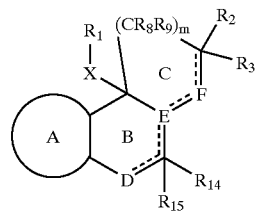

isomers thereof, prodrugs of said compounds and isomers, and pharmaceutically acceptable salts of said compounds, isomers and prodrugs;

wherein m is 1 or 2;

— represents an optional bond;

A is selected from the group consisting of

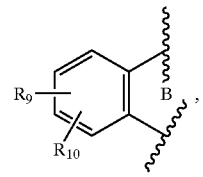

A-1

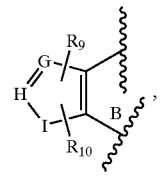

A-2

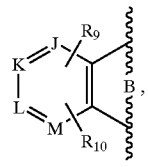

A-3

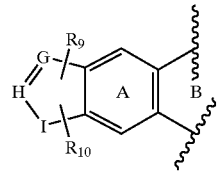

A-4 and

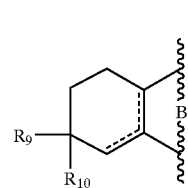

A-5

D is $CR_7$, $CR_7R_{16}$, N, $NR_7$ or O;
E is C, $CR_6$ or N;
F is $CR_4$, $CR_4R_5$ or O;

G, H and I together with 2 carbon atoms from the A-ring or 2 carbon atoms from the B-ring form a 5-membered heterocyclic ring comprising one or more N, O or S atoms; provided that there is at most one of O and S per ring; J, K, L and M together with 2 carbon atoms from the B-ring forms a 6-membered heterocyclic ring comprising 1 or more N atoms;

X is a) absent, b) —$CH_2$—, c) —CH(OH)—or d) —C(O)—;

$R_1$ is a) —H, b) —Z—$CF_3$, c) —($C_1$–$C_6$)alkyl, d) —($C_2$–$C_6$)alkenyl, e) —($C_2$–$C_6$)alkynyl, f) —CHO, g) —CH=N—$OR_{12}$, h) —Z—C(O)$OR_{12}$, i) —Z—C(O)—$NR_{12}R_{13}$, j) —Z—C(O)—$NR_{12}$—Z-het, k) —Z—$NR_{12}R_{13}$, l) —Z—$NR_{12}$het, m) —Z-het, n) —Z—O-het, o) —Z-aryl', p) —Z—O-aryl', q) —CHOH-aryl' or r) —C(O)-aryl'; wherein aryl' in substituents o) to r) is substituted independently with 0, 1 or 2 of the following: —Z—OH, —Z—$NR_{12}R_{13}$, —Z—$NR_{12}$-het, —C(O)$NR_{12}R_{13}$, —C(O)O($C_1$–$C_6$)alkyl, —C(O)OH, —C(O)—het, —$NR_{12}$—C(O)—($C_1$–$C_6$)alkyl, —$NR_{12}$—C(O)—($C_2$–$C_6$)alkenyl, —$NR_{12}$—C(O)—($C_2$–$C_6$)alkynyl, —$NR_{12}$—C(O)—Z-het, —CN, —Z-het, —O—($C_1$–$C_3$)alkyl-C(O)—$NR_{12}R_{13}$, —O—($C_1$–$C_3$)alkyl-C(O)O($C_1$–$C_6$)alkyl, —$NR_{12}$—Z—C(O)O($C_1$–$C_6$)alkyl, —N(Z—C(O)O($C_1$–$C_6$)alkyl)$_2$, —$NR_{12}$—Z—C(O)—$NR_{12}R_{13}$, —Z—$NR_{12}$—$SO_2$—$R_{13}$, —$NR_{12}$—$SO_2$-het, —C(O)H, —Z—$NR_{12}$—Z—O($C_1$–$C_6$)alkyl, —Z—$NR_{12}$—Z—$NR_{12}R_{13}$, —Z—$NR_{12}$—($C_3$–$C_6$)cycloalkyl, —Z—N(Z—O($C_1$–$C_6$)alkyl)$_2$, —$SO_2R_{12}$, —$SOR_{12}$, —$SR_{12}$, —$SO_2NR_{12}R_{13}$, —O—C(O)—($C_1$–$C_4$)alkyl, —O—$SO_2$—($C_1$–$C_4$)alkyl, -halo or —$CF_3$;

Z for each occurrence is independently a) —($C_0$–$C_6$)alkyl, b) —($C_2$–C6)alkenyl or c) —($C_2$–$C_6$)alkynyl;

$R_2$ is a) —H, b) —halo, c) —OH, d) —($C_1$–$C_6$)alkyl substituted with 0 or 1 —OH, e) —$NR_{12}R_{13}$, f) —Z—C(O)O($C_1$–$C_6$)alkyl, g) —Z—C(O)$NR_{12}R_{13}$, h) —O—($C_1$–$C_6$)alkyl, i) —Z—O—C(O)—($C_1$–$C_6$)alkyl, j) —Z—O—($C_1$–$C_3$)alkyl-C(O)—$NR_{12}R_{13}$, k) —Z—O—($C_1$–$C_3$)alkyl-C(O)—O($C_1$–$C_6$)alkyl, l) —O—($C_2$–$C_6$)alkenyl, m) —O—($C_2$–$C_6$)alkynyl, n) —O—Z-het, o) —COOH, p) —C(OH)$R_{12}R_{13}$ or q) —Z—CN;

$R_3$ is a) —H, b) —($C_1$–$C_{10}$)alkyl wherein 1 or 2 carbon atoms, other than the connecting carbon atom, may optionally be replaced with 1 or 2 heteroatoms independently selected from S, O and N and wherein each carbon atom is substituted with 0, 1 or 2 $R_y$, c) —($C_2$–$C_{10}$)alkenyl substituted with 0, 1 or 2 $R_y$, d) —($C_2$–$C_{10}$)alkynyl wherein 1 carbon atom, other than the connecting carbon atom, may optionally be replaced with 1 oxygen atom and wherein each carbon atom is substituted with 0, 1 or 2 $R_y$, e) —CH=C=$CH_2$, f) —CN, g) —($C_3$–$C_6$)cycloalkyl, h) —Z-aryl, i) —Z-het, j) —C(O)O($C_1$–$C_6$)alkyl, k) —O($C_1$–$C_6$)alkyl, l) —Z—S—$R_{12}$, m) —Z—S(O)—$R_{12}$, n) —Z—S(O)$_2$—$R_{12}$, o) —$CF_3$, p) —$NR_{12}$O—($C_1$–$C_6$)alkyl or q) —$CH_2OR_y$.

provided that one of $R_2$ and $R_3$ is absent when there is a double bond between $CR_2R_3$ (the 7 position) and the F moiety (the 8 position) of the C-ring;

$R_y$ for each occurrence is independently a) —OH, b) -halo, c) —Z—$CF_3$, d) —Z—CF($C_1$–$C_3$ alkyl)$_2$, e) —CN, f) —$NR_{12}R_{13}$, g) —($C_3$–$C_6$)cycloalkyl, h) —($C_3$–$C_6$)cycloalkenyl, i) —($C_0$–$C_3$)alkyl-aryl, j) -het or k) —$N_3$;

or $R_2$ and $R_3$ are taken together to form a) =$CHR_{11}$, b) =$NOR_{11}$, c) =O, d) =N—$NR_{12}$, e) =N—$NR_{12}$—C(O)—$R_{12}$, f) oxiranyl or g) 1,3-dioxolan-4-yl;

$R_4$ and $R_5$ for each occurrence are independently a) —H, b) —CN, c) —($C_1$–$C_6$)alkyl substituted with 0 to 3 halo, d) —($C_2$–$C_6$)alkenyl substituted with 0 to 3 halo, e) —($C_2$–$C_6$)alkynyl substituted with 0 to 3 halo, f) —O—($C_1$–$C_6$)alkyl substituted with 0 to 3 halo, g) —O—($C_2$–$C_6$)alkenyl substituted with 0 to 3 halo, h) —O—($C_2$–$C_6$)alkynyl substituted with 0 to 3 halo, i) halo, j) —OH, k) ($C_3$–$C_6$)cycloalkyl or l) ($C_3$–$C_6$)cycloalkenyl;

or $R_4$ and $R_5$ are taken together to form =O;

$R_6$ is a) —H, b) —CN, c) —($C_1$–$C_6$)alkyl substituted with 0 to 3 halo, d) —($C_2$–$C_6$)alkenyl substituted with 0 to 3 halo, e) —($C_2$–$C_6$)alkynyl substituted with 0 to 3 halo or f) —OH;

$R_7$ and $R_{16}$ for each occurrence are independently a) —H, b) -halo, c) —CN, d) —($C_1$–$C_6$)alkyl substituted with 0 to 3 halo, e) —($C_2$–$C_6$)alkenyl substituted with 0 to 3 halo or f) —($C_2$–$C_6$)alkynyl substituted with 0 to 3 halo; provided that $R_7$ is other than —CN or -halo when D is $NR_7$;

or $R_7$ and $R_{16}$ are taken together to form =O;

$R_8$, $R_9$, $R_{14}$ and $R_{15}$ for each occurrence are independently a) —H, b) -halo, c) ($C_1$–$C_6$)alkyl substituted with 0 to 3 halo, d) —($C_2$–$C_6$)alkenyl substituted with 0 to 3 halo, e) —($C_2$–$C_6$)alkynyl substituted with 0 to 3 halo, f) —CN, g) —($C_3$–$C_6$)cycloalkyl, h) —($C_3$–$C_6$)cycloalkenyl, i) —OH, j) —O—($C_1$–$C_6$)alkyl, k) —O—($C_1$–$C_6$)alkenyl, l) —O—($C_1$–$C_6$)alkynyl, m) —$NR_{12}R_{13}$, n) —C(O)$OR_{12}$ or o) —C(O)$NR_{12}R_{13}$;

or $R_8$ and $R_9$ are taken together on the C-ring to form =O; provided that when m is 2, only one set of $R_8$ and $R_9$ are taken together to form =O;

or $R_{14}$ and $R_{15}$ are taken together to form =O; provided that when $R_{14}$ and $R_{15}$ are taken together to form =O, D is other than $CR_7$ and E is other than C;

$R_{10}$ is a) —($C_1$–$C_{10}$)alkyl substituted with 0 to 3 substituents independently selected from -halo, —OH and —$N_3$, b) —($C_2$–$C_{10}$)alkenyl substituted with 0 to 3 substituents independently selected from -halo, —OH and —$N_3$, c) —$C_2$–$C_{10}$)alkynyl substituted with 0 to 3 substituents independently selected from -halo, —OH and —$N_3$, d) -halo, e) —Z—CN, f) —OH, g) —Z-het, h) —Z—$NR_{12}R_{13}$, i) —Z—C(O)-het, j) —Z—C(O)—($C_1$–$C_6$)alkyl, k) —Z—C(O)—$NR_{12}R_{13}$, l) —Z—C(O)—$NR_{12}$—Z—CN, m) —Z—C(O)—$NR_{12}$—Z-het, n) —Z—C(O)—$NR_{12}$—Z-aryl, o) —Z—C(O)—$NR_{12}$—Z—$NR_{12}R_{13}$, p) —Z—C(O)—$NR_{12}$—Z—O($C_1$–$C_6$)alkyl, q) —($C_0$–$C_6$)alkyl-C(O)OH, r) —Z—C(O)O($C_1$–$C_6$)alkyl, s) —Z—O—($C_0$–$C_6$)alkyl-het, t) —Z—O—($C_0$–$C_6$)alkyl-aryl, u) —Z—O—($C_1$–$C_6$)alkyl substituted with 0 to 2 $R_x$, v) —Z—O—($C_1$–$C_6$)alkyl-CH(O), w) —Z—O—($C_1$–$C_6$)alkyl-$NR_{12}$-het, x) —Z—O—Z-het-Z-het, y) —Z—O—Z-het-Z—$NR_{12}R_{13}$, z) —Z—O—Z-het-C(O)-het, a1) —Z—O—Z—C(O)-het, b1) —Z—O—Z—C(O)-het-het, c1) —Z—O—Z—C(O)—($C_1$–$C_6$)alkyl, d1) —Z—O—Z—C(S)—$NR_{12}R_{13}$, e1) —Z—O—Z—C(O)—$NR_{12}R_{13}$, f1) —Z—O—Z—($C_1$–$C_3$)alkyl-C(O)—$NR_{12}R_{13}$, g1) —Z—O—Z—C(O)—O($C_1$–$C_6$)alkyl, h1) —Z—O—Z—C(O)—OH, i1) —Z—O—Z—C(O)—$NR_{12}$—O($C_1$–$C_6$)alkyl, j1) —Z—O—Z—C(O)—$NR_{12}$—OH, k1) —Z—O—Z—C(O)—$NR_{12}$—Z—$NR_{12}R_{13}$, l1) —Z—O—Z—C(O)—$NR_{12}$-Z-het, m1) —Z—O—Z—C(O)—$NR_{12}$—$SO_2$—($C_1$–$C_6$)alkyl, n1) —Z—O—Z—C(=$NR_{12}$)($NR_{12}R_{13}$), o1) —Z—O—Z—C(=$NOR_{12}$)($NR_{12}R_{13}$), p1) —Z—$NR_{12}$—C(O)—O—Z—$NR_{12}R_{13}$, q1) —Z—S—C(O)—$NR_{12}R_{13}$, r1) —Z—O—$SO_2$—($C_1$–$C_6$)alkyl, s1) —Z—O—$SO_2$-aryl, t1) —Z—O—$SO_2$—$NR_{12}R_{13}$, u1) —Z—O—$SO_2$—$CF_3$, v1) —Z—$NR_{12}$C(O)$OR_{13}$ or w1) —Z—$NR_{12}$C(O)$R_{13}$;

or $R_9$ and $R_{10}$ are taken together on the moiety of formula A-5 to form a) =O or b)=$NOR_{12}$;

$R_{11}$ is a) —H, b) —($C_1$–$C_5$)alkyl, c) —($C_3$–$C_6$)cycloalkyl or d) —($C_0$–$C_3$)alkyl-aryl;

$R_{12}$ and $R_{13}$ for each occurrence are each independently a) —H, b) —$C_1$–$C_6$)alkyl wherein 1 or 2 carbon atoms, other than the connecting carbon atom, may optionally be replaced with 1 or 2 heteroatoms independently selected from S, O and N and wherein each carbon atom is substituted with 0 to 6 halo, c) —($C_2$–$C_6$)alkenyl substituted with 0 to 6 halo, or d) —($C_1$–$C_6$)alkynyl wherein 1 carbon atom, other than the connecting carbon atom, may optionally be replaced with 1 oxygen atom and wherein each carbon atom is substituted with 0 to 6 halo;

or R$_{12}$ and R$_{13}$ are taken together with N to form het;

or R$_6$ and R$_{14}$ or R$_{15}$ are taken together to form 1,3-dioxolanyl;

aryl is a) phenyl substituted with 0 to 3 R$_x$, b) naphthyl substituted with 0 to 3 R$_x$ or c) biphenyl substituted with 0 to 3 R$_x$;

het is a 5-,6- or 7-membered saturated, partially saturated or unsaturated ring containing from one (1) to three (3) heteroatoms independently selected from the group consisting of nitrogen, oxygen and sulfur; and including any bicyclic group in which any of the above heterocyclic rings is fused to a benzene ring or another heterocycle; and the nitrogen may be in the oxidized state giving the N-oxide form; and substituted with 0 to 3 R$_x$;

R$_x$ for each occurrence is independently a) -halo, b) —OH, c) —(C$_1$-C$_6$)alkyl, d) —C$_2$-C$_6$)alkenyl, e) —C$_2$-C$_6$) alkynyl, f) —O(C$_1$-C$_6$)alkyl, g) —O(C$_2$-C$_6$)alkenyl, h) —O(C$_2$-C$_6$)alkynyl, i) —(C$_0$-C$_6$)alkyl-NR$_{12}$R$_{13}$, j) —C(O)—NR$_{12}$R$_{13}$, k) —Z—SO$_2$R$_{12}$, l) —Z—SOR$_{12}$, m) —Z—SR$_{12}$, n) —NR$_{12}$—SO$_2$R$_{13}$, o) —NR$_{12}$—C(O)—R$_{13}$, p) —NR$_{12}$—OR$_{13}$, q) —SO$_2$—NR$_{12}$R$_{13}$, r) —CN, s) —CF$_3$, t) —C(O)(C$_1$-C$_6$)alkyl, u) =O, v) —Z—SO$_2$-phenyl or w) —Z—SO$_2$-het';

aryl' is phenyl, naphthyl or biphenyl;

het' is a 5-,6- or 7-membered saturated, partially saturated or unsaturated ring containing from one (1) to three (3) heteroatoms independently selected from the group consisting of nitrogen, oxygen and sulfur; and including any bicyclic group in which any of the above heterocyclic rings is fused to a benzene ring or another heterocycle;

provided that:
1) X—R$_1$ is other than hydrogen or methyl;
2) when R$_9$ and R$_{10}$ are substituents on the A-ring, they are other than mono- or di-methoxy;
3) when R$_2$ and R$_3$ are taken together to form =CHR$_{11}$ or =O wherein R$_{11}$ is —O(C$_1$-C$_6$)alkyl, then —X—R$_1$ is other than (C$_1$-C$_4$)alkyl;
4) when R$_2$ and R$_3$ are taken together to form =O and R$_9$ is hydrogen on the A-ring; or when R$_2$ is hydroxy, R$_3$ is hydrogen and R$_9$ is hydrogen on the A-ring, then R$_{10}$ is other than —O—(C$_1$-C$_6$)alkyl or —O—CH$_2$-phenyl at the 2-position of the A-ring;
5) when X—R, is (C$_1$-C$_4$)alkyl, (C$_2$-C$_4$)alkenyl or (C$_2$-C$_4$)alkynyl, R$_9$ and R$_{10}$ are other than monohydroxy or =O, including the diol form thereof, when taken together; and
6) when X is absent, R$_1$ is other than a moiety containing a heteroatom selected from N, O or S directly attached to the juncture of the B-ring and the C-ring.

More particularly, the present invention provides: compounds of formula I, isomers thereof, prodrugs of said compounds or isomers, or pharmaceutically acceptable salts of said compounds, isomers or prodrugs;

wherein the A-ring is selected from the group consisting of:

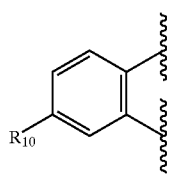

A-1a

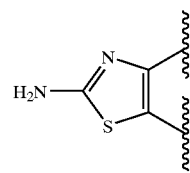

A-2a

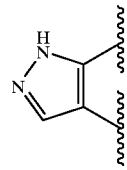

A-2b

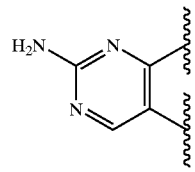

A-3a

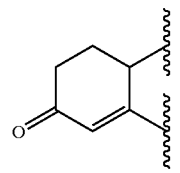

A-5a

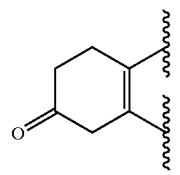

A-5b

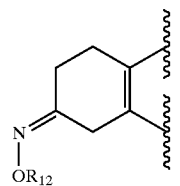

A-5c

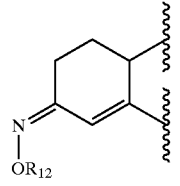

A-5d

D is CR$_7$, CR$_7$R$_{16}$ or O;

E is C, CR$_6$ or N;

F is CR$_4$, CR$_4$R$_5$ or O; and

X is —CH$_2$—.

More particularly, the present invention provides: compounds of formula I, isomers thereof, prodrugs of said compounds or isomers, or pharmaceutically acceptable salts of said compounds, isomers or prodrugs; wherein D is CH$_2$; E is CH; F is CH$_2$; R$_8$ is —H; R$_9$ is —H on the C-ring; m is 2; R$_{14}$ is —H; R$_{15}$ is —H; and the A-ring is the moiety of formula A-1a.

More particularly, the present invention provides:

compounds of formula II

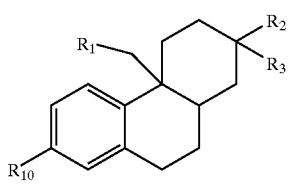

isomers thereof, prodrugs of said compounds or isomers, or pharmaceutically acceptable salts of said compounds, isomers or prodrugs; wherein $R_2$ is a) —OH or b) —O—$CH_2$-het;

$R_3$ is a) —($C_1$-$C_6$)alkyl substituted with 0 or 1 of the following: —$CF_3$, —CN, —($C_3$-$C_6$)cycloalkyl, -phenyl or —$N_3$, b) —C≡C— substituted with 1 of the following: —($C_1$-$C_5$)alkyl, —Cl, —$CF_3$, —($C_3$-$C_6$)cycloalkyl, -phenyl or -benzyl; c) —$CH_2$OH, d) —$CH_2$O($C_1$-$C_5$)alkyl wherein 1 carbon atom may optionally be replaced with 1 oxygen atom, e) —$CH_2$O($C_2$-$C_5$)alkenyl, f) —$CH_2$O($C_2$-$C_5$)alkynyl wherein 1 carbon atom may optionally be replaced with 1 oxygen atom, g) —$CH_2$O$R_y$, h) —CN or i) —$CF_3$;

$R_y$ is a) —($C_1$-$C_3$)alkyl —$CF_3$, b) —($C_3$-$C_6$)cycloalkyl, c) -phenyl or d) -benzyl;

or $R_2$ and $R_3$ are taken together to form a) -1,3-dioxolan-4-yl or b) =$NOR_{11}$;

$R_{11}$ is a) —H, b) —($C_1$-$C_5$)alkyl, c) —($C_3$-$C_6$)cycloalkyl, d) -phenyl or e) -benzyl.

In addition, more particularly, the present invention provides:
compounds of formula II

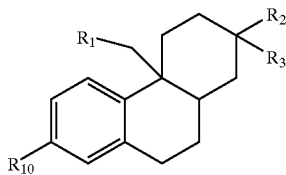

isomers thereof, prodrugs of said compounds or isomers, or pharmaceutically acceptable salts of said compounds, isomers or prodrugs; wherein $R_1$ is a) —($C_1$-$C_4$)alkyl, b) —($C_2$-$C_4$)alkenyl, c) -phenyl substituted with 0 or 1 of the following: —OH, —$NR_{12}R_{13}$, —$NR_{12}$—C(O)—($C_1$-$C_4$)alkyl, —CN, —Z-het, —O—($C_1$-$C_3$)alkyl-C(O)—$NR_{12}R_{13}$, —$NR_{12}$—Z—C(O)—$NR_{12}R_{13}$, —Z—$NR_{12}$—$SO_2$—$R_{13}$, —$NR_{12}$—$SO_2$-het, —O—C(O)—($C_1$-$C_4$)alkyl or —O—$SO_2$—($C_1$-$C_4$)alkyl; d) —O-phenyl substituted with 0 or 1 of the following: —Z—$NR_{12}R_{13}$ or —C(O)$NR_{12}R_{13}$, or e) —CH=CH-phenyl wherein phenyl is substituted with 0 or 1 of the following: —Z—$NR_{12}R_{13}$ or —C(O)$NR_{12}R_{13}$;

Z for each occurrence is independently —($C_0$-$C_2$)alkyl;

$R_{10}$ is a) —CH(OH)($C_1$-$C_5$)alkyl, b) —CN, c) —OH, d) -het, e) —C(O)—($C_1$-$C_4$)alkyl, f) —C(O)—$NR_{12}R_{13}$, g) —C(O)—NH—Z-het, h) —O—($C_0$-$C_2$)alkyl-het, i) —O—Z—C(O)—$NR_{12}R_{13}$, j) —O—Z—C(O)—NH—($C_0$-$C_3$)alkyl-het or k) —O—Z—C(O)—NH—($C_0$-$C_3$)alkyl-$NR_{12}R_{13}$;

$R_{12}$ and $R_{13}$ are independently a) —H or b) —($C_1$-$C_4$)alkyl;

or $R_{12}$ and $R_{13}$ are taken together with N to form het.

Yet, even more particularly, the present invention provides:

compounds of formula II

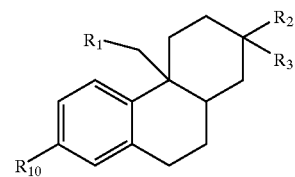

isomers thereof, prodrugs of said compounds or isomers, or pharmaceutically acceptable salts of said compounds, isomers or prodrugs; wherein $R_1$ is a) —($C_2$-$C_4$)alkyl, b) —$CH_2$—CH=$CH_2$ or c) -phenyl;

$R_2$ is —OH;

$R_3$ is a) —($C_1$-$C_6$)alkyl substituted with 0 or 1 $CF_3$, b) —C≡C—$CH_3$, c) —C≡C—Cl, d) —C≡C—$CF_3$, e) —$CH_2$O($C_1$-$C_3$)alkyl substituted with 0 or 1 $CF_3$, or f) —$CF_3$;

$R_{10}$ is —OH.

Most particularly, the present invention provides:

compounds of formula III

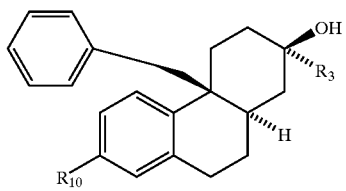

prodrugs thereof, or pharmaceutically acceptable salts of said compounds or prodrugs; wherein $R_3$ and $R_{10}$ are as defined immediately above.

In addition, the present invention more particularly provides:

compounds of formula II

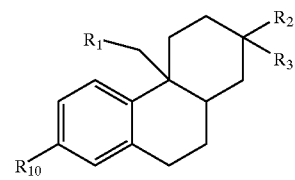

isomers thereof, prodrugs of said compounds or isomers, or pharmaceutically acceptable salts of said compounds, isomers or prodrugs; wherein $R_1$ is a) —($C_2$-$C_4$)alkyl, b) —$CH_2$—CH=$CH_2$ or c) -phenyl;

$R_2$ is —OH;

$R_3$ is a) —($C_1$-$C_5$)alkyl substituted with 0 or 1 $CF_3$, b) —C≡C—$CH_3$, c) —C≡C—Cl, d) —C≡C—$CF_3$, e) —$CH_2$O($C_1$-$C_3$)alkyl substituted with 0 or 1 $CF_3$, or f) —$CF_3$; $R_{10}$ is —CN.

Most particularly, the present invention provides:

compounds of formula III

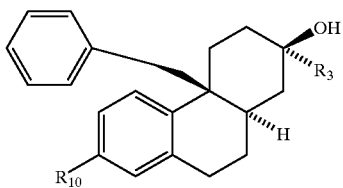

prodrugs thereof, or pharmaceutically acceptable salts of said compounds or prodrugs;
wherein $R_3$ and $R_{10}$ are as defined immediately above. Preferably, it provides a compound of formula III wherein $R_3$ is —C≡C—$CH_3$ and $R_{10}$ is —CN; a compound of formula III wherein $R_3$ is —$(CH_2)_2$—$CH_3$ and $R_{10}$ is —CN; a compound of formula III wherein $R_3$ is —$CF_3$ and $R_{10}$ is —CN; and a compound of formula III wherein $R_3$ is —$CH_2CH_2CF_3$ and $R_{10}$ is —CN; and pharmaceutically acceptable salts thereof.

In addition, the present invention more particularly provides:
compounds of formula II

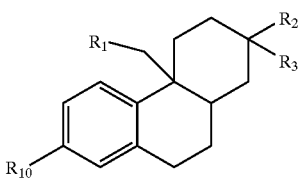

isomers thereof, prodrugs of said compounds or isomers, or pharmaceutically acceptable salts of said compounds, isomers or prodrugs; wherein $R_1$ is a) —$(C_2-C_4)$alkyl, b) —$CH_2$—CH=$CH_2$ or c) -phenyl;
$R_2$ is —OH;
$R_3$ is a) —$(C_1-C_6)$alkyl substituted with 0 or 1 $CF_3$, b) —C≡C—$CH_3$, c) —C≡C—Cl, d) —C≡C—$CF_3$, e) —$CH_2O(C_1-C_3)$alkyl substituted with 0 or 1 $CF_3$, or f) —$CF_3$;
$R_{10}$ is —C(O)—NH—Z-het wherein het is selected from the group consisting of a) pyridinyl substituted with 0 or 1 methyl, b) pyrimidinyl, c) pyrazinyl, d) morpholinyl and e) oxadiazolyl;
Z is —$(C_0-C_2)$ alkyl.

Most particularly, the present invention provides:
compounds of formula III

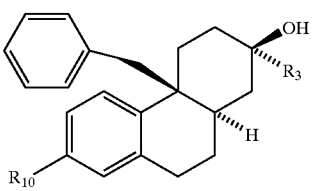

prodrugs thereof, or pharmaceutically acceptable salts of said compounds or prodrugs; wherein $R_3$ is a) —$(CH_2)_2$—$CF_3$, b) —$(CH_2)_2$—$CH_3$, c) —$CH_3$, d) —C≡C—$CH_3$, e) —C≡C—Cl or f) —$CF_3$;
$R_{10}$ is as defined immediately above. Preferably, it provides a compound of formula III or a pharmaceutically acceptable salt thereof as follows: a compound of formula III wherein $R_3$ is —C≡C—$CH_3$ and $R_{10}$ is —C(O)—NH—$CH_2$—(4-pyridinyl); a compound of formula III wherein $R_3$ is —C≡C—$CH_3$ and $R_{10}$ is —C(O)—NH—$CH_2$—(2-pyridinyl); a compound of formula III wherein $R_3$ is —C≡C—$CH_3$ and $R_{10}$ is —C(O)—NH—$CH_2$—(3-pynidinyl); a compound of formula III wherein $R_3$ is —C≡C—$CH_3$ and $R_{10}$ is —C(O)—NH—(2-pyrazinyl); a compound of formula III wherein $R_3$ is —C≡C—$CH_3$ and $R_{10}$ is —C(O)—NH—$CH_2$—(2-methyl-3-pyridinyl); a compound of formula III wherein $R_3$ is —$(CH_2)_2$—$CH_3$ and $R_{10}$ is —C(O)—NH—$CH_2$—(2-methyl-3-pyridinyl); a compound of formula III wherein $R_3$ is —$(CH_2)_2$—$CH_3$ and $R_{10}$ is —C(O)—NH—$CH_2$—(2-pyridinyl); a compound of formula III wherein $R_3$ is —$(CH_2)_2$—$CF_3$ and $R_{10}$ is —C(O)—NH—$CH_2$—(2-methyl-3-pyridinyl); a compound of formula III wherein $R_3$ is —$CH_3$ and $R_{10}$ is —C(O)—NH—$CH_2$—(2-methyl-3-pyridinyl); a compound of formula III wherein $R_3$ is —$CH_3$ and $R_{10}$ is —C(O)—NH—(3-pyridinyl); and a compound of formula III wherein $R_3$ is —$CF_3$ and $R_{10}$ is —C(O)—NH—$CH_2$—(2-methyl-3-pyridinyl).

In addition, the present invention more particularly provides:
compounds of formula II

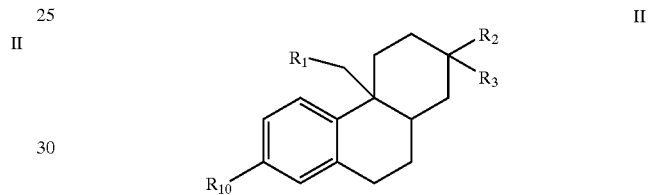

isomers thereof, prodrugs of said compounds or isomers, or pharmaceutically acceptable salts of said compounds, isomers or prodrugs; wherein $R_1$ is a) —$(C_2-C_4)$alkyl, b) —$CH_2$—CH=$CH_2$ or c) -phenyl;
$R_2$ is —OH;
$R_3$ is a) —$(C_1-C_4)$alkyl substituted with 0 or 1 $CF_3$, b) —C≡C—$CH_3$, c) —C≡C—Cl, d) —C≡C—$CF_3$, e) —$CH_2O(C_1-C_3)$alkyl substituted with 0 or 1 $CF_3$, or f) —$CF_3$;
$R_{10}$ is —O—$(C_1-C_2)$alkyl-het wherein het is selected from the group consisting of a) pyridinyl substituted with 0 or 1 methyl, b) pyrimidinyl, c) pyrazinyl, d) morpholinyl and f) oxadiazolyl.

Most particularly, the present invention provides:
compounds of formula III

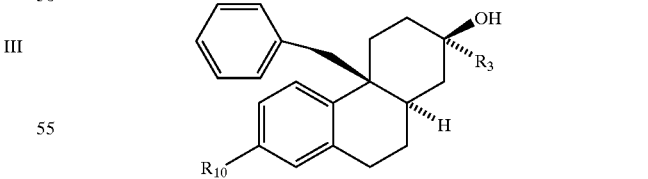

prodrugs thereof, or pharmaceutically acceptable salts of said compounds or prodrugs;
wherein $R_3$ is a) —$(CH_2)_2$—$CF_3$, b) —$(CH_2)_2$—$CH_3$, c) —$CH_3$, d) —C≡C—$CH_3$, e) —C≡C—Cl or f) —$CF_3$;
$R_{10}$ is —O—$(C_1-C_2)$alkyl-het wherein het is selected from the group consisting of a) 2-pyridinyl, b) 3-pyridinyl, c) 4-pyridinyl, d) 2-methyl-3-pyridinyl and e) pyrazinyl. Preferably, it provides a compound of formula III and pharmaceutically acceptable salts thereof as follows: a compound of formula III wherein $R_3$ is —C≡C—CH$_3$ and $R_{10}$ is —O—CH$_2$—(4-pyridinyl); a compound of formula III wherein $R_3$ is —C≡C—CH$_3$ and $R_{10}$ is —O—CH$_2$—(2-pyridinyl); a compound of formula III wherein $R_3$ is —(CH$_2$)$_2$—CF$_3$ and $R_{10}$ is —O—CH$_2$—(3-pyridinyl); a compound of formula III wherein $R_3$ is —(CH$_2$)$_2$—CF$_3$ and $R_{10}$ is —O—CH$_2$—(2-methyl-3-pyridinyl); a compound of formula III wherein $R_3$ is —(CH$_2$)$_2$—CF$_3$ and $R_{10}$ is —O—CH$_2$—(2-pyridinyl); and a compound of formula III wherein $R_3$ is —CF$_3$ and $R_{10}$ is —O—CH$_2$—(2-methyl-3-pyridinyl).

In addition, the present invention more particularly provides:
compounds of formula II

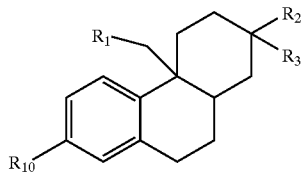

isomers thereof, prodrugs of said compounds or isomers, or pharmaceutically acceptable salts of said compounds, isomers or prodrugs; wherein $R_1$ is a) —(C$_2$-C$_4$)alkyl, b) —CH$_2$—CH═CH$_2$ or c) -phenyl;

$R_2$ is—OH;

$R_3$ is a) —(C$_1$-C$_4$)alkyl substituted with 0 or 1 CF$_3$, b) —C≡C—CH$_3$, c) —C≡C—Cl, d) —C≡C—CF$_3$, e) —CH$_2$O (C$_1$-C$_3$)alkyl substituted with 0 or 1 CF$_3$,or f) —CF$_3$;

$R_{10}$ is a) —O—Z—C(O)—NH—(C$_0$-C$_3$)alkyl-N((C$_1$-C$_2$)alkyl)$_2$, b) —O—Z—C(O)—NR$_{12}$R$_{13}$, or c) —O—Z—C(O)—NH—(C$_0$-C$_3$)alkyl-het wherein het is selected from the group consisting of 1) pyridinyl substituted with 0 or 1 methyl, 2) pyrimidinyl, 3) pyrazinyl, 4) morpholinyl, 5) pyrrolidinyl, 6) imidazolyl and 7) oxadiazolyl;

$R_{12}$ and $R_{13}$ are independently a) —H or b) —(C$_1$-C$_2$) alkyl; or $R_{12}$ and $R_{13}$ are taken together with N to form pyrrolidinyl;

Z is —(C$_0$-C$_1$) alkyl.

Most particularly, the present invention provides:
compounds of formula III

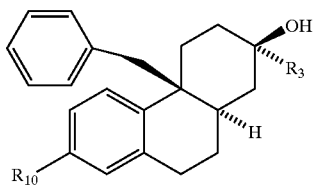

prodrugs thereof, or pharmaceutically acceptable salts of said compounds or prodrugs; wherein $R_3$ is a) —(CH$_2$)$_2$—CF$_3$, b) —(CH$_2$)$_2$—CH$_3$, c) —CH$_3$, d) —C≡C—CH$_3$, e) —C≡C—Cl or f) —CF$_3$;

$R_{10}$ is a) —O—C(O)—NH—(C$_0$-C$_3$)alkyl-N((C$_1$-C$_2$) alkyl)$_2$, b) —O—C(O)—N(CH$_3$)$_2$, c) —O—C(O)—(1-pyrrolidinyl) or d) —O—C(O)—NH—(C$_0$-C$_3$)alkyl-het wherein het is selected from the group consisting of 1) 2-pyridinyl, 2) 3-pyridinyl, 3) 4-pyridinyl, 4) 2-methyl-3-pyridinyl, 5) pyrazinyl, 6) morpholinyl, 7) pyrrolidinyl and 8) imidazolyl. Preferably, it provides a compound of formula III wherein $R_3$ is —C≡C—CH$_3$ and $R_{10}$ is —O—C(O)—NH—(CH$_2$)$_2$—(1-pyrrolidinyl); a compound of formula III wherein $R_3$ is —C≡C—CH$_3$ and $R_{10}$ is —O—C(O)—NH—(CH$_2$)$_2$—N(CH$_3$)$_2$; a compound of formula III wherein $R_3$ is —C≡C—CH$_3$ and $R_{10}$ is —O—C(O)—NH—CH$_2$-2-pyridyl; a compound of formula III wherein $R_3$ is —C≡C—CH$_3$ and $R_{10}$ is —O—C(O)—NH—CH$_2$-4-pyridyl; and a compound of formula III wherein $R_3$ is —C≡C—CH$_3$ and $R_{10}$ is —O—C(O)—NH—CH$_2$-3-pyridyl; and pharmaceutically acceptable salts of the above compounds.

The present invention also provides:
compounds of formula IV

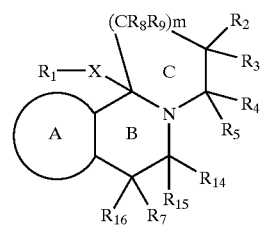

isomers thereof, prodrugs of said compounds or isomers, or pharmaceutically acceptable salts of said compounds, isomers or prodrugs; wherein the variables are as defined above for formula I.

More particularly, the present invention provides compounds of formula V, isomers thereof, prodrugs of said compounds or isomers, or pharmaceutically acceptable salts of said compounds, isomers or prodrugs; wherein $R_8$ is —H; $R_9$ is —H on the C-ring; m is 2; $R_7$ is —H; $R_{14}$ is —H; $R_{15}$ is —H; $R_{16}$ is —H; and the A-ring is the moiety of formula A-1a.

Even more particularly, the present invention provides compounds of formula V

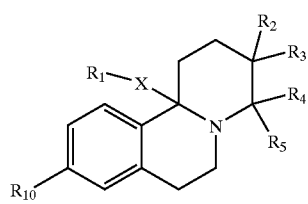

isomers thereof, prodrugs of said compounds or isomers, or pharmaceutically acceptable salts of said compounds, isomers or prodrugs; wherein X is —CH$_2$—;

$R_1$ is a) —(C$_1$-C$_4$)alkyl, b) —(C$_2$-C$_4$)alkenyl, c) -phenyl substituted with 0 or 1 of the following: —OH, —NR$_{12}$R$_{13}$, —NR$_{12}$—C(O)—(C$_1$-C$_4$)alkyl, —CN, —Z-het, —O—(C$_1$-C$_3$)alkyl-C(O)—NR$_{12}$R$_{13}$, —NR$_{12}$—Z—C(O)—NR$_{12}$R$_{13}$, —Z—NR$_{12}$—SO$_2$—R$_{13}$, —NR$_{12}$—SO$_2$-het, —O—C(O)—(C$_1$-C$_4$)alkyl or —O—SO$_2$—(C$_1$-C$_4$)alkyl; d) —O-phenyl substituted with 0 or 1 of the following: —Z—NR$_{12}$R$_{13}$ or —C(O)NR$_{12}$R$_{13}$; or e) —CH═CH-phenyl wherein phenyl is substituted with 0 or 1 of the following: —Z—NR$_{12}$R$_{13}$ or —C(O)NR$_{12}$R$_{13}$;

Z is for each occurrence independently —(C$_0$-C$_2$)alkyl;

$R_4$ and $R_5$ are each hydrogen or are taken together to form ═O;

$R_{10}$ is a) —CH(OH)(C$_1$-C$_5$)alkyl, b) —CN, c) —OH, d) -het, e) —C(O)—(C$_1$-C$_4$)alkyl, f) —C(O)—NR$_{12}$R$_{13}$, g) —C(O)—NH—Z-het, h) —O—(C$_0$-C$_3$)alkyl-het, i) —O—Z—C(O)—NR$_{12}$R$_{13}$, j) —O—Z—C(O)—NH—(C$_0$-C$_3$)alkyl-het, or k) —O—(C$_0$-C$_3$)alkyl-phenyl;

$R_{12}$ and $R_{13}$ for each occurrence are independently a) —H or b) —($C_1$–$C_4$)alkyl.

Most particularly, the present invention provides compounds of formula VI

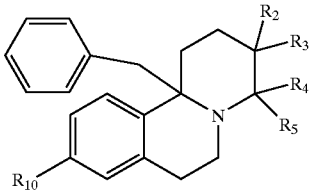

VI isomers thereof, prodrugs of said compounds or isomers, or pharmaceutically acceptable salts of said compounds, isomers or prodrugs; wherein $R_2$ is a) —C(O)OH, b) —C(O)OCH$_3$, c) —C(O)OCH$_2$CH$_3$ or d) —CH$_2$OH;

$R_3$ is a) —(CH$_2$)$_2$—CF$_3$, b) —(CH$_2$)$_2$—CH$_3$, c) —CH$_3$ or d) —CF$_3$;

$R_4$ and $R_5$ are each hydrogen or are taken together to form =O;

$R_{10}$ is a) —OH, b) —O—(C$_0$–C$_3$)alkyl-phenyl or c) —O—(C$_0$–C$_3$)alkyl-het wherein het is selected from the group consisting of a) 2-pyridinyl, b) 3-pyridyl, c) 4-pyridyl, d) 2-methyl-3-pyridyl and e) pyrazinyl.

The present invention also provides:
compounds of formula VII

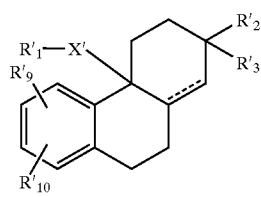

VII and isomers thereof; wherein —is an optional bond;

X' is —CH$_2$—;

R'$_1$ is phenyl substituted with 0, 1 or 2 R'$_x$;

R'$_2$ is —OH;

R'$_3$ is a) —(C$_1$–C$_6$)alkyl substituted with 0 or 1 R'$_y$ or b) —(C$_2$–C$_6$)alkynyl substituted with 0 or 1 R'$_y$;

R'$_y$ is —CF$_3$;

or R'$_2$ and R'$_3$ are taken together to form =O;

R'$_9$ is —H;

R'$_{10}$ is a) -halo, b) —C(O)OH, c) —C(O)O(C$_1$–C$_6$)alkyl, d) —C(O)—NR'$_{12}$R'$_{13}$, e) —CN, f) —OH or g) —O—(C$_1$–C$_3$)alkyl;

R'$_x$ is a) -halo, b) —OH, c) —(C$_1$–C$_6$)alkyl, d) —CN, e) —CF$_3$, f) —(C$_0$–C$_6$)alkyl-NR'$_2$R'$_{13}$, g) —C(O)—NR'$_{12}$R'$_{13}$, h) —NR'$_{12}$—SO$_2$R'$_{13}$, i) —NR'$_{12}$—C(O)—R'$_{13}$, j) —SO$_2$R'$_{12}$ or k) —SO$_2$—NR'$_{12}$R'$_{13}$;

R'$_{12}$ and R'$_{13}$ for each occurrence are each independently a) —H or b) —(C$_1$–C$_6$)alkyl. More particularly, the present invention provides the compound, 2(3H)-phenanthrenone, 4,4a,9,10-tetrahydro-7-bromo-4a-(phenylmethyl-,(S)—.

The present invention also provides:
compounds of formula VIII

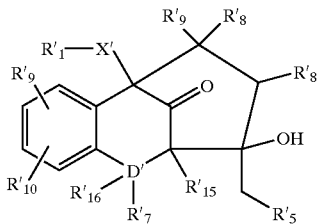

VIII and isomers thereof;
wherein D' is C;

X' is —CH$_2$—;

R'$_1$ is phenyl substituted with 0 to 2 R'$_x$;

R'$_5$, R'$_7$, R'$_8$, R'$_9$, R'$_{15}$ and R'$_{16}$ for each occurrence are independently a) —H, b) —O—(C$_1$–C$_6$)alkyl, c) —(C$_1$–C$_6$)alkyl or d) halo;

R'$_{10}$ is a) -halo, b) —CN, c) —OH, d) —C(O)—NR'$_{12}$R'$_{13}$, e) —C(O)—NR'$_{12}$—Z'-het wherein het is substituted with 0 or 1 R'$_x$, f) —C(O)—NR'$_{12}$—Z'-aryl wherein aryl is substituted with 0 or 1 R'$_x$, g) —O—(C$_0$–C$_6$)alkyl-het wherein het is substituted with 0 or 1 R'$_x$, or h) —O—(C$_0$–C$_6$)alkyl-aryl wherein aryl is substituted with 0 or 1 R'$_x$;

Z' is a) —(C$_0$–C$_6$)alkyl, b) —(C$_2$–C$_6$)alkenyl, or c) —(C$_2$–C$_6$)alkynyl;

R'$_x$ is a) -halo, b) —OH, c) —(C$_1$–C$_6$)alkyl, d) —CN, e) —CF$_3$, f) —(C$_0$–C$_6$)alkyl-NR'$_{12}$R'$_{13}$, g) —C(O)—NR'$_{12}$R'$_{13}$, h) —NR'$_{12}$—SO$_2$R'$_{13}$, i) —NR'$_{12}$—C(O)—R'$_{13}$, j) —SO$_2$R'$_{12}$ or k) —SO$_2$—NR'$_{12}$R'$_{13}$;

R'$_{12}$ and R'$_{13}$ for each occurrence are each independently a) —H or b) —(C$_1$–C$_6$)alkyl;

aryl is phenyl;

het is a 5-,6- or 7-membered saturated, partially saturated or unsaturated ring containing from one (1) to three (3) heteroatoms independently selected from the group consisting of nitrogen, oxygen and sulfur. More particularly, the present invention provides the compound, 1(R)-benzyl-6-methoxy-1-(S)—(3-oxo-butyl)-3,4-dihydro-1H-naphthalen-2-one.

In addition, the present invention provides compounds of formula II

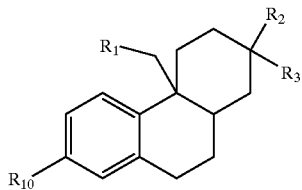

II an isomer thereof, a prodrug of said compound or isomer, or a pharmaceutically acceptable salt of said compound, isomer or prodrug; wherein $R_1$ is -phenyl;

$R_2$ is —OH;

$R_3$ is a) —(C$_1$–C$_6$)alkyl substituted with 0 or 1 CF$_3$, b) —C≡C—CH$_3$, c) —C≡C—Cl, d) —C≡C—CF$_3$, e) —CH$_2$O(C$_1$–C$_3$)alkyl substituted with 0 or 1 CF$_3$, or f) —CF$_3$;

$R_{10}$ is —OH, —CN, —C(O)OH or —C(O)O(C$_1$–C$_6$)alkyl.

More particularly, the present invention provides compounds of formula III

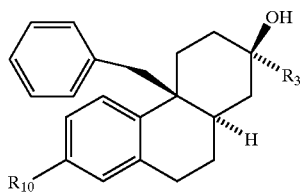

a prodrug thereof, or a pharmaceutically acceptable salt of said compound or prodrug; wherein $R_3$ is a) —$(CH_2)_2$—$CF_3$, b) —$(CH_2)_2$—$CH_3$, c) —$CH_3$, d) —C≡C—$CH_3$, e) —C≡C—Cl or f) —$CF_3$; and $R_{10}$ is as defined immediately above. Most particularly, it provides a compound of formula III wherein $R_3$ is —C≡C—$CH_3$ and $R_{10}$ is —OH; or a pharmaceutically acceptable salt thereof; a compound of formula III wherein $R_3$ is —C≡C—$CH_3$ and $R_{10}$ is —CN; or a pharmaceutically acceptable salt thereof; a compound of formula III wherein $R_3$ is —C≡C—$CH_3$ and $R_{10}$ is —COOH; or a pharmaceutically acceptable salt thereof; a compound of formula III wherein $R_3$ is —$(CH_2)_2$—$CH_3$ and $R_{10}$ is —OH; or a pharmaceutically acceptable salt thereof; a compound of formula III wherein $R_3$ is —$(CH_2)_2$—$CH_3$ and $R_{10}$ is —CN; or a pharmaceutically acceptable salt thereof; a compound of formula III wherein $R_3$ is —$(CH_2)_2$—$CH_3$ and $R_{10}$ is —COOH; or a pharmaceutically acceptable salt thereof; a compound of formula III wherein $R_3$ is —$(CH_2)_2$—$CF_3$ and $R_{10}$ is —OH; or a pharmaceutically acceptable salt thereof; a compound of formula III wherein $R_3$ is —$(CH_2)_2$—$CF_3$ and $R_{10}$ is —CN; or a pharmaceutically acceptable salt thereof; a compound of formula III wherein $R_3$ is —$(CH_2)_2$—$CF_3$ and $R_{10}$ is —COOH; or a pharmaceutically acceptable salt thereof; a compound of formula III wherein $R_3$ is —$CH_3$ and $R_{10}$ is —OH; or a pharmaceutically acceptable salt thereof; a compound of formula III wherein $R_3$ is —$CH_3$ and $R_{10}$ is —CN; or a pharmaceutically acceptable salt thereof; a compound of formula III wherein $R_3$ is —$CH_3$ and $R_{10}$ is —COOH; or a pharmaceutically acceptable salt thereof; a compound of formula III wherein $R_3$ is —$CF_3$ and $R_{10}$ is —OH; or a pharmaceutically acceptable salt thereof; a compound of formula III wherein $R_3$ is —$CF_3$ and $R_{10}$ is —CN; or a pharmaceutically acceptable salt thereof; and a compound of formula III wherein $R_3$ is —$CF_3$ and $R_{10}$ is —COOH; or a pharmaceutically acceptable salt thereof.

The present invention provides methods of treating obesity in a mammal comprising administering to said mammal a therapeutically effective amount of a compound of formula I, an isomer thereof, a prodrug of said compound or isomer, or a pharmaceutically acceptable salt of said compound, isomer or prodrug. More particularly, the present invention provides such methods wherein the mammal is a female or male human.

The present invention also provides pharmaceutical compositions comprising a therapeutically effective amount of a compound of formula I, an isomer thereof, a prodrug of said compound or isomer, or a pharmaceutically acceptable salt of said compound, isomer or prodrug; and a pharmaceutically acceptable carrier, vehicle or diluent.

The present invention also provides pharmaceutical compositions for the treatment of obesity comprising an obesity treating amount of a compound of formula I, an isomer thereof, a prodrug of said compound or isomer, or a pharmaceutically acceptable salt of said compound, isomer or prodrug; and a pharmaceutically acceptable carrier, vehicle or diluent.

The present invention also provides pharmaceutical combination compositions comprising: a therapeutically effective amount of a composition comprising:
a first compound, said first compound being a compound of formula 1, an isomer thereof, a prodrug of said compound or isomer, or a pharmaceutically acceptable salt of said compound, isomer or prodrug;
a second compound, said second compound being a $β_3$ agonist, a thyromimetic agent, an eating behavior modifying agent or a NPY antagonist; and
a pharmaceutical carrier, vehicle or diluent. More particularly, it provides such compositions wherein the second compound is orlistat or sibutramine.

In addition, the present invention provides methods of treating obesity comprising administering to a mammal in need of such treatment
an amount of a first compound, said first compound being a compound of formula I, an isomer thereof, a prodrug of said compound or isomer, or a pharmaceutically acceptable salt of said compound, isomer or prodrug;
a second compound, said second compound being a $β_3$ agonist, a thyromimetic agent, an eating behavior modifying agent or a NPY antagonist; and
wherein the amounts of the first and second compounds result in a therapeutic effect. More particularly, it provides such methods wherein the second compound is orlistat or sibutramine.

The present invention also provides kits comprising:
a) a first compound, said first compound being a compound of formula I, an isomer thereof, a prodrug of said compound or isomer, or a pharmaceutically acceptable salt of said compound, isomer or prodrug and a pharmaceutically acceptable carrier, vehicle or diluent in a first unit dosage form;
b) a second compound, said second compound being a $β_3$ agonist, a thyromimetic agent, an eating behavior modifying agent or a NPY antagonist; and a pharmaceutically acceptable carrier, vehicle or diluent in a second unit dosage form; and
c) a container for containing said first and second dosage forms; wherein the amounts of said first and second compounds result in a therapeutic effect.

In addition, the present invention provides methods of inducing weight loss in a mammal comprising administering to said mammal a therapeutically effective amount of a compound of formula I, an isomer thereof, a prodrug of said compound or isomer, or a pharmaceutically acceptable salt of said compound, isomer or prodrug. The present invention also provides pharmaceutical compositions for inducing weight loss comprising a weight loss-treating amount of a compound of formula I, an isomer thereof, a prodrug of said compound or isomer, or a pharmaceutically acceptable salt of said compound, isomer or prodrug; and a pharmaceutically acceptable carrier, vehicle or diluent.

Another aspect of the present invention provides methods of treating diabetes in a mammal comprising administering to said mammal a therapeutically effective amount of a compound of formula I, an isomer thereof, a prodrug of said compound or isomer, or a pharmaceutically acceptable salt of said compound, isomer or prodrug.

The present invention also provides pharmaceutical compositions for the treatment of diabetes comprising a diabetes-treating amount of a compound of formula I, an isomer thereof, a prodrug of said compound or isomer, or a pharmaceutically acceptable salt of said compound, isomer or prodrug; and a pharmaceutically acceptable carrier, vehicle or diluent.

In addition, the present invention provides pharmaceutical combination compositions comprising: a therapeutically effective amount of a composition comprising:

a first compound, said first compound being a compound of formula I, an isomer thereof, a prodrug of said compound or isomer, or a pharmaceutically acceptable salt of said compound, isomer or prodrug;

a second compound, said second compound being an aldose reductase inhibitor, a glycogen phosphorylase inhibitor, a sorbitol dehydrogenase inhibitor, insulin, troglitazone, sulfonylurea, glipizide, glyburide, or chlorpropamide; and a pharmaceutical carrier, vehicle or diluent. More particularly, the present invention provides such pharmaceutical combinationcompositions wherein the aldose reductase inhbitior is 1-phthalazineacetic acid, 3,4-dihydro-4-oxo-3-[[5-trifluoromethyl)-2-benzothiazolyl]methyl]-or a pharmaceutically acceptable salt thereof.

The present invention also provides methods of treating diabetes comprising administering to a mammal in need of such treatment an amount of a first compound, said first compound being a compound of formula I, an isomer thereof, a prodrug of said compound or isomer, or a pharmaceutically acceptable salt of said compound, isomer or prodrug;

a second compound, said second compound being an aldose reductase inhibitor, a glycogen phosphorylase inhibitor, a sorbitol dehydrogenase inhibitor, insulin, troglitazone, sulfonylurea, glipizide, glyburide, or chlorpropamide; and wherein the amounts of the first and second compounds result in a therapeutic effect.

In another aspect, the present invention provides pharmaceutical combination compositions comprising:

therapeutically effective amounts of a compound of formula I, an isomer thereof, a prodrug of said compound or isomer, or a pharmaceutically acceptable salt of said compound, isomer or prodrug; and a compound selected from the group consisting of a glucocorticoid receptor agonist, a cholinomimetic drug, an anti-Parkinson's drug, an antianxiolytic drug, an antidepressant drug and an antipsychotic drug; and a pharmaceutical carrier, vehicle or diluent. More particularly, it provides such compositions wherein the anti-Parkinson's drug is selected from the group consisting of L-dopa, bromocriptine and selegiline. More particularly, it provides such compositions wherein the antianxiolytic drug is selected from the group consisting of benzodiazepine, valium and librium. More particularly, it provides such compositions wherein the antidepressant drug is selected from the group consisting of desipramine, sertraline hydrochloride and fluoxetine hydrochloride. More particularly, it provides such compositions wherein the antipsychotic drug is selected from the group consisting of haloperidol and clozapine.

The present invention also provides kits comprising:

a) a first compound, said first compound being a compound of formula I, an isomer thereof, a prodrug said compound or isomer, or a pharmaceutically acceptable salt of said compound, isomer or prodrug; and a pharmaceutically acceptable carrier, vehicle or diluent in a first unit dosage form;

b) a second compound, said second compound being selected from the group consisting of a glucocorticoid receptor agonist; a cholinomimetic drug; an anti-Parkinson's drug; an antianxiolytic drug; an antidepressant drug; and an antipsychotic drug; and a pharmaceutically acceptable carrier, vehicle or diluent in a second unit dosage form; and c) a container for containing said first and second dosage forms wherein the amounts of said first and second compounds result in a therapeutic effect. More particularly, it provides such kits wherein the anti-Parkinson's drug is selected from the group consisting of L-dopa, bromocriptine and selegiline. More particularly, it provides such kits wherein the antianxiolytic drug is selected from the group consisting of benzodiazepine, valium and librium. More particularly, it provides such kits wherein the antidepressant drug is selected from the group consisting of desipramine, sertraline hydrochloride and fluoxetine hydrochloride. More particularly, it provides such kits wherein the antipsychotic drug is selected from the group consisting of haloperidol and clozapine.

In another aspect, the present invention provides methods of treating anxiety in a mammal comprising administering to said mammal a therapeutically effective amount of a compound of formula I, an isomer thereof, a prodrug of said compound or isomer, or a pharmaceutically acceptable salt of said compound, isomer or prodrug. It also provides pharmaceutical compositions for the treatment of anxiety comprising an anxiety-treating amount of a compound of formula I, an isomer thereof, a prodrug of said compound or isomer, or a pharmaceutically acceptable salt of said compound, isomer or prodrug; and a pharmaceutically acceptable carrier, vehicle or diluent.

In another aspect, the present invention provides methods of treating depression in a mammal comprising administering to said mammal a therapeutically effective amount of a compound of formula I, an isomer thereof, a prodrug of said compound or isomer, or a pharmaceutically acceptable salt of said compound, isomer or prodrug. It also provides pharmaceutical compositions for the treatment of depression comprising a depression-treating amount of a compound of formula I, an isomer thereof, a prodrug of said compound or isomer, or a pharmaceutically acceptable salt of said compound, isomer or prodrug; and a pharmaceutically acceptable carrier, vehicle or diluent.

In another aspect, the present invention provides methods of treating neurodegeneration in a mammal comprising administering to said mammal a therapeutically effective amount of a compound of formula I, an isomer thereof, a prodrug of said compound or isomer, or a pharmaceutically acceptable salt of said compound, isomer or prodrug. It also provides pharmaceutical compositions for the treatment of neurodegeneration comprising a neurodegeneration-treating amount of a compound of formula I, an isomer thereof, a prodrug of said compound or isomer, or a pharmaceutically acceptable salt of said compound, isomer or prodrug; and a pharmaceutically acceptable carrier, vehicle or diluent.

In other aspects, the present invention provides the following methods: methods of affecting glucocorticoid receptor activity comprising administering to a mammal in need thereof a therapeutically effective amount of a compound of formula I, an isomer thereof, a prodrug of said compound or isomer, or a pharmaceutically acceptable salt of said compound, isomer or prodrug; methods of modulating a process mediated by glucocorticoid receptor comprising administering to a mammal in need thereof a therapeutically effective amount of a compound of formula I, an isomer thereof, a prodrug of said compound or isomer, or a pharmaceutically acceptable salt of said compound, isomer or prodrug; methods of treating a mammal requiring glucocorticoid receptor therapy comprising administering to said mammal a therapeutically effective amount of a glucocorticoid receptor modulator compound of formula I, an isomer thereof, a prodrug of said compound or isomer, or a pharmaceutically acceptable salt of said compound, isomer or prodrug.

In another aspect, the present invention provides methods of treating an inflammatory disease in a mammal comprising administering to said mammal a therapeutically effective amount of a compound of formula I, an isomer thereof, a prodrug of said compound or isomer, or a pharmaceutically acceptable salt of said compound, isomer or prodrug. More particularly, it provides such methods wherein the mammal is a female or male human.

The present invention also provides pharmaceutical compositions for the treatment of an inflammatory disease comprising an inflammatory-treating amount of a compound of formula I, an isomer thereof, a prodrug of said compound or isomer, or a pharmaceutically acceptable salt of said compound, isomer or prodrug; and a pharmaceutically acceptable carrier.

In another aspect, the present invention provides methods for the treatment of an inflammatory disease in a mammal which comprises: administering to said mammal therapeutically effective amounts of a glucocorticoid receptor modulator and a glucocorticoid receptor agonist. More particularly, it provides such methods which further comprise reducing the undesirable side effects of said treatment. Also, it provides such methods wherein the inflammatory disease is selected from the group consisting of arthritis, asthma, rhinitis and immunomodulation. More particularly, it provides such methods wherein the glucocorticoid receptor modulator is a compound of formula I, an isomer thereof, a prodrug of said compound or isomer, or a pharmaceutically acceptable salt of said compound, isomer or prodrug. Also, more particularly, it provides such methods wherein the glucocorticoid receptor agonist is a compound selected from the group consisting of prednisone, prednylidene, prednisolone, cortisone, dexamethasone and hydrocortisone.

The present invention also provides a process for preparing a compound of formula III

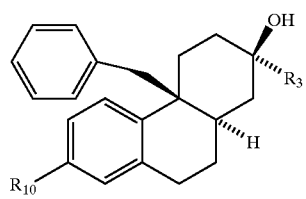

III wherein $R_3$ is a) —$(CH_2)_2$—$CF_3$, b) —$(CH_2)_2$—$CH_3$, c) —$CH_3$, d) —C≡C—$CH_3$, e) —C≡C—Cl or f) —$CF_3$; and $R_{10}$ is —O—$CH_2$-het wherein het is pyridinyl substituted with 0 or 1 methyl;

which comprises reacting a compound of formula III-A

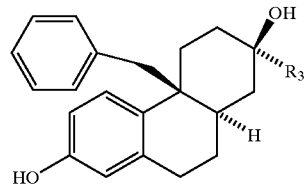

III-A wherein $R_3$ is as defined above, with a base in an aprotic solvent at room temperature to 200° C.; and then with a compound of formula $R_{10}$—$X_1$ wherein $R_{10}$ is as defined above and —$X_1$ is halo, mesylate or tosylate. More particularly, it provides this process wherein the base is NaH, t-butoxide or $Et_3N$; and the solvent is DMF or THF.

The present invention also provides a process for the preparing a compound of formula III

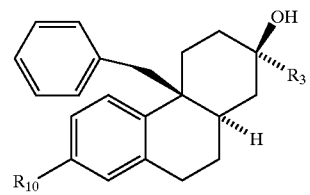

III wherein $R_3$ is a) —$(CH_2)_2$—$CF_3$, b) —$(CH_2)_2$—$CH_3$, c) —$CH_3$, d) —C≡C—$CH_3$, e) —C≡C—Cl or f) —$CF_3$; $R_{10}$ is —C(O)—NH—Z-het wherein het is selected from the group consisting of a) pyridinyl substituted with 0 or 1 methyl, b) pyrimidinyl, c) pyrazinyl, d) morpholinyl and e) oxadiazolyl; and Z is —$(C_0-C_1)$ alkyl;

which comprises reacting a compound of formula III-B

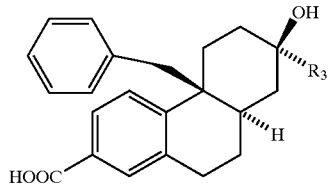

III-B wherein $R_3$ is as defined above, with a coupling reagent and a compound of formula $NH_2$—Z-het or a salt thereof wherein —Z and -het are as defined above in an aprotic solvent at 0° C. to 1000° C. More particularly, it provides this process wherein the coupling reagent is selected from the group consisting of 1-(3-dimethylaminopropyl-3-ethylcarbodiimide (EDC), dicyclohexyl carbodiimide (DCC) and hydroxybenzotriazole hydrate (HOBt).

In addition, the present invention provides a process for preparing a compound of formula III

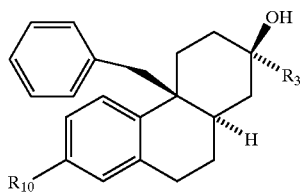

III wherein R₃ is a) —(CH₂)₂—CF₃, b) —(CH₂)₂—CH₃, c) —CH₃, d) —C≡C—CH₃, e) —C≡C—Cl or f) —CF₃; $R_{10}$ is —C(O)—NH—Z-het wherein het is selected from the group consisting of a) pyridinyl substituted with 0 or 1 methyl, b) pyrimidinyl, C) pyrazinyl, d) morpholinyl and e) oxadiazolyl; and Z is —(C₀-C₁) alkyl;

which comprises reacting a compound of formula III-C

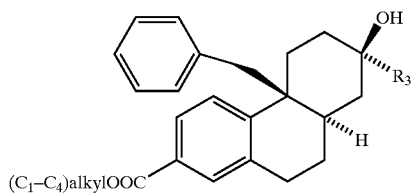

III-C wherein R₃ is as defined above, with a tri(C₁-C₄)alkyl-aluminum compound and a compound of formula NH₂—Z-het wherein —Z and -het are as defined above in a solvent at 0° C. to 40° C. More particularly, it provides this process wherein the tri(C₁-C₄)alkyl-aluminum compound is Al(CH₃)₃ and the solvent is methylene chloride.

Further, the present invention provides a process for preparing a compound of formula III

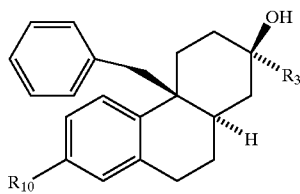

III wherein R₃ is a) —(CH₂)₂—CF₃, b) —(CH₂)₂—CH₃, c) —CH₃, d) —C≡C—CH₃, e) —C≡C—Cl or f) —CF₃; $R_{10}$ is a) —O—C(O)—N(CH₃)₂, b) —O —C(O)—(1-pyrrolidinyl) or c) —O—C(O)—NH—(C₀-C₃)alkyl-het wherein het is selected from the group consisting of 1) 2-pyridinyl, 2) 3-pyridinyl, 3) 4-pyridinyl, 4) 2-methyl-3-pyridinyl, 5) pyrazinyl, 6) morpholinyl, 7) pyrrolidinyl and 8) imidazolyl;

which comprises reacting a compound of formula III-A

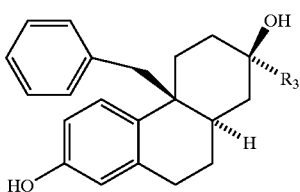

III-A wherein R₃ is as defined above, with phosgene or triphosgene in an aprotic solvent and then with a compound selected from the group consisting of NH(CH₃)₂, 1-pyrrolidinyl and NH₂—(C₀-C₃)alkyl-het wherein het is as defined above at 0° C. to room temperature. More particularly, it provides this process wherein the solvent is toluene.

In addition, the present invention provides a process for preparing a compound of formula III

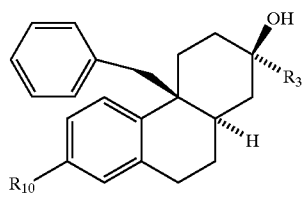

III wherein R₃ is a) —(CH₂)₂—CF₃, b) —(CH₂)₂—CH₃, c) —CH₃, d) —C≡C—CH₃, e) —C≡C—Cl or f) —CF₃; and $R_{10}$ is —O—(C₁-C₂)alkyl-het wherein het is pyridinyl substituted with 0 or 1 methyl;

which comprises reacting a compound of formula III-D

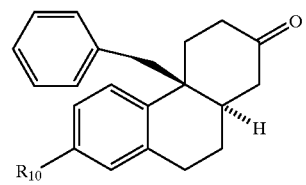

III-D wherein $R_{10}$ is as defined above, with R₃-metal selected from the group consisting of R₃Li, R₃MgBr and R₃MgCl wherein R₃ is as defined above in an aprotic solvent at −78° C. to room temperature.

Further, the present invention provides a process for preparing a compound of formula III

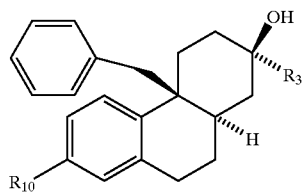

III wherein R₃ is —CF₃; and $R_{10}$ is —O—(C₁-C₂)alkyl-het wherein het is pyridinyl substituted with 0 or 1 methyl;

which comprises a) reacting a compound of formula III-D

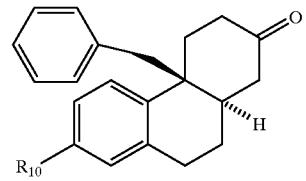

III-D wherein $R_{10}$ is as defined above, with trimethylsilyl-CF₃ in the presence of tert-butylammonium fluoride or cesium fluoride in a protic solvent; and b) hydrolyzing the resulting intermediate with tert-butylammonium fluoride or hydrochloric acid.

The present invention also provides process for preparing a compound of formula III

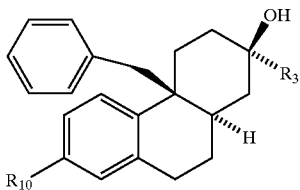

III wherein $R_3$ is a) —$(CH_2)_2$—$CF_3$, b) —$(CH_2)_2$—$CH_3$, c) —$CH_3$, d) —C≡C—$CH_3$, e) —C≡C—Cl or f) —$CF_3$; $R_{10}$ is —C(O)—NH—Z-het wherein het is selected from the group consisting of a) pyridinyl substituted with 0 or 1 methyl, b) pyrimidinyl, c) pyrazinyl, d) morpholinyl and e) oxadiazolyl; and Z for each occurrence is independently —($C_0$-$C_2$) alkyl;

which comprises reacting a compound of formula III-D

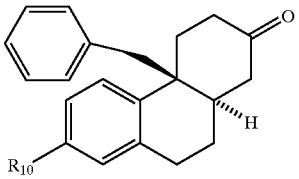

III-D wherein $R_{10}$ is as defined above, with $R_3$-metal selected from the group consisting of $R_3$Li, $R_3$MgBr and $R_3$MgCl wherein $R_3$ is as defined above in an aprotic solvent at −78° C. to room temperature.

Finally, the present invention provides a process for preparing a compound of formula II

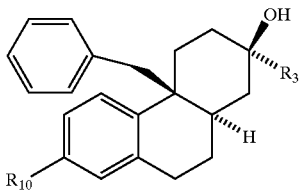

III wherein $R_3$ is a) —$(CH_2)_2$—$CF_3$, b) —$(CH_2)_2$—$CH_3$, c) —$CH_3$, d) —C≡C—$CH_3$, e) —C≡C—Cl or f) —$CF_3$; $R_{10}$ is —C(O)—NH—Z-het wherein het is selected from the group consisting of a) pyridinyl substituted with 0 or 1 methyl, b) pyrimidinyl, c) pyrazinyl, d) morpholinyl and e) oxadiazolyl; and Z for each occurrence is independently —($C_0$-$C_2$) alkyl;

which comprises a) reacting a compound of formula III-D

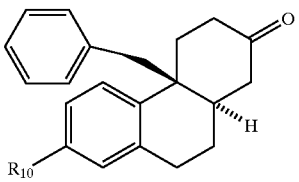

III-D wherein $R_{10}$ is as defined above, with trimethylsilyl-$CF_3$ in the presence of tert-butylammonium fluoride or cesium fluoride in a protic solvent; and b) hydrolyzing the resulting intermediate with tert-butylammonium fluoride or hydrochloric acid.

DETAILED DESCRIPTION OF THE INVENTION

The compounds of the present invention are named according to the IUPAC or CAS nomenclature system.

In one way of naming the compounds of the present invention, the carbon atoms in the ring may be numbered as shown in the following simplified structure:

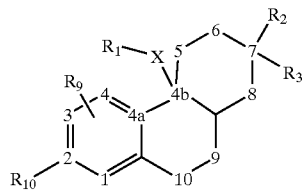

Alternatively, another way of naming the compounds of the present invention, the carbon atoms in the ring may be numbered as shown in the following simplified structure:

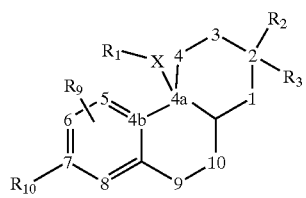

The carbon atom content of various hydrocarbon-containing moieties is indicated by a prefix designating the minimum and maximum number of carbon atoms in the moiety, i.e., the prefix $C_i$-$C_j$ indicates a moiety of the integer "i" to the integer "j" carbon atoms, inclusive. Thus, for example, $C_1$-$C_3$ alkyl refers to alkyl of one to three carbon atoms, inclusive, or methyl, ethyl, propyl and isopropyl, and all isomeric forms and straight and branched forms thereof.

Examples of alkyl of one to nine carbon atoms, inclusive, are methyl, ethyl, propyl, butyl, pentyl, hexyl, heptyl, octyl, and nonyl, and all isomeric forms and straight and branched thereof.

Examples of alkenyl of two to five carbon atoms, inclusive, are ethenyl, propenyl, butenyl, pentenyl, and all isomeric forms and straight and branched forms thereof.

Examples of alkynyl of two to five carbon atoms, inclusive, are ethynyl, propynyl, butynyl, pentynyl and all isomeric forms and straight and branched forms thereof.

The terms cycloalkyl, cycloalkenyl and cycloalkynyl refer to cyclic forms of alkyl, alkenyl and alkynyl, respectively. Exemplary ($C_3$-$C_8$)cycloalkyl groups are cyclopropyl, cyclobutyl, cyclopentyl, cyclohexyl, cycloheptyl and cyclooctyl.

The term halo includes chloro, bromo, iodo and fluoro.

The term aryl refers to an optionally substituted six-membered aromatic ring, including polyaromatic rings. Examples of aryl include phenyl, naphthyl and biphenyl.

The term het refers to an optionally substituted 5-, 6- or 7-membered saturated, partially saturated or unsaturated heterocyclic ring containing from 1 to 3 heteroatoms selected from the group consisting of nitrogen, oxygen and sulfur; and including any bicyclic group in which any of the above heterocyclic rings is fused to a benzene ring or another heterocyclic ring; and the nitrogen atom may be in the oxidized state giving the N-oxide form; and substituted by 0 to 3 independent substituents.

The following paragraphs describe exemplary ring(s) for the generic ring descriptions contained herein.

Exemplary five-membered rings are furyl, thienyl, 2H-pyrrolyl, 3H-pyrrolyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyi, 1,2,5-oxadiazolyi, 1,3,4-oxadiazolyl, 1,2,3-triazolyl, 1,2,4-trizaolyl, 1,3,4-thiadiazolyl, 1,2,3,4-oxatriazolyl, 1,2,3,5-oxatrizaolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl.

Exemplary six-membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-trizainyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, 1,4,2-oxadiazinyl and 1,3,5,2-oxadiazinyl.

Exemplary seven-membered rings are azepinyl, oxepinyl, thiepinyl and 1,2,4-diazepinyl.

Exemplary eight membered rings are cyclooctyl, cyclooctenyl and cyclooctadienyl.

Exemplary bicyclic rings consisting of combinations of two fused partially saturated, fully saturated or fully unsaturated five or six membered rings, taken independently, optionally having one to four heteroatoms selected independently from nitrogen, sulfur and oxygen are indolizinyl, indolyl, isoindolyl, 3H-indolyl, 1H-isoindolyl, indolinyl, cyclopenta(b)pyridinyl, pyrano(3,4-b)pyrrolyl, benzofuryl, isobenzofuryl, benzo(b)thienyl, benzo(c)thienyl, 1 H-indazolyl, indoxazinyl, benzoxazolyl, anthranilyl, benzimidazolyl, benzthiazolyl, purinyl, 4Hquinolizinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

As used herein the term "mammals" is meant to refer to all mammals, including, for example, primates such as humans and monkeys. Examples of other mammals included herein are rabbits, dogs, cats, cattle, goats, sheep and horses.

The term "treating", "treat" or "treatment" as used herein includes preventative (e.g., prophylactic) and palliative treatment.

By "pharmaceutically acceptable" it is meant the carrier, vehicle, diluent, excipient and/or salt must be compatible with the other ingredients of the formulation, and not deleterious to the recipient thereof.

The expression "prodrug" refers to compounds that are drug precursors which following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the Formula I compounds include but are not limited to those having a carboxyl moiety wherein the free hydrogen is replaced by $(C_1-C_4)$alkyl, $(C_2-C_7)$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

The compounds of formula I of the present invention are prepared as described in the Schemes, Preparations and Examples below, or are prepared by methods analogous thereto, which are readily known and available to one of ordinary skill in light of this disclosure. In each of the Schemes, the R groups (e.g., $R_1$, $R_2$, etc . . . ) correspond to those noted in the Summary above. In addition, the variable n is defined as 0 to 6. However, it will be understood by those skilled in the art that other functionalities disclosed herein at the indicated positions of compounds of Formula I also comprise potential substituents for the analogous positions on the structures within the Schemes.

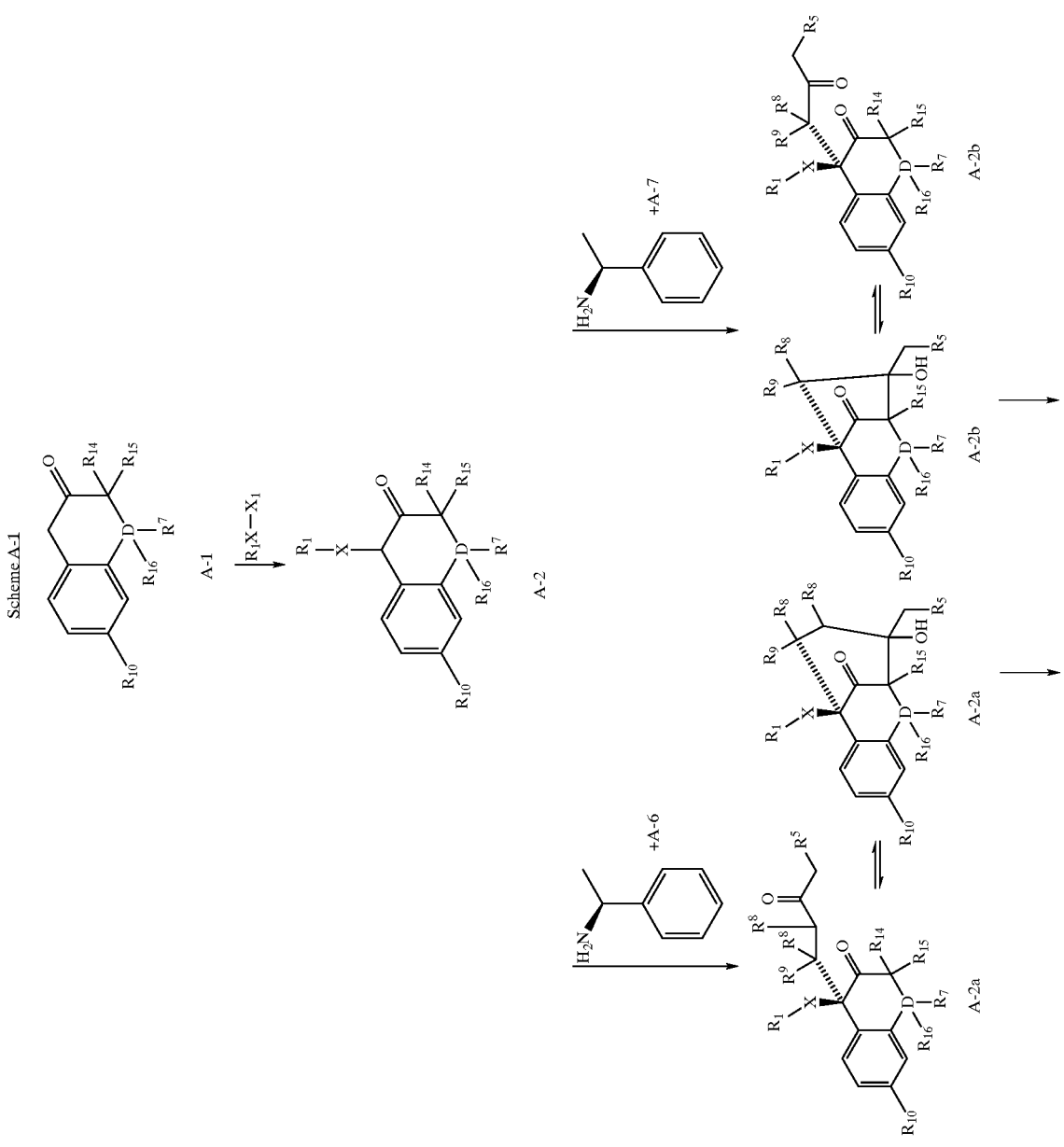

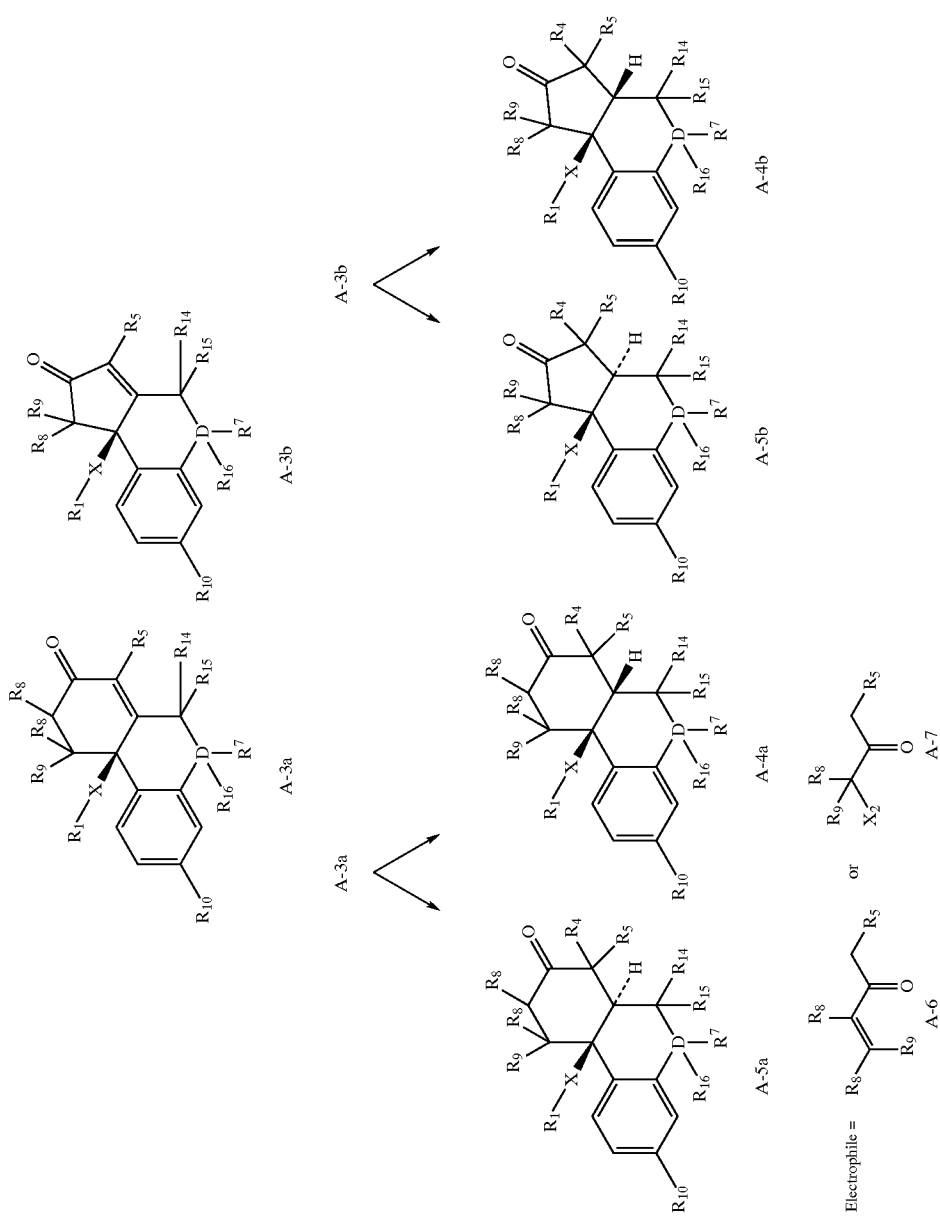

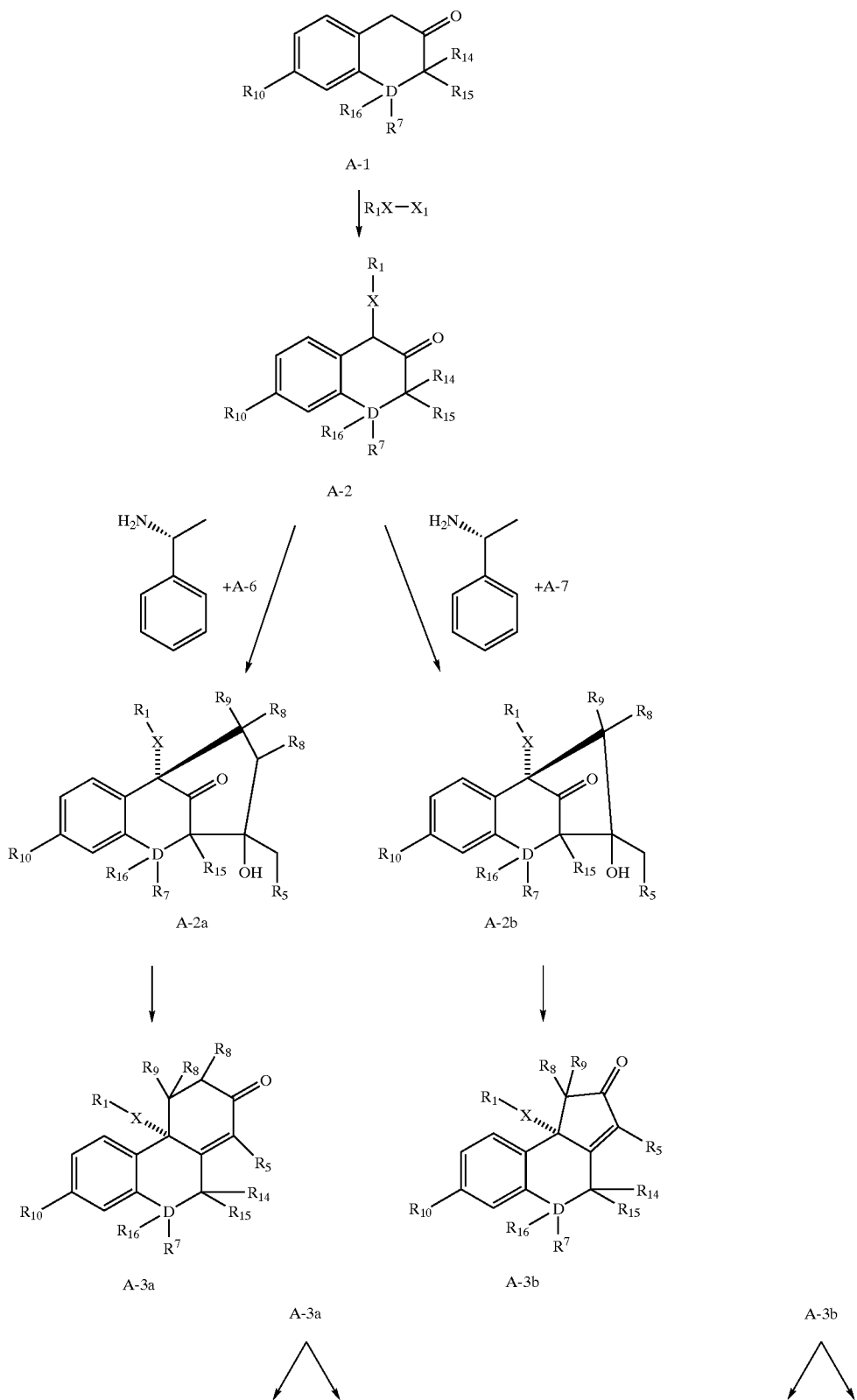

-continued

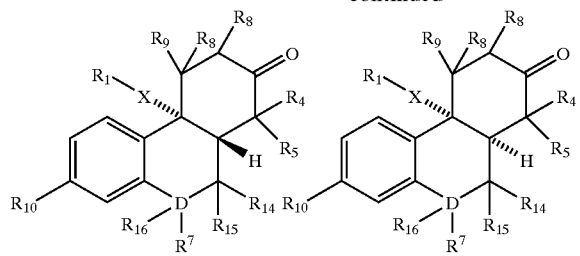

A-5a    A-4a

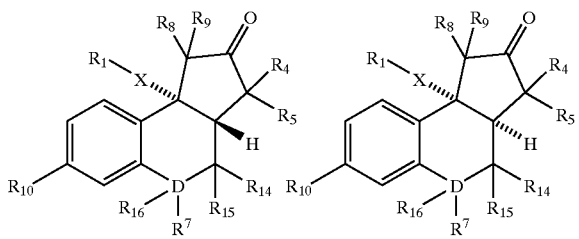

A-5b    A-4b

Electrophile =

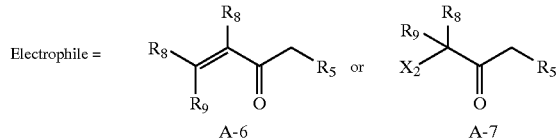

A-6    A-7

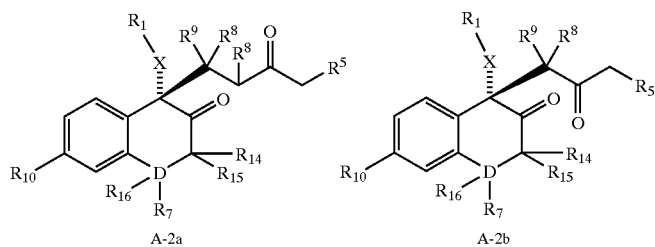

A-2a    A-2b

Scheme A-3

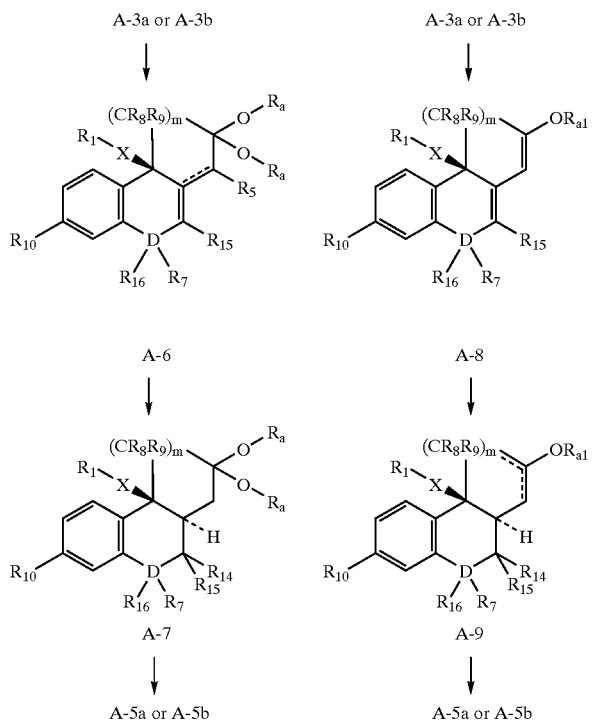

Schemes A-1, A-2 and A-3

The compound of formula A-1 (prepared as described in Org. Syn. 1971, 51, 109–112) (wherein D is methylene, substituted carbon, oxygen, sulfur or optionally protected nitrogen, $R_{10}$ is halogen, hydrogen, methyl ether, or benzyl ether or is as described in the Summary above, and the other variables are as defined in the Summary above) is reacted with a nitrogen-containing base, such as pyrrolidine, piperidine or morpholine, at a refluxing temperature in an aprotic solvent such as toluene, benzene, dichloromethane or dioxane, and then reacted with the alkylating agent of formula $R_1X$—$X_1$ wherein $R_1X$—is $(C_2-C_4)$alkyl straight chain or an isopropyl, t-butyl or benzyl group or is as described in the Summary above, and $X_1$ is a leaving group (see Francis A. Carey, in *Advanced Organic Chemistry*, Part A, Chapter 5.6 for examples) in dioxane, methanol, ethanol, isopropanol, DMF, DMSO or THF to give the compound of formula A-2. Typical alkylating agents are primary, secondary, benzylic or allylic halides and are preferably alkyl bromides or alkyl iodides.

Alternatively, the compound of formula A-1 is converted to its anion with a strong base, such as sodium hydride, sodium methoxide, lithium diisopropylamide, lithium bis (trimethylsilyl)amide, potassium bis(trimethylsilyl)amide, potassium t-butoxide or others, in an aprotic solvent, such as dimethylformamide (DMF) or tetrahydrofuran (THF). This reaction is conducted at −78° C. to room temperature depending on the nature of the base used. The resulting anion is alkylated with the appropriate alkylating agent of formula $R_1X$—$X_1$ as defined previously to give the compound of formula A-2.

Alternatively, the compound of formula A-1 is reacted with $R_1X$—CHO and a base, such as pyrrolidine or an acid, such as acetic acid or hydrochloric acid, in a solvent such as toluene, benzene, methanol or ethanol. The intermediate thus obtained is then hydrogenated using a palladium on carbon catalyst or numerous other reagents such as platinum oxide or rhodium on aluminum oxide (see P. N. Rylander in *Hydrogenation Methods*, Academic Press, New York, 1985; Herbert O. House in *Modern Synthetic Reactions*, Chapter 1, pp. 1–45; and John Fried and John A. Edwards in *Organic Reactions in Steroid Chemistry*, Chapter 3, pp. 111–145) to give the compound of formula A-2. Alternatively, the intermediate is reacted with a reducing metal reagent, such as an alkali (group IA in the periodic table) or alkaline metal (group IIA in the periodic table), including Li, Na, or Ca, and an amine, such as $NH_3$ or ethylene diamine, in an aprotic solvent, such as THF or dioxane, at −78° C. to room temperature to give the compound of formula A-2.

The compound of formula A-2 is reacted with (R)-(+)-α-methylbenzylamine (as shown in Scheme A-2) or (S)-(−)-α-methylbenzylamine (as shown in Scheme A-1) and an electrophile of formula A-6 (to form a 6-membered ring) or an electrophile of formula A-7 (to form a 5-membered ring) wherein $R_5$, $R_8$ and $R_9$ are as defined above in the Summary and $X_2$ is a leaving group that is typically a halogen such as bromide (see Francis A. Carey, in *Advanced Organic Chemistry*, Part A, Chapter 5.6 for examples), in an aprotic solvent such as toluene to give the C2-S or C2-R substituted intermediates of formula A-2a (which will form a six-membered ring) and of formula A-2b (which will form a five-membered ring), as shown in Schemes A-1 and A-2. These intermediates of formula A-2a and A-2b may be ring closed or ring opened as illustrated in the schemes.

Alternatively, the compound of formula A-2 is reacted with an electrophile of formula A-6 (to form a 6-membered ring) or with an electrophile of formula A-7 (to form a 5-membered ring) and a base, such as sodium methoxide or KOH, in a solvent, such as methanol, to give a racemic mixture of the intermediates of formula A-2a of Schemes A-1 and A-2 (which will form a six-membered ring) or to give a racemic mixture of the intermediates of formula A-2b of Schemes A-1 and A-2 (which will form a five-membered ring). This reaction may also give directly a racemic mixture of the products A-3a of Schemes A-1 and A-2 (which have a six-membered ring) or give directly a racemic mixture of the products A-3b of Schemes A-1 and A-2 (which have a five-membered ring), which mixtures may be resolved by chiral HPLC or by other literature methods.

The resulting intermediate of formula A-2a or A-2b is reacted with a base, such as sodium methoxide or KOH, in a solvent, such as methanol, or is reacted with an acid such as p-toluenesulfonic acid in a solvent such as toluene to give the compound of formula A-3a or A-3b, respectively, wherein the variables are as defined in the Summary above and wherein $R_{10}$ is halogen, hydrogen, methyl ether, or benzyl ether or is as described in the Summary above.

Alternatively, the compounds of formula A-3a or A-3b are prepared from the compound of formula A-2a or A-2b, respectively, by other reported, annulation methods, some of which are described in M. E. Jung, *Tetrahedron*, 1976, 32, pp. 3–31.

The compound of formula A-3a or A-3b wherein $R_{10}$ is, for example, methoxy is reacted with $BBr_3$ or $BCl_3$ and tetrabutylammonium iodide or dimethylboron bromide in an aprotic solvent, such as dichloromethane or toluene at −78° C. to room temperature to give the compound of formula A-3a or A-3b wherein $R_{10}$ is, for example, hydroxy.

Alternatively, the compound of formula A-3a or A-3b wherein $R_{10}$ is, for example, methoxy is reacted with sodium ethanethiol in DMF or is reacted with methionine in methanesulfonic acid to give the compound of formula A-3a or A-3b wherein $R_{10}$ is, for example, hydroxy.

Also, the compound of formula A-3a or A-3b wherein $R_{10}$ is, for example, hydroxy may be prepared by other literature methods as described in *Protecting Groups in Organic Synthesis*, Second Edition, T. W. Greene and P. G. M. Wuts, John Wiley and Sons, Inc. (1991) or as illustrated in *Comprehesive Organic Transformation*, R. C. Larock, VCH Publishers Inc. (1989), pp. 501–527.

The compound of formula A-3a or A-3b wherein $R_{10}$ is halogen, hydrogen, methyl ether, or hydroxy or is as described in the Summary above is hydrogenated with a palladium on carbon catalyst or other reagents such as platinum oxide or rhodium on aluminum oxide (see P. N. Rylander in *Hydrogenation Methods*, Academic Press, New York, 1985; Herbert O. House in *Modern Synthetic Reactions*, Chapter 1, pp. 1–45; and John Fried and John A. Edwards in *Organic Reactions in Steroid Chemistry*, Chapter 3, pp. 111–145) in a variety of solvents including methanol, ethanol, and THF to yield the compound of formula A4a or A-4b or A-5a or A-5b wherein the variables are as described in the Summary above and wherein the cis compounds are the major products.

The compound of formula A-3a or A-3b wherein $R_{10}$ is hydrogen, methyl ether, hydroxy or is as described in the Summary above is reacted with a reducing metal reagent, such as an alkali (group IA in the periodic table) or alkaline metal (group IIA in the periodic table), including Li, Na, or Ca, and an amine, such as $NH_3$ or ethylene diamine, in an aprotic solvent, such as THF or dioxane, at −78° C. to room temperature to give the compound of formula A-5a or A-5b or A-4a or A-4b wherein the variables are as described in the Summary above and wherein the trans compounds are the major products.

Alternatively, as shown in Scheme A-3, for example, the compound of formula A-3a or A-3b of Scheme A-1 wherein $R_{10}$ is halogen, hydrogen, methyl ether, hydroxy, carboxyl or is as described in the Summary above is treated with an alcohol or diol, such as methanol or ethylene glycol, and a strong acid, such as p-toluenesulfonic acid, in an aprotic solvent, such as toluene or benzene, to form a ketal intermediate of formula A-6 wherein m is one or two, $R_a$ is lower alkyl or wherein the $R_a$'s taken together with the two oxygen atoms form, for example, 1,3-dioxolane and wherein the other variables are as defined in the Summary above. Alternatively, this ketal intermediate may be prepared by other literature methods such as those described in *Protecting Groups in Organic Synthesis*, Second Edition, T. W. Greene and P. G. M. Wuts, John Wiley and Sons, Inc. (1991). The ketal intermediate is hydrogenated using $Pd(OH)_2$ on carbon or other reagents, such as platinum oxide or rhodium on aluminum oxide (see P. N. Rylander in *Hydrogenation Methods*, Academic Press, New York, 1985; Herbert O. House in *Modern Synthetic Reactions*, Chapter 1, pp. 1–45; and John Fried and John A. Edwards in *Organic Reactions in Steroid Chemistry*, Chapter 3, pp. 111–145) in a solvent such as toluene from 15–2000 psi (which is about 1 to about 133 atm) $H_2$ at room temperature to 100° C. The resultant intermediate of formula A-7 is then reacted with an acid, such as p-toluenesulfonic acid, in acetone or is reacted using various literature methods, such as those described in *Protecting Groups in Organic Synthesis*, Second Edition, T. W. Greene and P. G. M. Wuts, John Wiley and Sons, Inc. (1991), to yield the compound of formula A-5a of Scheme A-1 or the compound of formula A5-b of Scheme A-1 wherein $R_{10}$ is halogen, hydrogen, methyl ether, hydroxy or is as described in the Summary above, and the other variables are as defined in the Summary above. The corresponding stereoisomers of these compounds are prepared by procedures analogous to those described above.

Alternatively, as shown in Scheme A-3, for example, the compound of formula A-3a or A-3b of Scheme A-1, wherein $R_{10}$ is halogen, hydrogen, methyl ether, hydroxy or is as described in the Summary above, is reacted with triethylorthoformate and p-toluenesulfonic acid in ethanol or toluene to form an enol ether intermediate of formula A-8 wherein m is one or two, $R_{a1}$ is ethyl or other acyclic or cyclic lower alkyl or acyl, depending on the reagent used, and the other variables are as defined in the Summary above. Alternatively, this enol ether intermediate may be prepared by other literature methods such as those described in *Protecting Groups in Organic Synthesis*, Second Edition, T. W. Greene and P. G. M. Wuts, John Wiley and Sons, Inc. (1991). The enol ether intermediate is then hydrogenated using Pd on $CaCO_3$ or other reagents, such as platinum oxide or rhodium on aluminum oxide (see P. N. Rylander in *Hydrogenation Methods*, Academic Press, New York, 1985, Herbert O. House in *Modern Synthetic Reactions*, Chapter 1 pp. 1–45, and John Fried and John A. Edwards in "Organic Reactions in Steroid Chemistry," Chapter 3 pp. 111–145) in a variety of solvents including ethanol, methanol, and THF at 15–60 psi $H_2$ pressure. The resulting intermediate of formula A-9 is then reacted with an acid such as aqueous HCl, in a protic solvent, such as ethanol, or is reacted under other literature conditions, such as those described in *Protecting Groups in Organic Synthesis*, Second Edition, T. W. Greene and P. G. M. Wuts, John Wiley and Sons, Inc. (1991), to yield the compound of formula A-5a of Scheme A-1 (which has a six-membered ring) or the compound of formula A-5b of Scheme A-1 (which has a five-membered ring) wherein $R_{10}$ is halogen, hydrogen, methyl ether, hydroxy or is as described in the Summary above, and the other variables are as defined in the Summary above. The corresponding stereoisomers of these compounds are prepared by procedures analogous to those described above.

Alternatively, the resulting intermediate of formula A-3a or A-3b of Scheme A-1 is hydrogenated using $Pd/BaSO_4$ in a solvent such as ethanol at 15 to 200 psi $H_2$ pressure to yield the compound of formula A-5a of Scheme A-1 (which has a six-membered ring) or the compound of formula A-5b of Scheme A-1 (which has a five-membered ring) wherein $R_5$ is $COOR_{a2}$ and wherein $R_{a2}$ is, for example, $C_1$–$C_6$ alkyl. Other reagents which may be used in the above hydrogenation reactions are described in P. N. Rylander in *Hydrogenation Methods*, Academic Press, New York, 1985.

Alternatively, in Schemes A-1 and A-2, the compounds of formula A-5a or A-5b are prepared from the compounds of formula A-3a or A-3b, respectively, by other reported reduction methods, some of which are described in P. Jankowski, S. Marczak, J. Wicha, *Tetrahedron*, 1998, 12071–12150.

Scheme B

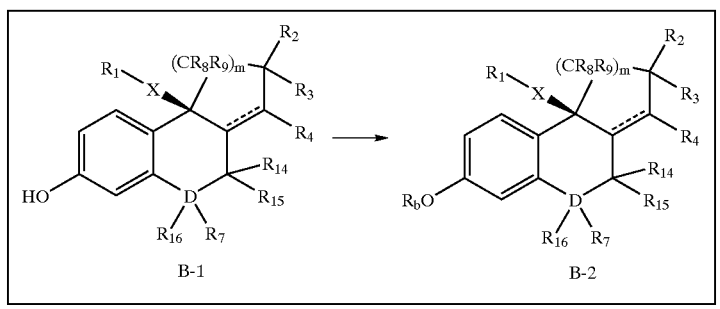

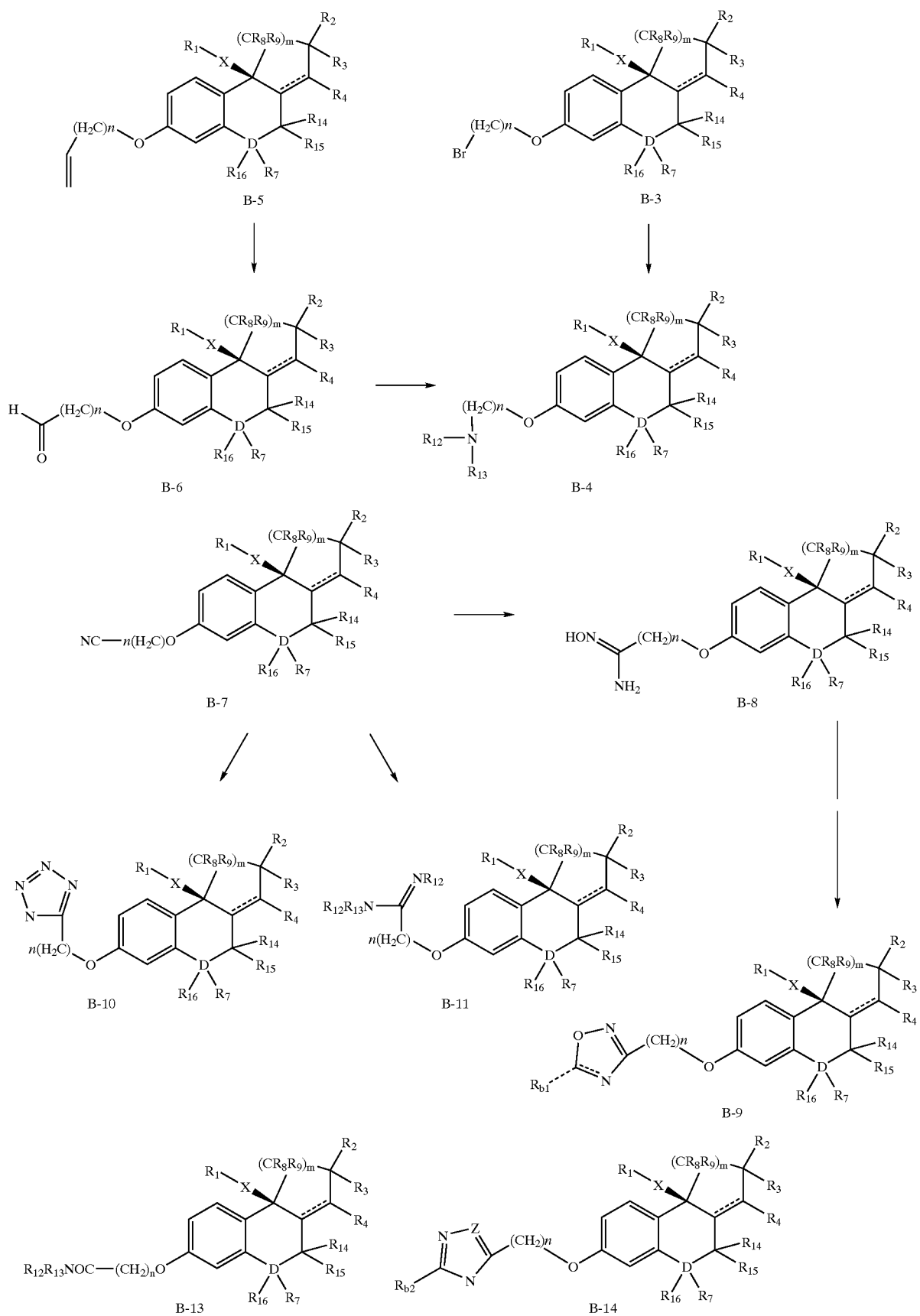

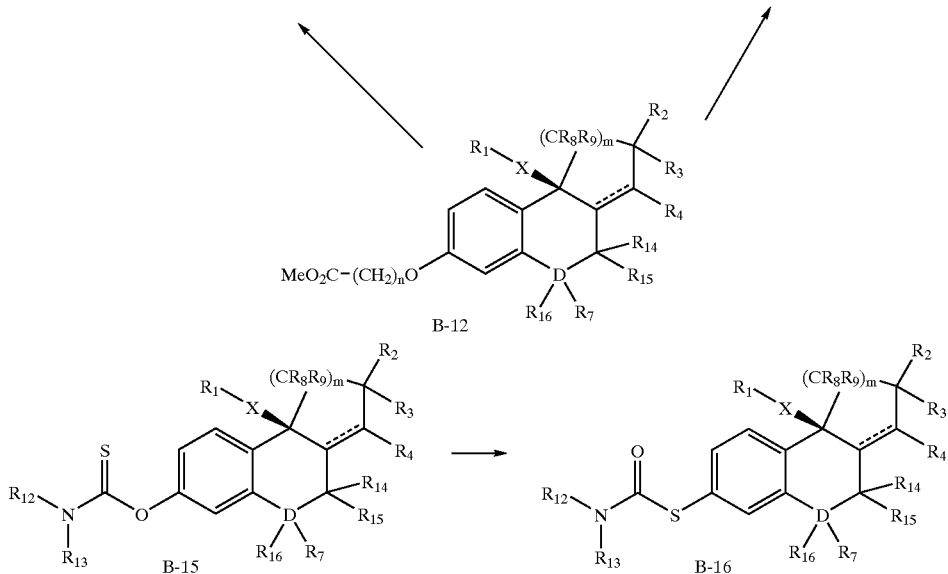

SCHEME B

The compound of formula B-1, which is obtained as described in Scheme A-1 and Scheme H, is reacted with a base, such as NaH, t-butoxide or Et$_3$N, in an aprotic solvent, such as DMF or CH$_3$CN, at a temperature which is between room temperature and 200° C. depending on the nature of the solvent used, and is then reacted with an alkylating agent of formula R$_b$—X$_1$ wherein X$_1$ is a leaving group, to give the compound of formula B-2 wherein R$_b$ is, for example, alkyl or alkyl-heterocycle and is further illustrated by a variety of different groups within the definition of R$_{10}$ in the Summary above. To obtain compounds of formula B-2 which are carbamates wherein R$_b$ is, for example, —C(O)NR$_{12}$R$_{13}$ and wherein R$_{12}$ and R$_{13}$ are as defined in the Summary above, the compound of formula B-1 is reacted with a compound of formula R$_{12}$R$_{13}$—NC(O)Cl. Alternatively, to obtain compounds of formula B-2, which are carbamates wherein R$_b$ is, for example, C(O)NR$_{12}$R$_{13}$, the compound of formula B-1 is reacted with phosgene or triphosgene in an aprotic solvent such as toluene and then with an amine of the formula R$_{12}$R$_{13}$NH. To obtain compounds of formula B-2 which are thiocarbamates wherein R$_b$ is, for example, —C(S)NR$_{12}$R$_{13}$ and R$_{12}$ and R$_{13}$ are defined in the Summary above, the compound of formula B-1 is reacted with a compound of the formula R$_{12}$R$_{13}$NC(S)Cl. Throughout this scheme, the other variables are as defined in the Summary above.

The compound of formula B-3 wherein n is, for example, one to six (prepared by the procedures for the formula B-2 compound) is reacted with a base such as Na$_2$CO$_3$ with or without sodium iodide in an aprotic solvent, such as DMF, at a temperature which is between room temperature and 200° C., depending on the nature of the solvent used, and is then reacted with an amine of formula R$_{12}$R$_{13}$NH to obtain the compound of formula B-4 wherein n is, for example one to six and R$_{12}$ and R$_{13}$ are as defined in the Summary above.

The compound of formula B-5 wherein n is, for example, one to six, (prepared by the procedures for the formula B-2 compound) is reacted with OsO$_4$, N-methylmorpholine-N-oxide or K$_2$MnO$_4$ to give the corresponding diol. The diol is oxidatively cleaved with NaIO4 or Pb(OAc)4 to give the compound of formula B-6 wherein n is one to six, for example. Alternatively, the compound of formula B-5 is reacted with ozone and quenched with dimethyl sulfite, triphenylphosphine or other known reagent to give the compound of formula B-6. Alternatively, the compound of formula B-6 is obtained from the compound of formula B-5 by the methods illustrated in *Comprehensive Organic Transformation*, R. C. Larock, VCH Publisher, Inc. (1989) pp. 595–596, pp. 615–616.

Alternatively, the compound of formula B-4 wherein n is, for example, one to six, and R$_{12}$ and R$_{13}$ are as defined in the Summary above, is obtained from the compound of formula B-6 wherein n is one to six, for example, by reductive amination. The reductive amination is typically carried out with a reducing agent, such as sodium cyanoborohydride or sodium triacetoxyborohydride, preferably at a pH of between 6 and 8. The reaction is normally performed in a protic solvent, such as methanol or ethanol, or in a mixture of solvents, such as dichloroethane/methanol, at temperature of about −78° C. to about 40° C. (See A. Abdel-Magid, C. Maryanoff, K. Carson, Tetrahedron Lett. Vol. 34, Issue 31, 5595–98, 1990). Other conditions involve the use of titanium isopropoxide and sodium cyanoborohydride (R. J. Mattson et al., J. Org. Chem. 1990, 55, 2552–4) or involve the formation of the imine under dehydrating conditions followed by reduction (*Comprehensive Organic Transformation*, R. C. Larock, VCH Publisher, Inc (1989) pp. 421–425).

The compound of formula B-7 wherein n is, for example, one to six (prepared by the procedures for the formula B-2 compound) is reacted with a hydroxyamine or its HCl salt in a protic solvent, such as ethanol or methanol, and a base such as K$_2$CO$_3$ at a temperature between room temperature and 150° C., depending on the nature of the solvent used, to give the compound of formula B-8 wherein n is one to six, for example.

To obtain compounds of formula B-9 wherein, for example, R$_{b1}$ is alkyl, and n is one to six, the compound of formula B-8 wherein n is one to six, for example, is reacted with a base, such as NaH and R$_{b1}$—CH$_2$CO$_2$Et in an aprotic solvent such as THF at a temperature between room temperature to 140° C., depending on the nature of the solvent used. To obtain compounds of formula B-9 wherein $R_{b1}$ is =O and n is, for example one to six, the compound of formula B-8 wherein n is one to six, for example, is reacted with a base, such as pyridine and 2-ethylhexylchloroformate in an aprotic solvent, such as DMF. The intermediate thus obtained is refluxed in xylene or other high boiling point aromatic solvent to give the compound of formula B-9 wherein $R_{b1}$ is =O. To obtain compounds of formula B-9 wherein $R_{b1}$ is =S and n is, for example, one to six, the compound of formula B-8 wherein n is one to six, for example, is reacted with a base such as DBU in an aprotic solvent, such as $CH_3CN$ and TCDI (1,1-thiocarbonyidiimidazole).

The compound of formula B-7 wherein n is, for example, one to six, is reacted with $TMSN_3$ and $AlMe_3$ in an aprotic solvent such as toluene at between 40° C. to 200° C., depending on the nature of the solvent used, to give the compound of formula B-10 wherein n is one to six, for example. Alternatively, the compound of formula B-10 is obtained by reacting the above compound of formula B-7 with $NaN_3$ and triethylamine or ammonium chloride in an aprotic solvent, such as DMF, at elevated temperatures.

The compound of formula B-7 wherein n is, for example, one to six, is reacted with an amine and $Al(Me)_3$ in an aprotic solvent, such as toluene, at a temperature between room temperature and 180° C., depending on the nature of the solvent used, to give the compound of formula B-11 wherein n is, for example, one to six and $R_{12}$ and $R_{13}$ are as defined in the Summary above. Alternatively, this compound of formula B-11 is obtained by reacting the above compound of formula B-7 with an amine in the presence of a Lewis acid, such as $AlCl_3$ or $ZnCl_2$ at 150° C. to 200° C., or in the presence of an organometallic reagent, such as CuCl, CuBr or lanthanide (III) triflate. (See Tetrahedron Lett. 1993, Vol. 34, Issue 40, 6395–6398.)

The compound of formula B-12 wherein n is, for example, one to six (prepared by the procedures for the formula B-2 compound) is reacted with an amine or its salt and $Al(Me)_3$ in an aprotic solvent, such as dichloromethane, to give the compound of formula B-13 wherein n is, for example, one to six and $R_{12}$ and $R_{13}$ are independently hydrogen, alkyl, hydroxy or methoxy, for example or as defined in the Summary above. Alternatively, the compound of formula B-12 is hydrolyzed by the methods mentioned in Greene and Wuts, *Protecting Groups in Organic Synthesis*, Wiley, New York (1981) to give the corresponding free acid. The free acid thus obtained is reacted with an amine and a coupling reagent, such as DCC or EDCl, to give the above compound of formula B-13 (as illustrated in *Comprehensive Organic Transformation*, R. C. Larock, VCH Publisher, Inc. (1989) pp. 972–976).

To obtain compounds of formula B-14 wherein, for example, n is one to six, Z is O and $R_{b2}$ is alkyl or halo, the compound of formula B-12 wherein n is one to six, for example, is reacted with a base, such as NaH, in an aprotic solvent, such as THF, and $NH_2C(=N—OH)R_{b2}$ wherein $R_1$ is alkyl at refluxing temperatures. To obtain compounds of formula B-14 wherein, for example, n is one to six, Z is N and $R_{b2}$ is alkyl or halo, the compound of formula B-12 wherein n is one to six, for example, is reacted with a base, such as NaOMe, in a protic solvent, such as MeOH, and aminoguanidine nitrate.

The compound of formula B-15 wherein $R_{12}$ and $R_{13}$ are as defined in the Summary above (prepared by the procedures for the formula B-2 compound) is dissolved in an aprotic solvent such as toluene and refluxed to give the compound of formula B-16 wherein $R_{12}$ and $R_{13}$ are as defined in the Summary above.

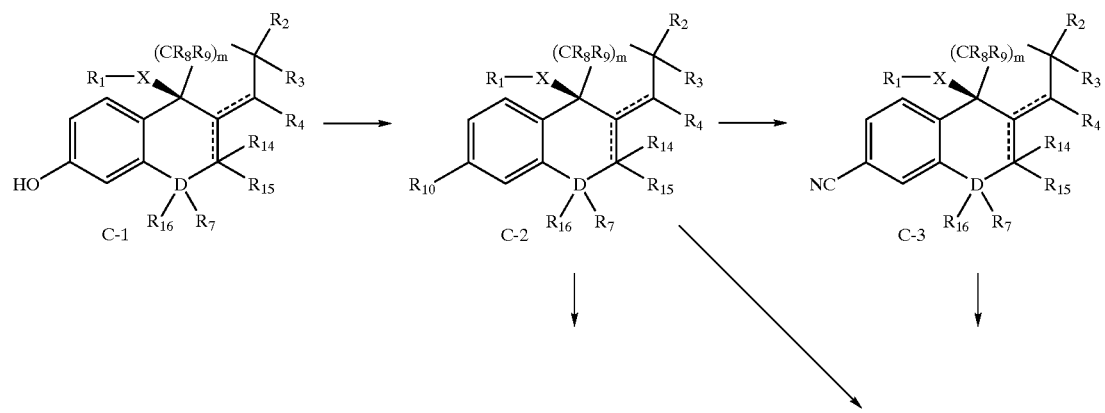

Scheme C

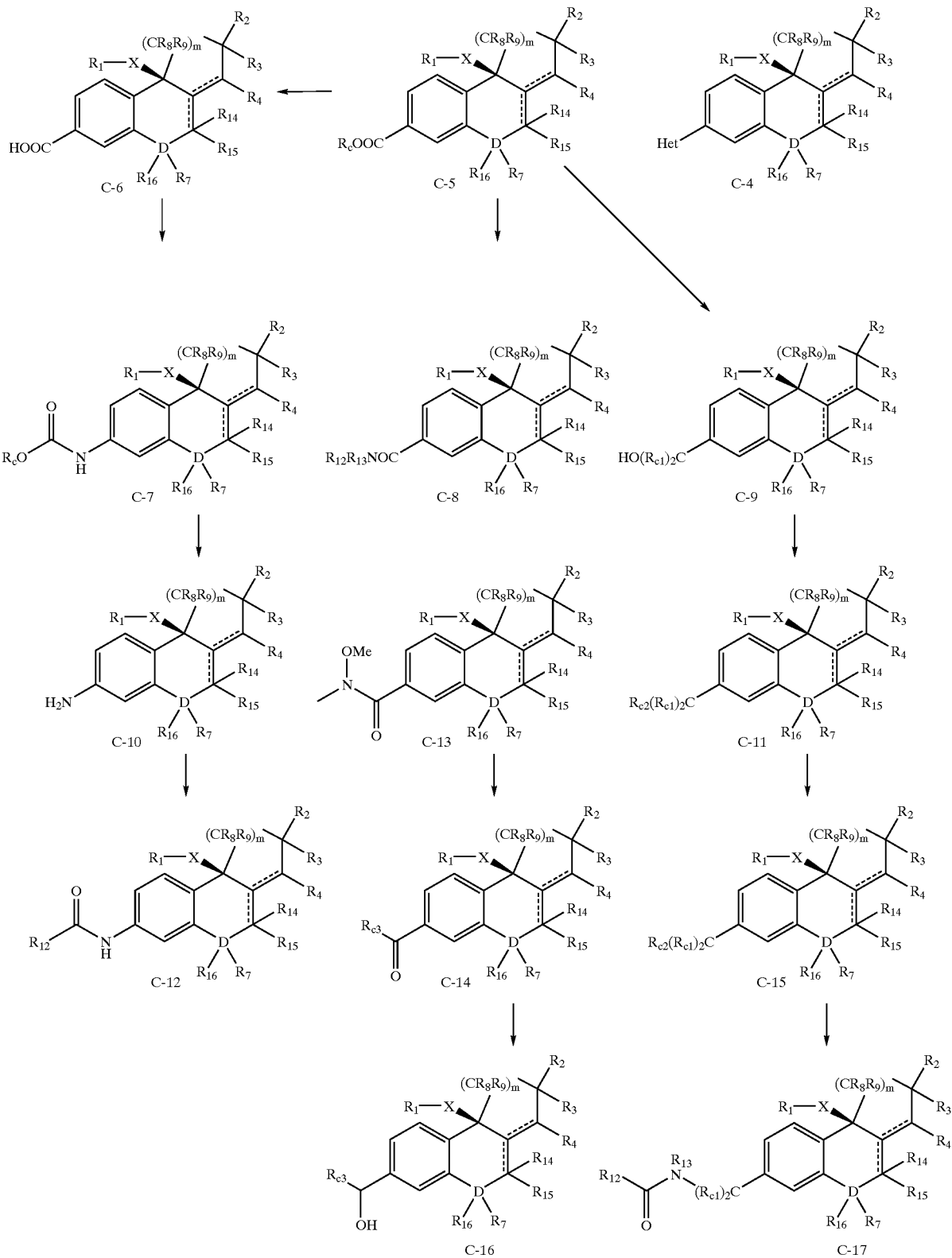

SCHEME C

The compound of formula C-1 (which is the same as the compound of formula B-1, see Scheme B) is treated with an acid scavenger, such as 2,6-lutidine, diisopropylethylamine, or potassium carbonate, with a trifluoromethylsulfonylation reagent, such as trifluoromethylsulfonic anhydride, N-phenyltrifluoromethane-sulfonamide, or 4-nitrophenyltrifluoromethanesulfonate, with or without a catalyst, such as 4-dimethylaminopyridine (DMAP), in a solvent, such as dichloromethane, DMF or methyl-2-pyrrolidinone (NMP), from −78° C. to room temperature to obtain the compound of formula C-2 wherein $R_{10}$ is —OS(O)$_2$CF$_3$. Throughout this scheme, the other variables are as defined in the Summary above. Alternatively, the above compounds of formula C-2 are prepared from the compound of formula C-1 by other reported fluoroalkylsulfonylation methods, some of which are described in K. Ritter, *Synthesis*, 1993, pp. 735–762.

The compound of formula C-2 wherein the group at the $R_{10}$ position is —OS(O)$_2$CF$_3$ or a halogen is reacted with metalcyanide, preferably zinc(II)cyanide (Zn(CN)$_2$), and with a palladium source, such as tetrakis(triphenylphosphine) palladium(O) (Pd(PPh$_3$)$_4$), palladium (II)acetate, or tris(dibenzylidenacetone) dipalladium(O), in a solvent such as N-methyl-2-pyrrolidinone (NMP), DMF or acetonitrile, at room temperature to 120° C. to give the cyano-substituted compound of formula C-3.

To obtain the compound of formula C-4 wherein, for example, Het is tetrazolyl, the compound of formula C-3 is reacted with dibutyltin oxide (Bu$_2$SnO) and trimethylsilylazide (TMSN$_3$) in toluene from room temperature to reflux. Alternatively, the compounds of formula C-4 wherein, for example, Het is tetrazolyl are prepared from the compound of formula C-3 by other reported methods, some of which are described in S J. Wittenberger, *Organic Preparations and Procedures Int.* 1994, 26(5), pp. 499–531. Alternatively, the compound of formula C-4 wherein Het is, for example, 2-pyridyl or 3-pyridyl, is obtained by reacting the compound of formula C-2 with a heterocycle-metal, such as bromo-2-pyridyl zinc or diethyl-(3-pyridyl)borane, and a catalyst, such as Pd(PPh$_3$)$_2$Cl$_2$, tetrakis(triphenylphosphine) palladium(O) (Pd(PPh$_3$)$_4$), or palladium acetate, and 1,1'-bis(diphenylphosphino)ferrocene, in an organic solvent, such as THF, DMF, or NMP at room temperature to 150° C., depending on the nature of the solvent used.

The compound of formula C-2 is reacted under CO 1-3 atm, with a catalyst such as palladium acetate (Pd(OAc)$_2$) and 1,1'-bis(diphenylphospino)ferrocene (DPPF) or bis(diphenylphosphino)propane (DPPP), tetrakis(triphenylphosphine) palladium(O) (Pd(PPh$_3$)$_4$), or tris(dibenzylidenacetone) dipalladium(O), and a base, such as triethylamine or potassium carbonate, with an alcohol, such as methanol, ethanol, or benzyl alcohol, in a solvent, such as DMF, NMP, or DMSO, at room temperature to 150° C., depending on the nature of the solvent used, to give the ester of formula C-5, wherein R$_c$ is, for example, alkyl or aryl.

An aqueous base, such as KOH, in a solvent, such as THF, is added to a solution of the compound of formula C-5 in a solvent, such as THF. The resulting solution is stirred at room temperature to reflux to give the acid of formula C-6.

A solution of the compound of formula C-6, diphenylphosphoryl azide (DPPA), triethylamine, and an alcohol of the formula R$_c$OH, such as t-butanol, is stirred at room temperature to reflux to give the carbamate of formula C-7, wherein, for example, R$_c$ is t-butyl.

The compound of formula C-6 is treated with a coupling reagent, such as 1,3-dimethylaminopropyl-3-ethylcarbodiimide (EDC) or dicyclohexyl carbodiimide (DCC) and hydroxybenzotriazole hydrate (HOBt), with or without a catalyst, such as 4-dimethylaminopyridine (DMAP), and an amine, $R_{12}R_{13}$NH, in an aprotic solvent, such as dichloromethane or DMF, at 0° C. to room temperature to give the amide of formula C-8 wherein $R_{12}$ and $R_{13}$ are defined in the Summary above. Also, the compounds of formula C-8 can be prepared from the compound of formula C-6 by other reported, coupling methods, such as those described in *Comprehensive Organic Transformation*, R. C. Larock, VCH Publishers Inc. (1989), p 972–988.

Alternatively, the ester of formula C-5 is added to a mixture of trimethylaluminum (Al(CH$_3$)$_3$) and $R_{12}R_{13}$NH, such as 1-(3-aminopropyl)imidazole, in a solvent, such as dichloromethane, dichloroethane (DCE), or toluene at 0° C. to room temperature. The resulting mixture is stirred at room temperature to reflux to obtain the amide of formula C-8 wherein, for example, $R_{12}$ is hydrogen and $R_{13}$ is propylimidazol-1-yl, and are further defined in the Summary above.

The ester of formula C-5 is reacted with a reducing agent, such as sodium borohydride or diisobutylaluminum hydride, in an organic solvent, such as methanol, THF or hexane depending on the nature of the reducing agent used, at −78° C. to room temperature, to obtain the alcohol of formula C-9 wherein $R_{c1}$ is H. To obtain other compounds of formula C-9, wherein, for example, $R_{c1}$ is methyl, the compound of formula C-5 is reacted with $R_{c1}$-metal, such as methylmagnesium bromide, in an organic solvent, such as THF or toluene, at −78° C. to room temperature.

The carbamate of formula C-7, wherein R$_c$ is, for example, t-butyl, is reacted with an acid, such as trifluoroacetic acid (TFA), in a solvent, such as dichloromethane, at −78° C. to room temperature to give the amine of formula C-10. Also, the compound of formula C-10 may be prepared from the compound of formula C-7, wherein R$_c$ is t-butyl, benzyl, or other protecting groups, by other literature methods, some of which are described in *Protecting Groups in Organic Synthesis*, Second Edition, T. W. Greene and P. G. M. Wuts, John Wiley and Sons, Inc. (1991).

To obtain the compound of formula C-11 wherein $R_{c2}$ is —OSO$_2$-methyl, the compound of formula C-9 wherein $R_{c1}$ is hydrogen or alkyl is reacted with a methylsulfonating reagent, such as methanesulfonyl chloride (MsCl), and an acid scavenger, such as diisopropylethylamine, in an organic solvent, such as THF or toluene at −78° C. to room temperature. To obtain the compound of formula C-11 wherein $R_{c2}$ is Cl, the compound of formula C-9 wherein $R_{c1}$ is hydrogen or alkyl is reacted with a chlorinating reagent, such as thionyl chloride, an acid scavenger, such as pyridine, in an organic solvent, such as methylene chloride, at −78° C. to room temperature.

The amine of formula C-10 is reacted with an acylating reagent, such as CH$_3$COCl and an acid scavenger, such as triethylamine or pyridine, in a solvent, such as methylene chloride or THF, at −78° C. to room temperature to give the amide of formula C-12 wherein $R_{12}$ is as defined in the Summary above.

The compound of formula C-13 (which is obtained from the compound of formula C-6 by reacting it with N,O-dimethylhydroxylamine hydrochloride, 1-(3-dimethylaminopropyl)-3-ethylcarbodiimide hydrochloride, HOBt and DMAP) is reacted with $R_{c3}$-Metal, such as ethylmagnesium bromide, in a solvent, such as THF or toluene, at −78° C. to room temperature to give the compound of formula C-14, wherein $R_{c3}$ is, for example, ethyl.

The compound of formula C-11 and an amination reagent, such as sodium azide, in a solvent, such as DMF, NMP, or DMSO, are stirred at room temperature to 150° C., depending on the nature of the solvent used, to give the compound of formula C-15 wherein $R_{c1}$ is hydrogen or alkyl and $R_{c4}$ is N$_3$. The resulting azide is treated with a reducing reagent, such as triphenylphosphine (PPh$_3$), in a solvent or mixture of solvents, such as THF, methanol and water, at −20° C. to reflux, to give the compound of formula C-15 wherein $R_{c4}$ is $NH_2$.

The aldehyde of formula C-14 wherein $R_{c3}$ is hydrogen or the ketone of formula C-14 wherein $R_{c3}$ is alkyl is treated with a reducing agent such as sodium borohydride or diisobutylaluminum hydride, in an organic solvent, such as methanol, THF, or hexane depending on the nature of the reducing agent used, at −78° C. to room temperature, to obtain the alcohol of formula C-16 wherein $R_{c3}$ is, for example, ethyl.

The amine of formula C-15 wherein $R_{c1}$ is hydrogen or alkyl and $R_{c4}$ is —$NH_2$ is reacted with an acylating reagent, such as $CH_3COCl$ and an acid scavenger, such as triethylamine or pyridine, in a solvent, such as methylene chloride or THF, at −78° C. to room temperature to give the amide of formula C-17 wherein $R_{12}$ and $R_{13}$ are as defined in the Summary above.

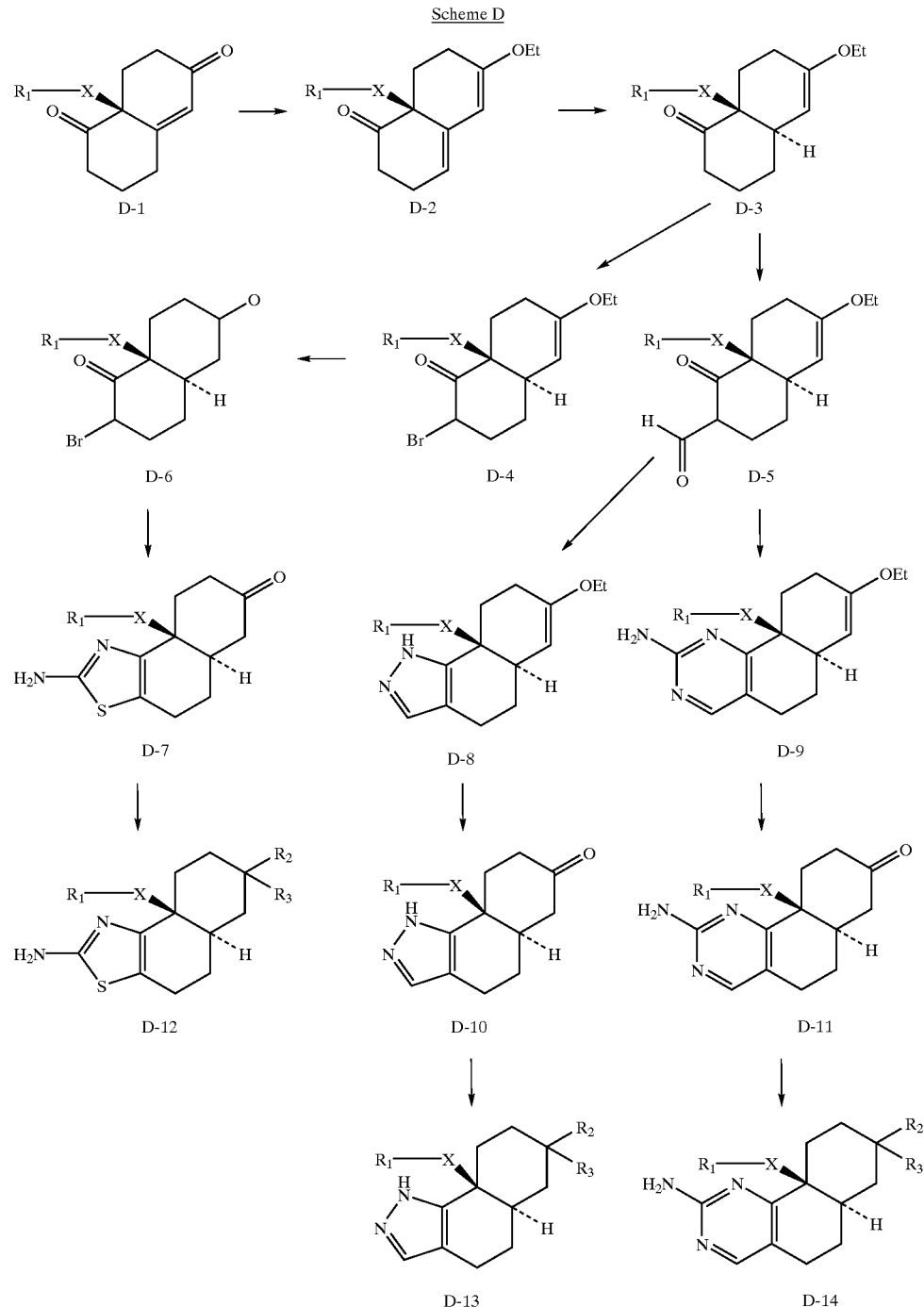

Scheme D

SCHEME D

The compound of formula D-1 is prepared from commercially available cyclohexane-1,3-dione by literature procedures described in Chem. Ber., 85, 1061 (1952); Org. Syn., Coll. Vol. V, page 486; and S. Ramachandran and M. S. Newman, Org. Syn. 41, 38 (1961). It is reacted with triethylorthoformate, p-toluenesulfonic acid and ethanol in toluene to obtain the dienol ether of formula D-2. Throughout this scheme, the other variables are as defined in the Summary above.

The compound of formula D-2 in ethanol or methanol is hydrogenated using 1 atm of $H_2$ over $Pd/CaCO_3$ or strontium carbonate to obtain the compound of formula D-3. The compound of formula D-3 is reacted with lithium diisopropylamide (prepared from diisopropylamine and n-butyllithium) and n-bromo-succinimide in THF to obtain the brominated compound of formula D-4. The compound of formula D-3 is reacted with ethyl formate in THF and potassium t-butoxide to obtain the carboxaldehyde of formula D-5.

The compound of formula D-4 is hydrolyzed with an aqueous acid, such as sulfuric acid, to obtain the compound of formula D-6. Likewise, once the compounds of formula D-8 and D-9 are obtained, as described below, they are hydrolyzed with aqueous acid to obtain the compounds of formula D-10 and D-11, respectively.

The compound of formula D-6 is reacted with thiourea in acetonitrile and then heated to reflux to obtain the amine-substituted thiazole compound of formula D-7. The carboxaldehyde of formula D-5 is reacted with hydrazine in ethanol/water to obtain the pyrazole compound of formula D-8. The carboxaldehyde compound of formula D-5 is reacted with a refluxing solution of sodium metal and guanidine sulfate in isopropyl alcohol to obtain the amino-substituted pyrimidine compound of formula D-9.

The compound of formula D-7 is reacted with an organometallic compound, $R_3$-Metal, such as $R_3Li$, $R_3MgBr$ or $R_3MgCl$, (for example, lithio-2-chloroethyne), in an aprotic solvent such as THF at −78° C. to room temperature to obtain the compound of formula D-12 wherein $R_2$ and $R_3$ are, for example, hydroxy and chloroethynyl, respectively, and are further defined in the Summary above. Likewise, the compounds of formula D-13 and D-14 are obtained from the compounds of formula D-10 and D-11, respectively, by analogous procedures.

Scheme E

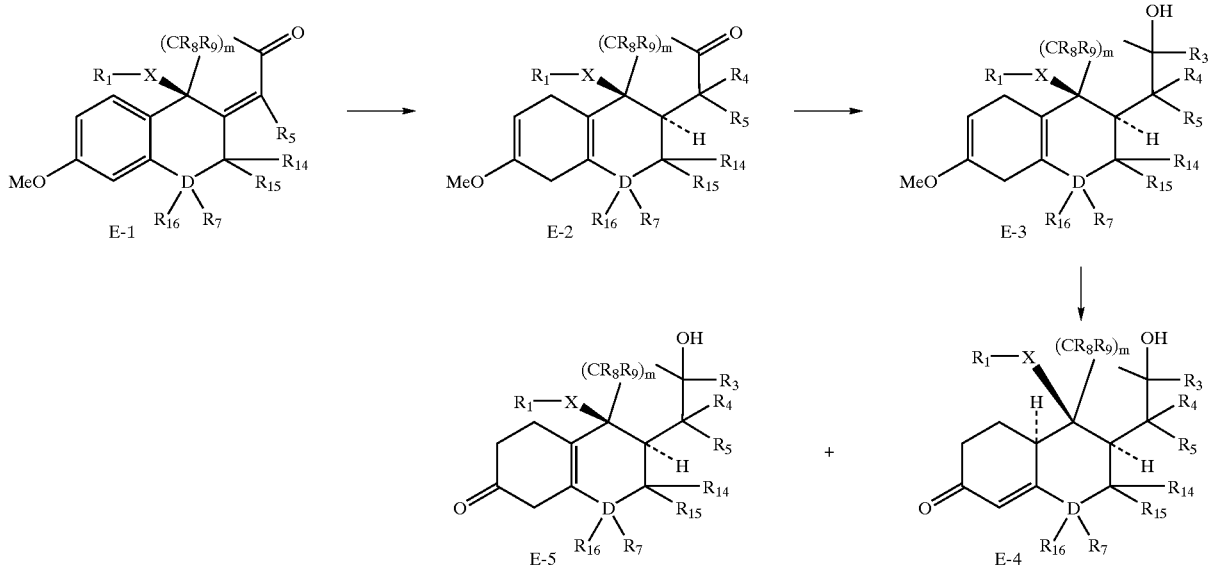

SCHEME E

The compound of formula E-1 (which is the same as the compound of formula A-3a (see Scheme A) wherein $R_{10}$ is methoxy and the other variables are as defined in the Summary above) is treated with a reducing metal reagent, such as an alkali (group IA in the periodic table) or alkaline metal (group IIA in the periodic table), including Li, Na, or Ca, an amine, such as $NH_3$ or ethylene diamine, and a proton source, such as t-butyl alcohol or ethanol, in an aprotic solvent, such as THF or dioxane, at −78° C. to room temperature to give the compound of formula E-2, wherein the variables are as described in the Summary above.

The compound of formula E-2 wherein the variables are as described in the Summary above is reacted with $R_3$-Metal, such as $R_3Li$, $R_3MgBr$ or $R_3MgCl$, wherein $R_3$ is, for example, alkynyl, in an aprotic solvent such as THF at low temperature to give the compound of formula of E-3 wherein the variables are as described in the Summary above.

The compound of formula E-3 is treated with an aqueous acid, such as HCl, acetic acid, or oxalic acid, in a solvent, such as THF or dioxane, at −20° C. to reflux to give the compounds of formula E-4 and E-5 wherein the variables are as defined in the Summary above in various ratios depending on the nature of the aqueous acid and the solvent used. Also, the compounds of formula E4 and E-5 may be prepared by other literature methods as described in *Protecting Groups in Organic Synthesis*, Second Edition, T. W. Greene and P. G. M. Wuts, John Wiley and Sons, Inc. (1991).

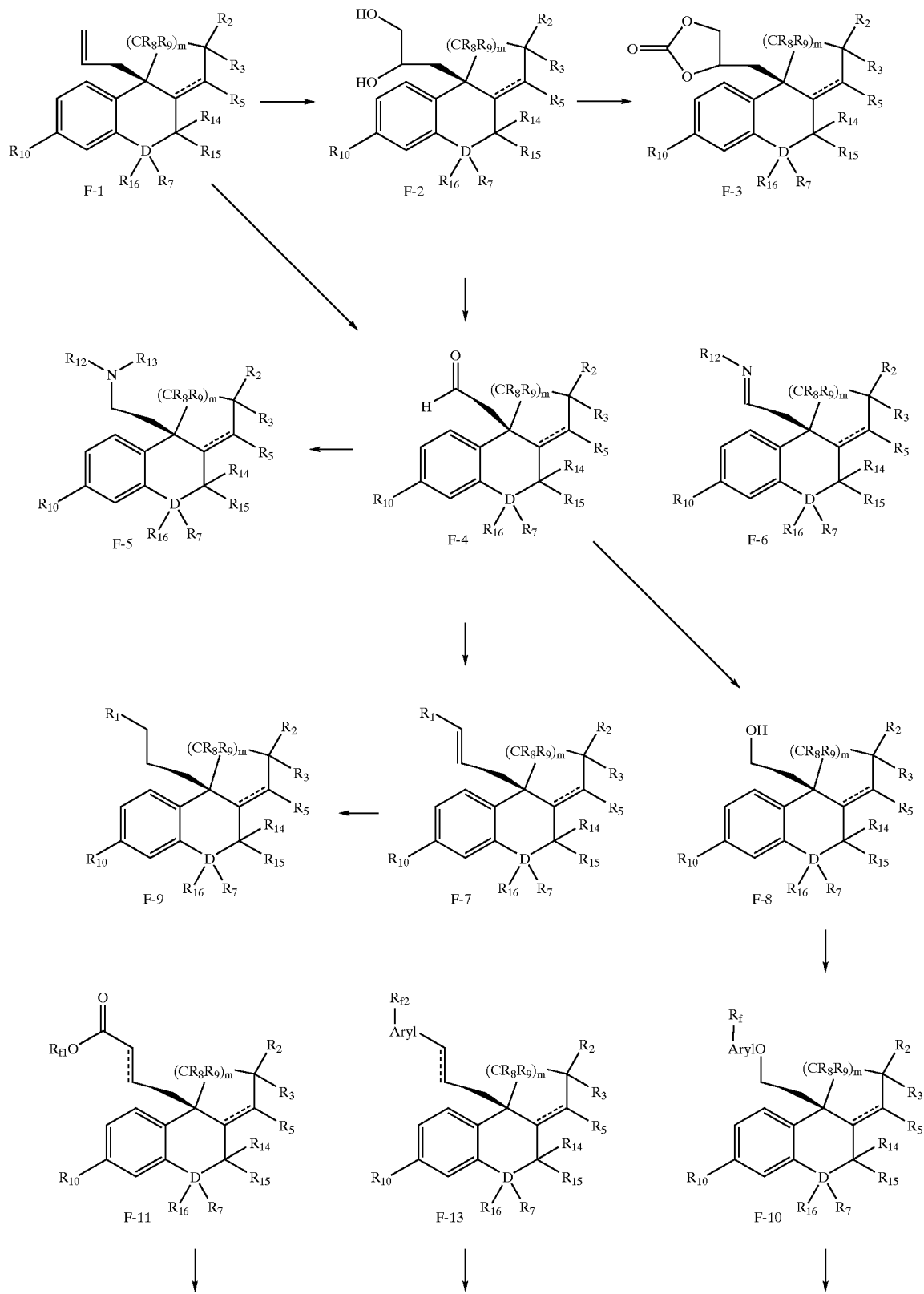

-continued

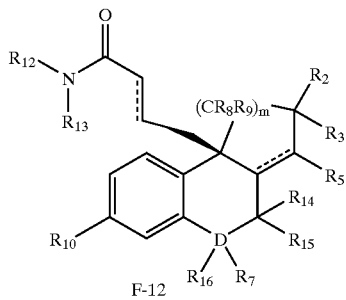
F-12

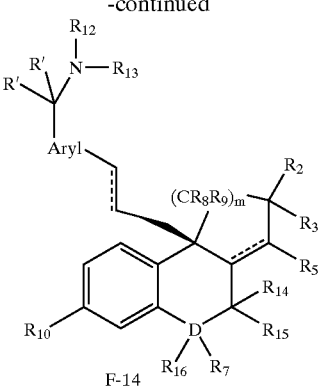
F-14

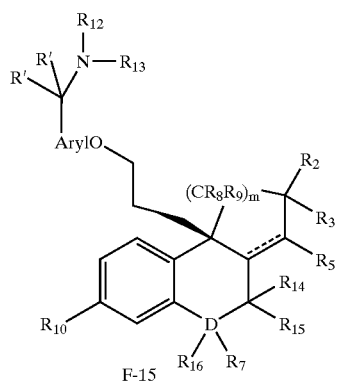
F-15

SCHEME F

The compound of formula F-1 (prepared as described in Schemes A, B, C, and H) wherein the variables are as described in the Summary above is treated with an oxidizing agent, such as osmium tetroxide in t-butanol, with or without an agent to regenerate the oxidizing agent, such as N-methylmorpholine-N-oxide, with or without a catalyst, such as pyridine, in a solvent, such as methylene chloride, at 0° C. to room temperature to obtain the diol compound of formula F-2 wherein the variables are as described in the Summary above.

The compound of formula F-2 wherein the variables are as described in the Summary above is reacted with a carbonylation reagent, such as carbonyldiimidazole, diphosgene or phosgene, in a solvent, such as THF or methylene chloride, at 0° C. to reflux to obtain the (2-oxo-1,3-dioxolan-4-yl)methyl compound of formula F-3 wherein all the variables are as described in the Summary above.

The diol compound of formula F-2 wherein the variables are as described in the Summary above is oxidatively cleaved with an oxidation reagent, such as sodium periodate (NaIO4), with or without an acid scavenger, such as sodium bicarbonate, in a solvent, such as methylene chloride, at 0° C. to room temperature to obtain the aldehyde of formula F-4 wherein the variables are as described in the Summary above.

Alternatively, the compound of formula F-1 wherein the variables are as described in the Summary above is treated concomitantly with an oxidation reagent, such as osmium tetroxide in t-butanol, and an oxidative cleavage reagent, such as sodium periodate ($NaIO_4$), with or without an agent to regenerate the oxidizing agent, such as N-methylmorpholine-N-oxide, with or without a catalyst, such as pyridine, in a solvent mixture, such as dioxane and water, at 0° C. to room temperature to obtain the aldehyde of formula F-4 wherein the variables are as described in the Summary above.

Alternatively, the compound of formula F-1 wherein the variables are as described in the Summary above is treated with ozone in a solvent, such as THF, at −78° C. to 0° C. followed by treatment with a reducing agent, such as dimethyl sulfide, at −78° C. to room temperature to obtain the aldehyde of formula F-4 wherein the variables are as described in the Summary above.

The aldehyde of formula F-4 wherein the variables are as described in the Summary above is treated with an amine, ($NHR_{12}R_{13}$, for example, piperidine), with or without a drying agent, such as molecular sieves or magnesium sulfate, with a reducing agent, such as sodium triacetoxyborohydride ($NaBH(OAc)_3$) or sodium cyanoborohydride ($NaCNBH_3$), in a solvent or a mixture of solvents, such as acetic acid and/or dichoromethane, at 0° C. to room temperature to obtain the compound of formula F-5, wherein, for example, $R_{12}$ and $R_{13}$ taken together are piperidinyl and wherein the other variables are as described in the Summary above.

The oxime-containing compound of formula F-6 wherein $R_{12}$ is hydroxy or alkoxy and wherein the other variables are as described in the Summary above, is prepared by reacting the formula F-4 compound wherein the variables are as described in the Summary above with hydroxylamine or an alkoxyamine or an HCl salt, with or without a base, such as $KHCO_3$ or pyridine, in a solvent, such as methanol, ethanol or pyridine, at 0° C. to reflux.

An olefination reagent, such as $PO(OR_1)_2CH_2R_1$, is treated with a base, such as lithium diisopropyl amine (LDA) or n-butyl lithium, and is reacted with the aldehyde of formula F4 wherein the variables are as described in the Summary above in a solvent, such as THF at −78° C. to room temperature to obtain the alkenyl compound of formula F-7 wherein the variables are as described in the Summary above.

The aldehyde of formula F-4 wherein the variables are as described in the Summary above is treated with a reducing agent, such as diisobutylaluminum hydride (DiBAl) in hexane or sodium borohydride ($NaBH_4$), in a solvent, such as THF or methanol, at −78° C. to room temperature to obtain the alcohol of formula F-8 wherein the variables are as described in the Summary above.

The alkenyl compound of formula F-7 wherein the variables are as described in the Summary above is hydrogenated using hydrogen with a palladium on carbon catalyst or other reagents such as platinum oxide or rhodium on aluminum oxide (see P. N. Rylander in *Hydrogenation Methods*, Academic Press, New York, 1985; Herbert O. House in *Modern Synthetic Reactions*, Chapter 1, pp. 1–45; and John Fried and John A. Edwards in *Organic Reactions in Steroid Chemistry*, Chapter 3, pp. 111–145) in a variety of solvents including methanol, ethanol and THF to obtain the compound of formula F-9 wherein the variables are as described in the Summary above.

The alcohol of formula F-8 is coupled with $R_f$ArylOH, utilizing an azocarboxylate such as diethylazodicarboxylate (DEAD), a trialkyl phosphine such as triphenylphosphine (PPh$_3$) in a solvent, such as methylene chloride, to obtain the compound of formula F-10 wherein $R_f$ is formyl and other aromatic substituents as described in the Summary above and the other variables are as defined in the Summary above. Alternatively, formula F-10 compounds are prepared by reacting the compound of formula F-8 with p-toluenesulfonyl chloride. The resulting intermediate in DMF is reacted with an alkali metal salt of $R_f$-ArylOH to give the compound of formula F-10.

The ester of formula F-11 (prepared from the aldehyde of formula F-4 by an olefination procedure described above) wherein $R_{f1}$ is, for example, methyl, and the other variables are as described in the Summary above is reacted with an aqueous base, such as KOH, in a solvent, such as THF, and the resulting solution is heated and stirred at room temperature to reflux to obtain the acid of formula F-11 wherein $R_{f1}$ is hydrogen and all the additional variables are as described in the Summary above.

The compound of formula F-11 wherein $R_{f1}$, is hydrogen and the other variables are as described in the Summary above is treated with a coupling reagent, such as 1,3-dimethylaminopropyl-3-ethylcarbodiimide (EDC) or dicyclohexyl carbodiimide (DCC) and hydroxybenzotriazole hydrate (HOBt), with or without a catalyst, such as 4-dimethylaminopyridine (DMAP), and an amine ($R_{12}R_{13}$NH, such as pyrrolidine), in an aprotic solvent, such as dichloromethane or DMF, at 0° C. to room temperature to obtain the compound of formula F-12 wherein, for example $R_{12}$ and $R_{13}$ taken together are pyrrolidinyl, and the other variables are as described in the Summary above. Also, the compounds of formula F-12 are prepared from the compounds of formula F-11 by other reported, coupling methods, some of which are described in *Comprehensive Organic Transformation*, R. C. Larock, VCH Publishers Inc. (1989), pp. 972–988.

The compound of formula F-13 wherein $R_{f2}$ is COOR$_{f3}$, wherein $R_{f3}$ is, for example, methyl, and wherein the other variables are as defined in the Summary above (prepared from the aldehyde of formula F-4 by an olefination procedure described above) is hydrolyzed with an aqueous base, such as KOH, in a solvent, such as THF, and the resulting solution is stirred at room temperature to reflux to give the compound of formula F-13 wherein $R_{f2}$ is COOH and the other variables are as described in the Summary above.

The compound of formula F-13 wherein $R_{f2}$ is COOH is treated with a coupling reagent, such as 1-(3-dimethylaminopropyl)-3-ethylcarbodiimide (EDC) or dicyclohexyl carbodiimide (DCC) and hydroxybenzotriazole hydrate (HOBt), with or without a catalyst, such as 4-dimethylaminopyridine (DMAP), and an amine ($R_{12}R_{13}$NH, such as pyrrolidine), in an aprotic solvent, such as dichloromethane or DMF, at 0° C. to room temperature to obtain the compound of formula F-14 wherein, for example $R_{12}$ and $R_{13}$ taken together are pyrrolidinyl, R' and R' are taken together to form =O, and the other variables are as described in the Summary above. Also, the compounds of formula F-14 are prepared from the compounds of formula F-13 by other reported, coupling methods, some of which are described in *Comprehensive Organic Transformation*, R. C. Larock, VCH Publishers Inc. (1989), pp. 972–988.

The compound of formula F-13 wherein $R_{f2}$ is CHO and the other variables are as described in the Summary above (which is prepared analogously to the compound of formula F-7) is treated with an amine, (NHR$_{12}$R$_{13}$, for example, piperidine), with or without a drying agent, such as molecular sieves or magnesium sulfate, and with a reducing agent, such as sodium triacetoxyborohydride (NaBH(OAc)$_3$) or sodium cyanoborohydride (NaCNBH$_3$), in a solvent or a mixture of solvents, such as acetic acid and/or dichloromethane, at 0° C. to room temperature to obtain the compound of formula F-14, wherein, for example, $R_{12}$ and $R_{13}$ taken together with the nitrogen atom are piperidinyl, each R' is H, and wherein the other variables are as described in the Summary above.

The protected compound of formula F-13 wherein $R_{f2}$ is, for example, —CH$_2$OTBDMS is prepared from the aldehyde of formula F-4 by Wittig coupling as described above. This compound is deprotected to the alcohol by using tetabutylammonium fluoride in a solvent, such as tetrahydrofuran. This alcohol wherein $R_{f2}$ is CH$_2$OH is reacted with methanesulfonyl chloride, diisopropylethylamine and a primary or secondary amine, such as morpholine, to give the compound of formula F-14 wherein $R_{12}$ and $R_{13}$ taken together are, for example, morpholinyl, each R' is H and the other variables are as described in the Summary above.

The compound of formula F-10 wherein $R_f$ is CHO and the other variables are as described in the Summary above (which is prepared as described above) is treated with an amine, (NHR$_{12}$R$_{13}$, for example, piperidine), with or without a drying agent, such as molecular sieves or magnesium sulfate, and with a reducing agent, such as sodium triacetoxyborohydride (NaBH(OAc)$_3$) or sodium cyanoborohydride (NaCNBH$_3$), in a solvent or a mixture of solvents, such as acetic acid and/or dichloromethane, at 0° C. to room temperature to obtain the compound of formula F-15, wherein, for example, $R_{12}$ and $R_{13}$ taken together with N are piperidinyl, R' is H and the other variables are as described in the Summary above. The compounds of formula F-15, wherein R' and R' taken together to form =O, may be prepared by procedures analogous to those described above.

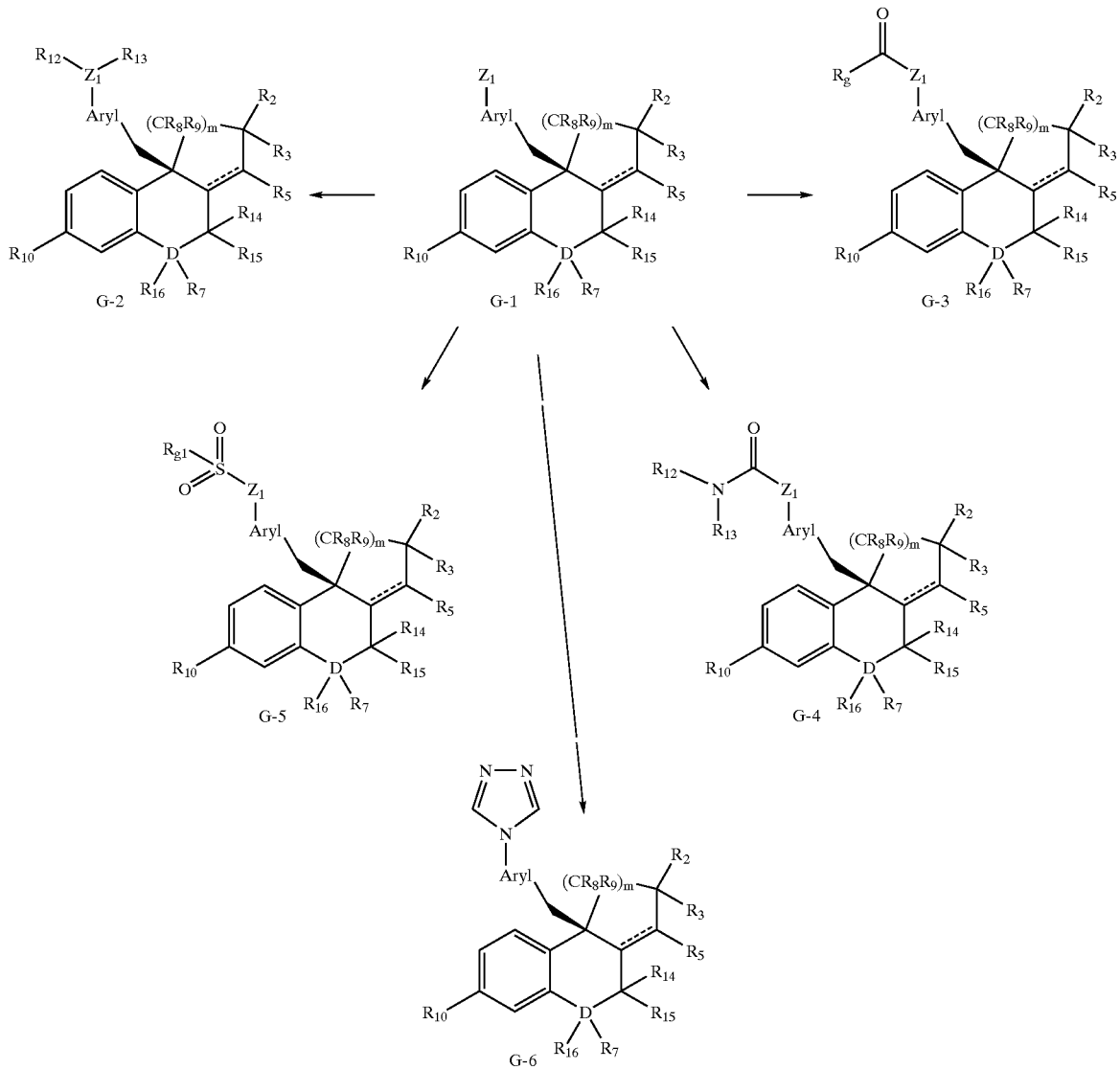

Scheme G

SCHEME G

The compound of formula G-1 wherein Z is $NH_2$ and the other variables areas defined in the Summary above (which is prepared according to the procedures in Schemes A and H) is reacted with an aldehyde or ketone such as $R_{12}C(O)R_{13}$ and with sodium triacetoxyborohydride ($Na(OAc)_3BH$) or sodium cyanoborohydride ($NaCNBH_3$) as reducing agents to give the reductive amination product of formula G-2 wherein $Z_1$ is N and the other variables are as defined in the Summary above. Alternatively, the compound of formula G-2 is prepared from the compound of formula G-1 by other reductive amination methods known in the art, such as those disclosed for the preparation of the compound of formula B-4 in Scheme B above.

The compound of formula G-1 wherein Z. is $NH_2$ or OH is reacted with a coupling reagent, such as 1,3-dimethylaminopropyl-3-ethylcarbodiimide (EDC) or dicyclohexyl carbodiimide (DCC) and hydroxybenzotriazole hydrate (HOBt), and a base, such as 4-dimethylaminopyridine (DMAP) or triethylamine, in an aprotic solvent, such as methylene chloride, and an acid to give the compound of formula G-3 wherein $Z_1$ is O or $NR_{12}$, $R_g$ is for example, alkyl and the other variables are as defined in the Summary above. Alternatively, the compound of formula G-3 is obtained from the compound of formula G-1 by standard acylation, such as treating the compound of formula G-1 with a base, such as pyridine, and an acyl halide or acid anhydride in an aprotic solvent to give the compound of formula G-3.

The compound of formula G-4 wherein $Z_1$ is O or $NR_{12}$ and the other variables are as defined in the Summary above is obtained from the compound of formula G-1 according to the procedures described in Scheme B, such as the preparation of the carbamate of formula B-2 wherein $R_b$ is $—C(O)NR_{12}R_{13}$. Alternatively, the compound of formula G-4 wherein $Z_1$ is NHBoc is reacted with a base, such as n-BuLi, in an aprotic solvent and an amine to give the compound of formula G-4 wherein $Z_1$ is NH.

The compound of the formula G-1 is reacted with the compound of formula $R_{g1}SO_2Cl$ and a base, such as triethylamine, in an aprotic solvent, such as THF, to give the compound of formula G-5 wherein $Z_1$ is O or $NR_{12}$, $R_{g1}$ is, for example, alkyl and the other variables are as defined in the Summary above.

The compound of formula G-1 wherein $Z_1$ is $-NH_2$ and the other variables are as defined in the Summary above is reacted with $(Me_2NCH=N)_2$ in an aprotic solvent such as toluene and with an acid, such as p-toluenesulfonic acid, to give the compound of formula G-6 wherein the variables are as defined in the Summary above.

The compound of formula H-1 is reacted with $R_hOH$ wherein $R_h$ is, for example, lower alkyl or ethylene glycol, and an acid such as p-toluenesulfonic acid in an aprotic solvent such as toluene at reflux temperature under Dean-Stark trap to remove water to give the compound of the formula H-3 wherein $R_h$ is, for example, lower alkyl or wherein $R_h$'S taken together with the two oxygen atoms form, for example, 1,3-dioxolane, and the other variables are as defined in the Summary above.

The compound of the formula H-2 wherein Z is CH, $R_{12}$ is, for example, alkyl and the other variables are as defined Scheme H

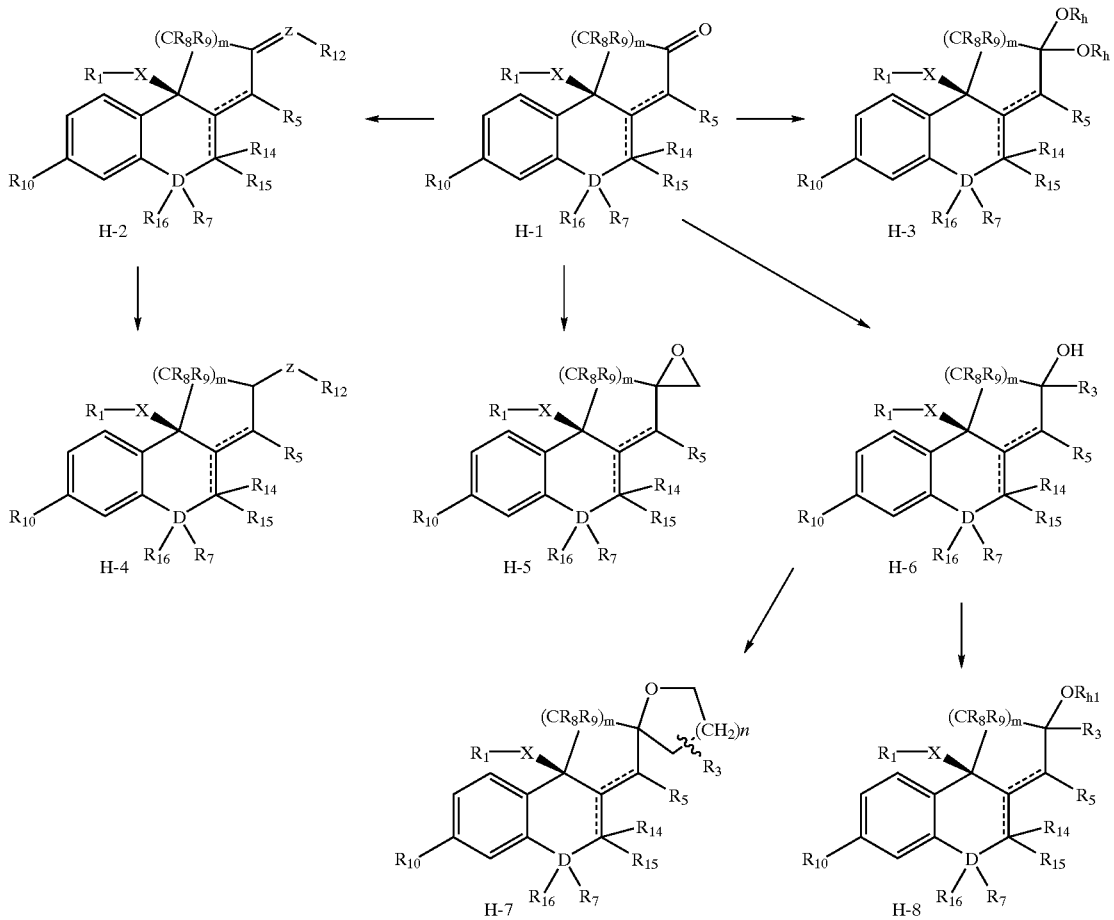

SCHEME H

The compound of formula H-1 wherein the variables are as described in the Summary above (which is prepared by the procedures in Scheme A above) is reacted with reagents such as $P(Rh_2)_3CH_2R_{12}$ or $PO(OR_{h2})_2CH_2R_{12}$ wherein $R_{h2}$ is lower alkyl or aryl and the other variables are as defined in the Summary above and a base such as lithium diisopropylamide (LDA) or sodium hydride (NaH) in an aprotic solvent, such as THF or DMF, to give the compound of formula H-2 wherein Z is CH, and $R_{12}$ and the other variables are as defined in the Summary above.

The compound of formula H-1 is reacted with the compound of formula $H_2NOR_{12}$ or its hydrochloride salt in ethanol or methanol, with or without sodium acetate (NaOAc), at room temperature or at the refluxing temperature of the solvent, to give the compound of formula H-2 wherein Z is N, and $R_{12}$ and the other variables are as defined in the Summary above.

in the Summary above is reacted with $H_2$, and Pd/C or other reagents as described by P. N. Rylander in *Hydrogenation Methods*, Academic Press, New York, 1985 in a solvent, such as methanol, to give the compound of formula H-4 wherein Z is CH, $R_{12}$ is, for example, alkyl, and the other variables are as defined in the Summary above.

The compound of the formula H-2 wherein Z is N, $R_{12}$ is, for example, alkyl and the other variables are as defined in the Summary above is reacted with hydrochloric acid in methanol and borane-trimethyl-amine complex ($Me_3N$, $BH_3$) or other reducing reagents to give the compound of formula H-4 wherein Z is NH, $R_{12}$ is alkyl and the other variables are as defined in the Summary above.

Alternatively, the compound of formula H-4 is obtained from the compound of formula H-2 by other hydrogenation procedures which are known and available in the art.

The compound of formula H-1 is reacted with trimethylsulfonium iodide ($(CH_3)_3S^+I^-$) or trimethylsulfoxonium iodide ((CH$_3$)$_3$S$^+$→OI$^-$) and a base, such as potassium t-butoxide, in an aprotic solvent such as DMF to give the compound of formula H-5 wherein the variables are as defined in the Summary above. Alternatively, the compound of formula H-5 is obtained from the compound of formula H-1 by an analogous method to that illustrated in *Comprehensive Organic Transformation*, R. C. Larock, VCH Publishers Inc. (1989), pp. 468–470.

The compound of formula H-1 is reacted with R$_3$-Metal, such as R$_3$Li, R$_3$MgBr or R$_3$MgCl, wherein R$_3$ is, for example, alkynyl or alkyl in an aprotic solvent such as THF at low temperature to give the compound of formula H-6 wherein R$_3$ is alkynyl or alkyl and the other variables are as defined in the Summary above.

The compound of formula H-1 is reacted with TMSCF$_3$ and TBAF as described in G. A. Olah et al., *J. Am. Chem. Soc.* (1989) 111, 393, to give the compound of formula H-6 wherein R$_3$ is —CF$_3$ and the other variables are as defined in the Summary above. Alternatively, the compound of formula H-1 is treated with other —CF$_3$ nucleophiles which are known and available in the literature including, but not limited to, that disclosed by J. Russell, N. Roques, Tetrahedron, 1998, 54, 13771–13782.

Alternatively, the compound of formula H-5, wherein the variables are as defined in the Summary above, is reacted with R$_3$-Metal such as R$_3$Li, R$_3$MgBr, or R$_3$MgCl wherein R$_3$ is, for example, alkyl in an aprotic solvent such as THF at low temperature to give the compound of formula H-6 wherein R$_3$ is, for example, —CH$_2$-alkyl, and the other variables are as defined in the Summary above. Alternatively, the compound of formula H-5 wherein the variables are as defined in the Summary above is reacted with R$_3$—X-Metal, such as R$_3$ONa, R$_3$SNa, R$_3$OK, R$_3$OLi or R$_3$SLi wherein R$_3$ is, for example, alkynyl and X is O or S in an aprotic solvent such as THF, at room temperature to the refluxing temperature of the solvent used, to give the compound of the formula H-6 wherein R$_3$ is, for example, —O—CH$_2$-alkynyl or —S—CH$_2$-alkynyl and the other variables are as defined in the Summary above. Alternatively, the compound of formula H-5 wherein the variables are as defined in the Summary above is reacted with an amine in an aprotic solvent such as THF, at room temperature to the refluxing temperature of the solvent used, to give the compound of the formula H-6 wherein R$_3$ is —CH$_2$—NR$_{12}$R$_{13}$ and the other variables are as defined in the Summary above.

The compound of formula H-6 wherein R$_3$ is alkynyl and the other variables are as defined in the Summary above is reacted with H$_2$, Pd/C, or PtO$_2$ to give the corresponding saturated alkyl product. The compound of formula H-6 wherein R$_3$ is alkynyl and the other variables are as defined in the Summary above is reacted with LiAlH$_4$ in an aprotic solvent such as THF to give the corresponding trans-alkenyl product. The compound of formula H-6 wherein R$_3$ is alkynyl and the other variables are defined in the Summary above is reacted with H$_2$ and Lindlar catalyst to give the corresponding cis-alkenyl product. Alternatively, these compounds are obtained using other conditions as described in *Modern Synthetic Reactions*, Herbert O. House, Ed., Chapters 1 & 2.

The compound of formula H-6 wherein R$_3$ is hydroxyalkyl and the other variables are as defined in the Summary above is reacted with an acid such as p-toluenesulfonic acid in an aprotic solvent such as toluene at reflux temperature to give the compound of formula H-7 wherein n is 1 or 2 and the other variables are as defined in the Summary above.

Alternatively, the compound of formula H-6 wherein R$_3$ contains a leaving group such as halogen, mesylate, tosylate or triflate and the other variables are as defined in the Summary above is reacted with a base such as NaH in an aprotic solvent such as THF to give the compound with the formula H-7 wherein n is 1 or 2 and the other variables are as defined in the Summary above.

The compound of formula H-6 wherein the variables are as defined in the Summary above is reacted with a base such as Et$_3$N or NaH and R$_{h1}$X wherein, for example, R$_{h1}$ is methyl and X is halogen or other leaving group in an aprotic solvent such as THF or methylene chloride to give the compound of formula H-8 wherein, for example, R$_{h1}$ is methyl and the other variables are as defined in the Summary above. Alternatively, the compound of formula H-6 wherein the variables are as defined in the Summary above is reacted with N$_2$CHR$_{h1}$, wherein, for example, R$_{h1}$ is methyl, and Rh(OAc)$_3$, in an aprotic solvent such as methylene chloride to give the compound of formula H-8 wherein, for example, R$_{h1}$ is methyl and the other variables are as defined in the Summary above.

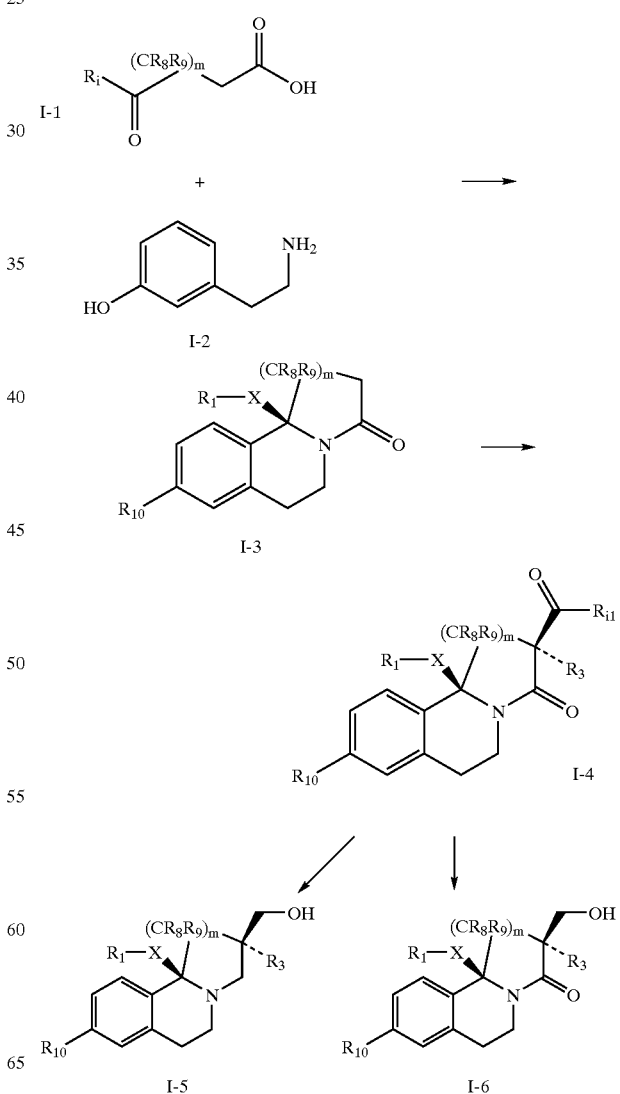

Scheme I

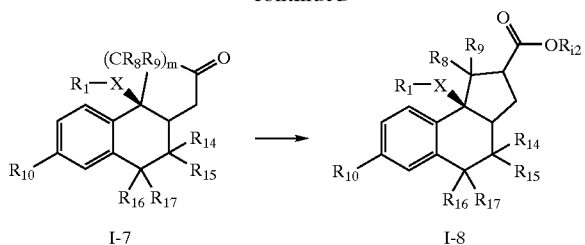

SCHEME I

The compound of formula I-1 wherein $R_i$ is, for example, benzyl, and wherein m is one, is prepared as described in L. M. Fuentes, G. L. Larson, *Tetrahedron Lett.* 1982, 23 (3), pp. 271–274. The compound of formula I-1 wherein $R_i$ is, for example, benzyl, and wherein m is two, is prepared as described in A. Ijima, K. Takashi, *Chem Pharm. Bull.* 1973, 21(1), pp. 215–219. The compound of formula I-1 and the compound of formula I-2 (which is commercially available) (or a salt of the compound of formula I-2, such as the hydrobromide or hydrochloride salt) are reacted in a solvent, such as isopropanol, at between 200° C. and 300° C. to obtain the compound of formula I-3 wherein $R_{10}$ is hydroxy and the other variables are as described in the Summary above.

The compound of formula I-3 wherein $R_{10}$ is hydroxy and the other variables are as described in the Summary above, which is in a solvent, such as DMF, is reacted with a base, such as potassium t-butoxide in t-butanol, and an electrophile, such as benzyl bromide, at 0° C. to 100° C. to obtain the compound of formula I-3 wherein $R_{10}$ is, for example, —O-benzyl.

The compound of formula I-3 wherein $R_{10}$ is, for example, —O-benzyl, and the other variables are as defined in the Summary above, which is in a solvent, such as THF, is treated with 2 eq. of a strong base, such as lithium diisopropylamide in THF, at −78° C. to 0° C., and is then treated with an electrophile, such as methylchloroformate (ClCOOMe), at −780° to 0° C. A second electrophile, such as propyl iodide, is added and the resulting mixture heated to between 0° C. to 55° C. to give the compound of formula I-4 wherein, for example, $R_{10}$ is —O-benzyl, $R_3$ is propyl, $R_{i1}$ is methoxy and the other variables are as defined in the Summary above.

The compound of formula I-4 wherein, for example, $R_{10}$ is —O-benzyl, $R_3$ is propyl, $R_{i1}$ is methoxy and the other variables are as defined in the Summary above is hydrogenated to obtain the compound of formula I-4 wherein, for example, $R_{10}$ is hydroxy, $R_3$ is propyl, $R_{i1}$ is methoxy and the other variables are as defined in the Summary above, using ammonium formate($NH_4{}^+HCOO-$) in methanol and a palladium on carbon catalyst at refluxing temperatures. The compound of formula I-5, which is prepared below, wherein, for example, $R_{10}$ is —O-benzyl or —O-methyl, $R_3$ is propyl and the other variables are as defined in the Summary above, is treated with boron tribromide ($BBr_3$) in methylene chloride at −78° C. to room temperature to obtain the corresponding compound wherein $R_{10}$ is hydroxy. Likewise, the compound of formula I-6, which is prepared below, wherein, for example, $R_{10}$ is —O-benzyl, $R_3$ is propyl and the other variables are as defined above, is cleaved under similar conditions. A variety of other hydrogenating agents and conditions are known and available in the art, such as using $H_2$ on a palladium on carbon catalyst in methanol.

The compound of formula I-4 wherein, for example, $R_{10}$ is —O-benzyl, $R_3$ is propyl, $R_{11}$ is methoxy and the other variables are as defined in the Summary above, is reacted with a reducing agent, such as lithium aluminum hydride ($LiAlH_4$), in a solvent, such as THF, at 0° C. to refluxing temperatures to obtain the compound of formula I-5 wherein, for example, $R_{10}$ is —O-benzyl, $R_3$ is propyl and the other variables are as defined in the Summary above.

The compound of formula I-4 wherein, for example, $R_{10}$ is —O-benzyl, $R_3$ is propyl, $R_{i1}$ is methoxy and the other variables are as defined in the Summary above, is reacted with a reducing agent, such as lithium borohydride ($LiBH_4$), in a solvent, such as THF, at 0° C. to room temperature to obtain the compound of formula I-6 wherein, for example, $R_{10}$ is —O-benzyl, $R_3$ is propyl and the other variables are as defined in the Summary above. A variety of other esterifying conditions are known and available in the art.

The compound of formula I-7 (which is prepared by procedures described in Scheme A) is reacted with thallium trinitrite·$3H_2O$ in a solvent, such as methylene chloride to obtain the acid of formula I-8 wherein $Ri_2$ is H and wherein, for example, $R_1$—X— is benzyl and $R_{10}$ is $CH_3$—C(O)—O—, and wherein these variables are further defined in the Summary above.

The acid of formula I-8 wherein $R_{i2}$ is H and wherein, for example, $R_1$—X— is benzyl and $R_{10}$ is $CH_3$—C(O)—O—, and wherein these variables are further defined in the Summary above, is reacted with an alcohol, such as methanol, and catalytic acid, such as sulfuric acid, at 0° C. to reflux to obtain the ester of formula I-8 wherein $R_{i2}$ is methyl and wherein, for example, $R_1$—X— is benzyl and $R_{10}$ is hydroxy, and wherein these variables are further defined in the Summary above.

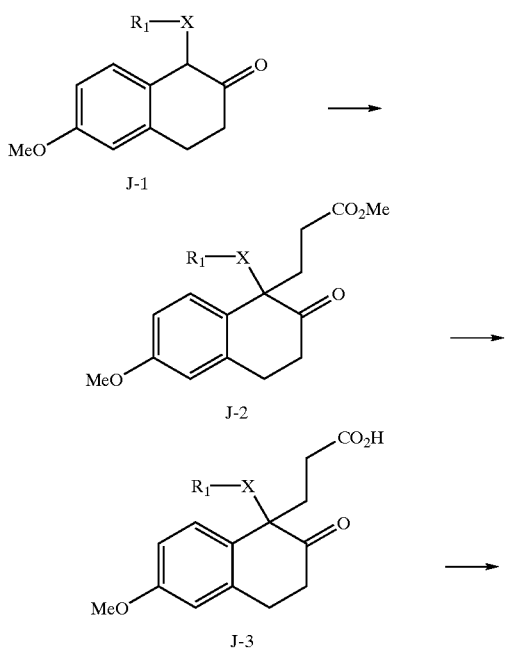

Scheme J

-continued

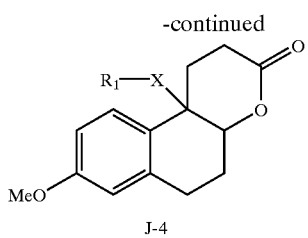
J-4

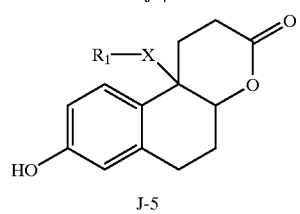
J-5

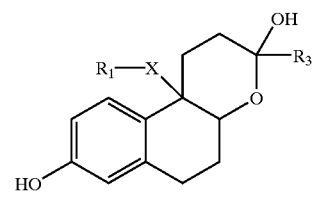
J-6

SCHEME J

The compound of formula J-1 wherein the variables correspond to those in the Summary above (see scheme A for its preparation) is reacted with a base such as sodium methoxide, in a protic solvent such as methanol, and methyl acrylate to give the compound of formula of J-2 wherein the variables correspond to those in the Summary above. Alternatively, the compound of formula of J-1 is prepared using the conditions described in Scheme A for the preparation of the compound of formula A-2 from the compound of formula A-1.

The compound of formula of J-2 wherein the variables correspond to those in the Summary above is reacted with a base such as sodium carbonate in a protic solvent or mixed solvents such as methanol/water at 90° C. to yield the compound of formula J-3 wherein the variables correspond to those in the Summary above. Alternatively, the compound of formula J-2 is hydrolyzed by the methods mentioned in *Protecting Groups in Organic Synthesis*, Second Edition, T. W. Greene and P. G. M. Wuts, John Wiley and Sons, Inc. (1991) to give the corresponding free acid of formula J-3 wherein the variables correspond with those in the Summary above.

The compound of formula J-3 wherein the variables correspond with those in the Summary above is reacted with a reducing agent, such as sodium borohydride in a protic solvent such as ethanol to give the compound of the formula J-4 wherein the variables are as defined in the Summary above. Alternatively, the compound of the formula J-4 is prepared from the compound of formula J-3 according to other F reducing methods described in *Modern Synthetic Reactions*, Chapters 2–3, pp. 45–227, Herbert O. House, ed., Academic Press, New York (1985).

The compound of formula J-5 wherein the variables are as defined in the Summary above is prepared from the compound of formula J-4 using $BBr_3$ or $BCl_3$ and tetrabutylammonium iodide or dimethylboron bromide in an aprotic solvent, such as dichloromethane or toluene, at −78° C. to room temperature.

The compound of formula J-6 is prepared from the compound of J-5 using the conditions described in Scheme H for the preparation of the compound of formula H-6 from the compound of formula H-1.

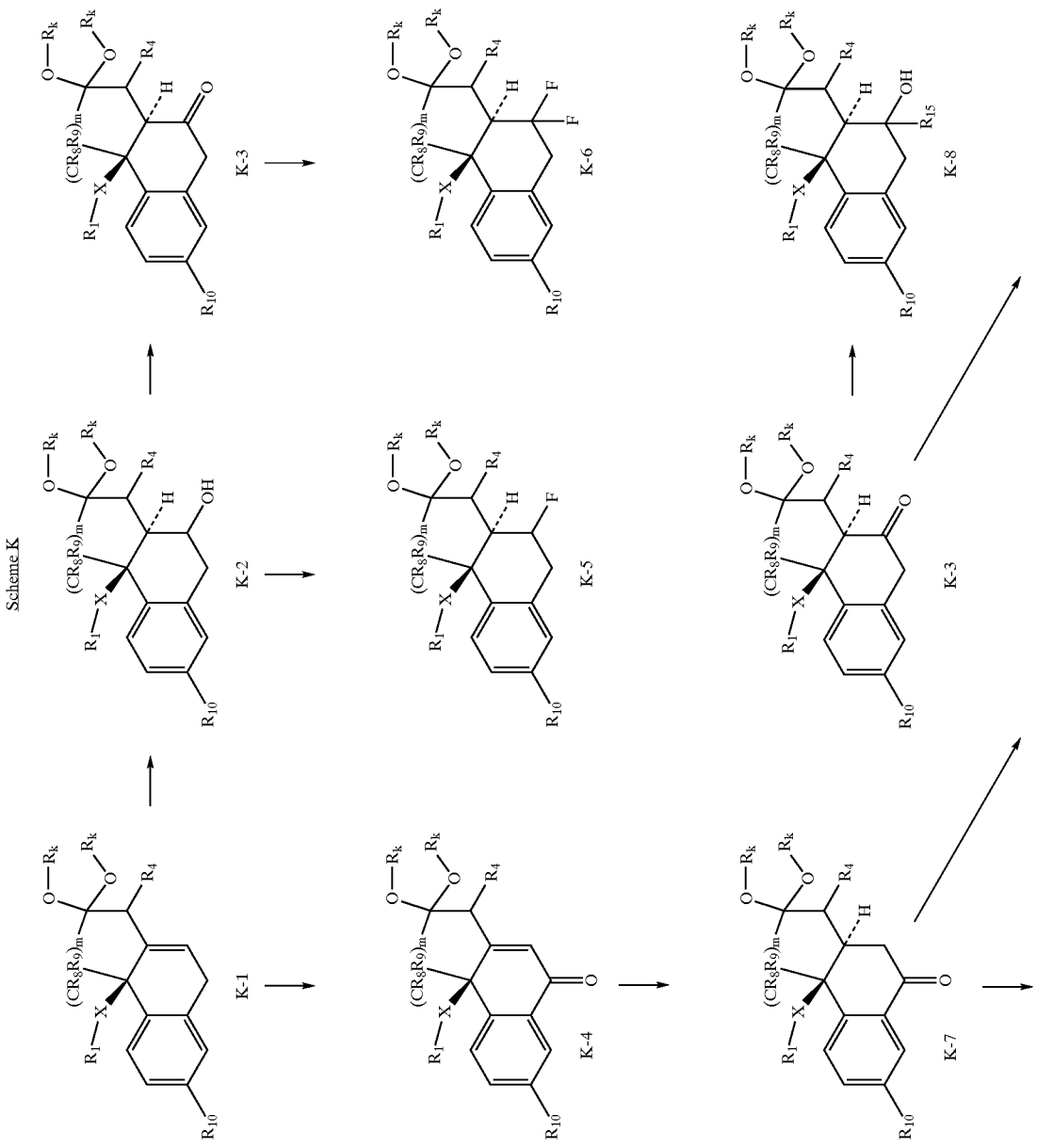

-continued
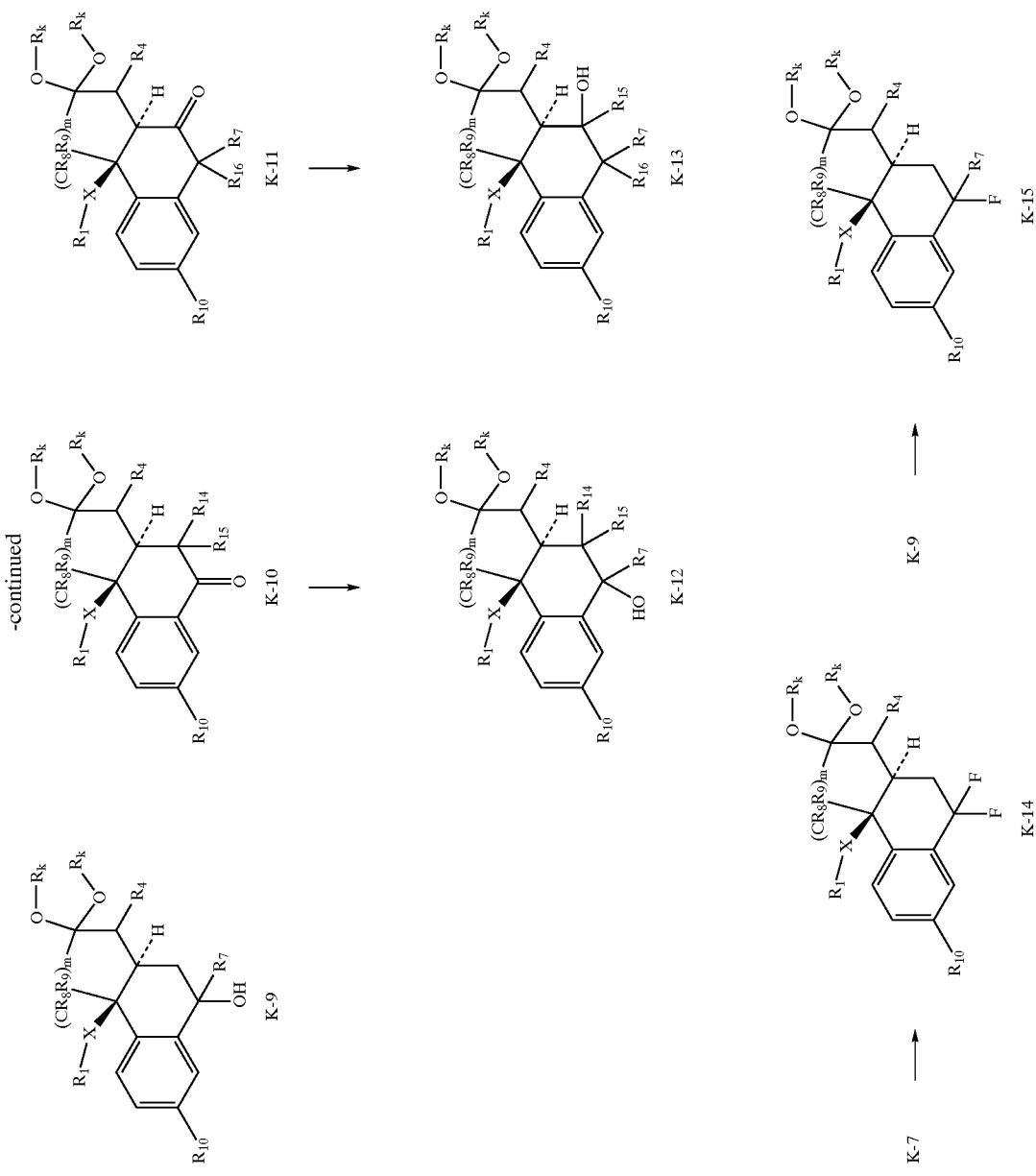

Scheme K

All compounds in this Scheme can serve as intermediates for Schemes A-3, B, C, F, G, or H.

The compound of formula K-1 (prepared as described in Scheme A-3), wherein $R_{10}$ is halogen, hydrogen, carboxylate, methyl ether, or benzyl ether or is as described in the Summary above, $R_k$ is, for example, lower alkyl or wherein $R_k$'s taken together are cyclic lower alkyl, and all other variables are as described in the Summary above, is treated with a hydroboration reagent, such as $BH_3$ in THF, in an aprotic solvent, such as THF or dioxane, from 0° C. to 60° C. and then treated with an oxidizing agent, such as hydrogen peroxide and aqueous sodium hydroxide, from 0° C. to 60° C. to give the compound of formula K-2. Alternatively, the compound of formula K-2 is prepared from the compound of formula K-1 by other methods known in the art, as exemplified in *Comprehensive Organic Transformations*, R. C. Larock, VCH Publishers Inc. (1989), pp. 497–498.

The compound of formula K-2, wherein $R_{10}$ is halogen, hydrogen, carboxylate, methyl ether, or benzyl ether or is as described in the Summary above, $R_K$ is, for example, lower alkyl or wherein $R_k$'s taken together are cyclic lower alkyl, and all other variables are as described in the Summary above, is treated with a fluorinating agent, such as diethylaminosulfur trifluoride (DAST), in an aprotic solvent, such as diglyme, from 0° C. to 60° C., depending on the nature of the solvent used, to give the compound in formula K-5. Alternatively, the compound of formula K-5 is prepared from the compound of formula K-2 by other halogenation methods known in the art, as exemplified in *Comprehensive Organic Transformations*, R. C. Larock, VCH Publishers Inc. (1989), pp. 353–363.

The compound of formula K-2, wherein $R_{10}$ is halogen, hydrogen, carboxylate, methyl ether, or benzyl ether or is as described in the Summary above, $R_k$ is, for example, lower alkyl or wherein $R_k$'s taken together are cyclic lower alkyl, and all other variables are as described in the Summary above, is treated with an oxidizing agent, such as (nPr)$_3$NRuO$_4$ and N-methylmorpholine-N-oxide, in a solvent, such as dichloromethane, from 0° C. to 60° C., depending on the nature of the solvent used, to give the compound in formula K-3. Alternatively, the compound of formula K-3 is prepared from the compound of formula K-2 by other oxidation methods known in the art, as exemplified in *Comprehensive Organic Transformations*, R. C. Larock, VCH Publishers Inc. (1989), pp. 604–614.

The compound of formula K-3, wherein $R_{10}$ is halogen, hydrogen, carboxylate, methyl ether, or benzyl ether or is as described in the Summary above, $R_k$ is, for example, lower alkyl or wherein $R_k$'s taken together are cyclic lower alkyl, and all other variables are as described in the Summary above, is treated with a fluorinating agent, such as diethylaminosulfur trifluoride (DAST), in an aprotic solvent, such as diglyme, from 0° C. to 60° C., depending on the nature of the solvent used, to give the compound in formula K-6. Alternatively, the compound of formula K-6 is prepared from the compound of formula K-3 by other halogenation methods known in the art, as exemplified in *Comprehensive Organic Transformations*, R. C. Larock, VCH Publishers Inc. (1989), pp. 353–363.

The compound of formula K-1, wherein $R_{10}$ is halogen, hydrogen, carboxylate, methyl ether, or benzyl ether or is as described in the Summary above, $R_k$ is, for example, lower alkyl or wherein $R_k$'s taken together are cyclic lower alkyl, and all other variables are as described in the Summary above, is treated with an oxidizing agent capable of allylic oxidation, such as selenium dioxide (SeO$_2$) and/or t-butyl hydrogen peroxide or chromium trioxide, in a solvent, such as dichloromethane, from 0° C. to 60° C., depending on the nature of the solvent used, to give the compound of formula K-4. Alternatively, the compound of formula K4 is prepared from the compound of formula K-2 by other oxidation methods known in the art, as exemplified in *Comprehensive Organic Transformations*, R. C. Larock, VCH Publishers Inc. (1989), pp. 592–593.

The compound of formula K-4, wherein $R_k$ is, for example, lower alkyl or wherein $R_k$'s taken together are cyclic lower alkyl, and the other variables are as described in the Summary above, is reduced using Pd(OH)$_2$ on carbon or other reagents, such as platinum oxide or rhodium on aluminum oxide (see P. N. Rylander in *Hydrogenation Methods*, Academic Press, New York, 1985; Herbert O. House in *Modern Synthetic Reactions*, Chapter 1, pp. 1–45; and John Fried and John A. Edwards in *Organic Reactions in Steroid Chemistry*, Chapter 3, pp. 111–145) under 15 to 1000 p.s.i (which is about 1 to about 133 atm) H$_2$ pressure in a solvent, such as toluene, t-butyl methyl ether, or ethanol, from 0° C. to 60° C., depending on the nature of the solvent used, to give the compound in formula K-7.

The compound of formula K-7, wherein $R_{10}$ is halogen, hydrogen, carboxylate, methyl ether, or benzyl ether or is as described in the Summary above, $R_k$ is, for example, lower alkyl or wherein $R_k$'s taken together are cyclic lower alkyl, and all other variables are as described in the Summary above, is treated with a reducing agent, such as sodium borohydride or lithium aluminum hydride, in a solvent, such as methanol or THF, from −78° C. to 60° C., depending on the nature of the reductant and/or solvent used, to give the compound in formula K-9, wherein $R_7$ is hydrogen. Alternatively, the compound of formula K-9 is prepared from the compound of formula K-4 by other reduction methods known in the art, as exemplified in *Comprehensive Organic Transformations*, R. C. Larock, VCH Publishers Inc. (1989), pp. 527–547. Alternatively, the compound of formula K-7, wherein $R_{10}$ is halogen, hydrogen, carboxylate, methyl ether, or benzyl ether or is as described in the Summary above, $R_k$ is, for example, lower alkyl or wherein $R_k$'s taken together are cyclic lower alkyl, and all other variables are as described in the Summary above, is treated with $R_7$-metal, such as $R_7$Li, $R_7$MgBr, or $R_7$MgCl, wherein $R_7$ is, for example, alkyl, in an aprotic solvent, such as THF or diethyl ether from −78° C. to 60° C., depending on the nature of $R_7$-metal and/or solvent used, to give the compound in formula K-9, wherein $R_7$ is, for example, alkyl.

The compound of formula K-3, wherein $R_{10}$ is halogen, hydrogen, carboxylate, methyl ether, or benzyl ether or is as described in the Summary above, $R_k$ is, for example, lower alkyl or wherein $R_k$'s taken together are cyclic lower alkyl, and all other variables are as described in the Summary above, is treated with a reducing agent, such as sodium borohydride or lithium aluminum hydride, in a solvent, such as methanol or THF, from −78° C. to 60° C., depending on the nature of the reductant and/or solvent used, to give the compound in formula K-8, wherein $R_{15}$ is hydrogen. Alternatively, the compound of formula K-8 is prepared from the compound of formula K-3 by other reduction methods known in the art, as exemplified in *Comprehensive Organic Transformations*, R. C. Larock, VCH Publishers Inc. (1989), pp. 527–547. Alternatively, the compound of formula K-3, wherein $R_{10}$ is halogen, hydrogen, carboxylate, methyl ether, or benzyl ether or is as described in the Summary above, $R_k$ is, for example, lower alkyl or wherein $R_k$'s taken together are cyclic lower alkyl, and all other variables are as described in the Summary above, is treated with $R_{15}$-metal, such as $R_{15}$Li, $R_{15}$MgBr, or $R_{15}$MgCl, wherein $R_{15}$ is, for example, alkyl, in an aprotic solvent, such as THF or diethyl ether from −78° C. to 60° C., depending on the nature of $R_{15}$-metal and/or solvent used, to give the compound in formula K-8, wherein $R_{15}$ is, for example, alkyl.

The compound of formula K-7, wherein $R_{10}$ is halogen, hydrogen, carboxylate, methyl ether, or benzyl ether or is as described in the Summary above, $R_k$ is, for example, lower alkyl or wherein $R_k$'s taken together are lower alkyl, and all other variables are as described in the Summary above, is converted to its anion with a base, such as sodium hydride, sodium methoxide, or lithium diisopropylamide, in a solvent, such as THF or DMF from −78° C. to 60° C., depending on the nature of the base and solvent used. The reaction mixture is treated with an alkylating agent of formula $R_{14}$-X, wherein $R_{14}$ is, for example, alkyl and X is a leaving group (see Francis A. Carey, in *Advanced Organic Chemistry*, Part A, Chapter 5.6 for examples) to give the compound of formula K-10, wherein $R_{14}$ and $R_{15}$ are, for example, alkyl or hydrogen or mixtures thereof.

The compound of formula K-3, wherein $R_{10}$ is halogen, hydrogen, carboxylate, methyl ether, or benzyl ether or is as described in the Summary above, $R_k$ is, for example, lower alkyl or wherein $R_k$'s taken together are cyclic lower alkyl, and all other variables are as described in the Summary above, is converted to its anion with a base, such as sodium hydride, sodium methoxide, or lithium diisopropylamide, in a solvent, such as THF or DMF from −78° C. to 60° C., depending on the nature of the base and solvent used. The reaction mixture is treated with an alkylating agent of formula $R_7$-X, wherein $R_7$ is, for example, alkyl and X is a leaving group (see Francis A. Carey, in *Advanced Organic Chemistry*, Part A, Chapter 5.6 for examples) to give the compound of formula K-11, wherein $R_7$ and $R_{16}$ are, for example, alkyl or hydrogen or mixtures thereof.

The compound of formula K-10, wherein $R_{10}$ is halogen, hydrogen, carboxylate, methyl ether, or benzyl ether or is as described in the Summary above, $R_k$ is, for example, lower alkyl or wherein $R_k$'s taken together are cyclic lower alkyl, and all other variables are as described in the Summary above, is treated with a reducing agent, such as sodium borohydride or lithium aluminum hydride, in a solvent, such as methanol or THF, from −78° C. to 60° C., depending on the nature of the reductant and/or solvent used, to give the compound of formula K-12, wherein $R_7$ is hydrogen. Alternatively, the compound of formula K-12 is prepared from the compound of formula K-10 by other reduction methods known in the art, as exemplified in *Comprehensive Organic Transformations*, R. C. Larock, VCH Publishers Inc. (1989), pp. 527–547. Alternatively, the compound of formula K-10, wherein $R_{10}$ is halogen, hydrogen, carboxylate, methyl ether, or benzyl ether or is as described in the Summary above, $R_k$ is, for example, lower alkyl or wherein $R_k$'s taken together are cyclic lower alkyl, and all other variables are as described in the Summary above, is treated with $R_7$-metal, such as $R_7$Li, $R_7$MgBr, or $R_7$MgCl, wherein $R_7$ is, for example, alkyl, in an aprotic solvent, such as THF or diethyl ether from −78° C. to 60° C., depending on the nature of $R_7$-metal and/or solvent used, to give the compound of formula K-12, wherein $R_7$ is, for example, alkyl.

The compound of formula K-11, wherein $R_{10}$ is halogen, hydrogen, carboxylate, methyl ether, or benzyl ether or is as described in the Summary above, $R_k$ is, for example, lower alkyl or wherein $R_k$'s taken together are cyclic lower alkyl, and all other variables are as described in the Summary above, is treated with a reducing agent, such as sodium borohydride or lithium aluminum hydride, in a solvent, such as methanol or THF, from −78° C. to 60° C., depending on the nature of the reductant and/or solvent used, to give the compound of formula K-13, wherein $R_{15}$ is hydrogen. Alternatively, the compound of formula K-13 is prepared from the compound of formula K-11 by other reduction methods known in the art, as exemplified in *Comprehensive Organic Transformations*, R. C. Larock, VCH Publishers Inc. (1989), pp. 527–547. Alternatively, the compound of formula K-11, wherein $R_{10}$ is halogen, hydrogen, carboxylate, methyl ether, or benzyl ether or is as described in the Summary above, $R_k$ is, for example, lower alkyl or wherein $R_k$'s taken together are cyclic lower alkyl, and all other variables are as described in the Summary above, is treated with $R_{15}$-metal, such as $R_{15}$Li, $R_{15}$MgBr, or $R_{15}$MgCl, wherein $R_{15}$ is, for example, alkyl, in an aprotic solvent, such as THF or diethyl ether from −78° C. to 60° C., depending on the nature of $R_{15}$-metal and/or solvent used, to give the compound of formula K-13, wherein $R_{15}$ is, for example, alkyl.

The compound of formula K-7, wherein $R_{10}$ is halogen, hydrogen, carboxylate, methyl ether, or benzyl ether or is as described in the Summary above, $R_k$ is, for example, lower alkyl or wherein $R_k$'s taken together are cyclic lower alkyl, and all other variables are as described in the Summary above, is treated with a fluorinating agent, such as diethylaminosulfur trifluoride (DAST), in an aprotic solvent, such as diglyme, from 0° C. to 60° C., depending on the nature of the solvent used, to give the compound in formula K-14. Alternatively, the compound of formula K-14 is prepared from the compound of formula K-7 by other halogenation methods known in the art, as exemplified in *Comprehensive Organic Transformations*, R. C. Larock, VCH Publishers Inc. (1989), pp. 353–363.

The compound of formula K-9, wherein $R_{10}$ is halogen, hydrogen, carboxylate, methyl ether, or benzyl ether or is as described in the Summary above, $R_k$ is, for example, lower alkyl or wherein $R_k$'s taken together are cyclic lower alkyl, and all other variables are as described in the Summary above, is treated with a fluorinating agent, such as diethylaminosulfur trifluoride (DAST), in an aprotic solvent, such as diglyme, from 0° C. to 60° C., depending on the nature of the solvent used, to give the compound in formula K-15. Alternatively, the compound of formula K-15 is prepared from the compound of formula K-9 by other halogenation methods known in the art, as exemplified in *Comprehensive Organic Transformations*, R. C. Larock, VCH Publishers Inc. (1989), pp. 353–363.

Some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds and of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples below, by substituting a readily available isotopically labelled reagent for a non-isotopically labelled reagent.

Any of the compounds and prodrugs of the present invention can be synthesized as pharmaceutically acceptable salts for incorporation into various pharmaceutical compositions. As used herein, pharmaceutically acceptable salts include, but are not limited to, hydrochloric, hydrobromic, hydroiodic, hydrofluoric, sulfuric, sulfonic, citric, camphoric, maleic, acetic, lactic, nicotinic, nitric, succinic, phosphoric, malonic, malic, salicyclic, phenylacetic, stearic, palmitic, pyridine, ammonium, piperazine, diethylamine, nicotinamide, formic, fumaric, urea, sodium, potassium, calcium, magnesium, zinc, lithium, cinnamic, methylamino, methanesulfonic, picric, p-toluenesulfonic, naphthalenesulfonic, tartaric, triethylamino, dimethylamino, and tris(hydroxymethyl)aminomethane. Additional pharmaceutically acceptable salts would be apparent to one of ordinary skill in the art. Where more than one basic moiety exists, the expression includes multiple salts (e.g., di-salt).

Some of the compounds of this invention are acidic and they form a salt with a pharmaceutically acceptable cation. Some of the compounds of this invention are basic and they form a salt with a pharmaceutically acceptable anion. All such salts, including di-salts, are within the scope of this invention and they can be prepared by conventional methods. They can be prepared simply by contacting the acidic and basic entities, in either an aqueous, non-aqueous or partially aqueous medium. For example, the mesylate salt is prepared by reacting the free base form of the compound of Formula I with methanesulfonic acid under standard conditions. Likewise, the hydrochloride salt is prepared by reacting the free base form of the compound of Formula I with hydrochloric acid under standard conditions. The salts are recovered either by filtration, by precipitation with a non-solvent followed by filtration, by evaporation of the solvent, or, in the case of aqueous solutions, by lyophilization, as appropriate.

In addition, when the compounds and prodrugs of the present invention form hydrates or solvates, they are also within the scope of the present invention.

The compounds and prodrugs of the present invention also includes racemates, stereoisomers and mixtures of these compounds, including isotopically-labeled and radiolabeled compounds. Such isomers can be isolated by standard resolution techniques, including fractional crystallization and chiral column chromatography.

For instance, the compounds of the present invention have asymmetric carbon atoms and are therefore enantiomers or diastereomers. Diasteromeric mixtures can be separated into their individual diastereomers on the basis of their physical/chemical differences by methods known in the art, for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered as part of this invention.

The following configurations of the compounds of the present invention (as represented by simplified structures) are preferred, with the first configuration being more preferred:

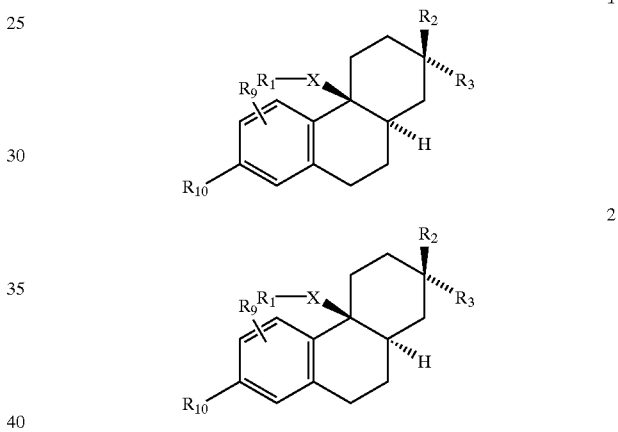

Also, the compounds and prodrugs of the present invention can exist in several tautomeric forms, including the enol form, the keto form and mixtures thereof. All such tautomeric forms are included within the scope of the present invention.

The GR agonists, partial agonists and antagonists of the present invention can be used to influence the basic, life sustaining systems of the body, including carbohydrate, protein and lipid metabolism, electrolyte and water balance, and the functions of the cardiovascular, kidney, central nervous, immune, skeletal muscle and other organ and tissue systems. In this regard, GR modulators are used for the treatment of diseases associated with an excess or a deficiency of glucocorticoids in the body. As such, they may be used to treat the following: obesity, diabetes, cardiovascular disease, hypertension, Syndrome X, depression, anxiety, glaucoma, human immunodeficiency virus (HIV) or acquired immunodeficiency syndrome (AIDS), neurodegeneration (for example, Alzheimer's and Parkinson's), cognition enhancement, Cushing's Syndrome, Addison's Disease, osteoporosis, frailty, inflammatory diseases (such as osteoarthritis, rheumatoid arthritis, asthma and rhinitis), tests of adrenal function, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism and prevention of muscle frailty.

The compounds of the present invention, isomers, prodrugs and pharmaceutically acceptable salts thereof are useful to induce weight loss in mammals needing or desiring to lose weight. While not intending to limit the present invention to a specific mechanism of action, the compounds of the present invention, isomers, prodrugs and salts thereof are able to induce weight loss by a variety of mechanisms, such as appetite suppression, decreasing food intake, and stimulation of the metabolic rate in peripheral tissue, thereby increasing energy expenditure. In addition, the compounds of the present invention, isomers, prodrugs and salts thereof are useful to induce a more favorable partitioning of nutrients from fat to muscle tissue in mammals. Thus, while not necessarily resulting in weight loss, this increase in muscle mass may be useful in preventing or treating diseases, such as obesity and frailty.

In addition, the compounds of the present invention, isomers, prodrugs and pharmaceutically acceptable salts thereof may also be useful to increase lean meat deposition, improve lean meat to fat ratio, and trim unwanted fat from non-human animals, as described further below.

It will be understood by those skilled in the art that while the compounds, isomers, prodrugs and pharmaceutically acceptable salts thereof of the present invention will typically be employed as selective agonists, partial agonists or antagonists, there may be instances where a compound with a mixed steroid receptor profile is preferred.

Furthermore, it will be understood by those skilled in the art that the compounds, isomers, prodrugs and pharmaceutically acceptable salts thereof of the present invention, including pharmaceutical compositions and formulations containing these compounds, isomers, prodrugs and salts can be used in a wide variety of combination therapies to treat the conditions and diseases described above. Thus, the compounds, isomers, prodrugs and pharmaceutically acceptable salts thereof of the present invention can be used in conjunction with other pharmaceutical agents for the treatment of the disease/conditions described herein. For example, they may be used in combination with pharmaceutical agents that treat obesity, diabetes, inflammatory disease, immunodefficiency, hypertension, cardiovascular disease, viral infection, HIV, Alzheimers's disease, Parkinson's disease, anxiety, depression, or psychosis. In combination therapy treatment, both the compounds, isomers, prodrugs and pharmaceutically acceptable salts thereof of this invention and the other drug therapies are administered to mammals (e.g., humans, male or female) by conventional methods.

For instance, glucocorticoid receptor agonists are efficacious agents for the treatment of various inflammatory diseases; however, treatment is often accompanied by undesirable side effects. These side effects include, but are not limited to, the following examples: metabolic effects, weight gain, muscle wasting, decalcification of the skeleton, osteoporosis, thinning of the skin and thinning of the skeleton. However, according to the present invention, glucocorticoid receptor modulators may be used in combination with glucocorticoid receptor agonists to block some of these side effects, without inhibiting the efficacy of the treatment. Thus, any glucocorticoid receptor agonist may be used as the second compound in the combination aspect of the present invention. This combination includes the treatment of various inflammatory diseases, such as arthritis (osteo and rheumatiod), asthma, rhinitis, or immunomodulation.

Examples of glucocorticoid receptor modulators include those known in the art (many of which are described above) as well as the novel compounds of formula I of the present invention. More particularly, examples of glucocorticoid receptor modulators known in the art include, but are not limited to, certain nonsteroidal compounds, such as 5H-chromeno[3,4-f]quinolines, which are selective modulators of steroid receptors, as disclosed in U.S. Pat. No. 5,696,127; and certain steroid compounds substituted at position 10, which possess antiglucocorticoid activity, and some of which have glucocorticoid activity, as disclosed in Published European Patent Application 0 188 396, published Jul. 23, 1986. Examples of glucocorticoid receptor agonists include those known in the art, such as prednisone (17,21-dihydroxypregnane-1,4-diene-3,11,20-trione), prednylidene ((11$\beta$)-11,17,21-trihydroxy-16-methylenepregna-1,4-diene-3, 20-dione), prednisolone ((11$\beta$)-11,17,21-trihydroxypregna-1,4-diene-3, 20-dione), cortisone (17$\alpha$, 21-dihydroxy-4-pregnene-3,11,20-trione), dexamethasone ((11$\beta$, 16$\alpha$)-9-fluoro-11, 17,21-trihydroxy-16-methylpregna-1,4-diene-3,20-dione), and hydrocortisone (11$\beta$, 17$\alpha$,21-trihydroxypregn-4-ene-3, 20-dione). These compounds, which are glucocorticoid receptor agonists, will generally be administered in the form of a dosage unit at a therapeutically effective amount of such compound. For example, prednisone or an equivalent drug may be administered from about 5 to about 80 mg, depending on the condition; hydrocortisone may be administered from about 100 to about 400 mg, depending on the condition; and dexamethasone may be administered from about 4 to about 16 mg, depending on the condition. These doses are typically administered once to twice daily, and for maintenance purposes, sometimes on alternate days.

For the treatment of Alzheimer's disease, any cholinomimetic drug, such as donepizil, may be used as the second compound in the combination aspect of this invention.

For the treatment of Parkinson's disease, any anti-Parkinson's drug, such as L-dopa, bromocriptine, or selegiline, may be used as the second compound in the combination aspect of this invention.

For the treatment of anxiety, any antianxiolytic drug, such as benzodiazepine, valium, or librium, may be used as the second compound in the combination aspect of this invention.

For the treatment of depression, any tricyclic antidepressant such as, desipramine, or any selective serotonin reuptake inhibitor (SSRI's), such as sertraline hydrochloride and fluoxetine hydrochloride, may be used as the second compound in the combination aspect of this invention.

For the treatment of psychosis, any typical or atypical antipsychotic drug, such as haloperidol or clozapine may be used as the second compound in the combination aspect of this invention.

Any aldose reductase inhibitor may be used as the second compound in the combination aspect of this invention. The term aldose reductase inhibitor refers to a compound which inhibits the bioconversion of glucose to sorbitol catalyzed by the enzyme aldose reductase. Such inhibition is readily determined by those skilled in the art according to standard assays (J. Malone, Diabetes, 29:861–864, 1980, "Red Cell Sorbitol, an Indicator of Diabetic Control"). A variety of aldose reductase inhibitors are described and referenced below; however other aldose reductase inhibitors will be known to those skilled in the art. Examples of aldose reductase inhibitors useful in the compositions and methods of this invention include, for example, zopolrestat, and other such compounds as disclosed and described in PCT/IB99/00206, filed Feb. 5, 1999 (the disclosure of which is hereby incorporated by reference), and assigned to the assignee hereof.

Any glycogen phosphorylase inhibitor may be used as the second compound in the combination aspect of this invention. The term glycogen phosphorylase inhibitor refers to any substance or agent or any combination of substances and/or agents which reduces, retards or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis). Such actions are readily determined by those skilled in the art according to standard assays (e.g., as described in PCT/IB99/00206, filed Feb. 5, 1999). A variety of these compounds are described in the following published international patent applications: WO 96/39384, published Dec. 12, 1996, and WO 96/39385, published Dec. 12, 1996; and in the following filed international patent application: PCT/IB99/00206, filed Feb. 5, 1999; the disclosures of all of these applications are hereby incorporated by reference herein.

Any sorbitol dehydrogenase inhibitor may be used as the second compound in the combination aspect of this invention. The term sorbitol dehydrogenase inhibitor refers to a compound which inhibits the enzyme sorbitol dehydrogenase, which catalyzes the oxidation of sorbitol to fructose. Such inhibition is readily determined by those skilled in the art according to standard assays (as described in U.S. Pat. No. 5,728,704 and references cited therein). A variety of these compounds are described and referenced below; however other sorbitol dehydrogenase inhibitors will be known to those skilled in the art. U.S. Pat. No. 5,728,704 (the disclosure of which is hereby incorporated by reference) discloses substituted pyrimidines which inhibit sorbitol dehydrogenase, lower fructose levels, and/or treat or prevent diabetic complications, such as diabetic neuropathy, diabetic retinopathy, diabetic nephropathy, diabetic microangiopathy and diabetic macroangiopathy.

Any known, commercially marketed antidiabetic compound may be used as the second compound in the combination aspect of this invention. A variety of such compounds are described and referenced below; however other such compounds will be known to those skilled in the art. Examples of such compounds useful in the compositions and methods of this invention include, for example, insulin, metformin, troglitazone (REZULIN®) and sulfonylureas, such as glipizide (GLUCOTROL®), glyburide (GLYNASE®, MICRONASE®) and chlorpropamide (DIABINASE®).

Any β-adrenergic agonist may be used as the second compound in the combination aspect of this invention. β-Adrenergic agents have been categorized into $\beta_1$, $\beta_2$, and $\beta_3$ subtypes. Agonists of β-receptors promote the activation of adenyl cyclase. Activation of $\beta_1$ receptors invokes increases in heart rate. Activation of $\beta_2$ receptors induces relaxation of smooth muscle tissue which produces a drop in blood pressure and the onset of skeletal muscle tremors. Activation of $\beta_3$ receptors is known to stimulate lipolysis, which is the breakdown of adipose tissue triglycerides to glycerol and fatty acids. Activation of $\beta_3$ receptors also stimulates the metabolic rate, thereby increasing energy expenditure. Accordingly, activation of $\beta_3$ receptors promotes the loss of fat mass. Compounds that stimulate β receptors are therefore useful as anti-obesity agents. Compounds which are $\beta_3$-receptors agonists have hypoglycemic and/or anti-diabetic activity. Such activity is readily determined by those skilled in the art according to standard assays (International Patent Application, Publication No. WO 96/35671). Several compounds are described and referenced below; however, other β-adrenergic agonists will be known to those skilled in the art. International Patent Application, Publication No. WO 96/35671 (the disclosure of which is incorporated herein by reference) discloses compounds, such as substituted aminopyridines, which are β-adrenergic agonists. International Patent Application, Publication No. 93/16189 (the disclosure of which is incorporated herein by reference) discloses the use of selective $\beta_3$ receptor agonists in combination with compounds which modify eating behavior for the treatment of obestiy.

Any thyromimetic antiobesity agent may be used as the second compound in the combination aspect of this invention. These compounds are tissue selective thyroid hormone agonists. These compounds are able to induce weight loss by mechanisms other than appetite suppression, e.g., through stimulation of the metabolic rate in peripheral tissue, which, in turn, produces weight loss. Such metabolic effect is readily measured by those skilled in the art according to standard assays. A variety of these compounds are described and referenced below; however other thyromimetic antiobesity agents will be known to those skilled in the art. It is well known to one of ordinary skill in the art that selectivity of thermogenic effect is an important requirement for a useful therapeutic agent in the treatment of, for example, obesity and related conditions.

Any eating behavior modifying compound may be used as the second compound of this invention. Compounds which modify eating behavior include anorectic agents, which are compounds which diminish the appetite. Such classes of anorectic agents are well known to one of ordinary skill in the art. A variety of these compounds are described in and referenced below; however, other anorectic agents will be known to those skilled in the art. Also, the following are antiobesity agents: phenylpropanolamine, ephedrine, pseudoephedrine, phentermine, a Neuropeptide Y (hereinafter also referred to as "NPY") antagonist, a cholecystokinin-A (hereinafter referred to as CCK-A) agonist, a monoamine reuptake inhibitor (such as sibutramine), a sympathomimetic agent, a serotoninergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a galanin antagonist or a Gl lipase inhibitor or decreaser (such as orlistat). Other antiobesity agents include phosphatase 1B inhibitors, bombesin agonists, dehydroepiandrosterone or analogs thereof, glucocorticoid receptor modulators, orexin receptor antagonists, urocortin binding protein antagonists or glucagon-like peptide-1 (insulinotropin) agonists. A particularly preferred monoamine reuptake inhibitor is sibutramine, which can be prepared as disclosed in U.S. Pat. No. 4,929,629, the disclosure of which is incorporated herein by reference. Preferred serotoninergic agents include fenfluramine and dexfenfluramine, which can be prepared as disclosed in U.S. Pat. No. 3,198,834, the disclosure of which is incorporated herein by reference. A particularly preferred dopamine agonist is bromocriptine, which can be prepared as disclosed in U.S. Pat. Nos. 3,752,814 and 3,752,888, the disclosures of which are incorporated herein by reference. Another preferred anorectic agent is phentermine, which can be prepared as disclosed in U.S. Pat. No. 2,408,345, the disclosure of which is incorporated herein by reference.

Any NPY receptor antagonist may be used as the second component in the combination aspect of this invention. The term NPY receptor antagonist refers to compounds which interact with NPY receptors and inhibit the activity of neuropeptide Y at those receptors and thus are useful in treating disorders associated with neuropeptide Y, such as feeding disorders, including obesity. Such inhibition is readily determined by those skilled in the art according to standard assays (such as those described in International Patent Application, Publication No. WO 99/07703). In addition, the compounds described and referenced below are NPY receptor antagonists; however, other NPY receptor antagonists will also be known to those skilled in the art. International Patent Application, Publication No. WO 99/07703 (the disclosure of which is hereby incorporated by reference) discloses certain 4-aminopyrrole (3,2-d) pyrimidines as neuropeptide Y receptor antagonists. International patent application, Publication No. WO 96/14307, published May 17, 1996; International patent application, Publication No. WO 96/40660, published Dec. 19, 1996; International patent application, Publication No. WO 98/03492; International patent application, Publication No. WO 98/03494; International patent application, Publication No. WO 98/03493; International patent application, Publication No. WO 96/14307, published May 17, 1996; International patent application, Publication No. WO 96/40660, published Dec. 19, 1996; (the disclosures of which are hereby incorporated by reference) disclose additional compounds, such as substituted benzylamine derivatives, which are useful as neuropeptide Y specific ligands.

In combination therapy treatment, both the compounds of this invention and the other drug therapies are administered to mammals (e.g., humans, male or female) by conventional methods. As recognized by those skilled in the art, the therapeutically effective amounts of the compounds of this invention and the other drug therapies to be administered to a patient in combination therapy treatment will depend upon a number of factors, including, without limitation, the biological activity desired, the condition of the patient, and tolerance for the drug.

For example, the second compound of this invention, when administered to a mammal, is dosed at a range between about 0.01 to about 50 mg/kg/day body weight, preferably about 0.1 mg/kg/day to about 10 mg/kg/day body weight, administered singly or as a divided dose. Particularly, when the second compound of this invention is (1) sibutramine, the dosage of sibutramine is about 0.01 mg/kg/day to about 30 mg/kg/day body weight, preferably about 0.1 mg/kg/day to about 1 mg/kg/day body weight; (2) dexfenfluramine, the dosage of dexfenfluramine is about 0.01 mg/kg/day to about 30 mg/kg/day body weight, preferably about 0.1 mg/kg/day to about 1 mg/kg/day body weight; (3) bromocriptine, the dosage of bromocriptine is about 0.01 to about 10 mg/kg/day body weight, preferably 0.1 mg/kg/day to about 10 mg/kg/day body weight; (4) phentermine, the dosage of phentermine is about 0.01 mg/kg/day to about 10 mg/kg/day, preferably about 0.1 mg/kg/day to about 1 mg/kg/day body weight. Also, for example, as noted above, an amount of an aldose reductase inhibitor that is effective for the activities of this invention may be used as the second compound of this invention. Typically, an effective dosage for aldose reductase inhibitors for this invention is in the range of about 0.1 mg/kg/day to about 100 mg/kg/day in single or divided doses, preferably about 0.1 mg/kg/day to about 20 mg/kg/day in single or divided doses.

As noted above, the compounds, isomers, prodrugs and pharmaceutically acceptable salts of the present invention can be combined in a mixture with a pharmaceutically acceptable carrier, vehicle or diluent to provide pharmaceutical compositions useful for treating the biological conditions or disorders noted herein in mammalian, and more preferably, in human, patients. The particular carrier, vehicle or diluent employed in these pharmaceutical compositions may take a wide variety of forms depending upon the type of administration desired, for example, intravenous, oral, topical, suppository or parenteral. Also, the compounds, isomers, prodrugs and salts thereof of this invention can be administered individually or together in any conventional dosage form, such as an oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tableftting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds, prodrugs and pharmaceutically acceptable salts thereof of this invention can be combined with various sweetening agents, flavoring agents, coloring agents, emulsifying agents and/or suspending agents, as well as such diluents as water, ethanol, propylene glycol, glycerin and various like combinations thereof.

Due to their ease of administration, tablets and capsules represent the most advantageous oral dosage form for the pharmaceutical compositions of the present invention.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

For topical administration, the compounds of the present invention may be formulated using bland, moisturizing bases, such as ointments or creams. Examples of suitable ointment bases are petrolatum, petrolatum plus volatile silicones, lanolin, and water in oil emulsions.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 15th Edition (1975).

The pharmaceutical compositions and compounds, isomers, prodrugs and pharmaceutically acceptable salts thereof of the present invention will generally be administered in the form of a dosage unit (e.g., tablet, capsule, etc.) at a therapeutically effective amount of such compound, prodrug or salt thereof from about 0.1 µg/kg of body weight to about 500 mg/kg of body weight, more particularly from about 1 µg/kg to about 250 mg/kg, and most particularly from about 2 µg/kg to about 100 mg/kg. More preferably, a compound of the present invention will be administered at an amount of about 0.1 mg/kg to about 500 mg/kg of body weight, and most preferably from about 0.1 mg/kg to about 50 mg/kg of body weight. As recognized by those skilled in the art, the particular quantity of pharmaceutical composition according to the present invention administered to a patient will depend upon a number of factors, including, without limitation, the biological activity desired, the condition of the patient, and tolerance for the drug.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of formula I, an isomer thereof, a prodrug thereof or a salt of such compound, isomer or prodrug and a second compound as described above. The kit comprises a container, such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of formula I compound (or an isomer, prodrug or pharmaceutically acceptable salt thereof) can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The following paragraphs describe exemplary formulations, dosages etc. useful for non-human animals. The administration of compounds of this invention can be effected orally or non-orally, for example by injection. An amount of a compound of formula I, an isomer, prodrug or pharmaceutically acceptable salt thereof, is administered such that a therapeutically effective dose is received, generally a daily dose which, when administered orally to an animal is usually between 0.01 and 500 mg/kg of body weight, preferably between 0.1 and 50 mg/kg of body weight. Conveniently, the medication can be carried in the drinking water so that a therapeutic dosage of the agent is ingested with the daily water supply. The agent can be directly metered into drinking water, preferably in the form of a liquid, water-soluble concentrate (such as an aqueous solution of a water soluble salt). Conveniently, the active ingredient can also be added directly to the feed, as such, or in the form of an animal feed supplement, also referred to as a premix or concentrate. A premix or concentrate of therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound according to the invention. The mixtures are thoroughly blended by standard procedures, such as in a twin shell blender, to ensure homogeneity.

If the supplement is used as a top dressing for the feed, it likewise helps to ensure uniformity of distribution of the active material across the top of the dressed feed.

The present invention has several advantagous veterinary features. For the pet owner or veterinarian who wishes to increase leanness and trim unwanted fat from pet animals, the present invention provides the means by which this can be accomplished. For poultry and swine raisers, using the method of the present invention yields leaner animals which command higher prices from the meat industry.

Drinking water and feed effective for increasing lean meat deposition and for improving lean meat to fat ratio are generally prepared by mixing a compound of the invention with a sufficient amount of animal feed to provide from about $10^{-3}$ to 500 ppm of the compound in the feed or water.

The preferred medicated swine, cattle, sheep and goat feed generally contain from 1 to 400 grams of active ingredient per ton of feed, the optimum amount for these animals usually being about 50 to 300 grams per ton of feed.

The preferred feed of domestic pets, such as cats and dogs, usually contain about 1 to 400 grams and preferably 10 to 400 grams of active ingredient per ton of feed.

For parenteral administration in animals, the compounds of the present invention may be prepared in the form of a paste or a pellet and administered as an implant, usually under the skin of the head or ear of the animal in which increase in lean meat deposition and improvement in lean mean to fat ratio is sought.

In general, parenteral administration involves injection of a sufficient amount of a compound of the present invention to provide the animal with 0.01 to 500 mg/kg/day of body weight of the active ingredient. The preferred dosage for poultry, swine, cattle, sheep, goats and domestic pets is in the range of from 0.1 to 50 mg/kg/day of body weight of active ingredient.

Paste formulations can be prepared by dispersing the active compound in a pharmaceutically acceptable oil such as peanut oil, sesame oil, corn oil or the like.

Pellets containing an effective amount of a compound of the present invention can be prepared by admixing a compound of the present invention with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body.

The activity of the compounds of the present invention are demonstrated by one or more of the assays described below:

The following is a description of an assay for the identification of glucocorticoid receptor antagonists/agonists: HeLa cells containing endogenous human glucocorticoid receptors are transfected with a 3xGRE-luciferase plasmid generated by standard procedures and a plasmid conferring neomycin resistance. Novel glucocorticoid responsive cell lines are generated and characterized. One such cell line designated HeLa-GRE9 is used for determining the activity of compounds at the glucocorticoid receptor. Cells are maintained in charcoal-stripped serum and transferred to 96-well microtiter plates one day prior to treatment with various concentrations ($10^{-12}$ to $10^{-5}$) of test compounds in the absence and presence of known glucocorticoid receptor agonists (i.e., dexamethasone, hydrocortisone) for up to 24 hours. Treatments are performed in triplicate. Cell lysates are prepared and luciferase activity is determined using a luminometer. Agonist activity is assessed by comparing the luciferase activity from cells treated with test compound to cells treated with the agonist dexamethasone. Antagonist activity is assessed by comparing the luciferase activity of an $EC_{50}$ concentration of dexamethasone in the absence and presence of test compound. The $EC_{50}$ (concentration that produced 50% of the maximal response) for dexamethasone is calculated from dose response curves.

The following is a description of an assay for determining the competitive inhibition binding of the Human Type II Glucocorticoid receptor expressed in Sf9 cells:

Binding protocol: Compounds are tested in a binding displacement assay using human glucocorticoid receptor expressed in Sf9 cells with $^3$H-dexamethasone as the ligand. Human glucorticoid receptor is expressed in Sf9 cells as described in Mol. Endocrinology 4:209, 1990. Pellets containing Sf9 cells expressing the human GR receptor from 1L vats are lysed with 40 ul of 20 mM AEBSF stock (Calbiochem, LaJolla, Calif.) containing 50 mg/ml leupeptin and 40 ml of homogenization buffer is added. The assay is carried out in 96-well polypropylene plates in a final volume of 130 ul containing 200 ug Sf9 lysate protein, 6.9 nM $^3$H-dexamethasone (Amersham, Arlington Heights, Ill.) in presence of test compounds, test compound vehicle (for total counts) or excess dexamethasone (7 uM non-radioactive, to determine non-specific binding) in an appropriate volume of assay buffer. All compounds are tested at 6 concentrations in duplicate (concentration range 0.1–30 nM or 3–1000 nM). Test compounds are diluted from a 25 mM stock in 100% DMSO with 70%EtOH and added in a volume of 2 $\mu$l. Once all additions are made the plates are shaken, sealed with sealing tape and incubated at 4° C. overnight.

After the overnight incubation, unbound counts are removed with dextran coated charcoal as follows: 75 $\mu$l of dextran coated charcoal (5.0 g activated charcoal, 0.5 g dextran adjusted to volume of 100 ml with assay buffer) is added, plates are shaken and incubated for five minutes at 4° C. Plates are then centrifuged in a refrigerated benchtop centrifuge at top speed for 15 minutes. 100 $\mu$l of the supernatant from each well is placed into a 96-well PET plate with 200 $\mu$l of scintillation cocktail and counted on a beta counter (1450 MicroBetaTrilux, from Wallac, Turku, Finland).

Data analysis: After subtracting non-specific binding, counts bound are expressed as % of total counts. The concentration response for test compounds are fitted to a sigmoidal curve to determine the IC50 (concentration of compound that displaces 50% of the bound counts).

Reagents: Assay Buffer: 2.0 ml 1M Tris, 0.2 ml 0.5 mM EDTA, 77.1 mg DTT, 0.243 g sodium molybdate in a volume of 100 ml water; Homogenization buffer: 2.0 ml 0.5M $K_2HPO_4$ (pH 7.6), 20 $\mu$l 0.5M EDTA (pH 8.0), 77.1 mg DTT, 0.486 g sodium molybdate in a volume of 100 ml water.

The following is a description of an assay for determining receptor selectivity: T47D cells from ATCC containing endogenous human progesterone and mineralocorticoid receptors are transiently transfected with a 3xGRE-luciferase using Lipofectamine Plus (GIBCO-DRL, Gaithersburg, Md.). Twenty-four hours post-transfection cells are maintained in charcoal-stripped serum and transferred to 96-well microtiter plates. The next day cells are treated with various concentrations ($10^{-12}$ to $10^{-5}$) of test compounds in the absence and presence of a known progesterone receptor agonist (progesterone) and a known mineralocorticoid receptor agonist (aldosterone) for up to 24 hours. Treatments are performed in triplicate. Cell lysates are prepared and luciferase activity is determined using a luminometer. Agonist activity is assessed by comparing the luciferase activity from cells treated with compound alone to cells treated with either the agonist progesterone or aldosterone. Antagonist activity is assessed by comparing the luciferase activity of an $EC_{50}$ concentration of progesterone or aldosterone in the absence and presence of compound. The $EC_{50}$ (concentration that produced 50% of maximal response) for progesterone and aldosterone is calculated from dose response curves.

The following is a description of an assay for determining anti-diabetes and anti-obesity activity: The obese, diabetic ob/ob mouse is used to assess the anti-diabetes and anti-obesity activity of the compounds. Six to 10 week old ob/ob male mice (Jackson Labs, Bar Harbor, Me.) are dosed with test compound for 2 to 10 days. Plasma glucose levels are determined by measuring glucose from samples obtained by orbital bleeding. Glucose is quantitated using an Abbott Autoanalyzer (Abbott, Inc., Abbott Park, Ill.). Food intake is monitored on a daily basis by differential weighing.

The following is a description of an assay for determining the ability of a compound to inhibit glucocorticoid agonist induction of liver tyrosine amino transferase (TAT) activity in conscious rats:

Animals: Male Sprague Dawley rats (from Charles River, Wilimington Mass.) (adrenal-intact or adrenalectomized at least one week prior to the screen) b.w. 90 g are used. The rats are housed under standard conditions for 7–10 d prior to use in the screen.

Experimental protocol: Rats (usually 3 per treatment group) are dosed with test compound, vehicle or positive control (Ru486) either i.p., p.o., s.c. or i.v. (tail vein). The dosing vehicle for the test compounds is typically one of the following: 100% PEG 400, 0.25% methyl cellulose in water, 70% ethanol or 0.1N HCl and the compounds are tested at doses ranging from 10 to 125 mg/kg. The compounds are dosed in a volume of 1.0 ml/100 g body weight (for p.o.) or 0.1 ml/100 g body weight for other routes of administration . Ten minutes after the administration of the test compound, the rats are injected with dexamethasone (0.03 mg/kg i.p. in a volume of 0.1 ml/100 g) or vehicle. To prepare the dexamethasone dosing solution, dexamethasone (from Sigma, St. Louis, Mo.) is dissolved in 100% ethanol and diluted with water (final: 10% ethanol:90% water, vol:vol). Groups treated with vehicle—vehicle, vehicle-dexamethasone, and Ru486-dexamethasone are included in each screen. The compounds are tested vs. dexamethasone only. Three hours after the injection of dexamethasone the rats are sacrificed by decapitation. A sample of liver (0.3 g) is excised and placed in 2.7 ml of ice cold buffer and homogenized with a polytron. To obtain cytosol the liver homogenate is centrifuged at 105,000 g for 60 min and the supernatant is stored at −80° C. until analysis. TAT is assayed on 100 ul of a 1:20 dilution of the 105,000 g supernatant using the method of Granner and Tomkins (Methods in Enzymology 17A: 633–637, 1970) and a reaction time of 8–10 minutes. TAT activity is expressed as umol product/min/g liver.

Interpretation: Treatment data are analyzed by using analysis of variance (ANOVA) with protected least significant difference (PLSD) post-hoc analysis. Compounds are considered active in this testif the TAT activity in the group pretreated with compound prior to dexamethasone administration is significantly (P<0.05) decreased relative to the TAT activity in the vehicle-dexamethasone treated group.

The following is a description of an assay for determining the effect of a compound on two typical genes that are upregulated during an inflammatory response. This assay, the glucocorticoid inhibition of IL-1 (Interleukin-1) induced MMP-1 (Matrix Metalloproteinase-1) and IL-8 (Interleukin-8) production in human chondrosarcoma cells, is conducted as follows: SW1353 human chondrosarcoma cells (obtained from ATCC) from passage 12 through passage 19 are used in a 96 well format assay. Cells are plated at confluence into 96 well plates in DMEM (Dulbecco's Modified Eagle Medium) with 10% fetal bovine serum and incubated at 37° C., 5% $CO_2$. After 24 hours, serum containing media is removed and replaced with 200 ul/well DMEM containing 1 mg/L insulin, 2 g/L lactalbumin hydrosylate, and 0.5 mg/L ascorbic acid and returned to incubation at 37° C., 5% $CO_2$. The following morning, the serum free media is removed and replaced with 150 ul/well fresh serum free media containing +/−20 ng/ml IL-1 beta, +/−5 nM dexamethasone, +/−compound. All conditions are completed in triplicate using only the inner 60 wells of the 96 well plate. Outside surrounding wells of plate contain 200 ul of serum free DMEM. Plates are incubated at 37° C., 5% $CO_2$. At 24 hours after addition of IL-1, 25 ul of sample from each well is removed under aseptic conditions for IL-8 production analysis. Samples are stored at −20° C. until time of analysis. IL-8 production is assessed using the Quantikine human IL-8 ELISA kit from R&D Systems (D8050) on samples diluted 60-fold in RD5P Calibrator Diluent, following the manufacturer's protocol. The percent of the average IL-1 control is determined for the average of each of the triplicate samples following subtraction of the average signal from untreated cells. $IC_{50}$'s are determined from log linear plots of the percent of control versus the concentration of inhibitor. At 72 hours after IL-1 addition, the remaining media is removed and stored at −20° C. until time of MMP-1 production analysis. MMP-1 production is assessed via the Bio-Trak MMP-1 ELISA kit from Amersham (RPN2610) on 100 ul of neat sample following the manufacturer's protocol.

The percent of the average IL-1 control is determined for the average of each of the triplicate samples following subtraction of the average signal from untreated cells. $IC_{50}$'s are determined from log linear plots of the percent of control versus the concentration of inhibitor. Dexamethasone has proven to be a good positive control inhibitor of both IL-8 and MMP1 expression ($IC_{50}$=5nM).

The following compounds of the present invention are preferred:

2-phenanthrenecarboxamide, 4b,5,6,7,8,8a,9,10-octahydro-7-hydroxy-4b-(phenylmethyl)-7-(1-propynyl)-N-(4-pyridinylmethyl)-, [4bS-(4bα,7α,8aβ)]-;

2-phenanthrenecarboxamide, 4b,5,6,7,8,8a,9,10-octahydro-7-hydroxy-4b-(phenylmethyl)-7-(1-propynyl)-N-(2-pyridinylmethyl)-, [4bS-(4bα,7α,8aβ)]-;

2-phenanthrenecarboxamide, 4b,5,6,7,8,8a,9,10-octahydro-7-hydroxy-4b-(phenylmethyl)-7-(1-propynyl)-N-(3-pyridinylmethyl)-, [4bS-(4bα,7α,8aβ)]-;

carbamic acid, [2-(dimethylamino)ethyl]-, 4b,5,6,7,8,8a, 9,10-octahydro-7-hydroxy-4b-(phenylmethyl)-7-(1-propynyl)-2-phenanthrenyl ester,[4bS-(4bα,7α,8aβ)]-;

2-phenanthrenecarboxamide, 4b,5,6,7,8,8a,9,10-octahydro-7-hydroxy-4b-(phenylmethyl)-7-(1-propynyl)-N-pyrazinyl-, [4bS-(4bα,7α,8aβ)]-;

2-phenanthrenol, 1,2,3,4,4a,9,10,10a-octahydro-4a-(phenylmethyl)-2-(1-propynyl)-7-(4-pyridinylmethoxy)-, [2R-(2α,4aα,10aβ)];

2-phenanthrenol, 1,2,3,4,4a,9, 10, 10a-octahydro-4a-(phenylmethyl)-2-(1-propynyl)-7-(2-pyridinylmethoxy)-, [2R-(2α,4aα,10aβ)];

2-phenanthrenecarbonitrile, 4b,5,6,7,8,8a,9,10-octahydro-7-hydroxy-4b-(phenylmethyl)-7-(1-propynyl)-, [4bS-(4bα,7α,8aβ)]-;

2-phenanthrenecarboxamide, 4b,5,6,7,8,8a,9,10-octahydro-7-hydroxy-N-[(2-methyl-3-pyridinyl)methyl]-4b-(phenylmethyl)-7-(1-propynyl)-, [4bS-(4bα,7α,8aβ)]-;

2-phenanthrenecarboxamide, 4b,5,6,7,8,8a,9,10-octahydro-7-hydroxy-N-[(2-methyl-3-pyridinyl)methyl]-4b-(phenylmethyl)-7-propyl-, [4bS-(4bα,7α,8aβ)]-;

2-phenanthrenecarboxamide, 4b,5,6,7,8,8a,9,10-octahydro-7-hydroxy-4b-(phenylmethyl)-7-propyl-N-(2-pyridinylmethyl)-, [4bS-(4bα,7α,8aβ)]-;

2-phenanthrenol, 1,2,3,4,4a,9,10,10a-octahydro-4a-(phenylmethyl)-7-(3-pyridinylmethoxy)-2-(3,3,3-trifluoropropyl)-, [2S-(2α,4aα,10aβ)]-;

2-phenanthrenol, 1,2,3,4,4a,9,10,10a-octahydro-7-[(2-methyl-3-pyridinyl) methoxy]-4a-(phenylmethyl)-2-(3,3,3-trifluoropropyl)-,[2S-(2α,4aα,10aβ)]-;

2-phenanthrenecarboxamide, 4b,5,6,7,8,8a,9,10-octahydro-7-hydroxy-N-[(2-methyl-3-pyridinyl)methyl]-4b-(phenylmethyl)-7-(3,3,3-trifluoropropyl)-, (4bS,7S,8aR);

2-phenanthrenecarboxamide, 4b,5,6,7,8,8a,9,10-octahydro-7-hydroxy-7-methyl-N-[(2-methyl-3-pyridinyl) methyl]-4b-(phenylmethyl)-, (4bS,7R,8aR)-;

2-phenanthrenecarboxamide, 4b,5,6,7,8,8a,9,10-octahydro-7-hydroxy-7-methyl-4b-(phenylmethyl)-N-3-pyridinyl-, (4bS,7R,8aR)-;

2-phenanthrenol, 1,2,3,4,4a,9,10,10a-octahydro-7-[(2-methyl-3-pyridinyl) methoxy]-4a-(phenylmethyl)-2-(trifluoromethyl)-, (2R,4aS,10aR)-; and 2-phenanthrenecarboxamide, 4b, 5, 6, 7, 8, 8a, 9, 10-octahydro-7-hydroxy-N-[(2-methyl-3-pyridinyl) methyl]-4b-(phenylmethyl)-7-(trifluoromethyl)-, (4bS, 7R, 8aR)-.

EXAMPLES

Preparation 1

1-Benzyl-6-methoxy-3,4-dihydro-1H-naphthalen-2-one

A solution of 51 g (0.289 mol) of 6-methoxy-2-tetralone of formula A-1 wherein D is C, $R_{10}$ is methoxy; $R_{14}$, $R_{15}$ and $R_{16}$ are each H, and 24.2 mL (0.289 mol) of pyrrolidine in 1.5L of toluene was heated to reflux, over a Dean-Stark trap, overnight. After removal of the azeotroped water, the reaction mixture was cooled to RT, concentrated to an oil, and dissolved in 725 mL of dioxane. To this solution was added 52 mL (0.434 mol) of benzyl bromide and the resulting solution was heated to reflux overnight. Water (100 mL) was added to the solution the resultant mixture was heated to reflux for an additional 2 h. The mixture was cooled to room temperature and poured into a solution of 1 N HCl and extracted 3 times with EtOAc. The organic layers were washed with $H_2O$ and saturated $NaHCO_3$, then dried over $Na_2SO_4$, filtered, and evaporated to dryness. The crude product was purified by flash chromatography over $SiO_2$ using 10% EtOAc to 15% EtOAc in hexanes as the gradient eluant to give 65.2 g of the title product of this preparation as a yellow oil (85%). IR (neat) 2937, 1712, 1500 cm$^{-1}$; $^1$H NMR (400 MHz, CDCl$_3$) δ 2.41–2.59 (m, 3H), 2.76 (dt, 1 H, J=5.4, 15.5), 3.15–3.70 (m, 2 H), 3.67 (t, 1 H, J=6.3), 3.77 (s, 3 H), 6.67–6.70 (m, 2 H), 6.81 (d, 1 H, J=8.1), 6.87–6.89 (m, 2 H), 7.13–7.17 (m, 3 H); $^{13}$C NMR (100 MHz, CDCl$_3$) δ 27.44, 38.19, 39.19, 54.13, 55.14, 112.11, 112.96, 126.30, 128.07, 128.26, 129.35, 129.53, 138.05, 138.20, 158.30, 212.41; MS m/z 267 (M+H)$^+$.

Preparation 2

1(R)-Benzyl-6-methoxy-1(S)-(3-oxo-butyl)-3,4-dihydro-1H-naphthelen-2-one

A solution of 62 g (0.23 mol) of the title product of Preparation 1 and 28 mL, (0.23 mol) of freshly distilled (S)-(−)-alpha-methyl benzylamine in 100 mL of toluene was heated to reflux, over a Dean-Stark trap, overnight. After removal of the azeotroped water, the imine solution was cooled to 0° C. and 21 mL (0.26 mol) of freshly distilled methylvinylketone was added dropwise to the solution. The solution was stirred at 0° C. for 30 min then heated to 40° C. overnight. The reaction solution was cooled to 0° C. and 17 mL of acetic acid and 14 mL of $H_2O$ were added and the resultant solution was allow to warm to RT for 2 h. The solution was poured into $H_2O$ and extracted three times with EtOAc. The combined organic layers were washed with 1 N HCl, $H_2O$, saturated $NaHCO_3$, then dried over $Na_2SO_4$, filtered, and evaporated to dryness. The crude product was purified by chromatography over $SiO_2$ using 15% EtOAc to 35% EtOAc in hexanes as the gradient eluant to give 48 g of the title product of this preparation as a yellow solid. $^1$HNMR (400 MHz, CDCl$_3$) δ 1.38 (s, 3H), 1.40–1.51 (m, 2H), 1.64 (ddd, 1H, J=2.1, 4.5, 13), 1.97 (broad s, 1H), 2.20 (dt, 1H, J=4.5, 13), 2.59 (d, 1H, J=6.6), 3.08 (d, 1H, J=18), 3.16 (d, 1H, J=16), 3.33 (dd, 1H, J=6.6, 18), 3.62 (d, 1H, J=16), 3.72 (s, 3H), 6.57 (d, 1H, J=2.5), 6.67 (dd, 1H, J=2.5, 8.8), 7.00–7.23 (m, 6H); $^{13}$C NMR (100 MHz, CDCl$_3$) δ 27.90 32.79, 34.40, 38.43, 41.49, 53.51, 55.12, 58.47, 79.06, 112.05, 113.09, 125.37, 127.63, 127.69, 130.27, 132.21, 135.45, 138.65, 157.88, 213.49; MS m/z 337 (M+H)$^+$, 319 (M-OH)$^+$.

Preparation 3

1(S)-Benzyl-6-methoxy-1(R)-(3-oxo-butyl)-3,4-dihydro-1H-naphthelen-2-one

The title product of this preparation was prepared using a method analogous to Preparation 2, using (R)-(+)-alphamethyl benzylamine in the initial imine formation. Starting with 4.64 g 1-benzyl-6-methoxy-3,4-dihydro-1H-naphthalen-2-one produced 3.58 g of the title product of this preparation as a yellow solid. $^1$HNMR (400 MHz, CDCl$_3$) δ 1.38 (s, 3H), 1.40–1.51 (m, 2H), 1.64 (ddd, 1H, J=2.1, 4.5, 13), 1.97 (broad s, 1H), 2.20 (dt, 1H, J=4.5, 13), 2.59 (d, 1H, J=6.6), 3.08 (d, 1H, J=18), 3.16 (d, 1H, J=16), 3.33 (dd, 1H, J=6.6, 18), 3.62 (d, 1H, J=16), 3.72 (s, 3H), 6.57 (d, 1H, J=2.5), 6.67 (dd, 1H, J=2.5, 8.8), 7.00–7.23 (m, 6H); $^{13}$C NMR (100 MHz, CDCl$_3$) δ 27.90, 32.79, 34.40, 38.43, 41.49, 53.51, 55.12, 58.47, 79.06, 112.05, 113.09, 125.37, 127.63, 127.69, 130.27, 132.21, 135.45, 138.65, 157.88, 213.49; MS m/z337 (M+H)$^+$, 319 (M-OH)$^+$.

Preparation 4

2(3H)-Phenanthrenone, 4a-[(4-isopropylaminophenyl)methyl]-4,4a,9,10-tetrahydro-7-hydroxy-, (S)-

To a stirring solution of 200 mg of the title product of Preparation 18 in 0.216 mL of AcOH , 3 mL of acetone and 3 mL of dichloroethane under $N_2$ atmosphere was added 373 mg of NaBH(OAc)$_3$ at RT. The reaction mixture was stirred at RT for 2 h, then quenched with NaHCO$_3$ (sat). The mixture was extracted with EtOAc (X3), washed with brine, dried over Na$_2$SO$_4$, filtered and concentrated to dryness. Purification by flash chromatography over SiO$_2$ using 30% EtOAc in hexanes as the eluant afforded 108 mg of the title product of this preparation as white powder (47%). MS m/z 362 (M+H)$^+$.

Preparation 5

2(1H)-Phenanthrenone, 4a-[[3-(dimethylamino) phenyl]methyl]-3, 4,4a,9,10,10a-hexahydro-7-hydroxy-, (4aS-cis)-

A solution of 255 mg of the title product of Preparation 19 in 0.11 mL of formaldehyde (37% w/w), 255 mg of 5% Pd(OH)$_2$/C and 10 mL of EtOH was shaken under 50 psi (which is about 3.3 atm.) H$_2$ pressure for 2 days. The mixture was filtered and concentrated to dryness. Purification by flash chromatography SiO$_2$ using 2% EtOAc in hexanes to 40% EtOAc in hexanes as the gradient elutant afforded 133 mg (48%) of the title product of this example as white fluffy powder. MS m/z 450 (M+H)$^+$.

Preparation 6

1-Naphthalenepropanoic acid, 1,2,3,4-tetrahydro-6-methoxy-2-oxo-1-(phenylmethyl)-, Methyl Ester To a solution of 3.18 g of the title compound of Preparation 1 in 30 mL of anhydrous MeOH was added 31 mL of 0.5 M NaOMe/MeOH at −15° C. under nitrogen atmosphere. This solution was stirred vigorously while 1.5 mL of fresh distilled methyl acrylate was added dropwise at −15° C. The mixture was stirred for 1 h at 0° C. and then allowed to settle for 5 min. The precipitate was collected by filtration and the filter cake was washed with MeOH to yield 2 g (52%) of the title product of this preparation as white solid. MS m/z 353 (M+H)$^+$.

Preparation 7

1-Naphthalenepropanoic acid, 1,2,3,4-tetrahydro-6-methoxy-2-oxo-1-(phenylmethyl)-

A solution of 200 mg of the title product of Preparation 6 and 92 mg of Na$_2$CO$_3$ in 8 mL of MeOH and 10 mL of water was heated to reflux for 30 min. The mixture was cooled and adjusted to pH around 5 with 1 N HCl solution. NaCl was added to make a saturated solution. The solution was extracted with EtOAc (X3), washed with brine, dried over Na$_2$SO$_4$, filtered and concentrated to dryness. The title product of this preparation was obtained in 98% yield as white solid. MS m/z 339 (M+H)$^+$.

Preparation 8

3H-Naphtho[2,1-b]pyran-3-one, 1,2,4a,5,6,10b-hexahydro-8-methoxy-10b-(phenylmethyl)-

To a solution of 199 mg of the title product of Preparation 7 in 5 mL of ethanol was added 67 mg of sodium borohydride at 0° C. under N$_2$ atmosphere. The mixture was then allowed to stirred overnight at room temperature. The solution was then acidified to pH 1 with 1 N HCl solution and extracted with EtOAc (X3), dried over Na$_2$SO$_4$, filtered and concentrated to dryness. Purification by preparative TLC SiO$_2$ using 35% EtOAc in hexanes as the elutant afforded 73 mg (37%) of the title product of this preparation as white fluffy powder. MS m/z 323 (M+H)$^+$.

Preparation 9

2,7-Phenanthrenediol, 2-(chloroethynyl)-1,2,3,4,4a, 9,10,10a-octahydro-4a-[3-[4-(t-butyldimethylsiloxymethyl)phenyl]-2-propenyl]-, [2R-[2α,4aα(E),10aβ]]-

The title compound of this preparation was prepared by procedures analogous to those described below in Example 35.

Preparation 9a

Carbamic acid, dimethyl-, 4b-[2-acetaldehydro]-4b, 5,6,7,8,8a,9, 10-octahydro-7-hydroxy-7-(1-propynyl)-2-phenanthrenyl ester, [4bS-(4bα,7α, 8aβ)]-

To a stirred solution of 4a(2H)-phenanthreneacetaldehyde, 2-(1-propynyl)-1, 3,4,9,10,10a-hexahydro-2,7-dihydroxy-, [2R-(2α,4aα,10aβ)]- (1.5 g) in THF were added sequentially 4-dimethylaminopyridine (0.12 g), triethylamine (1.8 g) and dimethylcarbamyl chloride (1.6 g). After 18 h, the heterogeneous mixture was quenched with saturated aqueous ammonium chloride, extracted with ethyl acetate, the organic layer was dried over sodium sulfate and concentrated in vacuo. The resulting oil was purified by flash chromatography on silica gel (30–50% ethyl acetate/hexanes) to afford the title compound of this preparation as a colorless solid, 2.3 g.

Preparation 10

Carbamic acid, dimethyl-, 4b-[2-hydroxyethyl]-4b, 5,6,7,8,8a,9,10-octahydro-7-hydroxy-7-(1-propynyl)-2-phenanthrenyl Ester, [4bS-(4bα,7α, 8aβ)]-

To a cooled (−78° C.), stirred solution of the title product of Preparation 9a (2.3 g) in tetrahydrofuran (60 mL) was added a 1 M solution of diisobutylaluminum hydride in cyclohexane (8 mL). After 2.5 h, the reaction was quenched with 0.5 M sodium potassium tartrate and the resulting mixture was stirred overnight at room temperature. The two-phase mixture was extracted with ethyl acetate (3x), the combined extracts washed with brine, dried over sodium sulfate and concentrated in vacuo to afford a colorless foam. Flash chromatography on silica gel (50–75% ethyl acetate/hexanes) afforded the title product of this preparation a colorless foam, 1.9 g.

Preparation 11

8-R,Sa-Benzyl-6-ethoxy-3,7,8,8a-tetrahydro-2H-naphthalen-1-one

A solution of 8-R,Sa-benzyl-3,4,8,8a-tetrahydro-2H,7H-naphthalene-1,6-dione (5.0 g), triethylorthoformate (13 mL), p-toluenesulfonic acid (200 mg), ethanol (1.5 mL) in toluene (100 mL) was heated at 80° C. for 1.5 h. The reaction solution was cooled, diluted into ethyl ether, washed with 1 N NaOH, water, brine, dried over sodium sulfate and concentrated in vacuo to afford a red oil. Filtration (20% ethyl ether/hexanes) through a pad of Florisil® provided the title product of this preparation as a red solid, 5.7 g.

Preparation 12

(cis/trans)-8-R,Sa-Benzyl-6-ethoxy-3,4,4a,5,8,8a-hexahydro-2H-naphthalen-1-one

A solution of the title product of Preparation 11 (2 g) in ethanol (56 mL) was hydrogenated at 1 atm of hydrogen pressure over 2% strontium carbonate (0.2 g) for 4.5 h. After removal of catalyst by filtration and concentration of the filtrate in vacuo, the trans and cis isomers of the title product of this preparation were separated by chromatography on silica gel (0–2% ethyl acetate/hexanes). The cis isomer (0.1 g) eluted first with the trans isomer (1.2 g) predominating.

Preparation 13

(trans)-8-R,Sa-Benzyl-2-bromo-6-ethoxy-3,4,4a,5,8, 8a-hexahydro-2H-naphthalen-1-one To a cooled (0° C.), stirred solution of lithium diisopropyamide (prepared from diisopropylamine (0.17 mL) and n-butyllithium (0.42 mL, 2.5 M in hexanes)) in tetrahydrofuran (9 mL) was added a solution of (trans)-8-R,Sa-benzyl-6-ethoxy-3, 4,4a,5,8,8a-hexahydro-2H-naphthalen-1-one (0.25 g) in tetrahydrofuran (4 mL). After 30 min, the solution was cooled to −78° C. and a solution of n-bromosuccinimide (0.2 g) in tetrahydrofuran (9 mL) was added. After 1 h, the reaction was quenched with saturated aqueous sodium bicarbonate, extracted with ethyl ether, the organic layers were combined, dried over sodium sulfate and concentrated in vacuo. The resulting oil was purified by flash chromatography on silica gel (0–1% ethyl acetate/hexanes) to afforded the title compound of this preparation as an oil (200 mg). The cis-isomer of the title product of Preparation 12 can be analogously reacted.

Preparation 14

(trans)-8a-Benzyl-2-bromo-hexahydro-naphthalene-1,6-dione

A solution of the title product of Preparation 13 (0.15 g) in a solution of ethanol (8 mL) containing 2.5% concentrated sulfuric acid and 1% water was stirred for 2 h. The reaction was diluted with ethyl ether, washed with sat. sodium bicarbonate, brine, dried over sodium sulfate and concentrated in vacuo to afford an oil. Flash chromatography on silica gel (15% ethyl acetate/hexanes) afforded the title compound of this preparation as a colorless solid, 53 mg. The cis-isomer can be similarly reacted.

Preparation 15

(trans)-8-R,Sa-Benzyl-6-ethoxy-1-oxo-1,2,3,4,4a,5, 8,8a-octahydro-naphthalene-2-carbaldehyde To a cooled (0° C.), stirred solution of the trans isomer of the title product of Preparation 12 (2.1 g) and ethyl formate (2.2 g) in tetrahydrofuran (8 mL) was added potassium t-butoxide (15.6 mL, 1 M in THF). The reaction solution was maintained at 0° C. for 0.5 h and at room temperature for 6 h, quenched with sat. aqueous ammonium chloride and extracted with ethyl acetate. The combined organic extracts were washed with brine, dried over sodium sulfate and concentrated in vacuo to afford the title compound of this preparation as a red oil, 2.3 g.

Preparation 16

Phenol, 4-[4-(chloroethynyl)-4-hydroxy-1-(phenylmethyl)cyclohexyl]-

The title compound of this preparation was prepared by procedures analogous to those described below in Example 8. MS: 342 (M+1)$^+$.

Preparation 17

2(1H)-Phenanthrenone, 3,4,4a,9,10,10a-hexahydro-7-hydroxy-4a -[(4-hydroxyphenyl)methyl]-, (4aS-cis)

The title compound of this preparation was prepared by procedures analogous to those described below in Example 7. MS: 323 (M+1)$^+$.

Preparation 18

2(3H)-Phenanthrenone, 4a-[(4-aminophenyl) methyl]-4,4a,9,10-tetrahydro-7-hydroxy-, (S)-

The title compound of this preparation was prepared by procedures analogous to those described below in Example 3. MS: 321 (M+1)$^+$.

Preparation 19

2(1H)-Phenanthrenone, 4a-[(3-aminophenyl) methyl]-3, 4,4a,9,10,10a-hexahydro-7-hydroxy-, (4aS-cis)-

The title compound of this preparation was prepared by procedures analogous to those described below in Preparation 5. MS: 322 (M+1)$^+$.

Preparation 20

Pyridine, 3-[[[(2R,4'aS,10'aR)-3',4',4'a,9',10',10'a-hexahydro-4'a-(phenylmethyl)spiro[oxirane-2,2' (1'H)-phenanthren]-7'-yl]oxy]methyl]-

The title compound of this preparation was prepared by procedures analogous to those described below in Example 76. MS: 413 (M+1)$^+$.

Preparation 21

Pyridine, 3-[[[(2R,4'aS,10'aR)-3',4',4'a,9',10'a-hexahydro-4'a-(ph enylmethyl)spiro[oxirane-2,2' (1'H)-phenanthren]-7'-yl]oxy]methyl]-2-methyl- The title compound of this preparation was prepared by procedures analogous to those described below in Example 76. MS: 427 (M+1)$^+$.

Preparation 22

Pyridine, 2-[[[(2R, 4'aS, 10'aR)-3',4',4'a,9', 10', 10'a-hexahydro-4'a-(phenylmethyl)spiro[oxirane-2,2' (1'H)-phenanthren]-7'-yl]oxy]methyl]-

The title compound of this preparation was prepared by procedures analogous to those described below in Example 76. MS: 413 (M+1)$^+$.

Example 1

2(3H)-Phenanthrenone, 4,4a,9,10-tetrahydro-7-methoxy-4a-(phenylmethyl)-, (S)-

A solution of 48 g (143 mmol) of the title product of Preparation 2 and 71 mL of 1 M sodium methoxide in 100 mL of methanol was stirred at room temperature for 15 min, then heated to 75° C. for 3 h. The solution was cooled to 0° C., 8.2 mL of acetic acid was added dropwise, and the solution was concentrated to an oil. The oil was dissolved in EtOAc, washed with saturated NaHCO$_3$ and brine, dried over Na$_2$SO$_4$, filtered, and evaporated to dryness. The crude product was purified by chromatography over SiO$_2$ using 15% EtOAc to 35% EtOAc in hexanes as the gradient eluant to give 44 g 2(3H)-phenanthrenone, 4,4a,9,10-tetrahydro-7-methoxy-4a-(phenylmethyl)-, (S)- as an off-white powder (60% from 1-benzyl-6-methoxy-3,4-dihydro-1H-naphthalen-2-one). Recrystallization from EtOAc/hexane afforded 35 g of the title product of this example as a white crystalline solid. mp 101–102° C.; IR (neat) 1667, 1500 cm$^{-1}$; $^1$HNMR (CDCl$_3$) 1.83–1.90 (m, 1H), 2.02 (dt, 1H, J=5.5, 14), 2.27 (dt, 1H, J=4.3, 14) 2.44–2.51 (m, 2H), 2.64–2.79 (m, 3H), 3.14 (d, 1H, J=13), 3.21 (d, 1H, J=13), 3.78 (s 3H), 5.96 (s, 1H), 6.54 (d, 1H, J=2.6), 6.71 (d, 2H, J=7.1), 6.77 (dd, 1H, J=2.6, 8.7), 7.06–7.23 (m, 4H)); $^{13}$C NMR (100 MHz, CDCl$_3$) δ 30.71, 32.10, 34.62, 36.09, 43.62, 46.36, 55.20, 112.78, 112.84, 125.53, 126.68, 127.96, 128.12, 130.08, 133.01, 137.24, 137.28, 157.75, 169.16, 198.81; MS m/z 319 (M+H)$^+$. Anal. Calcd. for $C_{22}H_{22}O_2$: C, 82.99; H, 6.96; N, 0. Found: C, 83.21; H, 7.08; N, <0.10.

Example 2

2(3H)-Phenanthrenone, 4,4a,9,10-tetrahydro-7-methoxy-4a-(phenylmethyl)-, (R)-

The title product of this preparation was prepared using a method analogous to Example 1. Starting with 3.53 g of the title product of Preparation 3 produced 2.78 g of the title product of this example as an off-white powder (51% from 1-benzyl-6-methoxy-3,4-dihydro-1H-naphthalen-2-one. Recrystallization from EtOAc/hexane afforded 2.15 g of the title product of this example as a white crystalline solid. All physical constants are the same as reported for the title product of Example 1. Anal. Calcd. for $C_{22}H_{22}O_2$: C, 82.99; H, 6.96; N, 0. Found: C, 83.17; H, 7.13; N, <0.10.

Example 3

2(3H)-Phenanthrenone, 4,4a,9,10-tetrahydro-7-hydroxy-4a-(phenylmethyl)-, (S)-

To a stirring solution of 40 g (0.126 mol) of the title product of Example 1 (which was made by procedures described in Example 1) and 46.5 g (0.126 mol) of tetrabutylammonium iodide in 630 mL of dichloromethane at −78° C. under N$_2$ atmosphere was added 300 mL of 1 M boron trichloride in methylene chloride. The resultant solution was allowed to warm to RT for 1.5 h, then poured into excess ice and stirred rapidly, overnight. The mixture was extracted with dichloromethane, dried over Na$_2$SO$_4$, filtered, and concentrated to dryness. Purification by flash chromatography over SiO$_2$ using 20%EtOAc to 60%EtOAc in hexanes as the gradient eluant afforded 33.3 g of the title product of this example as an off-white powder (87%). $^1$H NMR (400 MHz, CD$_3$OD) δ 1.81–2.00 (m, 2H), 2.26 (dt, 1H, J=4.2, 13), 2.40 (dd, 1H, J=4.5, 18), 2.53 (ddd, 1H, J=1.7, 5.6, 14), 2.58–2.80 (m, 3H), 3.20 (d, 1H, J=13), 3.26 (d, 1H, J=13), 5.92 (s, 1H), 6.45 (d, 1H, J=2.5), 6.67 (dd, 1H, J=2.5, 8.5), 6.76 (d, 2H, J=6.6), 7.05–7.14 (m, 4H); $^{13}$C NMR (100 MHz, CD$_3$OD) δ 30.22, 32.03, 34.08, 36.04, 43.73, 45.97, 113.76, 113.91, 124.50, 126.25, 127.49, 127.94, 129.84, 131.86, 137.0, 137.71, 155.34, 171.73, 200.33; MS m/z 305 (M+H)$^+$.

Example 4

2(3H)-Phenanthrenone, 4,4a,9,10-tetrahydro-7-hydroxy-4a-(phenylmethyl)-, (R)-

The title product of this example was prepared using a method analogous to Example 3. Starting with 1.8 g of the title product of Example 2 produced 1.3 g of the title product of this example as a white solid (75%). All physical constants are the same as reported for the title product of Example 3.

Example 5

2,7-Phenanthrenediol, 2,3,4,4a,9,10-hexahydro-4a-(phenylmethyl)-2-(1-propynyl)-, (2R-cis)- and 2,7-Phenanthrenediol, 2,3,4,4a,9,10-hexahydro-4a-(phenylmethyl)-2-(1-propynyl)-, (2S-trans)-

To a stirring solution of 5 mL of THF saturated with propyne gas at 0° C. was added 4 mL of 0.5 M lithium diisopropylamide in THF and the resultant mixture stirred under nitrogen atomosphere for 20 min. A solution of 50 mg (0.16 mmol) of the title product of Example 3 in 2 mL of THF was added dropwise, and the reaction mixture was warmed to RT and stirred for 16 h. Saturated, aqueous ammonium chloride was added, and the mixture was extracted with EtOAc, dried over Na$_2$SO$_4$, filtered, and concentrated to dryness. Purification by flash chromatography over SiO$_2$ using 2% acetone in dichloromethane to 4% acetone in dichloromethane with 0.5% triethylamine as the gradient eluant afforded 25 mg (45%) of the first listed title product of this example (higher Rf) and 5 mg (9%) of the second listed title product of this example.

The physical properties of the first listed title product of this example are as follows: $^1$H NMR (400 MHz, d$_6$acetone) δ 1.67 (s, 3H), 1.67–1.80 (m, 2H), 2.00–2. 22 (m, 2H+d$_6$acetone), 2.26 (ddd, 1H, J=2.9, 4.2, 7.0), 2.60–2.78 (m, 3H), 3.01, (d, 1H, J=13), 3.05 (d, 1H, J=13), 4.30 (s, 1H), 5.52 (s, 1H), 6.49, (d, 1H, J=2.6), 6.55 (dd, 1H, J=2.6, 8.5), 6.67 (d, 1H, J=8.5), 6.76–6.80 (m, 2H), 7.08–7.13 (m, 3H), 8.06, (s, 1H); $^{13}$C NMR (100 MHz, d$_6$acetone) δ 2.5, 31.4, 33.3, 35.6, 41.8, 46.8, 54.8, 65.8, 77.8, 83.9, 113.1, 114.4, 126.0, 127.4, 127.7, 128.4, 130.6, 134.0, 137.2, 138.7, 141.1, 155.1; MS m/z327 (M-OH)$^+$.

The physical properties of the second listed title product of this example are as follows: $^1$H NMR (400 MHz, d$_6$acetone) δ 1.77 (s, 3H), 1.77–2.30 (m, 5H+d$_6$acetone), 2.58–2.78 (m, 3H), 2.96, (d, 1H, J=13), 3.02 (d, 1H, J=13), 4.06 (s 1H), 5.60 (s, 1H), 6.47 (d, 1H, J=2.3), 6.56 (dd, 1H, J=2.3, 8.3), 6.78–6.82 (m, 3H), 7.10–7.14 (m, 3H), 8.03 (s, 1H); $^{13}$C NMR (100 MHz, d$_6$acetone) δ 2.5, 30.9, 31.6, 35.3, 41.9, 46.3, 54.6, 63.1, 76.8, 84.7, 113.1, 114.3, 126.0, 126.7, 127.4, 128.4, 130.5, 134.0, 137.3, 138.7, 142.3, 155.1; MS m/z 327 (M-OH)$^+$.

Example 6

2(1H)-Phenanthrenone, 3,4,4a,9,10,10a-hexahydro-7-hydroxy-4a- (phenylmethyl)-, (4aS-trans)-

Ammonia (1.5 L) was condensed into a round bottom flask at −78° C. equipped with a dry ice reflux condenser at −78° C. and a mechanical stirrer. To this flask was added 0.7 g (99 mmol) of lithium wire and the solution turned dark blue. A solution of 10 g (32.8 mmol) of the title product of Example 3 in 400 mL of 1:1 dioxane:ether was added to the mixture slowly in order to keep the reaction a dark blue. As the blue color dissipated, a small amount of lithium wire was added to the mixture to regenerate the blue color. The total amount of lithium added to the reaction mixture did not exceed 3.5 g (495 mmol). After the complete addition of 10 g of the title product of Example 3, the reaction was stirred an additional 30 min, then 14 g of solid ammonium chloride was added and immediate dissipation of the blue color was observed. H$_2$O was added to the mixture and it was extracted with EtOAc, dried over Na$_2$SO$_4$, filtered, and concentrated to dryness. The crude product was purified by flash chromatography over SiO$_2$ using 15% EtOAc to 20% EtOAc in hexanes as the gradient eluant to afford 8.16 g of the title product of this example as a white solid (81%). $^1$H NMR (400 MHz, CD$_3$OD) δ 1.52 (dt, 1H, J=4.5, 13), 1.64–1.71 (m, 1H), 1.90–2.15 (m, 2H), 2.27 (ddd, 1H, J=2.5, 3.7, 15), 2.39 (dm, 1H, J=15), 2.48 (ddd, 1H, J=2.0, 6.5, 13), 2.72 (t, 1H, J=14), 2.84 (d, 1H, J=13), 2.89–3.01 (m, 3H), 3.22 (d, 1H, J=13), 6.17 (d, 1H, J=8.5), 6.24 (dd, 1H, J=2.5, 8.5), 6.53 (d, 1H, J=2.5), 6.65–6.68 (m, 1H), 7.04–7.13, (m, 3H); $^{13}$C NMR (100 MHz, CD$_3$OD) δ; 27.9, 33.7, 34.8, 36.0, 37.6, 39.4, 43.6, 44.0, 111.3, 114.6, 125.7, 127.0, 127.9, 130.5, 133.4, 136.8, 138.0, 155.1, 212.7; MS m/z 307 (M+H)$^+$.

Example 7

2(1H)-Phenanthrenone, 3,4,4a,9,10,10a-hexahydro-7-hydroxy-4a-(phenylmethyl)-, (4aS-cis)-

To a solution of 1 g (3.6 mmol) of the title product of Example 3 in 75 mL of ethanol and 0.27 mL of 2M KOH was added 0.15 g of 10% Pd/C. The reaction mixture was shaken under 45 p.s.i. (which is about 3 atm) of $H_2$ gas for 4 h. Acetic acid (0.035 mL) was added then the mixture was filtered through Celite®, washing the Celite® with ethanol, and then the ethanol was removed under reduced pressure. The resultant residue was partitioned between EtOAc and sat. $NaHCO_3$, extracted with EtOAc, dried over $Na_2SO_4$, filtered, and concentrated to dryness. The crude product was purified by flash chromatography over $SiO_2$ using 25% EtOAc in hexanes as the eluant to afford 947 mg of the title product of this example as a white solid (86%). $^1$H NMR (400 MHz, $CD_3OD$) δ 1.52–1.60 (m, 1H), 1.87 (ddd, 1H, J=4.8, 11, 14), 2.00–2.35 (m, 6H), 2.39 (dt, 1H, J=5.2, 14), 2.69–2.92 (m, 2H), 2.96 (d, 1H, J=13), 3.00 (d, 1H, J=13), 6.56–6.58 (m, 2H), 6.88–6.92 (m, 3H), 7.13–7.15, (m, 3H); $^{13}$C NMR (100 MHz, $CD_3OD$) δ 23.7, 25.3, 34.7, 37.2, 39.6, 40.3, 42.8, 47.7, 113.1, 115.1, 127.3, 128.0, 130.5, 137.2, 137.8, 155.2, 213.9; MS m/z 307 (M+H)$^+$.

Example 8

2,7-Phenanthrenediol, 2-(chloroethynyl)-1,2,3,4,4a,9,10,10a-octahydro-4a-(phenylmethyl)-, [2R-(2α,4aα,10aβ)]- and 2,7-Phenanthrenediol,2-(chloroethynyl)-1,2,3,4,4a,9,10,10a-octahydro-4a-(phenylmethyl)-, [2S-(2α,4aβ,10aα)]-

To a stirring solution of 95 mg of cis-dichloroethylene (0.98 mM) in 5 mL of THF at 0° C. was added 2.5 mL of 0.5 M lithium diisopropylamide in THF and the resultant mixture was allowed to warm to RT for 30 min under nitrogen atomosphere. A solution of 30 mg (0.098 mmol) of the title product of Example 6 in 0.65 mL of THF was added dropwise, and the reaction mixture was stirred an additional 2 h. Saturated, aqueous ammonium chloride was added, and the mixture was extracted with EtOAc, dried over $Na_2SO_4$, filtered, and concentrated to dryness. Initial purification by flash chromatography over $SiO_2$ using 20% EtOAc in hexanes as the eluant afforded 30 mg of a light brown solid. Further purification by flash chromatography over $SiO_2$ using 2% acetone in dichloromethane to 4% acetone in dichloromethane as a gradient eluant afforded 20 mg (56%) of the first listed title product of this example (higher Rf) and 7.0 mg (19%) of the second listed title product of this example (lower Rf) as white solids. The physical characteristics of the first listed title product of this example are as follows: mp 230–232° C. (decomp.); $^1$H NMR (300 MHz, $CD_3OD$) δ 1.40 (mt, 1H, J=14), 1.64–1.70.(m, 1H), 1.80–2.13 (m, 7H), 2.59 (d, 1H, J=13), 2.93–2.97 (m, 3H), 6.13 (d, 1H, J=8.5), 6.25 (dd, 1H, J=2.6, 8.5), 6.54–6.57 (m, 3H), 7.00–7.07 (m, 3H); $^{13}$C NMR (75 MHz, $CD_3OD$) δ 25.5, 28.7, 31.8, 37.2, 40.52, 41.71, 43.43, 63.1, 70.7, 74.1, 112.4, 116.1, 126.8, 128.3, 138.9, 132.1, 136.2, 138.3,139.5, 156.3; MS m/z 366 (M+H)$^+$, 349 (M–OH)$^+$.

The physical characteristics of the second listed title product of this example are as follows: mp 216–219° C. (decomp.) $^1$H NMR (400 MHz, $CD_3OD$) δ 1.47 (mt, 1H, J=14), 1.56–1.62 (m, 1H), 1.80–2.00 (m, 5H), 2.08 (mt, 1H, J=13), 2.23 (dt, 1H, J=3.8, 14), 2.59 (d, 1H, J=13), 2.82–2.93 (m) and 2.95 (d, 1H, J=13), 6.08 (d, 1H, J=8.6), 6.20 (dd, 1H, J=2.2, 8.6), 6.50 (d, 1H, J=2.2), 6.54–6.56 (m, 2H), 7.03–7.06 (m, 3H); $^{13}$C NMR (75 MHz, $CD_3OD$) δ 25.4, 28.8, 28.9, 36.0, 36.7, 40.4, 42.5, 65.1, 67.3, 75.9, 112.3, 116.1, 126.8, 128.2, 128.8, 132.2, 136.3, 138.3, 139.7, 156.2; MS m/z 366 (M+H)$^+$, 349 (M–OH)$^+$.

Example 9

2,7-Phenanthrenediol, 1,2,3,4,4a,9,10,10a-octahydro-4a-(phenylmethyl)-2-(1-propynyl)-, [2R-(2α,4aα,10aβ)]- and 2,7-Phenanthrenediol, 1,2,3,4,4a,9,10,10a-octahydro-4a-(phenylmethyl)-2-(1-propynyl)-, [2S-(2α,4aβ,10aα)]-

To a stirring solution of 183 mL of THF saturated with propyne gas at 0° C. was added 143 mL of 1 M lithium diisopropylamide in THF and the resultant mixture was stirred under nitrogen atomosphere for 20 min. A solution of 7.3 g (23.8 mmol) of the title product of Example 6 in 250 mL of THF was added dropwise, and the reaction mixture was warmed to RT and stirred overnight. Saturated, aqueous ammonium chloride was added, and the mixture was extracted with EtOAc, dried over $Na_2SO_4$, filtered, and concentrated to dryness. Purification by flash chromatography over $SiO_2$ using 2% acetone in dichloromethane to 4% acetone as the eluant afforded 4.0 g (49%) of the first listed title product of this example (higher Rf) and 2.4 g (29%) of the second listed title product of this example as white solids.

Physical characteristics of the first listed title product of this example are as follows: mp 227–229° C. (decomp.), $^1$H NMR (400 MHz, $CD_3OD$) δ 1.42 (mt, 1H, J=14), 1.61.(ddd, 1H, J=3.4, 4.1, 8.8), 1.72 (s, 3H), 1.73–1.82 (m, 2H), 1.84–2.10 (m, 5H), 2.55 (d, 1H, J=13), 2.83–2.93 (m) and 2.94 (d, 3H, J=13), 6.10 (d, 1H, J=8.3), 6.23 (dd, 1H, J=2.5, 8.4), 6.52–6.55 (m, 3H), 7.00–7.05 (m, 3H); $^{13}$C NMR (62 MHz, $CD_3OD$) δ 2.5, 24.1, 27.3, 30.5, 35.8, 36.1, 39.1, 40.2, 42.4, 68.9, 79.5, 82.3, 110.9, 114.7, 125.4, 126.8, 127.5, 130.7, 135.1, 136.9, 138.3, 154.8; MS m/z 346 (M+H)$^+$, 329 (M–OH)$^+$.

Physical characteristics of the second listed title product of this example are as follows: mp 222–223° C. (decomp.); $^1$H NMR (400 MHz, $CD_3OD$) δ 1.46 (mt, 1H, J=14), 1.54–1.60.(m, 1H), 1.83 (s) overlap with 1.75–1.94 (m, 8H), 2.08 (mt, 1H, J=13), 2.20 (dt, 1H, J=4, 14), 2.57 (d, 1H, J=13), 2.88 (t, 2H, J=8.7), 2.94 (d, 1H, J=13), 6.08 (d, 1H, J=8.3), 6.20 (dd, 1H, J=2.4, 8.3), 6.50 (d, 1H, J=2.4), 6.53–6.56 (m, 2H), 7.01–7.06 (m, 3H); $^{13}$C NMR (62 MHz, $CD_3OD$) δ 1.7, 24.1, 27.4, 27.6, 35.0, 35.2, 36.4, 39.0, 41.6, 65.5, 76.9, 84.5, 110.8, 114.6, 125.3, 126.8, 127.4, 130.7, 135.0, 136.9, 138.4, 154.7; MS m/z 346 (M+H)$^+$, 329 (M–OH)$^+$.

Example 10

2,7-Phenanthrenediol, 1,2,3,4,4a,9,10,10a-octahydro-4a-(phenylmethyl)-2-propyl-[2R-(2α,4aα,10aβ)]-

A mixture of 975 mg of the first listed title product of Example 9, 195 mg of 10% Pd/C, and 100 mg $K_2CO_3$ in MeOH was shaken under 40 p.s.i. (which is about 2.6 atm) of $H_2$ gas for 16 h. The mixture was filtered through Celite® and concentrated to afford 945 mg of the title product of this example as a white solid. MS: 368 (M+18)$^+$.

Example 11

Pentanal, 5-[[4b,5,6,7,8,8a,9,10-octahydro-7-hydroxy-4b-(phenylmethyl)-7-propyl-2-phenanthrenyl]oxy]-, [4bS-(4bα,7α,8aβ)]-

To a stirring solution of 157 mg of the title compound of Example 314, below, in 4.8 mL of dioxane and 1.2 mL of $H_2O$ was added 72 mg of 4-methylmorpholine-N-oxide, 0.003 mL of pyridine, and 0.18 mL of 2.5 wt. % $OsO_4$ in t-butanol and the reaction mixture was stirred for 4 h. To this mixture was added 776 mg of NaIO4 and the resultant mixture was stirred overnight. The reaction mixture was poured into $H_2O$ and extracted with EtOAc. The organic layer was dried over $Na_2SO_4$, filtered, and concentrated to dryness. Purification by flash chromatography over $SiO_2$ using 25% EtOAc in hexanes to 10% EtOAc in hexanes as the gradient eluant afforded 141 mg of the title product of this example as colorless oil. MS: 417 $(M-17)^+$.

Example 12

2-Phenanthrenol, 1,2,3,4,4a,9,10,10a-octahydro-7-[[5-(4-morpholinyl) pentyl]oxy]-4a-(phenylmethyl)-2-propyl-, [2R-(2α,4aα,10aβ)]-

To a stirring solution of 34.6 mg of the title product of Example 11 in 1 mL of AcOH was added 0.014 mL of morpholine and 109 mg of $Na_2SO_4$ and the resultant mixture was stirred for 15 min. To this mixture was added 24 mg of $NaHB(OAc)_3$ and the resultant mixture was stirred for 1.5 h. The mixture was cooled to 0° C. and sat. $Na_2CO_3$ added until the pH of the mixture was approximately 8 to 9. The reaction mixture was extracted with EtOAc, dried over $Na_2SO_4$, filtered, and concentrated to dryness. Purification by flash chromatography over $SiO_2$ using 5% MeOH in dichloromethane to MeOH as the eluant afforded 26.6 mg of the title product of this example as a white solid. MS: 506 $(M+1)^+$.

Example 13

Methanesulfonic acid, trifluoro, 4b, 5, 6, 7, 8, 8a, 9, 10-octahydro-7-hydroxy-4b-(phenylmethyl)-7-(1-propynyl)-2-phenanthrenyl ester, [4bS-(4bα, 7α, 8aβ)]-

To a stirring solution of 4.14 g of the first listed title compound of Example 9 (which was prepared by procedures described in Example 9), 1.95 mL of 2,6-lutidine, and 292 mg of 4-dimethylaminopyridine in 150 mL of dichloromethane at −40° C. under nitrogen was added 2.6 mL of trifluoromethylsulfonic anhydride. The resultant mixture was stirred for 0.5 h at −40° C., 0.5 h at 0° C., then 1.5 h at RT. The reaction mixture was poured into 1 N HCL and extracted with dichloromethane. The organic layer was washed with water, sat. $NaHCO_3$, and brine, dried over $Na_2SO_4$, filtered, and concentrated to dryness. Purification by flash chromatography over $SiO_2$ using 15% EtOAc in hexanes to 20% EtOAc in hexane as the gradient eluant afforded 4.4 g (77%) of the title product of this example as a white solid. $^1H$ NMR (400 MHz, $C_6D_6$) δ 6.07 (d, 1H, J=8.4), 6.63 (d, 1H, J=2.5).

Example 14

2-Phenanthrenecarboxylic acid, 4b,5,6,7,8,8a,9,10-octahydro-7-hydroxy-4b-(phenylmethyl)-7-(1-propynyl)-, methyl ester, [4bS-(4bα,7α,8aβ)]-

A mixture of 1.18 g of the title product of Example 13, 0.27 g of 1,3-bis (diphenylphosphino)-propanol, 2.54 mL of triethylamine, and 0.1 g of palladium acetate in 40 mL of 1:1 DMF / MeOH was shaken under 60 p.s.i. (which is about 4 atm) carbon monoxide at 70° C. for 4 h. The reaction mixture was concentrated to remove MeOH. The mixture was poured into 1:1 hexane / EtOAc, washed with 50% brine, dried over $Na_2SO_4$, filtered, and concentrated to dryness. Purification by flash chromatography over $SiO_2$ using 23% EtOAc in hexanes to 28% EtOAc in hexane as the gradient eluant afforded 0.79 g (82%) of the title product of this example as a white solid. MS: 371 $(M-17)^+$.

Example 15

2-Phenanthrenecarbonitrile, 4b,5,6,7,8,8a,9,10-octahydro-7-hydroxy-4b-(phenylmethyl)-7-(1-propynyl)-, [4bS-(4bα,7α,8aβ)]-

A stirring mixture of 1.0 g of the title product of Example 13, 0.4 g of tetrakis(triphenylphosphine)palladium(0), and 0.17 g of zinc(II)cyanide in 9.5 mL of 1-methyl-2-pyrrolidinone (NMP) under nitrogen was heated to 90° C. for 4 h. The reaction mixture was poured into sat. $NaHCO_3$, filtered through Celite®, and extracted with EtOAc. The organic layer was dried over $Na_2SO_4$, filtered, and concentrated to dryness. Purification by flash chromatography over $SiO_2$ using 20% EtOAc in hexanes to 30% EtOAc in hexanes as the gradient eluant afforded 0.64 g (86%) of the title product of this example as a white solid. MS: 338 $(M-17)^+$.

Example 16

2-Phenanthrenol, 1,2,3,4,4a,9,10,10a-octahydro-4a-(phenylmethyl)-2-(1-propynyl)-7-(2-pyridinyl)-, [2R-(2α,4aα,10aβ)]-

Nitrogen gas was bubbled through a solution 300 mg of the title product of Example 13, 70 mg of 1,1'-bis (diphenylphosphino)ferrocene, and 28 mg of palladium acetate in THF for 5 min. Under nitrogen atmosphere, the solution was cooled to −78° C. and 3.78 mL of 0.5 M bromo-2-pyridyl zinc in THF was added. The solution was warmed to RT then heated to 70° C. overnight. After cooling to RT, sat. $NH_4Cl$ was added and the resultant mixture was extracted with EtOAc, dried over $Na_2SO_4$, filtered, and concentrated to dryness. Purification by flash chromatography over $SiO_2$ using 20% EtOAc in hexanes as the eluant afforded 173 mg (67%) of the title product of this example as a white solid. MS: 408 $(M+1)^+$.

Example 17

2-Phenanthrenecarboxylic acid, 4b,5,6,7,8,8a,9,10-octahydro-7-hydroxy-4b-(phenylmethyl)-7-(1-propynyl)-, [4bS-(4bα,7α,8aβ)]-

To a stirring solution of 170 mg of the title product of Example 14 in 4 mL of THF was added 0.26 mL of 2 N KOH and the resultant solution was heated to reflux for 3 days. An additional 0.75 mL of 2 N KOH was added and the mixture was heated to reflux overnight. The reaction mixture was cooled to RT, diluted with a small amount of water, and washed with diethyl ether. The aqueous layer was acidified with 2N HCl and extracted with EtOAc. The organic layer was dried over $Na_2SO_4$, filtered, and concentrated to dryness to yield 155 mg of the title product of this example as an off-white solid. MS: 357 $(M-17)^+$.

Example 18

2-Phenanthrenecarboxamide, 4b,5,6,7,8,8a,9,10-octahydro-7-hydroxy-N-[3-(1H-imidazol-1-yl) propyl]-4b-(phenylmethyl)-7-(1-propynyl)-,[4bS-(4bα,7α,8aβ)]-

To a stirring solution of 1-(3-aminopropyl)imidazole in 1 mL of dichloromethane at 0° C. under $N_2$ was added 0.1 mL of 2.0 M trimethylaluminum in hexane. The mixture was stirred at 0° C. for 20 min. then at RT for 1 h. To this mixture was added 20 mg of the title compound of Example 14 in 1 mL of dichloromethane. The mixture was heated to reflux for 6 h then removed from the heat and stirred at RT for 3 days. To the reaction mixture was added 1 N HCl dropwise until the aqueous layer was approximately pH 4. The resultant mixture was extracted with EtOAc, dried over $Na_2SO_4$, filtered, and concentrated to dryness. Purification by flash chromatography over $SiO_2$ using 5% MeOH in dichloromethane to 10% MeOH in dichloromethane as the gradient eluant afforded 22 mg (88%) of the title product of this example as a white solid. MS: 483 $(M+1)^+$.

Example 19

2-Phenanthrenemethanol, 4b,5,6,7,8,8a,9,10-octahydro-7-hydroxy-α,α-dimethyl-4b-(phenylmethyl)-7-(1-propynyl)-, [4bS-(4bα,7α,8aβ)]-

To a stirring solution of 100 mg of the title compound of Example 14 in 2 mL of THF at 0° C. under $N_2$ was added 0.77 mL of 1 M methyl magnesium bromide in butyl ether. The mixture was stirred at 0° C. for 2 h, warmed to RT and stirred an additional 1 h. To the reaction mixture was added 1.2 mL of 1 M methyl magnesium bromide in butyl ether and the resultant mixture was stirred at RT for 1 h. Sat. $NH_4Cl$ was added and the resultant mixture was extracted with EtOAc, dried over $Na_2SO_4$, filtered, and concentrated to dryness. Purification by flash chromatography over $SiO_2$ using 20% EtOAc in hexanes to 30% EtOAc in hexanes as the gradient eluant afforded 80.5 mg of the title product of this example as a white solid. MS: 371 $(M-17)^+$.

Example 20

2-Phenanthrenemethanol, 4b,5,6,7,8,8a,9,10-octahydro-7-hydroxy-4b-(phenylmethyl)-7-(1-propynyl)-, [4bS-(4bα,7α,8aβ)]-

To a stirring solution of 50 mg of the title compound of Example 14 in 2 mL of dichloromethane at −78° C. under $N_2$ was added 0.39 mL of 1 M diisobutylaluminum hydride in hexane and the resultant mixture was stirred for 35 min. Methanol (10 drops) was added dropwise to the reaction mixture followed by 2 mL of sat. Rochelle's salt. The mixture was extracted with dichoromethane. The organic layer was washed with $H_2O$ and brine, dried over $Na_2SO_4$, filtered, and concentrated to dryness. The resultant solid was washed with a small amount of EtOAc to afford 18 mg of the title product of this example as a white solid. MS: 343 $(M-17)^+$.

Example 21

2-Phenanthrenemethanol, 4b,5,6,7,8,8a,9,10-octahydro-7-hydroxy-4b-(phenylmethyl)-7-(1-propynyl)-, α-methanesulfonate, [4bS-(4bα,7α,8aβ)]-

To a stirring solution of 20 mg of the title product of Example 20 (which was prepared by procedures described in Example 20) in 0.5 mL of THF at 0° C. under $N_2$ was added 0.017 mL of methanesulfonyl chloride and 0.02 mL of diisopropylethylamine. After 3 h, the reaction mixture was diluted with EtOAc, washed with $H_2O$ and brine, dried over $Na_2SO_4$, filtered, and concentrated to give 18 mg of the title product of this example as a yellow solid. $^1$H NMR (400 MHz, $C_6D_6$) δ 4.79 (s, 2H).

Example 22

2-Phenanthrenol, 7-(azidomethyl)-1,2,3,4,4a,9,10,10a-octahydro-4a-(phenylmethyl)-2-(1-propynyl)-, [2R-(2α,4aα,10aδ)]-

The title product of Example 21 (18 mg) and 20 mg of sodium azide in 0.5 mL of DMF were heated to 100° C. under $N_2$ for 3 h. The reaction mixture was cooled to RT, diluted with EtOAc, washed with $H_2O$ and brine, dried over $Na_2SO_4$, filtered, and concentrated to dryness. Purification by flash chromatography over $SiO_2$ using 20% EtOAc in hexanes as the eluant afforded 18 mg of the title product of this example as a white solid. IR (neat) 2098 $cm^{-1}$; $^1$H NMR (400 MHz, $C_6D_6$) δ 4.24 (s, 2H).

Example 23

2-Phenanthrenol, 7-(aminomethyl)-1,2,3,4,4a,9,10,10a-octahydro-4a-(phenylmethyl)-2-(1-propynyl)-, [2R-(2α,4aα,10aβ)]-

To a stirring solution of 18 mg of the title product of Example 22 in 1 mL of 2: 1:1 THF: MeOH: $H_2O$ was added 25 mg of triphenylphosphine and the resultant mixture stirred at RT for 1.5 h. The reaction mixture was concentrated to a white residue. To this residue was added diethyl ether and the resultant mixture was extracted with 1 N HCl. The aqueous layer was taken to pH greater than 10 by the addition of 15% NaOH, extracted with EtOAc, dried over $Na_2SO_4$, filtered, and concentrated to dryness. Purification by flash chromatography over $SiO_2$ using 5% MeOH in dichloromethane to 50% MeOH in dichloromethane with 1% triethylamine as the gradient eluant afforded 10 mg of the title product of this example as a white solid. MS: 360 $(M+1)^+$.

Example 24

2-Phenanthrenol, 1,2,3,4,4a,9,10,10a-octahydro4a-(phenylmethyl)-2-(1-propynyl)-7-(1H-tetrazol-5-yl)-, [2R-(2α,4aα,10aβ)]-

To a stirring solution of 42 mg of the title compound of Example 15 in 1 mL of toluene under $N_2$ was added 4.7 g of dibutyltin oxide and 0.032 mL of trimethylsilylazide. The resultant mixture was stirred at 90° C. for 7 days then at RT for 7 additional days. The reaction mixture was concentrated in vacuo, dissolved in MeOH, and concentrated in vacuo. The residue was dissolved in EtOAc, washed with sat. $NaHCO_3$, dried over $Na_2SO_4$, filtered, and concentrated to dryness. Purification by flash chromatography over $SiO_2$ using 10% MeOH in dichloromethane as the eluant afforded 4 mg of the title product of this example as a white solid. MS: 399 $(M+1)^+$.

Example 25

2-Phenanthrenecarboxamide, 4b,5,6,7,8,8a,9,10-octahydro-7-hydroxy-N-methoxy-N-methyl-4b-(phenylmethyl)-7-(1-propynyl)-, [4bS-(4bα,7α,8aβ)]-

To a stirring solution of 168 mg of the title compound of Example 17 (which was prepared by procedures described in Example 17) dichloromethane was added sequentially 53 mg of N,O-dimethylhydroxylamine hydrochloride, 172 mg of 1-(3-dimethylaminopropyl)-3-ethylcarbodiimide hydrochloride, 121 mg of hydroxybenzotriazole hydrate, and 110 mg of 4-dimethylaminopyridine at RT under $N_2$.

The resultant mixture was stirred at RT overnight, poured into 2 N HCl, and extracted with EtOAc. The organic layer was washed sequentially with 2 N HCl, $H_2O$, and sat. $NaHCO_3$, dried over $Na_2SO_4$, filtered, and concentrated to dryness. Purification by flash chromatography over $SiO_2$ using 3% MeOH in dichloromethane as the eluant afforded 134 mg (71%) of the title product of this example as a colorless oil. MS: 418 (M+1)+.

Example 26

1-Propanone,1-[4b,5,6,7,8,8a,9,10-octahydro-7-hydroxy-4b-(phenylmethyl)-7-(1-propynyl)-2-phenanthrenyl]-, [4bS-(4bα,7α,8aβ)]-

To a stirring solution of 119 mg of the title product of Example 25 in 1.5 mL of THF at −78° C. under $N_2$ was added 0.86 mL of 1 M ethyl magnesium bromide in THF. The reaction mixture was stirred at −78° C. for 1 h, 0° C. for 2 h, then RT for 2 h. The reaction mixture was poured into 5% HCl in EtOH and stirred for 5 min. The resultant mixture was poured into brine, and extracted with EtOAc. The organic layer was dried over $Na_2SO_4$, filtered, and concentrated to dryness. Purification by flash chromatography over $SiO_2$ using 15% EtOAc in hexanes to 20% EtOAc in hexane as the gradient eluant afforded 49.5 mg (48%) the title product of this example as a white solid. MS: 387 (M+1)+.

Example 27

2-Phenanthrenemethanol, α-ethyl-4b,5,6,7,8,8a,9,10-octahydro-7-hydroxy-4b-(phenylmethyl)-7-(1-propynyl)-, [4bS-(4bα,7α,8aβ)]-

To a stirring solution of 32.3 mg of the title product of Example 26 in 0.8 mL of MeOH was added 3.2 mg of $NaBH_4$ and the resultant mixture stirred at RT for 2 days. An additional 2 mg of $NaBH_4$ was added and the reaction mixture was heated to reflux for 2 h. After cooling to RT, $H_2O$ was added and the mixture concentrated in vacuo to remove MeOH. The resultant mixture was extracted with EtOAc, dried over $Na_2SO_4$, filtered, and concentrated to dryness. Purification by flash chromatography over $SiO_2$ using 15% EtOAc in hexanes as the eluant afforded 24 mg of the title product of this example as a colorless oil. MS: 371 (M−17)+.

Example 28

Carbamic acid, [4b,5,6,7,8,8a,9,10-octahydro-7-hydroxy-4b-(phenylmethyl)-7-(1-propynyl)-2-phenanthrenyl]-, 1,1-dimethylethyl ester, [4bS-(4bα, 7α,8aβ)]-

A solution of 124 mg of the title compound of Example 17, 91 mg of diphenylphosphoryl azide, and 0.046 mL of triethylamine in 1mL of t-butanol was heated to reflux for 16 h. The solution was concentrated in vacuo and the resultant residue was dissolved in EtOAc. The EtOAc solution was washed with 5% citric acid, $H_2O$, sat. $NaHCO_3$, and brine, dried over $Na_2SO_4$, filtered, and concentrated to dryness. Purification by flash chromatography over $SiO_2$ using 30% EtOAc in hexanes to 50% EtOAc in hexanes as the gradient eluant afforded 34.1 mg of the title product of this example as a white solid. MS: 328 (M−17)+.

Example 29

2-Phenanthrenol, 7-amino-1,2,3,4,4a,9, 10,10a-octahydro-4a-(phenylmethyl)-2-(1-propynyl)-, [2R-(2α,4aα,10aβ)]-

To a stirring solution of 20 mg of the title product of Example 28 in 0.5 mL of dichloromethane was added 0.07 mL of trifluoroacetic acid. The solution was stirred at RT for approximately 1.5 h. Sat. $NaHCO_3$ was added to the solution. The resultant mixture was extracted with EtOAc, washed with brine, dried over $Na_2SO_4$, filtered, and concentrated to dryness. Purification by flash chromatography over $SiO_2$ using 20% EtOAc in hexanes as the eluant afforded 7.5 mg of the title product of this example as a white solid. MS: 328 (M+1)+.

Example 30

2-Phenanthrenecarboxamide, 4b-(2,3-dihydroxypropyl)-4b, 5,6,7,8,8a,9,10-octahydro-7-hydroxy-7-(1-propynyl)-, [4bS-(4bα,7α,8aβ)]-

To a stirring suspension of 303 mg of 2-phenanthrenecarboxamide, 4b,5,6,7,8,8a,9,10-octahydro-7-hydroxy-4b-(2-propenyl)-7-(1-propynyl)-, [4bS-(4bα,7α, 8aβ)]- in 13.5 mL of dioxane and 3.3 mL of $H_2O$ was added 186 mg of 4-methylmorpholine-N-oxide, 0.008 mL of pyridine, and 0.47 mL of 2.5 wt. % $OsO_4$ in t-butanol and the mixture was stirred at RT overnight. To this mixture was added 1:1 sat. $NaHCO_3$ and sat. $NaHSO_3$. The resultant mixture was extracted with EtOAc, dried over $Na_2SO_4$, filtered, and concentrated to afforded 292 mg of the title product of this example as a white solid. MS: 358 (M+1)+.

Example 31

2-Phenanthrenecarboxamide, 4b,5,6,7,8,8a,9,10-octahydro-7-hydroxy-4b-[(2-oxo-1,3-dioxolan-4-yl) methyl]-7-(1-propynyl)-, [4bS-(4bα,7α,8aβ)]-

To a stirring solution of 90 mg the title product of Example 30 in dichloromethane at 0° C. under $N_2$ was added 45 mg of carbonyidiimidazole. The reaction mixture was warmed to RT and stirred for 3 h. The mixture was concentrated to dryness and purified by flash chromatography over $SiO_2$ using 3% MeOH in dichloromethane to 5% MeOH in dichloromethane as the gradient eluant to afford 46 mg of the title product of this example as a white solid. MS: 384 (M+1)+.

Example 32

4a(2H)-Phenanthreneacetaldehyde, 2-(chloroethynyl)-1, 3,4,9,10,10a-hexahydro-2,7-dihydroxy-, [2R-(2α,4aα, 10aβ)]-

To a stirring solution of 1.77 g of the title compound of Example 172, below, in 100 mL of dioxane and 25 mL of $H_2O$ was added 1.11 g of 4-methylmorpholine-N-oxide, 0.045 mL pyridine, and 2.8 mL of 2.5 wt. % $OsO_4$ in t-butanol and the reaction mixture stirred for 6 h. To this mixture was added 12 g of $NaIO_4$ and the resultant mixture was stirred overnight. The reaction mixture was poured into $H_2O$ and extracted with EtOAc. The organic layer was dried over $Na_2SO_4$, filtered, and concentrated to dryness. Purification by flash chromatography over $SiO_2$ using 30% EtOAc in hexanes as the eluant afforded 1.04 g of the title product of this example as a white solid. $^1H$ NMR (400 MHz, $D_6$-acetone) δ 4.8 (s, 2H).

Example 33

2,7-Phenanthrenediol, 2-(chloroethynyl)-1,2,3,4,4a, 9,10,10a-octahydro-4a-[2-(1-piperidinyl)ethyl]-, [2R-(2α,4aα,10aβ)]-

To a stirring solution of 100 mg of the title product of Example 32 in 1.5 mL of AcOH was added 0.062 mL of piperidine and 446 mg of $Na_2SO_4$ and the resultant mixture was stirred for 15 min. To this mixture was added 100 mg of $NaHB(OAc)_3$ in two portions and the resultant mixture was stirred for 1.5 h. The mixture was cooled to 0° C. and sat. $Na_2CO_3$ added until the pH of the mixture was approximately 8 to 9. The reaction mixture was extracted with EtOAc, dried over $Na_2SO_4$, filtered, and concentrated to dryness. Purification by flash chromatography over $SiO_2$ using 5% MeOH in dichloromethane to MeOH as the gradient eluant afforded 95 mg of the title product of this example as a white solid. MS: 388 $(M+1)^+$.

Example 34

4a(2H)-Phenanthreneacetaldehyde, 2-(chloroethynyl)-1, 3,4,9,10,10a-hexahydro-2,7-dihydroxy-, oxime, [2R-[2α,4aα, 10aβ]]-

To a stirring solution of 150 mg of the title product of Example 32 in 6 mL of MeOH was added 147 mg of $KHCO_3$ and 141 mg of hydroxylamine hydrochloride. The reaction mixture was heated to reflux for 3 h then cooled to RT and concentrated to dryness. Purification by flash chromatography over $SiO_2$ using 5% MeOH in dichloromethane to 8% MeOH in dichloromethane as the gradient eluant afforded 64 mg of the title product of this example as a white solid. MS: 316 $(M-17)^+$.

Example 35

2,7-Phenanthrenediol, 2-(chloroethynyl)-1,2,3,4,4a, 9,10,10a-octahydro-4a-(3-phenyl-2-propenyl)-, [2R-[2α,4aα(E),10aβ]]-

To a stirring solution of 410 mg of diethyl benzylphosphonate in 5 mL of THF at −78° C. under $N_2$ was added 0.65 mL of 2.5 M butyl lithium in hexane. The reaction mixture was warmed to 0° C. and stirred for 1 h. To the reaction mixture was added 104 mg of the title product of Example 32 in 2 mL of THF and the mixture was stirred an additional 3.5 h. The reaction mixture was poured into sat. $NH_4Cl$, extracted with EtOAc, dried over $Na_2SO_4$, filtered, and concentrated to dryness. Purification by flash chromatography over $SiO_2$ using 10% EtOAc in hexanes to 20% EtOAc in hexane as the gradient eluant afforded 60 mg of the title product of this example as a white solid. MS: 375 $(M-17)^+$.

Example 36

2-Butenoic acid, 4-[2-(chloroethynyl)-1,3,4,9,10, 10a-hexahydro-2,7-dihydroxy-4a(2H)-phenanthrenyl]-, [2R-[2α,4aα(E), 10aβ]]-

To a stirring solution of 2.2 g of the title compound of Example 183, below, in 40 mL of THF was added 11 mL of 2 N KOH and the resultant solution was heated to reflux for 4 h. The reaction mixture was cooled to RT, diluted with a small amount of water, and washed with diethyl ether. The aqueous layer was acidified with 2N HCl and extracted with EtOAc, dried over $Na_2SO_4$, filtered, and concentrated to dryness to yield 1.55 g of the title product of this example as an off-white solid. $^1$H NMR (400 MHz, $CD_3OD$) δ 5.66 (d, 1H, J=15), 6.67–6.80 (m, 1H).

Example 37

Pyrrolidine, 1-[4-[2-(chloroethynyl)-1,3,4,9,10,10a-hexahydro-2,7-dihydroxy-4a(2H)-phenanthrenyl]-1-oxo-2-butenyl]-, [2R-[2α, 4aα(E),10aβ]]- (Formula F-12: $R_2$ is OH, $R_3$ is chloroethynyl, $R_5$ is H, $R_8$ is H, $R_9$ is H, $R_{10}$ is OH, $R_7$, $R_{14}$, $R_{15}$, $R_{16}$ are each H, m is 2, $R_{12}$ and $R_{13}$ taken together with N are pyrrolidinyl) Refer to Scheme F.

To a stirring solution of 168 mg of the title product of Example 36 in dichloromethane was added sequentially 0.67 mL of pyrrolidine, 140 mg of dicyclohexylcarbodiimide, 91 mg of hydroxybenzotriazole hydrate, and 10 mg of 4-dimethylaminopyridine at RT under $N_2$. The resultant mixture was stirred at RT overnight. The mixture was diluted with MeOH, filter through Celite®, and concentrated to dryness. Purification by flash chromatography over $SiO_2$ using 90% acetonitrile and 10% dichloromethane with 0.5% to 1% $H_2O$ as the gradient eluant afforded 90 mg of the title product of this example as a white solid. MS: 414 $(M+1)^+$.

Example 38

4H-Benzo[a]quinolizin-4-one, 1,2,3,6,7,11b-hexahydro-9-hydroxy-11b-(phenylmethyl)-

A solution of 973 mg of 2-(3-hydroxyphenyl)ethylamine hydrobromide and 920 mg of 5-oxo-6-phenyl-hexanoic acid in 3 mL of isopropanol was heated to 210° C. open to the air for 5 h. The resultant residue was purified by flash chromatography over $SiO_2$ using 5% MeOH in dichloromethane to 20% MeOH in dichloromethane as the gradient eluant to afford 774 mg (56%) of the title product of this example as an off-white solid. MS: 307 $(M+1)^+$.

Example 39

4H-Benzo[a]quinolizin-4-one, 1,2,3,6,7,11b-hexahydro-9-(phenylmethoxy)-11b-(phenylmethyl)-

To a stirring solution of 770 mg of the title product of Example 38 in DMF was added sequentially 3 mL of 1 M potassium t-butoxide in t-butanol followed by 0.35 mL of benzyl bromide. The reaction mixture was heated to 60° C. for 2 h. The mixture was cooled to room temperature and 1 N HCl was added. The resultant mixture was extracted with EtOAc, dried over $Na_2SO_4$, filtered, and concentrated to dryness. Purification by flash chromatography over $SiO_2$ using 60% EtOAc in hexanes to 100% EtOAc as the gradient eluant afforded 797 mg (80%) of the title product of this example as an off-white solid. MS: 398 $(M+1)^+$.

Example 40

2H-Benzo[a]quinolizine-3-carboxylic acid, 1,3,4,6, 7,11b-hexahydro-4-oxo-9-(phenylmethoxy)-11b-(phenylmethyl)-3-propyl-, methyl ester, (3-cis)-

To a stirring solution of 0.61 mL of diisopropylamine in 9 mL of THF at 0° C. under $N_2$ was added 1.75 mL of 2.5 M n-butyl lithium in hexane. The resultant solution was stirred for 10 min. at 0° C. then cooled to −78° C. To this solution was added 790 mg of the title product of Example 39 in 10 mL of THF dropwise over 30 min. The resultant solution was stirred at −78° C. for 30 min., warmed to 0° C. for 2 h, then cooled to −78° C. To this solution was added 0.17 mL of methyl chloroformate. The resultant mixture was stirred for 30 min at −78° C. then warmed to RT and stirred for 1 h. To the reaction mixture was added 0.42 mL of propyl iodide and the resultant mixture was stirred at 0° C. for 1 h then warmed to RT for 14 h. To the reaction mixture was added an additional 0.5 mL of propyl iodide and the resultant mixture heated to 55° C. for 4 h. The mixture was poured into EtOAc and washed with 1 N HCl, $H_2O$, sat $NaHCO_3$, and brine. The organic solution was dried over $Na_2SO_4$, filtered, and concentrated to dryness. Purification by flash chromatography over $SiO_2$ using 40% EtOAc in hexanes as the eluant afforded 768 mg (78%) of the title product of this example as an off-white solid. MS: 498 $(M+1)^+$.

Example 41

2H-Benzo[a]quinolizine-3-methanol, 1,3,4,6,7,11b-hexahydro-9(phenylmethoxy)-11b-(phenylmethyl)-3-propyl-, (3-cis)-

To a stirring solution of 50 mg of the title product of Example 40 in 1 mL of THF was added 3 mL of 1.0 M lithium aluminum hydride in THF. The reaction mixture was heated to reflux under $N_2$ overnight. The mixture was cooled to 0° C. and 0.12 mL $H_2O$, 0.12 mL 15% NaOH, and 0.36 mL $H_2O$ was added slowly and sequentially with stirring to the reaction mixture. After 5 min of rapid stirring, the mixture was filtered through Celite® and concentrated to dryness. Purification by flash chromatography over $SiO_2$ using 3% MeOH in dichloromethane to 10% MeOH in dichloromethane as the gradient eluant afforded 36 mg (79%) of the title product of this example as a white solid. MS: 456 $(M+1)^+$.

Example 42

2H-Benzo[a]quinolizine-3-methanol, 1,3,4,6,7,11b-hexahydro-9-hydroxy-11b-(phenylmethyl)-3-propyl-, (3-cis)-

To a stirring solution of 31 mg of the title product of Example 41 in dichloromethane at −78° C. under $N_2$ was added 0.05 mL of $BBr_3$ and the reaction mixture allowed to warm to RT. The reaction mixture was cooled to −78° C. and MeOH was added dropwise to quench the reaction. The mixture was concentrated to dryness, dissolved in MeOH and concentrated to dryness. Purification by flash chromatography over $SiO_2$ using 5% MeOH in dichloromethane with 0.1% triethylamine to 10% MeOH in dichloromethane with 0.1% triethylamine as the gradient eluant afforded a white solid. This solid was partitioned between EtOAc and sat. $NaHCO_3$. The EtOAc layer was dried over $Na_2SO_4$, filtered, and concentrated to afford 10 mg of the title product of this example as a white solid. $^1H$ NMR (400 MHz, $CD_3OD$) δ 2.45 (d, 1H, J=12), 2.66 (d, 1H, J=12).

Example 43

2H-Benzo[a]quinolizine-3-carboxylic acid, 1,3,4,6,7,11b-hexahydro-9-hydroxy-4-oxo-11b-(phenylmethyl)-3-propyl-, methyl ester, (3-cis)-

A mixture of 50 mg of the title product of Example 40, 63 mg of ammonium formate, and 20 mg of 20% palladium hydroxide on carbon in 5 mL of MeOH was heated to reflux for 3 h. The mixture was cooled to RT, filtered through Celite®, and concentrated to dryness. Purification by flash chromatography over $SiO_2$ using 50% EtOAc in hexanes as the eluant afforded 41 mg of the title product of this example as a white solid. MS: 408 $(M+1)^+$.

Example 44

4H-Benzo[a]quinolizin-4-one, 1,2,3,6,7,11b-hexahydro-3-(hydroxymethyl)-9-(phenylmethoxy)-11b-(phenylmethyl)-3-propyl-, (3-cis)-

To a stirring solution of 50 mg of the title product of Example 40 in 5 mL of THF under $N_2$ was added 10 mg of lithium borohydride. The resultant mixture was stirred for 2 h at RT then warmed to 40° C. and stirred an additional 2 h. After cooling to RT, sat. ammonium chloride was added and the mixture was extracted with EtOAc. The EtOAc solution was dried over $Na_2SO_4$, filtered, and concentrated to dryness. Purification by flash chromatography over $SiO_2$ using 40% EtOAc in hexanes to 80% EtOAc in hexanes as the gradient eluant afforded 17 mg of the title product of this example as a white solid. MS: 470 $(M+1)^+$.

Example 45

2(1H)-Phenanthrenone, 7-(acetyloxy)-3,4,4a,9,10,10a-hexahydro-4a-(phenylmethyl)-, (4aS-trans)-

To a stirring solution of 54 mg of the title compound of Example 6 in 2 mL of dichloromethane was added 0.037 mL of triethylamine and 0.015 mL of acetyl chloride and the resultant mixture was stirred overnight. The mixture was poured into 1 N HCl and extracted with dichloromethane. The dichloromethane solution was dried over $Na_2SO_4$, filtered, and concentrated to dryness. Purification by flash chromatography over $SiO_2$ using 20% EtOAc in hexanes as the eluant afforded 55 mg of the title product of this example. $^1H$ NMR (400 MHz, $CDCl_3$) δ 2.27 (s, 3H)

Example 46

1H-Benz[e]indene-2-carboxylic acid, 7-(acetyloxy)-2,3,3a,4,5,9b-hexahydro-9b-(phenylmethyl)-, [2R-(2α,3aα,9bβ)]-

To a stirring solution of 50 mg of the title product of Example 45 in 1 mL of dichloromethane was added 75 mg of thallium trinitrate ● $3H_2O$ under $N_2$ and the mixture stirred overnight. To the reaction mixture was added an additional 75 mg of thallium trinitrate ● $3H_2O$ and the mixture was again stirred overnight. The mixture was filtered through Celite® and concentrated to afford the title product of this example as an off-white solid. MS: 363 $(M-1)^+$.

Example 47

1H-Benz[e]indene-2-carboxylic acid, 2,3,3a,4,5,9b-hexahydro-7-hydroxy-9b-(phenylmethyl)-, methyl ester, [2R-(2α,3aα,9bβ)]-

Continuing the procedure began in Example 46, a solution of the title product of Example 46 in methanol and catalytic sulfuric acid was heated to reflux under a soxlet extractor filled with 3 angstroms molecular sieves for 4 h. After cooling to RT, a small amount of solid $NaHCO_3$ was added to the solution, and it was concentrated to dryness. Purification by flash chromatography over $SiO_2$ using 20% EtOAc in hexanes as the eluant afforded 28 mg of the title product of this example. MS: 335 $(M-1)^+$.

Example 48

2,7-Phenanthrenediol, 1,2,3,4,4a,9,10,10a-octahydro-4a-(phenylmethyl)-2-(1H-1,2,4-triazol-1-ylmethyl)-, [2R-(2α,4aα, 10aβ)]-

A solution of 50 mg of the title compound of Example 79 below (which was prepared by procedures described in Example 79), 54 mg of 1,2,4-triazole, and 108 mg of potassium carbonate in 4 mL of DMF was heated to 90° C. for 2 h. After cooling to RT, sat. ammonium chloride was added and the resultant mixture was extracted with EtOAc. The EtOAc solution was dried over $Na_2SO_4$, filtered, and concentrated to dryness. Purification by flash chromatography over $SiO_2$ using 5% MeOH in dichloromethane as the eluant afforded 50 mg of the title product of this example as a white solid. MS: 391 $(M+1)^+$.

Example 49

2(1H)-Phenanthrenone, 4a-(2-butenyl)-3,4,4a,5,8,9,10,10a-octahydro-7-methoxy-,[4aS-[4aα(E), 10aβ]]-

Ammonia (200 mL) was condensed into a round bottom flask at −78° C. equipped with a dry ice reflux condenser at −78° C. and a mechanical stirrer. To this flask was added 80 mL of t-butanol followed by lithium wire until the solution turned dark blue. A solution of 5 g of 2(3H)-phenanthrenone, 4a-(2-butenyl)-4,4a,9,10-tetrahydro-7-methoxy-, [S-(E)]- in 80 mL of THF was added to the mixture slowly in order to keep the reaction a dark blue. As the blue color dissipated, a small amount of lithium wire was added to the mixture to regenerate the blue color. The total amount of lithium added to the reaction mixture did not exceed 4 g. After the complete addition of the starting compound the reaction was stirred an additional 40 min, then 100 mL of sat. ammonium chloride was added and immediate dissipation of the blue color was observed. $H_2O$ was added to the mixture and it was extracted with EtOAc, dried over $Na_2SO_4$, filtered, and concentrated to dryness. The crude product was purified by flash chromatography over $SiO_2$ using 10% EtOAc to 25% EtOAc in hexanes as the gradient eluant to afford 2.0 g of the title product of this example as a white solid. MS: 287 $(M+1)^+$.

Example 50

2-Phenanthrenol, 4a-(2-butenyl)-1,2,3,4,4a,5,8,9,10, 10a-decahydro-7-methoxy-2-(1-propynyl)-, [2R-[2α,4aα(E),10aβ]]-

To a stirring solution of 200 mL of THF saturated with propyne gas at 0° C. was added 16.4 mL of 2.5 M n-butyl lithium in hexane and the resultant mixture stirred under nitrogen atomosphere for 20 min. A solution of 1.96 g of the title product of Example 49 in 50 mL of THF was added dropwise, and the reaction mixture was warmed to RT and stirred for 40 min. Saturated, aqueous ammonium chloride was added, and the mixture was extracted with EtOAc, dried over $Na_2SO_4$, filtered, and concentrated to dryness. Purification by flash chromatography over $SiO_2$ using 10% EtOAc in hexanes to 15% EtOAc in hexanes as the eluant afforded 879 mg of the title product of this example as a white solid. MS: 327 $(M+1)^+$.

Example 51

2(3H)-Phenanthrenone, 4b-(2-butenyl)-4, 4a,4b,5,6, 7,8,8a,9,10-decahydro-7-hydroxy-7-(1-propynyl)-, [4aR-[4aα,4bβ(E),7β,8aα]]- and 2(1H)-Phenanthrenone, 4b-(2-butenyl)-3,4,4b,5,6,7,8,8a,9, 10-decahydro-7-hydroxy-7-(1-propynyl)-, [4bS-[4bα(E),7α,8aβ]]-

Continuing the procedures began in Example 50, to a stirring solution of the title product of Example 50 in 20 mL of THF was added 1 mL of 2 N HCl. After 3 h at RT, sat. $NaHCO_3$ was added and the mixture was extracted with EtOAc. The organic layer was dried over $Na_2SO_4$, filtered, and concentrated to dryness. Purification by flash chromatography over $SiO_2$ using 20% EtOAc in hexanes to 35% EtOAc in hexanes as the gradient eluant afforded 154 mg of the second listed title product of this example as a white solid. MS: 313 $(M+1)^+$. Further purification of lower Rf material by flash chromatography over $SiO_2$ using 3% acetone in dichloromethane to 4% acetone in dichloromethane as the gradient eluant afforded 215 mg of the first listed title product of this example as a white solid. MS: 313 $(M+1)^+$.

Example 52

2,7-Phenanthrenediol, 1,2,3,4,4a,9,10,10a-octahydro-4a-[[4-[(methylsulfonyl) oxy]phenyl] methyl]-2-propyl-, 7-methanesulfonate, (4aS,10aS)-; and 2,7-Phenanthrenediol, 1,2,3,4,4a,9, 10,10a-octahydro-4a-[[4-[(methylsulfonyl)oxy] phenyl] methyl]-2-propyl-, (4aS,10aS)-

To a stirring solution of 50 mg of 2,7-Phenanthrenediol, 1,2,3,4,4a,9,10,10a-octahydro-4a-[(4-hydroxyphenyl) methyl]-2-propyl-, (4aS ,10aS)- in 0.039 mL of triethylamine and 3 mL of anhydrous THF was added slowly 0.011 mL of $MeSO_2Cl$ at 0° C. under $N_2$ atmosphere. The reaction was allowed to warm to RT for 2 h, then quenched with water. The mixture was extracted with EtOAc (X3), washed with brine, dried over $Na_2SO_4$, filtered and concentrated to dryness. Purification by flash chromatography over $SiO_2$ using 25% EtOAc in hexanes to 45% EtOAc in hexanes as the gradient eluant afforded 18 mg of the second listed title product of this example and 35 mg of the first listed title product of this example as white powder. MS m/z 540 $(M+NH_4)^+$.

Example 53

1-Piperazinecarboxamide, N-[4-[[1,3,4,9,10,10a-hexahydro-2,7-dihydroxy-2-(1-propynyl)-4a(2H)-phenanthrenyl]methyl] phenyl]-4-methyl-,(4aS, 10aR)-

To a stirring solution of 97 mg of carbamic acid, [4-[[1, 3,4,9,10,10a-hexahydro-2,7-dihydroxy-2-(1-propynyl)-4a (2H)-phenanthrenyl]methyl]phenyl]-, 1,1-dimethylethyl ester, [2R-(2α,4aα,10aβ)]- in 0.078 mL of 1-methylpiperazine and 5 mL of anhydrous THF under $N_2$ atmosphere was added 0.56 mL of 2.5 M n-BuLi and the mixture was heated to 65° C. After 2 h, the reaction was quenched with $NH_4Cl$ (sat), extracted with EtOAc (X3), washed with brine, dried over $Na_2SO_4$, filtered and concentrated to dryness. Purification by flash chromatography over $SiO_2$ using 5% MeOH in $CH_2Cl_2$ as the elutant afforded 40 mg (40%) of the title product of this example as white fluffy powder. MS m/z 472 $(M-Me)^+$.

Example 54

Acetic acid, [4-[[1,3,4,9, 10,10a-hexahydro-2-hydroxy-7-(2-methoxy-2-oxoethoxy)-2-(1-propynyl)-4a(2H)-phenanthrenyl]methyl]phenoxy]-, methyl ester,[2R-(2α,4aα, 10aβ)]-

A solution of 50 mg of 2,7-phenanthrenediol, 1,2,3,4,4a, 9,10,10a-octahydro-4a-[(4-hydroxyphenyl)methyl]-2-(1-propynyl)-, [2R-(2a,4aa, 10ab)]- in 5 mL anhydrous $CH_3CN$, 109.5 mg of $Cs_2CO_3$ and 0.067 mL of methyl bromoacetate was stirred at RT under $N_2$ atmosphere overnight. The reaction was quenched with $NH_4Cl$ (sat.), extracted with EtOAc (X3), washed with brine, dried over $Na_2SO_4$, filtered and concentrated to dryness. Purification by $SiO_2$ preparative TLC using 45% EtOAc in hexanes as the elutant afforded 20 mg (28%) of the title product of this example as white fluffy powder. MS m/z 489 $(M-17)^+$.

Example 55

Acetamide, 2-[4-[[7-(2-amino-2-oxoethoxy)-1,3,4,9, 10,10a-hexahydro-2-hydroxy-2-(1-propynyl)-4a (2H)-phenanthrenyl]methyl]phenoxy]-, [2R-(2α, 4aα, 10aβ)]-

A solution of 17 mg of the title product of Example 54 in 2 mL of $NH_4OH$ (aq), 0.5 mL of toluene and 10 drops of MeOH was heated at 60° C. overnight. The reaction was quenched with $NH_4Cl$ (sat.), extracted with EtOAc (X3), washed with brine, dried over $Na_2SO_4$, filtered and concentrated to dryness. Purification by flash chromatography $SiO_2$ using 2% MeOH in $CH_2Cl_2$ to 4% MeOH in $CH_2Cl_2$ as the elutant afforded 5 mg (30%) of the title product of this example as white fluffy powder. MS m/z 478 $(M+H)^+$.

Example 56

2(1H)-Phenanthrenone, 4a-[[3-(dimethylamino) phenyl]methyl]-3, 4,4a,9, 10,10a-hexahydro-7-hydroxy-, (4aS-cis)-. See also Preparation 5 above.

Example 57

2,7-Phenanthrenediol, 1,2,3,4,4a,9, 10,10a-octahydro-2-(1-propynyl)-4a-[[4-(4H-1,2,4-triazol-4-yl)phenyl]methyl]-, [2R-(2α,4aα, 10aβ)]-

A solution of 50 mg of the title product of Example 776, below, 20 mg of dimethyl formamideazine and 3 mg of p-toluenesulfonic acid in 5 mL of toluene was refluxed overnight. The reaction was quenched with NaHCO$_3$ (sat.), extracted with EtOAc (X3), washed with brine, dried over Na$_2$SO$_4$, filtered and concentrated to dryness. Purification by flash chromatography SiO$_2$ using 1% MeOH in CH$_2$Cl$_2$ to 5% MeOH in CH$_2$Cl$_2$ as the elutant afforded 18 mg (31%) of the title product of this example as white fluffy powder. MS m/z 398 (M−Me)$^+$.

Example 58

4-Morpholinecarboxylic acid, 7-(chloroethynyl)-4b, 5,6,7,8,8a,9,10-octahydro-7-hydroxy-4b-(phenylmethyl)-2-phenanthrenyl ester, (4bS,8aR)-

To a solution of 50 mg of 2,7-phenanthrenediol, 2-(chloroethynyl)-1, 2,3,4,4a,9,10,10a-octahydro-4a-(phenylmethyl)-, [2S-(2α,4aα,10aβ)]-, in 3 mL of anhydrous THF was added 0.019 mL of triethylamine, 1.7 mg of DMAP and followed by slow addition of 0.020 mL of 4-morpholinecarbonyl chloride at 0° C. under N$_2$ atmosphere. The reaction was warmed up to RT for 4 h and then quenched with NH$_4$Cl (sat.), extracted with EtOAc (X3), washed with brine, dried over Na$_2$SO$_4$, filtered and concentrated to dryness. Purification by flash chromatography SiO$_2$ using 2% EtOAc in hexanes to 30% EtOAc in hexanes as the gradient elutant afforded 57 mg (85%) of the title product of this example as white fluffy powder. MS m/z 480 (M)$^+$.

Example 59

Carbamic acid, [2-(dimethylamino)ethyl]-, 4b-[[3-(dimethylamino) phenyl]methyl]-4b, 5, 6, 7, 8, 8a, 9, 10-octahydro-7-hydroxy-7-(1-propynyl)-2-phenanthrenyl ester, [4bS-(4bα,7α,8aβ)]-

A solution of 68 mg of 2,7-phenanthrenediol, 4a-[[3-(dimethylamino)phenyl] methyl]-1,2,3,4,4a,9, 10, 10a-octahydro-2-(1-propynyl)-, (4aS, 10aR)- in 64 mg of triphosgene, 0.03 mL of triethylamine and 2 mL of anhydrous dichloromethane was stirred at RT for 1.5 h under N$_2$ atmosphere. To the mixture, 0.099 mL of N, N-dimethylethylenediamine was added dropwise and stirred overnight under N$_2$ atmosphere. The reaction was quenched with NH$_4$Cl (sat.), extracted with EtOAc (X3), washed with brine, dried over Na$_2$SO$_4$, filtered and concentrated to dryness. Purification by flash chromatography SiO$_2$ using 100% CHCl$_3$ and 0.1% of triethylamine to 2% EtOH in CHCl$_3$ and 0.1% of triethylamine as the gradient elutant afforded 20 mg (23%) of the title product of this example as white fluffy powder. MS m/z 504 (M+H)$^+$.

Example 60

2-Phenanthrenol, 4a-[[3-(dimethylamino)phenyl] methyl]-1, 2,3,4,4a,9, 10, 10a-octahydro-7-(2-hydroxyethoxy)-2-(1-propynyl)-, [2R-(2α,4aα, 10aβ)]-

To a solution of 76 mg of 2,7-phenanthrenediol, 4a-[[3-(dimethylamino)phenyl] methyl]-1,2,3,4,4a,9,10,10a-octahydro-2-(1-propynyl)-, (4aS, 10aR)- in 3 mL anhydrous DMF was added 1.4 mg of TBAI and 17 mg of ethylene carbonate, and the mixture was heated to 100° C. for 2 h. The reaction was quenched with water, extracted with EtOAc (X3), washed with brine, dried over Na$_2$SO$_4$, filtered and concentrated to dryness. Purification by flash chromatography SiO$_2$ using 5% EtOAc in hexanes and 0.1% of triethylamine to 40% EtOAc in hexanes and 0.1% of triethylamine as the gradient elutant afforded 30 mg (36%) of the title product of this example as white fluffy powder. MS m/z 435 (M+H)$^+$.

Example 61

2-Phenanthrenol, 1,2,3,4,4a,9,10,10a-octahydro-4a-(phenylmethyl)-2-(1-propynyl)-7-[(3-pyrazinyl-1,2, 4-oxadiazol-5-yl) methoxy]-, [2R-(2α,4aα,10aβ)]-

To a solution of 29 mg of acetic acid, [[4b,5,6,7,8,8a,9, 10-octahydro-7-hydroxy-4b-(phenylmethyl)-7-(1-propynyl)-2-phenanthrenyl]oxy]-, methyl ester, [4bS-(4bα, 7α,8aβ)]- and 19.5 mg of pyrazine-2-carboxamide oxime in 3 mL of anhydrous THF was added 24 mg of NaH (60%) and refluxed overnight. The reaction was cooled to RT, filtered and concentrated to dryness. Purification by preparative TLC SiO$_2$ using 5% MeOH in dichloromethane as the elutant afforded 7 mg (20%) of the title product of this example. MS m/z 507 (M+H)$^+$.

Example 62

2-Phenanthrenol, 7-[(5-amino-1H-1,2,4-triazol-3-yl) methoxy]-1, 2,3,4,4a,9,10,10a-octahydro-4a-(phenylmethyl)-2-(1-propynyl)-, (4aS, 10aR)-

To a cooled (0° C.) solution of NaOMe prepared from 7 mg of sodium and 1 mL of anhydrous MeOH was added 40 mg of amino guanidine nitrate. Then 30 mg acetic acid, [[4b,5,6,7,8,8a,9,10-octahydro-7-hydroxy-4b-(phenylmethyl)-7-(1-propynyl)-2-phenanthrenyl]oxy]-, methyl ester, [4bS-(4bα,7α,8aβ)]-in 1 mL of anhydrous MeOH was added dropwise to the resultant mixture and refluxed under N$_2$ atmosphere overnight. The mixture was concentrated to dryness and purified with preparative TLC using 10% MeOH in dichloromethane as the elutant to yield 11 mg of the title product of this example (33%) as white fluffy powder. MS m/z 443 (M+H)$^+$.

Example 63

Acetic acid, [[4b,5,6,7,8,8a,9,10-octahydro-7-hydroxy-4b-(phenylmethyl)-7-(1-propynyl)-2-phenanthrenyl]oxy]-, [4bS-(4bα,7α,8aβ)]-

A solution of 20 mg of acetic acid, [[4b,5,6,7,8,8a,9,10-octahydro-7-hydroxy-4b-(phenylmethyl)-7-(1-propynyl)-2-phenanthrenyl]oxy]-, methyl ester, [4bS-(4bα, 7α,8aβ)]- and 5.36 mg of KOH in 3 mL of MeOH and 0.5 mL of H$_2$O was heated at 80° C. for 4 h. The reaction was cooled to RT, extracted with EtOAc (X3), washed with brine, dried over Na$_2$SO$_4$, filtered and concentrated to dryness. Purification by a plug of SiO$_2$ using 5% MeOH in CH$_2$Cl$_2$ as the elutant afforded 18 mg (93%) of the title product of this example as white fluffy powder. MS m/z 387 (M−17)$^+$.

Example 64

Acetonitrile, [[4b,5,6,7,8,8a,9,10-octahydro-7-hydroxy-4b-(phenylmethyl)-7-(1-propynyl)-2-phenanthrenyl]oxy]-, [4bS-(4bα,7α,8aβ)]-

To a solution of 54 mg of the first listed title product of Example 8 (which was prepared by procedures analogous to those described in Example 8) and 8 mg of 60% NaH in 5 mL of anhydrous $CH_3CN$ was added 0.056 mL bromoacetonitrile under $N_2$ atmosphere. The reaction was heated to 85° C. overnight. The reaction was quenched with $NH_4Cl$ (sat), extracted with EtOAc (X3), washed with brine, dried over $Na_2SO_4$, filtered and concentrated to dryness. Purification by flash chromatography $SiO_2$ using 0.5% acetone in $CH_2Cl_2$ to 1% acetone in $CH_2Cl_2$ as the gradient elutant afforded 46 mg (76%) of the title product of this example as white fluffy powder. MS m/z (M−17)+.

Example 65

2-Phenanthrenol, 7-(2-bromoethoxy)-1,2,3,4,4a,9, 10,10a-octahydro-4a-(phenylmethyl)-2-(1-propynyl)-, [2R-(2α,4aα, 10aβ)]-

To a solution of 5 mg of the first listed title product of Example 8 and 7 mg of 60% NaH in 5 mL of anhydrous $CH_3CN$ was added 0.125 mL 1,2-dibromoethane under $N_2$ atmosphere. The reaction was heated to 85° C. overnight. The reaction was quenched with $NH_4Cl$ (sat.), extracted with EtOAc (X3), washed with brine, dried over $Na_2SO_4$, filtered and concentrated to dryness. Purification by flash chromatography $SiO_2$ using 2% EtOAc in hexanes to 20% EtOAc in hexanes as the gradient elutant afforded 29 mg (44%) of the title product of this example as white fluffy powder. MS m/z 453 (M+H)+.

Example 66

2-Phenanthrenol, 1,2,3,4,4a,9,10,10a-octahydro-4a-(phenylmethyl)-2-(1-propynyl)-7-(1H-tetrazol-5-ylmethoxy)-, [2R-(2α,4aα, 10aβ)]- (Refer to Scheme B: B-7→B-10)

A solution of 0.019 mL of $TMSN_3$ and 0.067 mL of $Me_3Al$ in 5 mL of anhydrous toluene was stirred at 0° C. under $N_2$ atmosphere. To the resultant solution was added 43 mg of the title product of Example 64 in 1 mL of toluene slowly to keep the temperature below 5° C. The reaction was then allowed to warm to RT and heated to 80° C. overnight. The reaction was cooled to 0° C. and quench with 5 mL of 10% HCl and 5 mL of EtOAc. The aqueous phase was acidified with 1 N HCl to pH around 3 and extracted with EtOAc (X3), dried over $Na_2SO_4$, filtered and concentrated to dryness. Purification by flash chromatography $SiO_2$ using 1% MeOH in $CH_2Cl_2$ and a couple of drops of AcOH to 10% MeOH in $CH_2Cl_2$ and a couple of drops of AcOH as the gradient elutant afforded 17 mg (36%) of the title product of this example as white fluffy powder. MS m/z 427 (M−H)+.

Example 67

2-Phenanthrenol, 1,2,3,4,4a,9,10,10a-octahydro-7-[2-(4-methyl-1-piperazinyl)ethoxy]-4a-(phenylmethyl)-2-(1-propynyl)-, [2R-(2α,4aα, 10aβ)]-

To a solution of 30 mg of the title product of Example 65 (which was prepared by procedures described in Example 65), 8 mg of anhydrous $Na_2CO_3$ and 12 mg of NaI in 2 ml of anhydrous DMF was added 0.015 mL of 1-methylpiperazine under $N_2$ atmosphere. The reaction was heated to 60° C. overnight. The reaction was quenched with $NaHCO_3$ (sat.), extracted with EtOAc (X3), washed with brine, dried over $Na_2SO_4$, filtered and concentrated to dryness. Purification by preparative TLC on $SiO_2$ using 5% MeOH in methylene chloride as the elutant afforded 19 mg (60%) of the title product of this example as white fluffy powder. MS m/z 473 (M+H)+.

Example 68

Ethanimidamide, N-hydroxy-2-[[4b,5,6,7,8,8a,9,10-octahydro-7-hydroxy-4b-(phenylmethyl)-7-(1-propynyl)-2-phenanthrenyl]oxy]-, [4bS-(4bα,7α, 8aβ)]-

To a solution of 30 mg of the title product of Example 64 and 22 mg of $K_2CO_3$ in 2 mL of anhydrous EtOH was added 8 mg of $NH_2OH.HCl$ and heated to reflux for 6 h. The reaction was then concentrated to dryness and purified by preparative TLC using 5% MeOH in $CH_2Cl_2$ as the elutant to yield 11 mg of the title product of this example as white powder (34%). MS m/z 419 (M+H)+.

Example 69

2-Phenanthrenol, 7-[[5-[(dimethylamino)methyl]-1, 2,4-oxadiazol-3-yl]methoxy]-1,2,3,4,4a,9,10,10a-octahydro-4a-(phenylmethyl)-2-(1-propynyl)-,[2R-(2α,4aα, 10aβ)]-

A solution of 30 mg of the title product of Example 68 (which was prepared by procedures described in Example 68) and 3 mg of 60% NaH in 3 mL of anhydrous THF was heated to 60° C. for 20 min. The solution was cooled to RT and 0.02 mL of ethyl-N, N-dimethyl glycine was added to the solution. The resultant mixture was heated to reflux for 1 h then cooled to RT, filtered and concentrated to dryness. Purification by preparative TLC using 10% acetone in $CH_2Cl_2$ and 0.05% of $NH_4OH$ as the elutant yielded 4 mg of the title product of this example (11%). MS m/z 486 (M+H)+.

Example 70

1,2,4-Oxadiazol-5(2H)-one, 3-[[[4b,5,6,7,8,8a,9,10-octahydro-7-hydroxy-4b-(phenylmethyl)-7-(1-propynyl)-2-phenanthrenyl]oxy]methyl]-,[4bS-(4bα, 7α,8aβ)]-

To a solution of 30 mg of the title product of Example 68 (which was prepared by procedures described in Example 68), 0.006 mL of pyridine a and 1 mL of anhydrous DMF in 2 mL of xylene was slowly added 0.014 mL of 2-ethyl hexyl chloroformate at 0° C. under $N_2$ atmosphere. After the reaction was stirred for 30 min, it was diluted with water, extracted with EtOAc (X3), washed with brine, dried over $Na_2SO_4$, filtered and concentrated to dryness. The residue was dissolved in xylene and refluxed for 2 days. The mixture was then concentrated to dryness and purified by preparative TLC on $SiO_2$ using 5% MeOH in methylene chloride as the elutant to afford 6 mg (19%) of the title product of this example. MS m/z 443 (M−H)+.

Example 71

1,2,4-Oxadiazole-5(2H)-thione, 3-[[[4b,5,6,7,8,8a,9, 10-octahydro-7-hydroxy-4b-(phenylmethyl)-7-(1-propynyl)-2-phenanthrenyl]oxy]methyl]-,[4bS-(4bα, 7α,8aβ)]-

To a solution of 20 mg of the title product of Example 68 (which was prepared by procedures described in Example 68) and 0.029 mL of DBU in 2 mL of anhydrous $CH_3CN$ was added 14 mg of 1,1-thiocarbonyidiimidazole at RT and stirred for 1.5 h. The solution was diluted with water, adjusted to pH around 4 with 10% HCl, extracted with EtOAc (X3), washed with brine, dried over $Na_2SO_4$, filtered and concentrated to dryness. Purification by preparative TLC on $SiO_2$ using 5% MeOH in methylene chloride as the elutant afforded 12 mg (54%) of the title product of this example as white fluffy powder. MS m/z 459 (M−H)+.

Example 72

2-Phenanthrenol, 1,2,3,4,4a,9,10,10a-octahydro-7-[[5-[2-(4-morpholinyl) ethyl]-1,2,4-oxadiazol-3-yl] methoxy]-4a-(phenylmethyl)-2-(1-propynyl)-,[2R-(2α,4aα, 10aβ)]-

To a solution of 30 mg of the title product of Example 68 (which was prepared by procedures described in Example 68) and 3 mg of 60% NaH in 3 mL of anhydrous THF was added 0.023 mL of methyl 4-morpholine propionate and heated to reflux for 2 h. The solution was cooled, filtered, concentrated to dryness and purified by preparative TLC using 20% acetone in $CH_2Cl_2$ and a few drops of $NH_4OH$ as the elutant to afford 14 mg of the title product of this example (36%) as white fluffy powder. MS m/z 542 (M+H)+.

Example 73

Carbamothioic acid, dimethyl-, S-[4b,5,6,7,8,8a,9,10-octahydro-7-hydroxy-4b-(phenylmethyl)-7-(1-propynyl)-2-phenanthrenyl] ester, [4bS-(4bα,7α,8aβ)]-

A solution of 55 mg of carbamothioic acid, dimethyl-, O-[4b,5,6,7,8,8a,9,10-octahydro-7-hydroxy-4b-(phenylmethyl)-7-(1-propynyl)-2-phenanthrenyl] ester, [4bS-(4ba,7a,8ab)]- of in 2 mL of phenol ether was refluxed overnight under $N_2$ atmosphere. The solution was concentrated to dryness and purified by preparative TLC using 2% MeOH in $CH_2Cl_2$ as the elutant to yield 5 mg of the title product of this example. MS m/z 434 (M+H)+.

Example 74

2-Phenanthrenol, 1,2,3,4,4a,9,10,10a-octahydro-4a-(phenylmethyl)-2-(1-propynyl)-7-(pyrazinyloxy)-, [2R-(2α,4aα, 10aβ)]-

To a solution of 30 mg of the first listed title product of Example 8 (which was prepared by procedures described in Example 8) and 4 mg of 60% NaH in 2 mL of anhydrous DMF was added 0.01 mL of chloropyrazine at 0° C. under $N_2$ atmosphere. The reaction was then heated to 60° C. for 2 h. The reaction was quenched with $NH_4Cl$ (sat.), extracted with EtOAc (X3), washed with brine, dried over $Na_2SO_4$, filtered and concentrated to dryness. Purification by flash chromatography $SiO_2$ using 2% EtOAc in hexanes to 25% EtOAc in hexanes as the gradient elutant afforded 20 mg (54%) of the title product of this example as white fluffy powder. MS m/z 426 (M+2)+.

Example 75

2-Phenanthrenol, 1,2,3,4,4a,9,10,10a-octahydro-7-[[2-(4-morpholinyl)-4-pyrimidinyl]oxy]-4a-(phenylmethyl)-2-(1-propynyl)-, [2R-(2α,4aα, 10aβ)]-

A solution of 12 mg of 2-phenanthrenol, 7-[(4-chloro-2-pyrimidinyl)oxy]-1, 2,3,4,4a,9,10,10a-octahydro-4a-(phenylmethyl)-2-(1-propynyl)-, [2R-(2α, 4aα, 10aβ)]-and 0.011 mL of morpholine in 2 mL of anhydrous THF was heated at 65° C. overnight under $N_2$ atmosphere. The reaction was quenched with $NH_4Cl$ (sat.), extracted with EtOAc (X3), washed with brine, dried over $Na_2SO_4$, filtered and concentrated to dryness. Purification by preparative TLC $SiO_2$ using 50% EtOAc in hexanes as the elutant afforded 10 mg (75%) of the title product of this example as white fluffy powder. MS m/z 510 (M+H)+.

Example 76

2-Phenanthrenol, 1,2,3,4,4a,9,10,10a-octahydro-4a-(phenylmethyl)-2-(1-propynyl)-7-(3-pyridinylmethoxy)-, [2R-(2α,4aβ, 10aβ)]-

To a solution of 30 mg of the first listed title product of Example 8 (which was prepared by procedures described in Example 8) and 8 mg of 60% NaH in 2 mL of anhydrous DMF was added 18 mg of 3-picolyl chloride hydrochloride at RT under $N_2$ atmosphere overnight. The reaction was quenched with $NH_4Cl$ (sat.), extracted with EtOAc (X3), washed with brine, dried over $Na_2SO_4$, filtered and concentrated to dryness. Purification by preparative TLC $SiO_2$ using 4% MeOH in $CH_2Cl_2$ as the elutant afforded 32 mg (80%) of the title product of this example as white fluffy powder. MS m/z 438 (M+H)+.

Example 77

2(1H)-Phenanthrenone, 3,4,4a,9,10,10a-hexahydro-7-hydroxy-4a-(phenylmethyl)-,O-ethyloxime To a solution of 150 mg of the first listed title product of Example 8 (which was prepared by procedures described in Example 8) and 80 mg of sodium acetate in 5 mL of EtOH was added 96 mg of O-ethylhydroxylamine hydrochloride and heated to 70° C. for 30 min. The solution was concentrated to dryness and purified by flash chromatography $SiO_2$ using 5% EtOAc in hexanes with 0.1% of $Et_3N$ to 7% EtOAc in hexanes with 0.1% of $Et_3N$ as the gradient elutant afforded 148 mg (86%) of the title product of this example as white fluffy powder. MS m/z 350 (M+H)+.

Example 78

2-Phenanthrenol, 4b,5,6,7,8,8a,9,10-octahydro-4b-[(4-hydroxyphenyl) methyl]-7-propylidene-, [4bS-(4bα,7Z,8aα)]-

A solution of 170 mg of propyltriphenylphosphonium bromide in 3 mL of anhydrous DMSO was added dropwise 0.44 mL of 1M sodium bis(trimethylsilane)amide in ether at RT under $N_2$ atmosphere for 10 min. To the resultant solution was added 35 mg of the title product of Preparation 17 in 1.5 mL DMSO dropwise and the mixture was heated at 70° C. overnight. The reaction was quenched with $NH_4Cl$ (sat.), extracted with EtOAc (X3), washed with brine, dried over $Na_2SO_4$, filtered and concentrated to dryness. Purification by flash chromatography $SiO_2$ using 10% EtOAc in hexanes to 25% EtOAc in hexanes as the gradient elutant afforded 34 mg (89%) of the title product of this example as white fluffy powder. MS m/z 349 (M+H)+.

Example 79

Spiro[oxirane-2,2'(1'H)-phenanthren]-7'-ol, 3',4',4'a, 9',10',10'a-hexahydro-4'a-(phenylmethyl)-, [2'R-(2'α, 4'aα, 10'aβ)]-

To a solution of 91 mg of trimethyl sulfonium iodide in 1 mL of anhydrous DMF was added 55 mg of t-BuOK at 0°

C. under $N_2$ atmosphere and the mixture was stirred for 5 min. To the resultant solution was added 20 mg of the title product of Example 6 in 1 mL of DMF slowly and stirred for another 1 h at 0° C. The reaction was quenched with $NH_4Cl$ (sat), extracted with EtOAc (X3), washed with brine, dried over $Na_2SO_4$, filtered and concentrated to dryness. Purification by flash chromatography $SiO_2$ using 100% $CH_2Cl_2$ to 2% acetone in $CH_2Cl_2$ as the gradient elutant afforded 13 mg (70%) of the title product of this example as white fluffy powder. MS m/z 303 (M–17)$^+$.

Example 80

2-Phenanthreneacetonitrile, 1,2,3,4,4a,9,10,10a-octahydro-2, 7-dihydroxy-4a-(phenylmethyl)-, (4aS, 10aR)-, -2R-, A solution of 9 mg of the title product of Example 79 and 22 mg of potassium cyanide in 1 mL of ethylene glycol was heated at 100° C. for 2 h. The reaction was cooled and diluted with water, extracted with EtOAc (X3), washed with brine, dried over $Na_2SO_4$, filtered and concentrated to dryness. Purification by preparative TLC $SiO_2$ using 35% EtOAc in hexanes as the elutant afforded 5 mg (51%) of the title product of this example as white fluffy powder. MS m/z330 (M–17)$^+$.

Example 81

2,7-Phenanthrenediol, 1,2,3,4,4a,9,10,10a-octahydro-2-(methoxymethyl)-4a-(phenylmethyl)-, [2R-(2α,4aα, 10aβ)]-

A solution of 20 mg of the title product of Example 79 (which was prepared by procedures described in Example 79) and 0.071 mL of 25% (w/w) sodium methoxide in 5 mL of anhydrous MeOH was heated to reflux for 3 h. The reaction was cooled and quenched with $NH_4Cl$(sat.), extracted with EtOAc (X3), washed with brine, dried over $Na_2SO_4$, filtered and concentrated to dryness. Purification by preparative TLC $SiO_2$ using 30% EtOAc in hexanes as the elutant afforded 15 mg (69%) of the title product of this example as white fluffy powder. MS m/z 335 (M–17)$^+$.

Example 82

2,7-Phenanthrenediol, 2-(azidomethyl)-1,2,3,4,4a,9,10,10a-octahydro-4a-(phenylmethyl)-, [2R-(2α,4aα, 10aβ)]-

A solution of 20 mg of the title product of Example 79 (which was prepared by procedures described in Example 79), 20 mg of sodium azide and 17 mg of $NH_4Cl$ in 0.8 mL of MeOH and 0.1 mL of water was heated to reflux for 3 h. The reaction was cooled and diluted with $NH_4Cl$ (sat.), extracted with EtOAc (X3), washed with brine, dried over $Na_2SO_4$, filtered and concentrated to dryness. Purification by preparative TLC $SiO_2$ using 27% EtOAc in hexanes as the elutant afforded 15 mg (66%) of the title product of this example as white fluffy powder. MS m/z 348 (M–17)$^+$.

Example 83

2,7-Phenanthrenediol, 1,2,3,4,4a,9,10,10a-octahydro-2-(4-morpholinylmethyl)-4a-(phenylmethyl)-, [2R-(2α,4aα, 10aβ)]-

A solution of 20 mg of the title product of Example 79 (which was prepared by procedures described in Example 79) and 0.055 mL of morphiline in 1 mL of anhydrous MeOH was heated to reflux for 2 h. The reaction was cooled and diluted with $NH_4Cl$ (sat.), extracted with EtOAc (X3), washed with brine, dried over $Na_2SO_4$, filtered and concentrated to dryness. Purification by preparative TLC $SiO_2$ using 5% MeOH in methylene chloride as the elutant afforded 14 mg (55%) of the title product of this example as white fluffy powder. MS m/z 408 (M+H)$^+$.

The following compounds were prepared by using methods analogous to those described in Example 8 above.

Example 84

Piperidine, 4-[[2-(chloroethynyl)-1,3,4,9,10,10a-hexahydro-2,7-dihydroxy-4a(2H)-phenanthrenyl] methyl]-1-(methylsulfonyl)-, [2R-(2α,4aα,10aβ)]-, m.p.=124–127° C.

Example 85

Piperidine, 4-[[2-(chloroethynyl)-1,3,4,9,10,10a-hexahydro-2,7-dihydroxy-4a(2H)-phenanthrenyl] methyl]-1-(ethylsulfonyl)-, [2R-(2α,4aα,10aβ)]-, m.p.=174–176° C.

Example 86

Piperidine, 4-[[2-(chloroethynyl)-1,3,4,9,10,10a-hexahydro-2,7-dihydroxy-4a(2H)-phenanthrenyl] methyl]-1-(2-thienylsulfonyl)-, [2R-(2α,4aα, 10aβ)]-, m.p.=145–148° C.

Examples 87–90

The following compounds were prepared by using methods analogous to those described in Example 35 above.

Example 87

Benzoic acid, 4-[3-[2-(chloroethynyl)-1,3,4,9,10, 10a-hexahydro-2,7-dihydroxy-4a(2H)-phenanthrenyl]-1-propenyl]-, methyl ester, [2R-[2α, 4aα(E),10aβ]]-, m.p.=199–208° C. (dec).

Example 88

Benzoic acid, 3-[3-[2-(chloroethynyl)-1,3,4,9,10, 10a-hexahydro-2,7-dihydroxy-4a(2H)-phenanthrenyl]-1-propenyl]-, methyl ester, [2R-[2α, 4aα(E),10aβ]]-, m.p.=93–95° C.

Example 89

4-Thiazolecarboxylic acid, 2-[3-[2-(chloroethynyl)-1, 3,4,9,10,10a-hexahydro-2,7-dihydroxy4a(2H)-phenanthrenyl]-1-propenyl]-, ethyl ester, [2R-[2α, 4aα(E),10aβ]]-, MS: 472.

Example 90

2,7-Phenanthrenediol, 2-(chloroethynyl)-1,2,3,4,4a, 9,10,10a-octahydro-4a-[3-[4-(hydroxymethyl) phenyl]-2-propenyl]-, [2R-[2α, 4aα(E),10aβ]]-, MS: 405 (M–18)$^+$.

Example 91

Benzoic acid, 4-[3-[2-(chloroethynyl)-1,3,4,9,10, 10a-hexahydro-2,7-dihydroxy-4a(2H)-phenanthrenyl]-1-propenyl]-, [2R-[2α,4aα(E), 10aβ]]-

To a stirred solution of the title compound of Example 87 in methanol (9 mL) was added a solution of potassium hydroxide (250 mg) in water (0.6 mL) and the resulting solution was refluxed for 3 h. The reaction was allowed to cool to room temperature, saturated aqueous ammonium chloride was added and the mixture was extracted with ethyl acetate (3×). The combined organic layers were dried over magnesium sulfate and concentrated in vacuo to afford the title compound of this example as an off-white solid, 381 mg. mp 145–146° C. (dec).

Example 92

Morpholine, 4-[4-[3-[2-(chloroethynyl)-1,3,4,9,10, 10a-hexahydro-2,7-dihydroxy-4a(2H)-phenanthrenyl]-1-propenyl]benzoyl]-, [2R-[2α,4aα(E),10aβ]]-

To a stirred solution of the title product of Example 91 (100 mg) and N-hydroxysuccinimide (26 mg) in dioxane (2.3 mL) at 0° C. was 1,3-dicyclohexylcarbodiimide (47 mg) and the resulting solution was allowed to warm to room temperature and stirred for 3 h. Acetonitrile (10 mL) was added and the resulting slurry was filtered through Celite®. Concentration of the filtrate afforded an oil (170 mg), which slowly crystallized upon standing. The solid residue and morpholine (0.08 mL) were suspended in acetonitrile (3.5 mL) and heated at 50° C. for 3 h. Saturated aqueous ammonium chloride was added, extracted with ethyl acetate (3×), the organic layers combined, dried over sodium sulfate and concentrated in vacuo to afford a foam. Flash chromatography on silica gel (1:1 to 3:1 ethyl acetate:hexanes) afforded the title compound of this example as an off-white foam, 60mg. m.p.=129–136° C., MS: 506.

Examples 93–100

The following styryl amide compounds were prepared using procedures analogous to those described above in Examples 91 and 92.

Example 93

Piperazine, 1-[4-[3-[2-(chloroethynyl)-1,3,4,9,10, 10a-hexahydro-2,7-dihydroxy-4a(2H)-phenanthrenyl]-1-propenyl]benzoyl]-4-methyl-, [2R-[2α,4aα(E),10aβ]]-MS: 519

Example 94

4-Piperidinol, 1-[4-[3-[2-(chloroethynyl)-1,3,4,9,10, 10a-hexahydro-2,7-dihydroxy-4a(2H)-phenanthrenyl]-1-propenyl]benzoyl]-, [2R-[2α,4aα(E),10aβ]]-MS: 520

Example 95

Benzamide, 4-[3-[2-(chloroethynyl)-1,3,4,9,10,10a-hexahydro-2, 7-dihydroxy-4a(2H)-phenanthrenyl]-1-propenyl]-, [2R-[2α, 4aα(E),10aβ]]-MS: 436

Example 96

Benzoic acid, 3-[3-[2-(chloroethynyl)-1,3,4,9,10, 10a-hexahydro-2,7-dihydroxy-4a(2H)-phenanthrenyl]-1-propenyl]-, [2R-[2α,4aα(E), 10aβ]]-m.p.=101–105° C.

Example 97

Morpholine, 4-[3-[3-[2-(chloroethynyl)-1,3,4,9,10, 10a-hexahydro-2,7-dihydroxy-4a(2H)-phenanthrenyl)-1-propenyl]benzoyl]-, [2R-[2α,4aα(E),10aβ]]-m.p.=135–141° C.

Example 98

Piperazine, 1-[3-[3-[2-(chloroethynyl)-1,3,4,9,10, 10a-hexahydro-2,7-dihydroxy-4a(2H)-phenanthrenyl]-1-propenyl]benzoyl]-4-methyl-, [2R-[2α,4aα(E),10aβ]]- MS: 519

Example 99

4-Piperidinol, 1-[3-[3-[2-(chloroethynyl)-1,3,4,9,10, 10a-hexahydro-2,7-dihydroxy-4a(2H)-phenanthrenyl]-1-propenyl]benzoyl]-, [2R-[2α,4aα(E),10aβ]]-MS: 520

Example 100

Morpholine, 4-[[2-[3-[2-(chloroethynyl)-1,3,4,9,10, 10a-hexahydro-2,7-dihydroxy-4a(2H)-phenanthrenyl]-1-propenyl]-4-thiazoly]carbonyl]-, [2R-[2α,4aα(E),10aβ]]-MS: 513

Example 101

2,7-Phenanthrenediol, 2-(chloroethynyl)-1,2,3,4,4a, 9,10,10a-octahydro-4a-[3-[4-(hydroxymethyl) phenyl]-2-propenyl]-, 7-acetate, [2R-[2α,4aα(E), 10aβ]]-

To a stirred solution of 2,7-Phenanthrenediol, 2-(chloroethynyl)-1, 2,3,4,4a,9,10,10a-octahydro-4a-[3-[4-(t-butyidimethylsiloxymethyl)phenyl]-2-propenyl]-, [2R-[2α,4aα(E),10aβ]]- (322mg), tetrabutylammonium hydroxide (0.7 mg) and sodium hydroxide (60 mg) in dioxane (1 mL) at 5° C. was added dropwise a solution of acetyl chloride (57 mg) in dioxane (1 mL). The reaction was allowed to warm to room temperature and stirred for 2 h. An additional portion of acetyl chloride (57 mg) was added and stirring was continued an additional 2 h. The reaction was quenched with aqueous ammonium chloride, extracted with ethyl acetate, the organic phase dried over sodium sulfate and the filtrate concentrated in vacuo. Flash chromatography on silica gel (10 to 20% ethyl acetate/hexanes) afforded an oil, 91 mg. To a cooled (0° C.), stirred solution of this oil in tetrahydrofuran (1.6 mL) was added a 1 M solution of tetrabutylammonium fluoride in tetrahydrofuran (0.23 mL). After 2 h, the reaction was quenched with saturated aqueous ammonium chloride, extracted with ethyl acetate, the organic layer dried over sodium sulfate, concentrated and flash chromatographed on silica gel (10–50% ethyl acetate/ hexanes) to afford the title compound of this example, 22 mg. mp 73–77° C.

Example 102

2,7-Phenanthrenediol, 2-(chloroethynyl)-1,2,3,4,4a, 9,10,10a-octahydro-4a-[3-[4-(4-morpholinylmethyl) phenyl]-2-propenyl]-, 7-acetate, [2R-[2α,4aα(E), 10aβ]]-

To a cooled (0° C.), stirred solution of the title product of Example 101 (40 mg) (which was prepared by procedures described in Example 101) in tetrahydrofuran (0.9 mL) were added sequentially methanesulfonyl chloride (39 mg) and diisopropylethylamine (33 mg). After 2 h, the reaction was cooled to −78° C., morpholine (0.12 mL) was added and the reaction solution was allowed to warm to 0° C. After 4 h, the reaction was quenched with aqueous ammonium chloride, extracted with ethyl ether, dried over sodium sulfate and concentrated in vacuo to afford a gum. Flash chromatography on silica gel (40–75% ethyl acetate/hexanes) afforded the title compound of this example as a colorless gum, 35 mg: MS: 534

Example 103

2,7-Phenanthrenediol, 2-(chloroethynyl)-1,2,3,4,4a, 9,10,10a-octahydro-4a-[3-[4-(4-morpholinylmethyl) phenyl]-2-propenyl]-, [2R-[2α,4aα(E),10aβ]]-

To a suspension of the title product of Example 102 (25 mg) in methanol (0.5 mL) and water (0.25 mL) was added saturated aqueous sodium bicarbonate (0.25 mL) and the reaction mixture was allowed to stir at room temperature for 2 h. The reaction was quenched with saturated aqueous ammonium chloride, extracted with ethyl acetate, the organic phase was dried over sodium sulfate and concentrated in vacuo to afford a colorless solid. Flash chromatography on silica gel (50–100% ethyl acetate/hexanes) afforded the title compound of this example as a colorless solid, 15 mg: MS: 492

Examples 104–106

The following aminomethyl substituted styryl compounds were prepared using procedures analogous to those described above in Examples 101–103.

Example 104

2,7-Phenanthrenediol, 2-(chloroethynyl)-1,2,3,4,4a, 9,10,10a-octahydro-4a-[3-[4-[(4-hydroxy-1-piperidinyl)methyl]phenyl]-2-propenyl]-, 7-acetate, [2R-[2α,4aα(E),10aβ]]-MS: 548

Example 105

2,7-Phenanthrenediol, 2-(chloroethynyl)-1,2,3,4,4a, 9,10,10a-octahydro-4a-[3-[4-[(4-hydroxy-1-piperidinyl)methyl]phenyll]-2-propenyl]-, [2R-[2α, 4aα(E),10aβ]]-MS: 506

Example 106

2,7-Phenanthrenediol, 2-(chloroethynyl)-4a-[3-[4-[(dimethylamino) methyl]phenyl]-2-propenyl]- 1,2, 3,4,4a,9,10,10a-octahydro-, [2R-[2α,4aα(E),10aβ]]- MS: 450.

Example 107

Carbamic acid, dimethyl-, 4b-[2-(4-formylphenoxy) ethyl]-4b, 5,6,7,8,8a,9,10-octahydro-7-hydroxy-7-(1-propynyl)-2-phenanthrenyl ester, [4bS-(4bα,7α, 8aβ)]-

To a stirred solution of the title product of Preparation 10 (1.9 g) in pyridine (50 mL) was added p-toluenesulfonyl chloride (2.0 g). After 18 h at room temperature, the reaction solution was partitioned between ethyl ether and 0.5 N aqueous sodium hydrogensulfate, the aqueous phase extracted with additional ethyl ether (2×), the combined organic layers dried over sodium sulfate, concentrated in vacuo and flash chromatographed on silica gel (50–60% ethyl acetate/hexanes) to afford a colorless foam, 1.5 g. To a solution of this oil in dimethylformamide (9 mL) was added a solution of p-hydroxybenzaldehyde (0.44 g) and potassium t-butoxide (1 M in tetrahydrofuran, 3.3 mL) in dimethylformamide (5 mL, stirred at ambient temperature for 0.5 h) and the resulting solution was heated at 80° C. for 4 h. The reaction was cooled, diluted into ethyl ether, washed with water, brine, dried over sodium sulfate and concentrated in vacuo. The resulting oil was flash chromatographed to afford the title compound of this example as a colorless foam, 1.3 g. MS: 476 (M+1)$^+$.

Example 108

Carbamic acid, dimethyl-, 4b,5,6,7,8,8a,9,10-octahydro-7-hydroxy-4b-[2-[4-(4-morpholinylmethyl)phenoxy]ethyl]-7-(1-propynyl)-2-phenanthrenyl ester, [4bS-(4bα,7α,8aβ)]-, HCl salt A solution of the title product of Example 107 (50 mg), acetic acid (7 mg), morpholine (18 mg) and sodium triacetoxyborohydride (33 mg) in 1,2-dichloroethane (2 mL) was stirred at room temperature for 3 h. The reaction was quenched with saturated aqueous sodium bicarbonate, extracted with dichloromethane, the organic phase was dried over sodium sulfate and concentrated in vacuo to afford an oil. Flash chromatography on silica gel (ethyl acetate) afforded the title compound of this example as colorless foam, 50 mg. MS: 547.

Examples 109–129

The following examples were prepared using procedures analogous to those described above in Examples 107 and 108.

Example 109

Carbamic acid, dimethyl-, 4b-[2-[4-[(dimethylamino) methyl]phenoxy]ethyl]-4b,5,6,7,8, 8a,9,10-octahydro-7-hydroxy-7-(1-propynyl)-2-phenanthrenyl ester,[4bS-(4bα,7α,8aβ)]-, HCl salt, MS: 505

Example 110

Carbamic acid, dimethyl-, 4b-[2-[4-[(ethylamino) methyl]phenoxy]ethyl]-4b,5,6,7,8,8a,9,10-octahydro-7-hydroxy-7-(1-propynyl)-2-phenanthrenyl ester,[4bS-(4bα,7α,8aβ)]-, HCl salt, MS: 505

Example 111

Carbamic acid, dimethyl-, 4b,5,6,7,8,8a,9,10-octahydro-7-hydroxy-4b-[2-[4-[(methylamino) methyl]phenoxy]ethyl]-7-(1-propynyl)-2-phenanthrenylester, [4bS-(4bα,7α,8aβ)]-, HCl salt, MS: 491

Example 112

Carbamic acid, dimethyl-, 4b,5,6,7,8,8a,9,10-octahydro-7-hydroxy-4b-[2-[4-[[methyl (methylsulfonyl)amino]methyl] phenoxy]ethyl]-7-(1-propynyl)-2-phenanthrenyl ester, [4bS-(4bα,7α, 8aβ)]-, m.p. 82–85° C.

Example 113

Carbamic acid, dimethyl-, 4b,5,6,7,8,8a,9,10-octahydro-7-hydroxy-7-(1-propynyl)-4b-[2-[4-(1-pyrrolidinylmethyl) phenoxy]ethyl]-2-phenanthrenyl ester, [4bS-(4bα,7α,8aβ)]-, HCl salt, MS: 531

Example 114

Carbamic acid, dimethyl-, 4b,5,6,7,8,8a,9,10-octahydro-7-hydroxy-4b-[2-[4-[(4-methyl-1-piperazinyl) methyl]phenoxy]ethyl]-7-(1-propynyl)-2-phenanthrenyl ester, [4bS-(4bα,7α,8aβ)]-, HCl salt, MS: 560

Example 115

Carbamic acid, dimethyl-, 4b,5,6,7,8,8a,9,10-octahydro-7-hydroxy-4b-[2-[4-[[methyl(1-methyl-4-piperidinyl) amino]methyl]phenoxy]ethyl]-7-(1-propynyl)-2-phenanthrenyl ester, [4bS-(4bα,7α, 8aβ)]-, HCl salt, MS: 588

Example 116

Carbamic acid, dimethyl-, 4b,5,6,7,8,8a,9,10-octahydro-7-hydroxy-4b-[2-[4-[[(2-methoxyethyl) amino]methyl]phenoxy]ethyl]-7-(1-propynyl)-2-phenanthrenyl ester, [4bS-(4bα,7α,8aβ)]-, HCl salt, MS: 535

Example 117

Carbamic acid, dimethyl-, 4b-[2-[4-[[[2-(dimethylamino) ethyl]amino]methyl]phenoxy] ethyl]-4b, 5,6,7,8,8a,9,10-octahydro-7-hydroxy-7-(1-propynyl)-2-phenanthrenyl ester, [4bS-(4bα,7α, 8aβ)]-, HCl salt, MS: 548

Example 118

Carbamic acid, dimethyl-, 4b-[2-[4-[[[2-(dimethylamino) ethyl]methylamino]methyl] phenoxy]ethyl]-4b,5,6,7,8,8a,9,10-octahydro-7-hydroxy-7-(1-propynyl)-2-phenanthrenyl ester, [4bS-(4bα,7α,8aβ)]-, HCl salt, MS: 562

Example 119

Carbamic acid, dimethyl-, 4b-[2-[4-[(diethylamino) methyl]phenoxy]ethyl]-4b ,5,6,7,8,8a,9,10-octahydro-7-hydroxy-7-(1-propynyl)-2-phenanthrenyl ester,[4bS-(4bα,7α,8aβ)]-, HCl salt, MS: 533

Example 120

Carbamic acid, dimethyl-, 4b-[2-[4-[(cyclopropylamino) methyl]phenoxy]ethyl]4b,5,6,7,8,8a,9,10-octahydro-7-hydroxy-7-(1-propynyl)-2-phenanthrenyl ester,[4bS-(4bα,7α,8aβ)]-, HCl salt, MS: 517

Example 121

Carbamic acid, dimethyl-, 4b-[2-[4-[[bis(2-methoxyethyl) amino]methyl]phenoxy]ethyl]4b,5,6,7,8,8a,9,10-octahydro-7-hydroxy-7-(1-propynyl)-2-phenanthrenyl ester,[4bS-(4bα,7α,8aβ)]-, HCl salt, MS: 593

Example 122

2,7-Phenanthrenediol, 2-(chloroethynyl)-1,2,3,4,4a,9,10,10a-octahydro-4a-[2-[4-(4-morpholinylmethyl) phenoxy]ethyl]-, [2R-(2α, 4aα,10aβ)]-, MS: 496

Example 123

Carbamic acid, dimethyl-, 7-(chloroethynyl)4b,5,6,7,8,8a,9,10-octahydro-7-hydroxy-4b-[2-[4-(4-morpholinylmethyl) phenoxy]ethyl]-2-phenanthrenyl ester,[4bS-(4bα,7α,8aβ)]-, HCl salt, MS: 567

Example 124

2,7-Phenanthrenediol, 2-(chloroethynyl)4a-[2-[4-[(dimethylamino) methyl]phenoxy]ethyl]-1,2,3,4,4a,9,10,10a-octahydro-, [2R-(2α,4aα,10aβ)]-, MS: 454

Example 125

Carbamic acid, dimethyl-, 7-(chloroethynyl)-4b-[2-[4-[(dimethylamino) methyl]phenoxy]ethyl]4b,5,6,7,8,8a,9,10-octahydro-7-hydroxy-2-phenanthrenyl ester, [4bS-(4bα,7α,8aβ)]-, HCl salt, MS: 525

Example 126

Sulfamic acid, dimethyl-, 7-(chloroethynyl)4b-[2-[4-[(dimethylamino) methyl]phenoxy]ethyl]-4b,5,6,7,8,8a,9,10-octahydro-7-hydroxy-2-phenanthrenyl ester, [4bS-(4bα,7α,8aβ)]-, HCl salt, MS: 561

Example 127

2,7-Phenanthrenediol, 2-(chloroethynyl)-1,2,3,4,4a,9,10,10a-octahydro-4a-[2-[4-(hydroxymethyl) phenoxy]ethyl]-, [2R-(2α, 4aα,10aβ)]-, m.p.= 179–186° C.

Example 128

Benzaldehyde, 4-[2-[2-(chloroethynyl)-1,3,4,9,10,10a-hexahydro -2,7-dihydroxy-4a(2H)-phenanthrenyl]ethoxy]-, [2R-(2α, 4aα,10aβ)]-, MS: 407 (M–18)+

Example 129

2,7-Phenanthrenediol, 2-(chloroethynyl)-1,2,3,4,4a,9,10,10a-octahydro -4a-(2-phenoxyethyl)-, [2R-(2α, 4aα,10aβ)]-, MS: 379 (M–18)+

Example 130

Naphtho[1,2-d]thiazol-7-ol, 2-amino-7-(chloroethynyl)-4, 5,5a,6,7,8,9,9a-octahydro-9a-(phenylmethyl)-, [5aR,S-(5aα,7β,9aβ)]-

A solution of the title product of Preparation 14 (46 mg) and thiourea (22 mg) in acetonitrile (2 mL) were heated at reflux for 8 h. The reaction was concentrated in vacuo, partitioned between sat. aqueous sodium bicarbonate and chloroform, the organic layer dried over sodium sulfate, concentrated in vacuo and flash chromatographed on silica gel (40% ethyl acetate/hexanes) to afford a colorless solid, 25 mg. Addition of lithio-2-chloroethyne was carried out using the general procedure described above in Example 8 to afford the title compound of this example as a tan solid, 7 mg. MS: 373

Example 131

Formamide, N-[7-(chloroethynyl)-4,5,5a,6,7,8,9,9a-octahydro-7-hydroxy-9a-(phenylmethyl)naphtho[1,2-d]thiazol-2-yl]-, [5aR,S-(5aα,7β,9aβ)]-

Using procedures analogous to those described in Preparations 11–14 and Example 130 above, except dimethylformamide was substituted in the thiourea cyclization reaction to afford the corresponding N-formyl derivative, which is the title product of this example. MS: 401

Example 132

2H-Benz[g]indazol-7-ol, 7-(chloroethynyl)-4,5,5a,6,7,8,9,9a-octahydro-9a-(phenylmethyl)-, [5aR,S-(5aα,7β,9aβ)]-

A solution of the title product of Preparation 15 (244 mg) and hydrazine (75 mg) in ethanol (7 mL)/water (1 mL) was stirred at room temperature for 16 h. The reaction was diluted into ethyl acetate, washed with water, brine, dried over sodium sulfate and flash chromatographed to afford a colorless foam, 190 mg. To this foam was added a solution of ethanol (10 mL), 20% sulfuric acid/water (v/v) and the resulting solution was refluxed for 5 h. The reaction was diluted into ethyl ether, washed with sat. aqueous sodium bicarbonate, brine, dried over sodium sulfate and concentrated in vacuo to afford a golden oil. Addition of lithio-2-chloroethyne was carried out using the general procedure described above in Example 8 to afford the title compound of this example as a tan foam, 129 mg. MS: 341

Example 133

2H-Benz[g]indazol-7-ol, 7-(chloroethynyl)-4,5,5a,6,7,7,9,9a-octahydro-9a-(phenylmethyl)-, [5aR,S-(5aα,7β,9aα)]-

The title compound of this example was prepared by procedures analogous to those described above in Example 132. MS: 341.

Example 134

Benzo[h]quinazolin-8-ol, 2-amino-8-(chloroethynyl)-5, 6,6a,7,8,9,10,10a-octahydro-10a-(phenylmethyl)-, [6aR,S-(6aα,8β,10aβ)]-

A solution of sodium metal (25 mg) in isopropyl alcohol (1.5 mL) and quanidine sulfate (107 mg) were refluxed for 1 h, then the title product of Preparation 15 (154 mg) was added and refluxing was continued for 24 h. Work-up and subsequent elaboration according to procedures analogous to those described in Example 132 afforded the title compound of this example as a colorless foam, 43 mg. MS: 368

Example 135

2-Phenanthrenol, 2-(chloroethynyl)-2,3,4,4a,9,10-hexahydro-7-methoxy-4a-(phenylmethyl)-, (2R-cis)-

The title compound of this example was prepared by procedures analogous to those described above in Example 8. MS: 361 (M–17)+.

Example 136

2-Phenanthrenol, 2,3,4,4a,9,10-hexahydro-7-methoxy-2-phenyl-4a-(phenylmethyl)-, (2R-cis)-

To a flame dried flask, 5 ml of THF and 1.3 ml of phenylmagnesium chloride were added. The title product of Example 3 (200 mg) in 5 ml THF was added dropwise to the solution (sat.) at 0° C. The reaction was stirred at 0° C. for an hour and quenched with $NH_4Cl$ extracted with EtOAc, dried over $Na_2SO_4$ and filtered. The mixture was purified with flash chromatography (25% EtOAc in hexane) on silica gel to afford the title product of this example as light yellow solid, 245 mg, yield 98%, MS: 379 (M–17)$^+$.

Example 137

2,7-Phenanthrenediol, 2,3,4,4a,9,10-hexahydro-2,4a-bis (phenylmethyl)-, (2S-cis)-

The title compound of this example was prepared by procedures analogous to those described above in Example 136. MS: 379 (M–17)$^+$.

Example 138

2,7-Phenanthrenediol, 2,3,4,4a,9,10-hexahydro-4a-(phenylmethyl)-2-(2-pyridinyl)-, (2R-cis)-

The title compound of this example was prepared by procedures analogous to those described above in Example 9. MS: 383 (M+1)$^+$.

Example 139

2(3H)-Phenanthrenone, 4,4a,9,10-tetrahydro-7-(4-nitrophenoxy)-4a-(phenylmethyl)-, (R)-

The title compound of this example was prepared by procedures analogous to those described above in Example 74. MS: 426 (M+1)$^+$.

Examples 140–143

The title compounds of Examples 140–143 were prepared by procedures analogous to those described above in Example 136.

Example 140

2,7-Phenanthrenediol, 1,2,3,4,4a,9,10,10a-octahydro-4a-(phenylmethyl)-2-(1,2-propadienyl)-, (4aS,10aR)-, MS: 329 (M–17)$^+$.

Example 141

2,7-Phenanthrenediol, 2,3,4,4a,9,10-hexahydro-2-(2-naphthalenylmethyl)-4a-(phenylmethyl)-, (4aS)-, MS: 429 (M–17)$^+$.

Example 142

2,7-Phenanthrenediol, 2,3,4,4a,9,10-hexahydro-2-(2-naphthalenylmethyl)-4a-(phenylmethyl)-, (4aS)-, MS: 429 (M–17)$^+$.

Example 143

2,7-Phenanthrenediol, 1,2,3,4,4a,9,10,10a-octahydro-2,4a-bis (phenylmethyl)-, (4aS)-, MS: 416 (M+18)$^+$.

Example 144

2,7-Phenanthrenediol, 2-(chloroethynyl)-2,3,4,4a,9,10-hexahydro-4a-(phenylmethyl)-, (2R-cis)-

The title compound of this example was prepared by procedures analogous to those described above in Example 8. MS: 347 (M–17)$^+$.

Example 145

2,7-Phenanthrenediol, 2-ethynyl-2,3,4,4a,9,10-hexahydro-4a-(phenylmethyl)-, (2R-cis)-

The title compound of this example was prepared by procedures analogous to those described above in Example 5. MS: 313 (M–17)$^+$.

Examples 146–147

The title compounds of Examples 146–147 were prepared by procedures analogous to those described above in Example 136.

Example 146

2,7-Phenanthrenediol, 1,2,3,4,4a,9,10,10a-octahydro-2-phenyl-4a-(phenylmethyl)-, (4aS, 10aR)-, MS: 367 (M–17)$^+$.

Example 147

2,7-Phenanthrenediol, 1,2,3,4,4a,9,10,10a-octahydro-2-phenyl-4a-(phenylmethyl)-, (4aS, 10aR)-, MS: 367 (M–17)$^+$.

Example 148

2,7-Phenanthrenediol, 2-ethynyl-1,2,3,4,4a,9,10,10a-octahydro-4a-(phenylmethyl)-, [2R-(2α,4aα,10aβ)]-

The title compound of this example was prepared by procedures analogous to those described above in Example 9. MS: 350 (M+18)$^+$.

Example 149

2,7-Phenanthrenediol, 2-cyclopropyl-1,2,3,4,4a,9,10,10a-octahydro-4a-(phenylmethyl)-, [2R-(2α,4aα,10aβ)]-

The title compound of this example was prepared by procedures analogous to those described above Example 136. MS: 331 (M–17)$^+$.

Example 150

2,7-Phenanthrenediol, 2-(cyclopropylethynyl)-1, 2, 3,4,4a,9,10,10a-octahydro-4a-(phenylmethyl)-, [2R-(2α, 4aα,10aβ)]-

The title compound of this example was prepared by procedures analogous to those described above Example 9. MS: 355 (M–17)$^+$.

Example 151

2,7-Phenanthrenediol, 2-butyl-1,2,3,4,4a,9,10,10a-octahydro-4a-(phenylmethyl)-, (4aS,10aR)-

The title compound of this example was prepared by procedures analogous to those described above in Example 136. MS: 382 (M+18)$^+$.

Examples 152–153

The title compounds of Examples 152–153 were prepared by procedures analogous to those described above in Example 9.

Example 152

2,7-Phenanthrenediol, 1,2,3,4,4a,9,10,10a-octahydro-4a-(phenylmethyl)-2-(2-thienyl)-, (4aS, 10aR)-, MS: 373 (M−17)$^+$.

Example 153

2,7-Phenanthrenediol, 1,2,3,4,4a,9,10,10a-octahydro-4a-(phenylmethyl)-2-(2-pyridinyl)-, [2R-(2α,4aβ,10aβ)]-, MS: 386 (M+1)$^+$.

example 154

2,7-Phenanthrenediol, 1,2,3,4,4a,9,10,10a-octahydro-4a-(phenylmethyl)-, [2R-(2α,4aα,10aβ)]-

The title compound of this example was prepared by procedures analogous to those described above in Example 6. MS: 309 (M+1)$^+$.

Example 155

2,7-Phenanthrenediol, 2-(chloroethynyl)-1,2,3,4,4a, 9,10,10a-octahydro-4a-(phenylmethyl)-, [2S-(2α, 4aα,10aβ)]-

The title compound of this example was prepared by procedures analogous to those described above in Example 8. MS: 349 (M−17)$^+$.

Example 156

2,7-Phenanthrenediol, 1,2,3,4,4a,9,10,10a-octahydro-4a-(phenylmethyl)-2-(3,3,3-trifluoro-1-propynyl)-, [2R-(2α,4aα,10aβ)]-

A 5-L three-necked, round-bottom flask was equipped with a dry ice condenser and a dropping funnel. The flask was charged with 1000 mL anhydrous THF, and 3,3,3-trifluoropropyne gas was bubbled through for 10 mins. About 100 g (~15 eqs) of the gas was condensed during this period. Solution was then cooled to −78° C. and 200 mL of n-BuLi (2.5 M solution in hexanes, ~8 eqs) was added slowly via the dropping funnel. The resultant mixture was stirred under −78° C. for 1 hour. Then 300 mL of anhydrous THF was added to the reaction flask. A solution of 20 g of the starting compound, 2(1H)-phenanthrenone, 4a-(benzyl)-3,4,4a,5,8,9,10,10a-octahydro-7-hydroxy-, [4aS-[4aα[E], 10aβ]]- in 200 mL of THF was added dropwise, followed by the addition of another 500 mL anhydrous THF, and the reaction mixture was stirred at −78° C. for another hour. Saturated, aqueous ammonium chloride solution was added and the mixture was extracted with EtOAc three times, dried and concentrated. Purification by flash chromatography over SiO$_2$ using 2% Ethyl Acetate in Methylene Chloride to 5% Ethyl Acetate in Methylene Chloride as the eluant afforded 20.8 g of the title product of this example as a yellow-white solid. MS: 399 (M−1)$^+$.

Example 157

2(1H)-Phenanthrenone, 3,4,4a,9,10,10a-hexahydro-7-hydroxy-4a-(phenylmethyl)-, (4aR-cis)-

The title compound of this example was prepared by procedures analogous to those described above in Example 7. MS: 307 (M+1)$^+$.

Examples 158–159

The title compounds of Examples 158–159 were prepared by procedures analogous to those described above in Example 8.

Example 158

2,7-Phenanthrenediol, 2-(chloroethynyl)-1,2,3,4,4a, 9,10,10a-octahydro-4a-(phenylmethyl)-, [2S-(2α, 4aα,10aα)]-, MS: 349 (M−17)$^+$.

Example 159

2,7-Phenanthrenediol, 2-(chloroethynyl)-1,2,3,4,4a, 9,10,10a-octahydro-4a-(phenylmethyl)-, [2R-(2α, 4aβ,10aβ)]-, MS: 349 (M−17)$^+$.

Example 160

2,7-Phenanthrenediol, 1,2,3,4,4a,9,10,10a-octahydro-4a-(phenylmethyl)-2-(2-thiazolyl)-, (4aS, 10aR)-

The title compound of this example was prepared by procedures analogous to those described above in Example 9. MS: 392 (M+1)$^+$.

Example 161

2,7-Phenanthrenediol, 2-(chloroethynyl)-1,2,3,4,4a, 9,10,10a-octahydro-4a-(phenylmethyl)-, [2R-(2α, 4aβ,10aα)]-

The title compound of this example was prepared by procedures analogous to those described above in Example 8. MS: 349 (M−17)$^+$.

Example 162

2,7-Phenanthrenediol, 1,2,3,4,4a,9,10,10a-octahydro-4a-(phenylmethyl)-2-(1-propynyl)-, [2S-(2α,4aβ,10aβ)]-

The title compound of this example was prepared by procedures analogous to those described above in Example 9. MS: 349 (M−17)$^+$.

Examples 163–164

The title compounds of Examples 163–164 were prepared by procedures analogous to those described above in Example 8.

Example 163

2,7-Phenanthrenediol, 2-(chloroethynyl)-1,2,3,4,4a, 9,10,10a-octahydro-4a-(phenylmethyl)-, [2R-(2α, 4aα,10aα)]-, MS: 349 (M−17)$^+$.

Example 164

2,7-Phenanthrenediol, 2-(chloroethynyl)-1,2,3,4,4a, 9,10,10a-octahydro-4a-(phenylmethyl)-, [2S-(2α, 4aβ,10aβ)]-, MS: 349 (M−17)$^+$.

Example 165

2-Phenanthrenecarbonitrile, 1,2,3,4,4a,9,10,10a-octahydro-2,7-dihydroxy-4a-(phenylmethyl)-, [2R-(2α,4aα,10aβ)]-

At room temperature and under nitrogen atmosphere, 159 mg of KCN was added into 75 mg of the title product of example 6 in methanol (4 ml) and followed by 0.070 mL of HOAc. The mixture was stirred overnight at room temperature, quenched with NaHCO$_3$ (sat.), extracted with EtOAc, dried over $Na_2SO_4$, filtered and concentrated to dryness. The crude product was purified with column chromatography with 0.5% acetone in $CH_2Cl_2$ as the eluant to yield 20.4 mg of the title product of this example as white solid. MS: 322 (M+1) $^{+13}$C NMR (100 MHz, $CD_3OD$) δ; 24.8, 27.8, 33.6, 36.0, 37.6, 39.3, 43.6, 44.0, 74.6, 111.3, 114.6, 125.6, 126.8, 127.0, 127.9, 130.7, 133.8, 136.8, 138.0, 155.1.

Example 166

2-Phenanthrenecarbonitrile, 1,2,3,4,4a,9,10,10a-octahydro-2,7-dihydroxy-4a-(phenylmethyl)-, (4aS, 10aR)-

The title compound of this example was prepared by procedures analogous to those described above in Example 165. $^{13}$C NMR (100 MHz, $CD_3OD$) δ; 26.2, 29.3, 35.1, 37.4, 39.1, 41.6, 45.1, 45.5, 71.5, 112.7, 116.0, 127.1, 128.3, 128.4, 129.4, 132.1, 134.9, 138.6, 139.5, 156.5.

Example 167

2-Phenanthrenecarbonitrile, 1,2,3,4,4a,9,10,10a-octahydro-7-[[(4-methylphenyl)sulfonyl]oxy]4a-(phenylmethyl)-, (4aS, 10aR)-

Tosyl chloride (0.13 mL) was added slowly to a stirring solution of 106 mg of the corresponding phenol in 0.1 mL of triethylamine and 1 mL of anhydrous $CH_2Cl_2$ at 0° C. under nitrogen atmosphere. The reaction was allowed to warm to room temperature for 4 h, then 40° C. overnight. It is quenched with water. The mixture was extracted with $CH_2Cl_2$ (X3), washed with brine, dried over $Na_2SO_4$, filtered and concentrated to dryness. Purification with flash chromatography over $SiO_2$ using 20% EtOAc in hexanes as the eluant afforded 63 mg of pure title product of this example as white crystalline solid. MS: 489 (M+18)$^+$.

Example 168

2,7-Phenanthrenediol, 4a-(2,3-dihydroxypropyl)-1,2,3,4,4a,9,10,10a-octahydro-,[2R-(2α,4aα,10aβ)]-

The title compound of this example was prepared by procedures analogous to those described above in Example 6. IR (neat) 3380, 2929, 1612 cm$^{-1}$.

Example 169

Acetamide, N-[5-[3-(3,4,9,10-tetrahydro-7-methoxy-2-oxo-4a (2H)-phenanthrenyl]-1-propenyl]-2-pyridinyl]-, [S-(E)]-

The title compound of this example was prepared by procedures analogous to those described above in Example 35. MS: 403 (M+1)$^+$.

Example 170

2-Phenanthrenecarbonitrile, 1,2,3,4,4a,9,10,10a-octahydro-7-hydroxy-4a-(phenylmethyl)-, (4aS, 10aR)-

The title product of Example 167 (20 mg) and KOH (38 mg) in EtOH (0.7 ml) and water (0.7 ml) were mixed. The mixture was refluxed overnight, then neutralized with HOAc, extracted with EtOAc, dried and concentrated to dryness. The crude mixture was purified with column chromatography with 5% isopropanol in hexane as the eluant to yield 1.2 mg of the pure title product of this example as the white solid. MS: 318 (M+1)$^+$.

The title compounds of Examples 171–174 were prepared by procedures analogous to those described above in Example 8.

Example 171

Acetamide, N-[5-[3-[2-(chloroethynyl)-3,4,9,10-tetrahydro-2,7-dihydroxy-4a(2H)-phenanthrenyl]-1-propenyl]-2-pyridinyl]-, [2R,4a(E)]-, MS: 449 (M+1)$^+$.

Example 172

2,7-Phenanthrenediol, 2-(chloroethynyl)-1,2,3,4,4a, 9,10,10a-octahydro-4a-(2-propenyl)-, [2R-(2α,4aα, 10aβ)]-, $^1$H NMR (400 MHz, $CD_3OD$) δ 4.90–4.97 (m, 2H), 5.45–5.61 (m, 1H), 6.51–6.53 (m, 2H), 6.95 (d, 1H, J=9).

Example 173

2,7-Phenanthrenediol, 2-(chloroethynyl)-1,2,3,4,4a, 9,10,10a-octahydro-4a-(2-propenyl)-, [2S-(2α,4aβ, 10aα)]-, $^1$H NMR (400 MHz, $CD_3OD$) δ 4.90–4.96 (m, 2H), 5.53–5.60 (m, 1H), 6.48–6.51 (m, 2H), 6.93 (d, 1H, J=9)

Example 174

2,7-Phenanthrenediol, 2-(chloroethynyl)-1,2,3,4,4a, 9,10,10a-octahydro-4a-(2-propenyl)-, [2S-(2α,4aβ, 10aβ)]-, $^1$H NMR (400 MHz, $CD_3OD$) δ 4.87–5.46 (m, 2H), 5.70–5.80 (m, 1H), 6.50 (d, 1H, J=2.7), 657 (dd, 1H, J=2.7, 8.5), 7.04 (d, 1H, J=8.5).

Example 175

2(3H)-Phenanthrenone, 4,4a,9,10-tetrahydro-7-hydroxy-4a-(2-propenyl)-, (S)-, $^1$H NMR (400 MHz, $CD_3OD$) δ 4.95–5.01 (m, 2H), 5.60–5.75 (m, 2H),5.95 (s, 1H), 6.58 (d, 1H, J=2.6), 6.73 (dd, 1H, J=2.6, 8.5), 7.12 (d, 1H, J=8.5).

The title compound of this example was prepared by procedures analogous to those described above in Example 3.

Example 176

2(1H)-Phenanthrenone, 3,4,4a,9,10,10a-hexahydro-7-hydroxy-4a a-(2-propenyl)-,(4aS-trans)-

The title compound of this example was prepared by procedures analogous to those described above or below in Example 6. MS: 357 (M+1)$^+$.

Example 177

2,7-Phenanthrenediol, 2-(chloroethynyl)-1,2,3,4,4a, 9,10,10a-octahydro-4a-[2-(4-morpholinyl)ethyl]-, (4aS,10aR)-

The title compound of this example was prepared by procedures analogous to those described above in Example 33. MS: 390 (M+1)$^+$.

Example 178

2,7-Phenanthrenediol, 2-(chloroethynyl)-1,2,3,4,4a, 9,10,10a-octahydro-4a-(2-propenyl)-, [2R-(2α,4aα, 10aα)]-

The title compound of this example was prepared by procedures analogous to those described above for the preparation of the title compound of Example 8. $^1$H NMR (400 MHz, CD$_3$OD) δ 4.95–4.99 (m, 2H), 5.60–5.80 (m, 2H), 6.50 (d, 1H, J=2.4), 657 (dd, 1H, J=2.4, 8.5), 7.03 (d, 1H, J=8.5).

Examples 179–181

The title compounds of Examples 179–181 were prepared by procedures analogous to those described above in Example 33.

Example 179

2,7-Phenanthrenediol, 2-(chloroethynyl)-1,2,3,4,4a, 9,10,10a-octahydro-4a-[2-(4-hydroxy-1-piperidinyl) ethyl]-, [2R-(2α, 4aα,10aβ)]-, MS: 404 (M+1)$^+$.

Example 180

2,7-Phenanthrenediol, 2-(chloroethynyl)-1,2,3,4,4a, 9,10,10a-octahydro-4a-[2-(4-methyl-1-piperazinyl) ethyl]-, [2R-(2α, 4aα,10aβ)]-, MS: 403 (M+1)$^+$.

Example 181

2,7-Phenanthrenediol, 2-(chloroethynyl)-1,2,3,4,4a, 9,10,10a-octahydro-4a-[2-[4-[2-(2-hydroxyethoxy) ethyl]-1-piperazinyl]ethyl]-, [2R-(2α,4aα,10aβ)]-, MS: 477 (M).

Example 182

2,7-Phenanthrenediol, 2-(chloroethynyl)-1,2,3,4,4a, 9,10,10a-octahydro-4a-(2-hydroxy-2-phenylethyl)-, [2R-(2α,4aα,10aβ)]-

The title compound of this example was prepared by procedures analogous to those described above in Example 136. MS: 396 (M).

Example 183

2-Butenoic acid, 4-[2-(chloroethynyl)-1,3,4,9,10, 10a-hexahydro-2,7-dihydroxy-4a(2H)-phenanthrenyl]-, ethyl ester, [2R-[2α,4aα(E), 10aβ]]-

The title compound of this example was prepared by procedures analogous to those described above in Example 35. MS: 406 (M+18)$^+$.

Example 184

4a(2H)-Phenanthreneacetaldehyde, 2-(chloroethynyl)-1, 3,4,9,10,10a-hexahydro-2,7-dihydroxy-, O-methyloxime, [2R-[2α,4aα,10aβ)]-

The title compound of this example was prepared by procedures analogous to those described above in Example 34. $^1$H NMR (400 MHz, CD$_3$OD) δ 3.70 (s) and 3.74 (s, 3H).

Example 185

(11H)-Phenanthrenone, 3,4,4a,9,10,10a-hexahydro-7-hydroxy-4a-propyl-, (4aR-cis)-

The title compound of this example was prepared by procedures analogous to those described above in Example 7. $^1$H NMR (400 MHz, CD$_3$OD) δ 0.826 (t, 3H, J=7). MS: 276 (M+18)$^+$.

Example 186

2-Phenanthrenol, 4b,5,6,7,8,8a,9,10-octahydro-4b-propyl-7-propylidene-, [4bR-(4bα,7Z,8aα)]-

The title compound of this example was prepared by procedures analogous to those described above in Example 78. MS: 285 (M+1)$^+$.

Example 187

2,7-Phenanthrenediol, 1,2,3,4,4a,9,10,10a-octahydro-4a-(2-propenyl)-2-(1-propynyl)-, [2R-(2α,4aα,10aβ)]-

The title compound of this example was prepared by procedures analogous to those described above in Example 9. MS: 279 (M−17)$^+$.

Examples 188–189

The title compounds of Examples 188–189 were prepared by procedures analogous to those described above in Example 7.

Example 188

2(1H)-Phenanthrenone, 3,4,4a,9,10,10a-hexahydro-7-hydroxy-4a -propyl-, (4aR-trans)-, MS: 259 (M+1)$^+$.

Example 189

2,7-Phenanthrenediol, 1,2,3,4,4a,9,10,10a-octahydro-2,4a-dipropyl-, [2R-(2α,4aα,10aβ)]-, MS: 285 (M−17)$^+$.

Example 190

Piperazine, 1-[4-[2-(chloroethynyl)-1,3,4,9,10,10a-hexahydro-2,7-dihydroxy-4a(2H)-phenanthrenyl]-1-oxo-2-butenyl]-4-[2-(2-hydroxyethoxy) ethyl]-, [2R-[2α,4aα(E),10aβ]]-

The title compound of this example was prepared by procedures analogous to those described above in Example 37. MS: 517 (M).

Example 191

2,7-Phenanthrenediol, 1,2,3,4,4a,9,10,10a-octahydro-4a-propyl-, [2S-(2α,4aβ,10aβ)]-

The title compound of this example was prepared by procedures analogous to those described above in Example 7. MS: 243 (M−17)$^+$.

Examples 192–193

The title compounds of Examples 192–193 were prepared by procedures analogous to those described above in Example 136.

Example 192

2,7-Phenanthrenediol, 1,2,3,4,4a,9,10,10a-octahydro-2,4a-dipropyl-, [2R-(2α,4aα,10aα)]-, MS: 285 (M−17)$^+$.

Example 193

2,7-Phenanthrenediol, 1,2,3,4,4a,9,10,10a-octahydro-2,4a-dipropyl-, [2S-(2α,4aβ,10aβ)]-, MS: 285 (M−17)$^+$.

Example 194

Piperazine,1-[4-[2-(chloroethynyl)-1,3,4,9,10,10a-hexahydro-2,7-dihydroxy-4a(2H)-phenanthrenyl]-1-oxo-2-butenyl]-4-methyl-, [2R-[2α,4aα(E),10aβ]]-

The title compound of this example was prepared by procedures analogous to those described above in Example 37. MS: 443 (M+1)$^+$.

Example 195

2,7-Phenanthrenediol, 2-(chloroethynyl)-1,2,3,4,4a,
9,10,10a-octahydro-4a-[3-(2-thienyl)-2-propenyl]-,
[4aS(E)]-

The title compound of this example was prepared by procedures analogous to those described above in Example 35. MS: 382 (M−18)+.

Example 196

2-Phenanthrenol, 4b,5,6,7,8,8a,9,10-octahydro-4b,7-dipropyl-, (4bR,8aS)-

The title compound of this example was prepared by procedures analogous to those described above in Example 10. MS: 287 (M+1)+.

Examples 197–202

The title compounds of Examples 197–202 were prepared by procedures analogous to those described above in Example 37.

Example 197

4-Piperidinol, 1-[4-[2-(chloroethynyl)-1,3,4,9,10,
10a-hexahydro-2,7-dihydroxy4a(2H)-phenanthrenyl]-1-oxo-2-butenyl]-, [2R-[2α,4aα(E),
10aβ]]-, MS: 426 (M−17)+.

Example 198

2-Butenamide, 4-[2-(chloroethynyl)-1,3,4,9,10,10a-hexahydro-2,7-dihydroxy-4a(2H)-phenanthrenyl]-N-[3-(dimethylamino)propyl]-, [2R-[2α,4aα(E),
10aβ]]-, MS: 446 (M+1)+.

Example 199

2-Butenamide, 4-[2-(chloroethynyl)-1,3,4,9,10,10a-hexahydro-2,7-dihydroxy-4a(2H)-phenanthrenyl]-N,N-diethyl-, [2R-[2α, 4aα(E),10aβ]]-, MS: 416 (M+1)+.

Example 200

2-Butenamide, 4-[2-(chloroethynyl)-1,3,4,9,10,10a-hexahydro-2,7-dihydroxy-4a(2H)-phenanthrenyl]-N-[3-(4-morpholinyl) propyl]-, [2R-[2α,4aα(E),
10aβ]]-, MS: 487 (M).

Example 201

2-Butenamide, 4-[2-(chloroethynyl)-1,3,4,9,10,10a-hexahydro-2,7-dihydroxy-4a(2H)-phenanthrenyl]-N-(2-pyridinylmethyl)-, [2R-[2α,4aα(E),10aβ]]-, MS: 452 (M+1)+.

Example 202

2-Butenamide, 4-[2-(chloroethynyl)-1,3,4,9,10,10a-hexahydro-2,7-dihydroxy4a(2H)-phenanthrenyl]-N-(4-pyridinylmethyl)-, [2R-[2α,4aα(E),10aβ]]-, MS: 451 (M+1)+.

Example 203

2,7-Phenanthrenediol, 2-(chloroethynyl)-1,2,3,4,4a,9,10,10a -octahydro 4a-[3-(2-pyridinyl)-2-propenyl]-, [2R-[2α, 4aα(E),10aβ]]-

The title compound of this example was prepared by procedures analogous to those described above in Example 35. MS: 394 (M+1)+.

Example 204

2-Butenamide, 4-[2-(chloroethynyl)-1,3,4,9,10,10a-hexahydro-2,7-dihydroxy-4a(2H-phenanthrenyl]-N-[2-(4-pyridinyl)ethyl]-, [2R-[2α,4aα(E),10aβ]]-

The title compound of this example was prepared by procedures analogous to those described above in Example 37. MS: 465 (M+1)+.

Example 205

2,7-Phenanthrenediol, 2-(chloroethynyl)-1,2,3,4,4a,
9,10,10a-octahydro-4a-[3-(5-isoxazolyn)-2-propenyl]-, [4aS(E),10aR]-

The title compound of this example was prepared by procedures analogous to those described above in Example 35. MS: 366 (M−17)+.

Example 206

2-Butenamide, 4-[2-(chloroethynyl)-1,3,4,9,10,10a-hexahydro-2,7-dihydroxy-4a(2H)phenanthrenyl]-N-ethyl-, [2R-[2α, 4aα(E),10aβ]]-

The title compound of this example was prepared by procedures analogous to those described above in Example 37. MS: 370 (M−17)+.

Example 207

2-Phenanthrenecarboxylic acid, 4b,5,6,7,8,8a,9,10-octahydro-7-hydroxy-4b-(2-propenyl)-7-(1-propynyl)-, [4bS-(4bα,7α,8aβ)]- , $^{13}$C NMR (100 MHz, CDCl$_3$) δ 116.6, 168.5

The title compound of this example was prepared by procedures analogous to those described above in Example 9.

Examples 208–209

The title compounds of Examples 208–209 were prepared by procedures analogous to those described above in Example 8.

Example 208

2,7-Phenanthrenediol, 2-(chloroethynyl)-1,2,3,4,4a,
9,10,10a-octahydro-4a-(3-phenylpropyl)-, (4aR)-, MS: 377 (M−17)+.

Example 209

2,7-Phenanthrenediol, 2-(chloroethynyl)-1,2,3,4,4a,
9,10,10a-octahydro-4a-(3-phenylpropyl)-, [2S-(2α,4aβ,10aα)]-, MS: 377 (M−17)+.

Examples 210–212

The title compounds of Examples 210–212 were prepared by procedures analogous to those described above in Example 18.

Example 210

2-Phenanthrenecarboxamide, 4b,5,6,7,8,8a,9,10-octahydro-7-hydroxy-4b-(2-propenyl)-7-(1-propynyl)-, [4bS-(4bα,7α,8aβ)]-, MS: 324 (M+1)+.

Example 211

2-Phenanthrenecarboxamide, 4b,5,6,7,8,8a,9,10-octahydro-7-hydroxy-N,N-dimethyl-4b-(2-propenyl)-7-(1-propynyl)-, [4bS-(4bα,7α,8aβ)]-, MS: 353 (M+1)+.

Example 212

2-Phenanthrenecarboxamide, 4b,5,6,7,8,8a,9,10-octahydro-7-hydroxy-4b-(phenylmethyl)-7-(1-propynyl)-, [4bS-(4bα,7α,8aβ)]-, MS: 374 (M+1)+.

Examples 213–214

The title compounds of Examples 213–214 were prepared by procedures analogous to those described above in Example 9.

Example 213

2-Phenanthrenol, 1,2,3,4,4a,9,10,10a-octahydro-4a-(phenylmethyl)-2-(1-propynyl)-, [2R-(2α,4aα, 10aβ)]-, MS: 313 (M−17)+.

Example 214

2-Phenanthrenol, 1,2,3,4,4a,9,10,10a-octahydro-4a-(phenylmethyl)-2-(1-propynyl)-, [2S-(2α,4aβ, 10aα)]-, MS: 313 (M−17)+.

Examples 215–216

The title compounds of Examples 215–216 were prepared by procedures analogous to those described above in Example 10.

Example 215

2-Phenanthrenol, 7-fluoro-1,2,3,4,4a,9,10,10a-octahydro-4a-(phenylmethyl)-2-propyl-, (4aS, 10aS)-, MS: 352 (M).

Example 216

2-Phenanthrenol, 7-fluoro-1,2,3,4,4a,9,10,10a-octahydro-4a-(phenylmethyl)-2-propyl-, (4aS, 10aS)-, MS: 352 (M).

Example 217

2-Phenanthrenecarboxamide, 4b,5,6,7,8,8a,9,10-octahydro-7-hydroxy-N-methyl-4b-(phenylmethyl)-7-(1-propynyl)-, [4bS-(4bα,7α,8aβ)]-

The title compound of this example was prepared by procedures analogous to those described above in Example 18. MS: 388 (M+1)+.

Examples 218–219

The title compounds of Examples 218–219 were prepared by procedures analogous to those described above in Example 9.

Example 218

2-Phenanthrenol, 7-fluoro-1,2,3,4,4a,9,10,10a-octahydro-4a-(phenylmethyl)-2-(1-propynyl)-, [2S-(2α,4aβ,10aα)]-, MS: 331 (M−17)+.

Example 219

2-Phenanthrenol, 7-fluoro-1,2,3,4,4a,9,10,10a-octahydro-4a-(phenylmethyl)-2-(1-propynyl)-, [2R-(2α,4aα,10aβ)]-, MS: 331 (M−17)+.

Example 220

2-Phenanthrenecarboxamide, 4b-[(2,2-dimethyl-1,3-dioxolan-4-yl) methyl]-4b,5,6,7,8,8a,9,10-octahydro-7-hydroxy-7-(1-propynyl)-, [4bS-(4bα, 7α,8aβ)]-

The title compound of this example was prepared by procedures analogous to those described above in Example 18. MS: 398 (M+1)+.

Example 221

2-Phenanthrenecarboxylic acid, 4b,5,6,7,8,8a,9,10-octahydro-7-hydroxy4b-(phenylmethyl)-7-(1-propynyl)-, methyl ester, [4bS-(4bα,7β,8aβ)]-

The title compound of this example was prepared by procedures analogous to those described above in Example 14. MS: 371 (M−17)+.

Example 222

2-Phenanthrenemethanol, 4b,5,6,7,8,8a,9,10-octahydro-7-hydroxy-a,a-dimethyl-4b-(phenylmethyl)-7-(1-propynyl)-, [4bS-(4bα,7α, 8aβ)]-

The title compound of this example was prepared by procedures analogous to those described above in Example 19. MS: 371 (M−17)+.

Example 223

Carbamic acid, [4b,5,6,7,8,8a,9,10-octahydro-7-hydroxy-4b-(phenylmethyl)-7-(1-propynyl)-2-phenanthrenyl]-, 2-(dimethylamino) ethyl ester, [4bS-(4bα,7α,8aβ)]-

The title compound of this example was prepared by procedures analogous to those described above in Example 28. MS: 461 (M+1)+.

Example 224

2-Phenanthrenol, 7-(chloromethyl)-1,2,3,4,4a,9,10, 10a-octahydro-4a-(phenylmethyl)-2-(1-propynyl)-, [2R-(2α,4aα,10aβ)]-

The title compound of this example was prepared by procedures analogous to those described above in Example 9. MS: 361 (M−17)+.

Examples 225–231

The title compounds of Examples 225–231 were prepared by procedures analogous to those described above in Example 18.

Example 225

2-Phenanthrenecarboxamide, 4b,5,6,7,8,8a,9,10-octahydro-7-hydroxy-4b-(3-phenyl-2-propenyl)-7-(1-propynyl)-, [4bS-(4bα,7α,8aβ)]-, MS: 400 (M+1)+.

Example 226

2-Phenanthrenecarboxamide, N-[2-(dimethylamino) ethyl]-4b,5,6,7,8,8a,9,10-octahydro-7-hydroxy-4b-(phenylmethyl)-7-(1-propynyl)-, [4bS-(4bα,7α, 8aβ)]-, MS: 445 (M+1)+.

Example 227

2-Phenanthrenecarboxamide, N-[6-(dimethylamino) hexyl]-4b,5,6,7,8,8a,9,10-octahydro-7-hydroxy-4b-(phenylmethyl)-7-(1-propynyl)-, [4bS-(4bα,7α, 8aβ)]-, MS: 501 (M+1)+.

Example 228

2-Phenanthrenecarboxamide, 4b,5,6,7,8,8a,9,10-octahydro-7-hydroxy-4b-(phenylmethyl)-7-(1-propynyl)-N-[2-(1-pyrrolidinyl) ethyl]-,[4bS-(4bα, 7α,8aβ)]-, MS: 471 (M+1)+.

Example 229

2-Phenanthrenecarboxamide, 4b,5,6,7,8,8a,9,10-octahydro-7-hydroxy-N-[3-(4-methyl-1-piperazinyl) propyl]-4b-(phenylmethyl)-7-(1-propynyl)-,[4bS-(4bα,7α,8aβ)]-, MS: 514 (M+1)+.

Example 230

2-Phenanthrenecarboxamide, N-[3-(dimethylamino) propyl]-4b,5,6,7,8,8a,9,10-octahydro-7-hydroxy-4b-(phenylmethyl)-7-(1-propynyl)-, [4bS-(4bα,7α, 8aβ)]-, MS: 459 (M+1)+.

Example 231

2-Phenanthrenecarboxamide, 4b,5,6,7,8,8a,9,10-octahydro-7-hydroxy -N-[2-(4-morpholinyl)ethyl]-4b-(phenylmethyl)-7-(1-propynyl)-, [4bS-(4bα,7α, 8aβ)]-, MS: 487 (M+1)+.

Example 232

2-Phenanthrenecarboxamide, 4b,5,6,7,8,8a,9,10-octahydro-7-hydroxy-N-[2-(4-morpholinyl)ethyl]-4b-(phenylmethyl)-7-(1-propynyl)-, [4bS-(4bα,7α,8aβ)]- HCl salt The title compound of this example is the HCl salt of the title compound of Example 231. MS: 487 (M+1)$^+$.

Examples 233–237

The title compounds of Examples 233–237 were prepared by procedures analogous to those described above in Example 18.

Example 233

2-Phenanthrenecarboxamide, 4b,5,6,7,8,8a,9,10-octahydro-7-hydroxy-4b-(phenylmethyl)-7-(1-propynyl)-, [4bS-(4bα,7β,8aβ)]-, MS: 374 (M+1)$^+$.

Example 234

2-Phenanthrenecarboxamide, 4b,5,6,7,8,8a,9,10-octahydro-7-hydroxy-N-[3-(1H-imidazol-1-yl)propyl]-4b-(phenylmethyl)-7-(1-propynyl)-, [4bS-(4bα,7α,8aβ)]-HCl salt, MS: 483 (M+1)$^+$.

Example 235

2-Phenanthrenecarboxamide, N-[4-(dimethylamino)butyl]-4b,5,6,7,8,8a,9,10-octahydro-7-hydroxy-4b-(phenylmethyl)-7-(1-propynyl)-, [4bS-(4bα,7α,8aβ)]-, MS: 473 (M+1)$^+$.

Example 236

2-Phenanthrenecarboxamide, 4b,5,6,7,8,8a,9,10-octahydro-7-hydroxy -N-[3-(4-morpholinyl)propyl]-4b-(phenylmethyl)-7-(1-propynyl)-, [4bS-(4bα,7α,8aβ)]-, MS: 501 (M+1)$^+$.

Example 237

2-Phenanthrenecarboxamide, 4b,5,6,7,8,8a,9,10-octahydro-7-hydroxy-N-[3-(4-morpholinyl)propyl]-4b-(phenylmethyl)-7-(1-propynyl)-, [4bS-(4bα,7α,8aβ)]-HCl salt, MS: 501 (M+1)$^+$.

Example 238

2,7-Phenanthrenediol, 1,2,3,4,4a,9,10,10a-octahydro-4a-propyl-2-(1-propynyl)-,[2R-(2α,4aα,10aβ)]-

The title compound of this example was prepared by procedures analogous to those described above in Example 9. MS: 281 (M−17)$^+$.

Examples 239–240

The title compounds of Examples 239–240 were prepared by procedures analogous to those described above in Example 18.

Example 239

2-Phenanthrenecarboxamide, 4b,5,6,7,8,8a,9,10-octahydro-7-hydroxy-N-(3-methoxypropyl)-4b-(phenylmethyl)-7-(1-propynyl)-, [4bS-(4bα,7α,8aβ)]-, MS: 446 (M+1)$^+$

Example 240

2-Phenanthrenecarboxamide, 4b,5,6,7,8,8a,9,10-octahydro-7-hydroxy-N-[3-(2-methoxyethoxy)propyl]-4b-(phenylmethyl)-7-(1-propynyl)-, [4bS-(4bα,7α,8aβ)]-, MS: 490 (M+1)$^+$

Example 241

2-Phenanthrenecarboxamide, 4b,5,6,7,8,8a,9,10-octahydro-7-hydroxy- 4b-(phenylmethyl)-7-(1-propynyl)-N-(4-pyridinylmethyl)-, [4bS-(4bα,7α,8aβ)]-

To a stirring solution of 779 mg of 4-aminomethylpyridine in 10 mL of dichloromethane at 0° C. under N$_2$ was added 3.6 mL of 2.0 M trimethylaluminum in toluene. The mixture was stirred at 0° C. for 20 min. then at RT for 1 h. To this mixture was added 350 mg of the title compound of Example 14 in 5 mL of dichloromethane. The mixture was heated to reflux overnight. To the reaction mixture was added 1 N HCl dropwise until the aqueous layer was approximately pH 4. The resultant mixture was extracted with EtOAc, dried over Na$_2$SO$_4$, filtered, and concentrated to dryness. Purification by flash chromatography over SiO$_2$ using 5% MeOH in dichloromethane to 10% MeOH in dichloromethane as the gradient eluant afforded 362 mg (87%) of the title product of this example as a white solid. MS: 465 (M+1)$^+$.

Example 242

2-Phenanthrenecarboxamide, 4b,5,6,7,8,8a,9,10-octahydro-7-hydroxy-4b-(phenylmethyl)-7-(1-propynyl)-N-(4-pyridinylmethyl)-, [4bS-(4bα,7α,8aβ)]-, HCl salt The title compound of this example is the HCl salt of the title compound of Example 241. MS: 465 (M+1)$^+$.

Example 243

2-Phenanthrenecarboxamide, 4b,5,6,7,8,8a,9,10-octahydro-7-hydroxy-4b-(phenylmethyl)-7-(1-propynyl)-N-[2-(4-pyridinyl)ethyl]-,[4bS-(4bα,7α,8aβ)]-

The title compound of this example was prepared by procedures analogous to those described above in Example 241. MS: 479 (M+1)$^+$.

Example 244

2-Phenanthrenecarboxamide, 4b,5,6,7,8,8a,9,10-octahydro-7-hydroxy-4b-(phenylmethyl)-7-(1-propynyl)-N-(2-pyridinylmethyl)-,[4bS-(4bα,7α,8aβ)]-

To a stirring solution of 6.2 g of 2-aminomethylpyridine in 80 mL of dichloromethane at 0° C. under N$_2$ was added 26 mL of 2.0 M trimethylaluminum in toluene. The mixture was stirred at 0° C. for 20 min. then at RT for 1 h. To this mixture was added 2.2 g of the title compound of Example 14 (which was made by procedures described in Example 14) in 50 mL of dichloromethane. The mixture was heated to reflux overnight. To the reaction mixture was added 1 N HCl dropwise until the aqueous layer was approximately pH 4. The resultant mixture was extracted with EtOAc, dried over $Na_2SO_4$, filtered, and concentrated to dryness. Purification by flash chromatography over $SiO_2$ using 5% MeOH in dichloromethane to 10% MeOH in dichloromethane as the gradient eluant afforded 1.4 g (53%) of the title product of this example as a white solid. MS: 465 $(M+1)^+$.

Examples 245–247

The compounds of Examples 245–247 were prepared by procedures analogous to those described above in Example 244.

Example 245

2-Phenanthrenecarboxamide, 4b,5,6,7,8,8a,9,10-octahydro-7-hydroxy-4b-(phenylmethyl)-7-(1-propynyl)-N-(2-pyridinylmethyl)-,[4bS-(4bα,7α,8aβ)]-HCl salt The title product of this example is the HCl salt of the title product of Example 244. MS: 465 $(M+1)^+$.

Example 246

2-Phenanthrenecarboxamide, 4b,5,6,7,8,8a,9,10-octahydro-7-hydroxy-4b-(phenylmethyl)-7-(1-propynyl)-N-[2-(2-pyridinyl)ethyl]-,[4bS-(4bα,7α,8aβ)]-, MS: 479 $(M+1)^+$.

Example 247

2-Phenanthrenecarboxamide, 4b,5,6,7,8,8a,9,10-octahydro-7-hydroxy-4b-(phenylmethyl)-7-(1-propynyl)-N-[(tetrahydro-2-furanyl)methyl]-,[4bS-(4bα,7α,8aβ)]-, MS: 458 $(M+1)^+$.

Example 248

2-Phenanthrenecarboxamide, 4b,5,6,7,8,8a,9,10-octahydro-7-hydroxy-4b-(phenylmethyl)-7-(1-propynyl)-N-(3-pyridinylmethyl)-,[4bS-(4bα,7α,8aβ)]-

To a stirring solution of 0.21 mL of 3-aminomethylpyridine in 1 mL of dichloromethane at 0° C. under $N_2$ was added 0.1 mL of 2.0 M trimethylaluminum in hexane. The mixture was stirred at 0° C. for 20 min. then at RT for 1 h. To this mixture was added 20 mg of the title compound of Example 14 in 1 mL of dichloromethane. The mixture was heated to reflux overnight. To the reaction mixture was added 1 N HCl dropwise until the aqueous layer was approximately pH 4. The resultant mixture was extracted with EtOAc, dried over $Na_2SO_4$, filtered, and concentrated to dryness. Purification by flash chromatography over $SiO_2$ using 5% MeOH in dichloromethane to 10% MeOH in dichloromethane as the gradient eluant afforded 18 mg (75%) of the title product of this example as a white solid. MS: 465 $(M+1)^+$.

Example 249

2-Phenanthrenecarboxamide, 4b,5,6,7,8,8a,9,10-octahydro-7-hydroxy-4b-(phenylmethyl)-7-(1-propynyl)-N-(3-pyridinylmethyl)-,[4bS-(4bα,7α,8aβ)]-HCl-salt The title product of this example is the HCl salt of the title product of Example 248. MS: 465 $(M+1)^+$ Example 250

2-Phenanthrenecarboxamide, 4b,5,6,7,8,8a,9,10-octahydro-7-hydroxy-N-[2-(1-methyl-2-pyrrolidinyl)ethyl]-4b-(phenylmethyl)-7-(1-propynyl)-,[4bS-(4bα,7α,8aβ)]-

The title compound of this example was prepared by procedures analogous to those described above in Example 248. MS: 485 $(M+1)^+$.

Example 251

2-Phenanthrenecarboxamide, 4b,5,6,7,8,8a,9,10-octahydro-7-hydroxy-N-[2-(1-methyl-2-pyrrolidinyl)ethyl]-4b-(phenylmethyl)-7-(1-propynyl)-,[4bS-(4bα,7α,8aβ)]-HCl salt The title product of this example is the HCl salt of the title product of Example 251. MS: 485 $(M+1)^+$.

Examples 252–253

The title compounds of Examples 252–253 were prepared by procedures analogous to those described above in Example 9.

Example 252

2,7-Phenanthrenediol, 1,2,3,4,4a,9,10,10a-octahydro-4a-pentyl-2-(1-propynyl)-,[2R-(2α,4aα,10aβ)]-, MS: 309 $(M-17)^+$.

Example 253

2,7-Phenanthrenediol, 4a-butyl-1,2,3,4,4a,9,10,10a-octahydro-2-(1-propynyl)-,[2R-(2α,4aα,10aβ)]-, MS: 295 $(M-17)^+$.

Example 254

2-Phenanthrenecarboxamide, 4b,5,6,7,8,8a,9,10-octahydro-7-hydroxy-4b-(phenylmethyl)-7-(1-propynyl)-N-[3-(1-pyrrolidinyl)propyl]-,[4bS-(4bα,7α,8aβ)]-

The title compound of this example was prepared by procedures analogous to those described above in Example 248. MS: 485 $(M+1)^+$.

Example 255

2-Phenanthrenecarboxamide, 4b,5,6,7,8,8a,9,10-octahydro-7-hydroxy-4b-(phenylmethyl)-7-(1-propynyl)-N-[3-(1-pyrrolidinyl)propyl]-,[4bS-(4bα,7α,8aβ)]-HCl salt The title product of this example is the HCl salt of the title product of Example 254. MS: 485 $(M+1)^+$.

Example 256

2-Phenanthrenecarboxamide, 4b,5,6,7,8,8a,9,10-octahydro-7-hydroxy-4b-(phenylmethyl)-7-(1-propynyl)-N-[3-(1H-1,2,4-triazol-1-yl)propyl]-,[4bS-(4bα,7α,8aβ)]-

The title compound of this example was prepared by procedures analogous to those described above in Example 248. MS: 483 $(M+1)^+$.

Example 257

2-Phenanthrenecarboxamide, 4b,5,6,7,8,8a,9,10-octahydro-7-hydroxy-4b-(phenylmethyl)-7-(1-propynyl)-N-[3-(1H-1,2,4-triazol-1-yl)propyl]-,[4bS-(4bα,7α,8aβ)]-HCl salt The title product of this example is the HCl salt of the title product of Example 256. MS: 483 $(M+1)^+$.

Example 258

2,7-Phenanthrenediol, 4a-(3-butenyl)-1,2,3,4,4a,9,10,10a-octahydro-2-(1-propynyl)-,[2R-(2α,4aα,10aβ)]-

The title compound of this example was prepared by procedures analogous to those described above in Example 9. MS: 293 $(M-17)^+$.

Example 259

2-Phenanthrenecarboxamide, 4b,5,6,7,8,8a,9,10-octahydro-7-hydroxy-N-[5-(4-morpholinyl)pentyl]-4b-(phenylmethyl)-7-(1-propynyl)-,[4bS-(4bα,7α, 8aβ)]-

The title compound of this example was prepared by procedures analogous to those described above in Example 248. MS: 529 (M+1)+.

Example 260

2-Phenanthrenecarboxamide, 4b,5,6,7,8,8a,9,10-octahydro-7-hydroxy-N-[5-(4-morpholinyl)pentyl]-4b-(phenylmethyl)-7-(1-propynyl)-,[4bS-(4bα,7α, 8aβ)]- HCl salt The title compound of this example is the HCl salt of the title compound of Example 259. MS: 529 (M+1)+.

Example 261

2-Phenanthrenecarboxamide, 4b,5,6,7,8,8a,9,10-octahydro-7-hydroxy-4b-pentyl-7-(1-propynyl)-N-[3-(1H-1,2,4-triazol-1-yl)propyl]-,[4bR-(4bα,7α, 8aβ)]-

The title compound of this example was prepared by procedures analogous to those described above in Example 248. MS: 463 (M+1)+.

Example 262

2-Phenanthrenecarboxamide, 4b,5,6,7,8,8a,9,10-octahydro-7-hydroxy-4b-pentyl-7-(1-propynyl)-N-[3-(1H-1,2,4-triazol-1-yl)propyl]-,[4bR-(4bα,7α, 8aβ)]-HCl salt The title product of this example is the HCl salt of the title product of Example 261. MS: 463 (M+1)+.

Examples 263–265

The title compounds of Examples 263–265 were prepared by procedures analogous to those described above for the preparation of the title compound of Example 59.

Example 263

Carbamic acid, dimethyl-, 7-(chloroethynyl)-4b,5,6, 7,8,8a,9,10-octahydro-7-methoxy-4b-(2-methoxyethyl)-2-phenanthrenyl ester,[4bS-(4bα,7α, 8aβ)]-, MS: 420 (M+1)+.

Example 264

Carbamic acid, dimethyl-, 7-(chloroethynyl)-4b,5,6, 7,8,8a,9,10-octahydro-7-hydroxy-4b-(2-methoxyethyl)-2-phenanthrenyl ester, [4bS-(4bα,7α, 8aβ)]-, MS: 406 (M+1)+.

Example 265

Carbamic acid, dimethyl-, 7-(chloroethynyl)-4b-[2-[2-(dimethylamino)-2-oxoethoxy]ethyl]-4b,5,6,7,8, 8a,9,10-octahydro-7-hydroxy-2-phenanthrenyl ester, [4bS-(4bα,7α,8aβ)]-, $^1$H NMR (400 MHz, CDCl$_3$) δ 2.94 (s 3H), 2.96 (s, 3H), 3.06 (s, 3H), 3.09 (s, 3H), 4.34 (s, 2H).

Example 266–267

The title compounds of Examples 266–267 were prepared by procedures analogous to those described above in Example 248.

Example 266

2-Phenanthrenecarboxamide, 4b,5,6,7,8,8a,9,10-octahydro-7-hydroxy-4b-(phenylmethyl)-7-(1-propynyl)-N-2-pyridinyl-,[4bS-(4bα,7α,8aβ)]-, MS: 451 (M+1)+.

Example 267

2-Phenanthrenecarboxamide, 4b,5,6,7,8,8a,9,10-octahydro-7-hydroxy-4b-(phenylmethyl)-7-(1-propynyl)-N-2-pyridinyl-,[4bS-(4bα,7α,8aβ)]-HCl salt, MS: 451 (M+1)+.

Example 268

2-Phenanthrenecarboxamide, 4b,5,6,7,8,8a,9,10-octahydro-7-hydroxy-4b-(phenylmethyl)-7-(1-propynyl)-N-pyrazinyl-,[4bS-(4bα,7α,8aβ)]-

The title compound of this example was prepared by procedures analogous to those described above in Example 244. MS: 452 (M+1)+.

Examples 269–270

The title products of Examples 269–270 are the HCl salt and the p-methanesulfonic acid salt, respectively, of the title product of Example 268.

Example 269

2-Phenanthrenecarboxamide, 4b,5,6,7,8,8a,9,10-octahydro-7-hydroxy-4b-(phenylmethyl)-7-(1-propynyl)-N-pyrazinyl-, [4bS-(4bα,7α,8aβ)]-HCl salt, MS: 452 (M+1)+.

Example 270

2-Phenanthrenecarboxamide, 4b,5,6,7,8,8a,9,10-octahydro-7-hydroxy-4b-(phenylmethyl)-7-(1-propynyl)-N-pyrazinyl-,[4bS-(4bα,7α,8aβ)]-p-methanesulfonic acid salt, MS: 452 (M+1)+.

Example 271

2-Phenanthrenecarboxamide, 4b,5,6,7,8,8a,9,10-octahydro-7-hydroxy-4b-(phenylmethyl)-7-(1-propynyl)-N-3-pyridinyl-,[4bS-(4bα,7α,8aβ)]-

The title compound of this example was prepared by procedures analogous to those described above in Example 248. MS: 450 (M).

Example 272

2-Phenanthrenecarboxamide, 4b,5,6,7,8,8a,9,10-octahydro-7-hydroxy-4b-(phenylmethyl)-7-(1-propynyl)-N-3-pyridinyl-,[4bS-(4bα,7α,8aβ)]-HCl salt The title product of this example is the HCl salt of the title product of Example 271. MS: 451 (M+1)+.

Examples 273–274

The title compounds of Examples 273–274 were prepared by procedures analogous to those described above in Example 248.

Example 273

2-Phenanthrenecarboxamide, 4b,5,6,7,8,8a,9,10-octahydro-7-hydroxy-4b-(phenylmethyl)-7-(1-propynyl)-N-4-pyrimidinyl-,[4bS-(4bα,7α,8aβ)]-, MS: 452 (M+1)$^+$.

Example 274

2- Phenanthrenecarboxamide, 4b,5,6,7,8,8a,9,10-octahydro-7-hydroxy-4b-propyl-7-(1-propynyl)-N-(4-pyridinylmethyl)-,[4bR-(4bα,7α,8aβ)]-, MS: 417 (M+1)$^+$.

Example 275

2-Phenanthrenecarboxamide, 4b,5,6,7,8,8a,9,10-octahydro-7-hydroxy-4b-propyl-7-(1-propynyl)-N-(4-pyridinylmethyl)-,[4bR-(4bα,7α,8aβ)]- HCl salt The title compound of this example is the HCl salt of the title compound of Example 274. MS: 417 (M+1)$^+$.

Example 276

2-Phenanthrenecarboxamide, 4b,5,6,7,8,8a,9,10-octahydro-7-hydroxy-4b-(phenylmethyl)-7-(1-propynyl)-N-1,3,4-thiadiazol-2-yl-,[4bS-(4bα,7α,8aβ)]-

The title compound of this example was prepared by procedures analogous to those described above in Example 248. MS: 458 (M+1)$^+$.

Example 277

2-Phenanthrenecarboxamide, 4b,5,6,7,8,8a,9,10-octahydro-7-hydroxy-4b-(phenylmethyl)-7-(1-propynyl)-N-1,3,4-thiadiazol-2-yl-,[4bS-(4bα,7α,8aβ)]-HCl salt The title product of this example is the HCl salt of the title product of Example 276. MS: 458 (M+1)$^+$.

Example 278

2-Phenanthrenecarboxamide, 4b,5,6,7,8,8a,9,10-octahydro-7-hydroxy-4b-(phenylmethyl)-7-(1-propynyl)-N-2-pyrimidinyl-,[4bS-(4bα,7α,8aβ)]-

The title compound of this example was prepared by procedures analogous to those described above in Example 248. MS: 452 (M+1)$^+$.

Example 279

2-Phenanthrenecarboxamide, 4b,5,6,7,8,8a,9,10-octahydro-7-hydroxy-4b-(phenylmethyl)-7-(1-propynyl)-N-2-pyrimidinyl-,[4bS-(4bα,7α,8aβ]-HCl salt The title product of this example is the HCl salt of the title product of Example 278. MS: 452 (M+1)$^+$.

Examples 280–283

The title compounds of Examples 280–283 were prepared by procedures analogous to those described above in Example 248.

Example 280

2-Phenanthrenecarboxamide, N-(cyanomethyl)-4b,5,6,7,8,8a,9,10-octahydro-7-hydroxy-4b-(phenylmethyl)-7-(1-propynyl)-,[4bS-(4bα,7α,8aβ)]-, MS: 413 (M+1)$^+$.

Example 281

2-Phenanthrenecarboxamide, 4b,5,6,7,8,8a,9,10-octahydro-7-hydroxy-4b-(phenylmethyl)-7-(1-propynyl)-N-(1H-tetrazol-5-ylmethyl)-,[4bS-(4bα,7α,8aβ)]-, MS: 454 (M−1)$^+$.

Example 282

2-Phenanthrenecarboxamide, 4b,5,6,7,8,8a,9,10-octahydro-7-hydroxy-4b-(phenylmethyl)-7-(1-propynyl)-N-1,2,4-triazin-3-yl-,[4bS-(4bα,7α,8aβ)]-, MS: 453 (M+1)$^+$.

Example 283

2-Phenanthrenecarboxamide, 4b,5,6,7,8,8a,9,10-octahydro-7-methoxy-4b-(phenylmethyl)-7-(1-propynyl)-N-pyrazinyl-,[4bS-(4bα,7α,8aβ)]-, MS: 466 (M+1)$^+$.

Example 284

2-Phenanthrenecarboxamide, 4b,5,6,7,8,8a,9,10-octahydro-7-methoxy-4b-(phenylmethyl)-7-(1-propynyl)-N-pyrazinyl-,[4bS-(4bα,7α,8aβ)]-HCl salt The title product of this example is the HCl salt of the title product of Example 283. MS: 466 (M+1)$^+$.

Example 285

2-Phenanthrenol, 1,2,3,4,4a,9,10,10a-octahydro-4a-propyl-2-(1-propynyl)-7-(2-thiazolyl)-,[2R-(2α,4aα,10aβ)]-

The title compound of this example was prepared by procedures analogous to those described above in Example 16. MS: 366 (M+1)$^+$.

Examples 286–287

The title compounds of Examples 286–287 were prepared by procedures analogous to those described above in Example 248.

Example 286

2-Phenanthrenecarboxamide, 4b,5,6,7,8,8a,9,10-octahydro-7-hydroxy-N-(5-methyl-1H-pyrazol-3-yl)-4b-(phenylmethyl)-7-(1-propynyl)-,[4bS-(4bα,7α,8aβ)]-, MS: 454 (M+1)$^+$.

Example 287

1H-Pyrazol-3-amine,5-methyl-1-[[4b,5,6,7,8,8a,9,10-octahydro-7-hydroxy-4b-(phenylmethyl)-7-(1-propynyl)-2-phenanthrenyl]carbonyl]-, [4bS-(4bα, 7α, 8aβ)]-, MS: 454 (M+1)$^+$.

Example 288

2-Phenanthrenol, 1,2,3,4,4a,9,10,10a-octahydro-4a-propyl-2-(1-propynyl)-7-(3-pyridinyl)-,[2R-(2α,4aα,10aβ)]-

The title compound of this example was prepared by procedures analogous to those described above in Example 16. MS: 360 (M+1)$^+$.

Example 289

2-Phenanthrenol, 1,2,3,4,4a,9,10,10a-octahydro-4a-propyl-2-(1-propynyl)-7-(3-pyridinyl)-,[2R-(2α,4aα,10aβ)]-HCl salt The title product of this example is the HCl salt of the title product of Example 288. MS: 360 (M+1)$^+$.

Example 290

Carbamic acid, [2-(4-morpholinyl)ethyl]-, 4b-butyl-4b,5,6,7,8,8a,9,10-octahydro-7-hydroxy-7-(1-propynyl)-2-phenanthrenyl ester, [4bR-(4bα,7α,8aβ)]-

The title compound of this example was prepared by procedures analogous to those described above in Example 59. MS: 469 (M+1)$^+$.

Example 291

Carbamic acid, [2-(4-morpholinyl)ethyl]-, 4b-butyl-4b,5,6,7,8,8a,9,10-octahydro-7-hydroxy-7-(1-propynyl)-2-phenanthrenyl ester,[4bR-(4bα,7α,8aβ)]-HCl salt The title product of this example is the HCl salt of the title product of Example 290. MS: 469 (M+1)$^+$.

Example 292

Carbamic acid, [2-(1-pyrrolidinyl)ethyl]-,4b-butyl-4b,5,6,7,8,8a,9,10-octahydro-7-hydroxy-7-(1-propynyl)-2-phenanthrenyl ester,[4bR-(4bα,7α,8aβ)]-

The title compound of this example was prepared by procedures analogous to those described above in Example 59. MS: 453 (M+1)$^+$.

Example 293

2(3H)-Phenanthrenone, 7-fluoro-4,4a,9,10-tetrahydro-4a-(phenylmethyl)-, (S)—, $^1$H NMR (400 MHz, CDCl$_3$) δ 5.99 (s, 1H), 6.88–6.93 (m, 1H).

The title compound of this example was prepared by procedures analogous to those described above in Example 1.

Example 294

Carbamic acid, [2-(dimethylamino)ethyl]-, 4b-butyl-4b,5,6,7,8,8a,9,10-octahydro-7-hydroxy-7-(1-propynyl)-2-phenanthrenyl ester,[4bR-(4bα,7α,8aβ)]-

The title compound of this example was prepared by procedures analogous to those described above in Example 59. MS: 427 (M+1)$^+$.

Examples 295–296

The title compounds of Examples 295–296 were prepared by procedures analogous to those described above in Example 16.

Example 295

2-Phenanthrenol, 1,2,3,4,4a,9,10,10a-octahydro-7-(5-methyl-1H-1,2,4-triazol-3-yl)-4a-(phenylmethyl)-2-(1-propynyl)-,[2R-(2α,4aα,10aβ)]- and 2-Phenanthrenol, 1,2,3,4,4a,9,10,10a-octahydro-7-(5-methyl-1H-1,2,4-triazol-3-yl)-4a-(phenylmethyl)-2-propyl-,[2R-(2α,4aα,10aβ)]-, MS: 413 (M+2)$^+$

Example 296

2-Phenanthrenecarbonitrile, 4b,5,6,7,8,8a,9,10-octahydro-7-hydroxy-4b-propyl-7-(1-propynyl)-, [4bR-(4bα,7α,8aβ)]-, MS:290 (M−17)$^+$.

Example 297

2-Phenanthrenol, 4a-butyl-1,2,3,4,4a,9,10,10a-octahydro-2-(1-propynyl)-7-(pyrazinyloxy)-,[2R-(2α,4aα,10aβ)]-

The title compound of this example was prepared by procedures analogous to those described above in Example 74. MS: 391 (M+1)$^+$.

Examples 298–299

The title compounds of Examples 298–299 were prepared by procedures analogous to those described above in Example 16.

Example 298

2-Phenanthrenol, 4a-butyl-1,2,3,4,4a,9,10,10a-octahydro-2-(1-propynyl)-7-(2-thiazolyl)-,[2R-(2α,4aα,10aβ)]-, MS: 380 (M+1)$^+$.

Example 299

2-Phenanthrenol, 4a-butyl-1,2,3,4,4a,9,10,10 a-octahydro-2-(1-propynyl)-7-(2-pyridinyl)-,[2R-(2α,4aα,10aβ)]-, MS: 3374 (M+1)$^+$.

Example 300

2-Phenanthrenol, 4a-butyl-1,2,3,4,4a,9,10,10a-octahydro-2-(1-propynyl)-7-(2-pyridinyl)-,[2R-(2α,4aα,10aβ)]-HCl salt The title product of this example is the HCl salt of the title product of Example 299. MS: 3374 (M+1)$^+$.

Example 301

2-Phenanthrenol, 4a-butyl-1,2,3,4,4a,9,10,10a-octahydro-2-(1-propynyl)-7-(2-pyrimidinyloxy)-, [2R-(2α,4aα,10aβ)]-

The title compound of this example was prepared by procedures analogous to those described above in Example 74. MS: 391 (M+1)$^+$.

Example 302

2-Phenanthrenol, 1,2,3,4,4a,9,10,10a-octahydro-4a-(phenylmethyl)-2-(1-propynyl)-7-(2-thiazolyl)-,[2R-(2α,4aα,10aβ)]-

The title compound of this example was prepared by procedures analogous to those described above in Example 16. MS: 414 (M+1)$^+$.

Example 303

2-Phenanthrenol, 1,2,3,4,4a,9,10,10a-octahydro-4a-(phenylmethyl)-2-(1-propynyl)-7-(2-pyridinyl)-,[2R-(2α,4aα,10aβ)]-HCl salt The title product of this example is the HCl salt of the title product of Example 16. MS: 408 (M+1)$^+$.

Example 304

2-Phenanthrenol, 1,2,3,4,4a,9,10,10a-octahydro-4a-(phenylmethyl)-2-(1-propynyl)-7-(3-pyridinyl)-,[2R-(2α,4aα,10aβ)]-

The title compound of this example was prepared by procedures analogous to those described above in Example 16. MS: 408 (M+1)$^+$.

Example 305

2-Phenanthrenol, 1,2,3,4,4a,9,10,10a-octahydro-4a-(phenylmethyl)-2-(1-propynyl)-7-(3-pyridinyl)-, [2R-(2α,4aα,10aβ)]-HCl salt The title product of this example is the HCl salt of the title product of Example 304. MS: 408 (M+1)$^+$.

Example 306

2-Phenanthrenol, 4a-butyl-1,2,3,4,4a,9,10,10a-octahydro-2-(1-propynyl)-7-(pyrazinylmethoxy)-, [2R-(2α,4aα,10aβ)]-

The title compound of this example was prepared by procedures analogous to those described above in Example 76. MS: 405 (M+1)$^+$.

Example 307

2-Phenanthrenol, 4a-butyl-1,2,3,4,4a,9,10,10a-octahydro-2-(1-propynyl)-7-(pyrazinylmethoxy)-, [2R-(2α,4aα,10aβ)]-HCl salt The title product of this example is the HCl salt of the title product of Example 306. MS: 405 (M+1)$^+$.

Example 308

4H-Benzo[a]quinolizin-4-one, 1,2,3,6,7,11b-hexahydro-9-hydroxy-11b-(phenylmethyl)-3-propyl- The title compound of this example was prepared by procedures analogous to those described above in Example 40. MS: 350 (M+1)$^+$.

Examples 309–311

The title compounds of Examples 309–311 were prepared by procedures analogous to those described above in Example 15.

Example 309

2-Phenanthrenecarbonitrile, 4b-butyl-4b,5,6,7,8,8a,9,10-octahydro-7-hydroxy-7-(1-propynyl)-,[4bR-(4bα,7α,8aβ)]-, MS: 322 (M+1)$^+$.

Example 310

2-Phenanthrenecarbonitrile, 4b,5,6,7,8,8a,9,10-octahydro-7-(2-propenyloxy)-4b-propyl-7-(1-propynyl)-,[4bR-(4bα,7α,8aβ)]-, $^1$H NMR (400 MHz, CD$_3$OD) δ 5.88–5.97 (m, 1H)

Example 311

Acetic acid, [[7-cyano-1,2,3,4,4a,9,10,10a-octahydro-4a-propyl-2-(1-propynyl)2-phenanthrenyl]oxy]-, ethyl ester,[2R-(2α,4aα,10aβ)]-, $^1$H NMR (400 MHz, CD$_3$OD) δ 4.25 (s, 1H).

Example 312

2-Phenanthrenol, 1,2,3,4,4a,9,10,10a-octahydro-4a-(phenylmethyl)-2-propyl-7-(4-pyridinylmethoxy)-, [2R-(2α,4aα,10aβ)]-

The title compound was obtained as described in Example 627, below, except 4-picolyl chloride hydrochloride was used instead of 2-picolyl chloride hydrochloride. Mass: 442 (M+1)$^+$

Example 313

2-Phenanthrenecarbonitrile, 4b,5,6,7,8,8a,9,10-octahydro-7-hydroxy-4b-(phenylmethyl)-7-propyl-, [4bS-(4bα,7α,8aβ)]-, $^1$H NMR (400 MHz, CD$_3$OD) δ 0.88 (t,3H, J=7.3), 6.43 (d,1H, J=8.3)

The title compound of this example was prepared by procedures analogous to those described above in Example 15.

Example 314

2-Phenanthrenol, 7-(5-hexenyloxy)-1,2,3,4,4a,9,10,10a-octahydro-4a-(phenylmethyl)-2-propyl-,[2R-(2α,4aα,10aβ)]-

The title compound of this example was prepared by procedures analogous to those described above in Example 63. MS: 415 (M−17)$^+$.

Example 315

2-Phenanthrenol, 7-[(4-ethenylphenyl)methoxy]-1,2,3,4,4a,9,10,10a-octahydro-4a-(phenylmethyl)-2-propyl-, (4aS,10aR)-

The title compound of this example was prepared by procedures analogous to those described above in Example 39. MS: 449 (M−17)$^+$.

Example 316

2-Phenanthrenecarboxamide, 4b,5,6,7,8,8a,9,10-octahydro-7-hydroxy-N-(6-methyl-2-pyridinyl)-4b-(phenylmethyl)-7-propyl-,[4bS-(4bα,7α,8aβ)]-

The title compound of this example was prepared by procedures analogous to those described above in Example 244. MS: 469 (M+1)$^+$.

Example 317

2-Phenanthrenecarboxamide, 4b,5,6,7,8,8a,9,10-octahydro-7-hydroxy-N-(6-methyl-2-pyridinyl)-4b-(phenylmethyl)-7-propyl-,[4bS-(4bα,7α,8aβ)]-HCl salt The title product of this example is the HCl salt of the title product of Example 316. MS: 534 (M+1)$^+$.

Example 318

2-Phenanthrenol, 7-[[5-(2,6-dimethyl-4-morpholinyl)pentyl]oxy]-1,2,3,4,4a,9,10,10a-octahydro-4a-(phenylmethyl)-2-propyl-,[2R-(2α,4aα,10aβ)]-

The title compound of this example was prepared by procedures analogous to those described above in Example 12. MS: 469 (M+1)$^+$.

Examples 319–320

The title compounds of Examples 319–320 were prepared by procedures analogous to those described above in Example 136.

Example 319

2,7-Phenanthrenediol, 2-(4-fluorophenyl)-1,2,3,4,4a, 9,10,10a-octahydro-4a-(phenylmethyl)-, (4aS, 10aR)-, MS: 385 (M−17)$^+$.

Example 320

2,7-Phenanthrenediol, 2-(4-fluorophenyl)-1,2,3,4,4a, 9,10,10a-octahydro-4a-(phenylmethyl)-, (4aS, 10aR)-, MS: 385 (M−17)$^+$.

Example 321

2-Phenanthrenol, 4b,5,6,7,8,8a,9,10-octahydro-7-phenyl-4b-(phenylmethyl)-,(4bS,8aR)-, $^1$H NMR (400 MHz, CDCl$_3$) δ 6.58–6.63 (m 2H)

The title compound of this example was prepared by procedures analogous to those described above in Example 10.

Examples 322–323

The title compounds of Examples 322–323 were prepared by procedures analogous to those described above in Example 12.

Example 322

2-Phenanthrenol, 1,2,3,4,4a,9,10,10a-octahydro-4a-(phenylmethyl)-7-[[5-(1-piperidinyl)pentyl]oxy]-2-propyl-,[2R-(2α,4aα,10aβ)]-, MS: 504 (M+1)$^+$.

Example 323

2-Phenanthrenol, 1,2,3,4,4a,9,10,10a-octahydro-4a-(phenylmethyl)-2-propyl-7-[[5-(1-pyrrolidinyl) pentyl]oxy]-,[2R-(2α,4aα,10aβ)]-, MS: 490 (M+1)$^+$

Example 324

2-Phenanthrenecarboxamide, 4b,5,6,7,8,8a,9, 10-octahydro-7-hydroxy-N-[(6-methyl-2-pyridinyl) methyl]-4b-(phenylmethyl)-7-propyl-, [4bS-(4bα, 7α,8aβ)]-

The title compound of this example was prepared by procedures analogous to those described below in Example 332. MS: 483 (M−17)$^+$.

Example 325

2-Phenanthrenecarboxamide, 4b,5,6,7,8,8a,9,10-octahydro-7-hydroxy-N-[(6-methyl-2-pyridinyl) methyl]-4b-(phenylmethyl)-7-propyl-,[4bS-(4bα,7α, 8aβ)]- HCl salt The title compound of this example is the HCl salt of the title compound of Example 324. MS: 483 (M−17)$^+$.

Example 326

2-Phenanthrenecarboxamide, 7-(4,6-dimethyl-2-pyridinyl)-4b,5,6,7,8,8a,9,10-octahydro-7-hydroxy-4b-(phenylmethyl)-7-propyl-,[4bS-(4bα,7α,8aβ)]-

The title compound of this example was prepared by procedures analogous to those described below in Example 332. MS: 483 (M−17)$^+$.

Example 327

2-Phenanthrenecarboxamide, N-(4,6-dimethyl-2-pyridinyl)-4b,5,6,7,8,8a,9, 10-octahydro-7-hydroxy-4b-(phenylmethyl)-7-propyl-,[4bS-(4bα,7α,8aβ)]- HCl salt The title compound of this example is the HCl salt of the title compound of Example 326. MS: 483 (M−17)$^+$.

Examples 328–331

The title compounds of Examples 328–331 were prepared by procedures analogous to those described below in Example 332.

Example 328

2-Phenanthrenecarboxamide, 7-(4,6-dimethyl-2-pyridinyl)-4b,5,6,7,8,8a,9,10-octahydro-7-hydroxy-4b-(phenylmethyl)-7-(1-propynyl)-,[4bS-(4bα,7α, 8aβ)]-, MS: 479 (M+1)$^+$.

Example 329

2-Phenanthrenecarboxamide, 4b,5,6,7,8,8a,9,10-octahydro-7-hydroxy-N-(6-methyl-2-pyridinyl)-4b-(phenylmethyl)-7-(1-propynyl)-,[4bS-(4bα,7α, 8aβ)]-, MS: 465 (M+1)$^+$.

Example 330

2-Phenanthrenecarboxamide, 4b,5,6,7,8,8a,9,10-octahydro-7-hydroxy-N-[(6-methyl-2-pyridinyl) methyl]-4b-(phenylmethyl)-7-(1-propynyl)-,[4bS-(4bα,7α,8aβ)]-, MS: 479 (M+1)$^+$.

Example 331

2-Phenanthrenecarboxamide, 4b,5,6,7,8,8a,9,10-octahydro-7-hydroxy-N-[(6-methyl-3-pyridinyl) methyl]-4b-(phenylmethyl)-7-(1-propynyl)-,[4bS-(4bα,7α,8aβ)]-, MS: 479 (M+1)$^+$.

Example 332

2-Phenanthrenecarboxamide, 4b,5,6,7,8,8a,9,10-octahydro-7-hydroxy-N-[(2-methyl-3-pyridinyl) methyl]-4b-(phenylmethyl)-7-(1-propynyl)-,[4bS-(4bα,7α,8aβ)]-

To a stirring solution of 250 mg of 2-methyl-3-aminomethylpyridine in 5 mL of dichloromethane at 0° C. under N$_2$ was added 1.02 mL of 2.0 M trimethylaluminum in toluene. The mixture was stirred at 0° C. for 20 min. then at RT for 1 h. To this mixture was added 100 mg of the title compound of Example 14 in 5 mL of dichloromethane. The mixture was heated to reflux overnight. To the reaction mixture was added 1 N HCl dropwise until the aqueous layer was approximately pH 4. The resultant mixture was extracted with EtOAc, dried over Na$_2$SO$_4$, filtered, and concentrated to dryness. Purification by flash chromatography over SiO$_2$ using 90% EtOAc in hexanes as the eluant afforded 99 mg (80%) of the title product of this example as a white solid. MS: 479 (M+1)$^+$.

Examples 333–336

The compounds of Examples 333–336 were prepared by procedures analogous to those described above in Example 244.

Example 333

2- Phenanthrenecarboxamide, N-(4,6-dimethyl-2-pyrimidinyl)-4b,5,6,7,8,8a,9,10-octahydro-7-hydroxy-4b-(phenylmethyl)-7-(1-propynyl)-,[4bS-(4bα,7α,8aβ)]-, MS: 480 (M+1)$^+$.

Example 334

2-Phenanthrenecarboxamide, 4b,5,6,7,8,8a,9,10-octahydro-7-hydroxy-N-(4-methyl-2-pyrimidinyl)-4b-(phenylmethyl)-7-(1-propynyl)-,[4bS-(4bα,7α,8aβ)]-, MS: 466 (M+1)$^+$. Example 335

2-Phenanthrenecarboxamide, N-(2,6-dimethyl4-pyrimidinyl)-4b,5,6,7,8,8a,9,10-octahydro-7-hydroxy-4b-(phenylmethyl)-7-(1-propynyl)-,[4bS-(4bα,7α,8aβ)]-, MS: 480 (M+1)$^+$.

Example 336

2,7-Phenanthrenediol, 1,2,3,4,4a,9,10,10a-octahydro-4a-(phenylmethyl)-2-(1-propenyl)-,[2R-[2α,2(E),4aα,10aβ]]-, MS: 347 (M−1)$^+$.

Example 337

2-Phenanthrenecarboxamide, 4b,5,6,7,8,8a,9,10-octahydro-7-hydroxy-N-[(2-methyl-3-pyridinyl)methyl]-4b-(phenylmethyl)-7-(1-propynyl)-,[4bS-(4bα,7α,8a)]-

The title compound of this example was prepared by procedures analogous to those described above in Example 332. MS: 479 (M+1)$^+$.

Example 338

2-Phenanthrenecarboxamide, 4b,5,6,7,8,8a,9,10-octahydro-7-hydroxy-N-[(2-methyl-3-pyridinyl)methyl]4b-(phenylmethyl)-7-propyl-,[4bS-(4bα,7α,8aβ)]-

To a stirring solution of 232 mg of 2-methyl-3-aminomethylpyridine in 10 mL of dichloromethane at 0° C. under N$_2$ was added 0.95 mL of 2.0 M trimethylaluminum in toluene. The mixture was stirred at 0° C. for 20 min. then at RT for 1 h. To this mixture was added 300 mg of 2-phenanthrenecarboxylic acid, 4b,5,6,7,8,8a,9,10-octahydro-7-hydroxy-4b-(phenylmethyl)-7-(1-propyl)-, methyl ester, [4bS-(4bα,7α,8aβ)]- in 10 mL of dichloromethane. The mixture was heated to reflux overnight. To the reaction mixture was added 1 N HCl dropwise until the aqueous layer was approximately pH 4. The resultant mixture was extracted with EtOAc, dried over Na$_2$SO$_4$, filtered, and concentrated to dryness. Purification by flash chromatography over SiO$_2$ using 10% isopropanol and 1% acetone in hexanes to 30% isopropanol and 5% acetone in hexanes as the gradient eluant afforded 303 mg (80%) of the title product of this example as a white solid. $^1$H NMR (400 MHz, CDCl$_3$) δ 2.56 (s, 2H), MS: 483 (M+1)$^+$.

Example 339

2-Phenanthrenecarboxamide, 4b,5,6,7,8,8a,9,10-octahydro-7-hydroxy-N-[(2-methyl-3-pyridinyl)methyl]-4b-(phenylmethyl)-7-propyl-,[4bS-(4bα,7α,8aβ)]-HCl salt The title product of this example is the HCl salt of the title product of Example 338. $^1$H NMR (400 MHz, CD$_3$OD) δ 2.56 (s, 2H), MS: 483 (M+1)$^+$.

Examples 340–342

The title compounds of Examples 340–342 were prepared by procedures analogous to those described above in Example 338.

Example 340

2-Phenanthrenecarboxamide, N-[(2-chloro-6-methyl-4-pyridinyl)methyl]-4b,5,6,7,8,8a,9,10-octahydro-7-hydroxy4b-(phenylmethyl)-7-propyl-, [4bS-(4bα,7α,8aβ)]-, MS: 517 (M).

Example 341

2-Phenanthrenecarboxamide, 4b,5,6,7,8,8a,9,10-octahydro-7-hydroxy-N-[(2-methyl-4-pyridinyl)methyl]-4b-(phenylmethyl)-7-propyl-,[4bS-(4bα,7α,8a≠)]-, MS: 483 (M+1)$^+$.

Example 342

2-Phenanthrenecarboxamide, 4b,5,6,7,8,8a,9,10-octahydro-7-hydroxy-4b-(phenylmethyl)-7-propyl-N-(2-pyridinylmethyl)-,[4bS-(4bα,7α,8aβ)]-, MS: 469 (M+1)$^+$.

Example 343

2-Phenanthrenecarboxamide, 4b,5,6,7,8,8a,9,10-octahydro-7-hydroxy-4b-(phenylmethyl)-7-propyl-N-(2-pyridinylmethyl)-,[4bS-(4bα,7α,8aβ)]-HCl salt The title product of this example is the HCl salt of the title product of Example 342. MS: 469 (M+1)$^+$.

Examples 344–345

The title compounds of Examples 344–345 were prepared by procedures analogous to those described above in Example 338.

Example 344

2-Phenanthrenecarboxamide, 4b,5,6,7,8,8a,9,10-octahydro-7-hydroxy-4b-(phenylmethyl)-7-propyl-N-(4-pyridinylmethyl)-,[4bS-(4bα,7α,8aβ)]-, MS: 469 (M+1)$^+$.

Example 345

2- Phenanthrenecarboxamide, 4b,5,6,7,8,8a,9,10-octahydro-7-hydroxy-4b-(phenylmethyl)-7-propyl-N-(3-pyridinylmethyl)-,[4bS-(4bα,7α,8aβ)]-, MS: 469 (M+1)$^+$.

Examples 346–347

The title compounds of Examples 346–347 were prepared by procedures analogous to those described above in Example 9.

Example 346

2,7-Phenanthrenediol, 1,2,3,4,4a,9,10,10a-octahydro-2-(4-methyl-1-pentynyl)-4a-(phenyl methyl)-,[2R-(2α,4aα,10aβ)]-, MS: 371 (M−17)$^+$.

Example 347

2,7-Phenanthrenediol, 1,2,3,4,4a,9,10,10a-octahydro-2-(3-methyl-1-butynyl)-4a-(phenylmethyl)-,[2R-(2α,4aα,10aβ)]-, MS: 357 (M−17)$^+$.

Example 348

2,7-Phenanthrenediol, 1,2,3,4,4a,9,10,10a-octahydro-4a-(phenylmethyl)-2-(3,3,3-trifluoropropyl)-,[2S-(2(2α,4aα,10aβ)]-

The title compound of this example was prepared by procedures analogous to those described above in Example 10. MS: 487 (M−17)$^+$.

Examples 349–350

The title compounds of Examples 349–350 were prepared by procedures analogous to those described above in Example 338.

Example 349

2-Phenanthrenecarboxamide, 4b,5,6,7,8,8a,9,10-octahydro-7-hydroxy4b-(phenylmethyl)-7-propyl-N-pyrazinyl-,[4bS-(4bα,7α,8aβ)]-, MS: 456 (M+1)$^+$.

Example 350

2-Phenanthrenecarboxamide, 4b,5,6,7,8,8a,9,10-octahydro-7-hydroxy-4b-(phenylmethyl)-7-propyl-N-2-pyridinyl-,[4bS-(4bα,7α,8aβ)]-, $^1$H NMR (400 MHz, CD$_3$OD) δ 7.22 (d, 1H, J=1).

Examples 351–353

The title compounds of Examples 351–353 were prepared by procedures analogous to those described above in Example 10.

Example 351

2,7-Phenanthrenediol, 1,2,3,4,4a,9,10,10a-octahydro-2-(2-methylpropyl)-4a-(phenylmethyl)-, [2R-(2α,4aα,10aβ)]-, MS: 347 (M−17)$^+$.

Example 352

2,7-Phenanthrenediol, 1,2,3,4,4a,9,10,10a-octahydro-2-(2-methylpropyl)-4a-(phenylmethyl)-, [2R-(2α,4aα,10aβ)]-, MS: 347 (M−17)$^+$.

Example 353

2,7-Phenanthrenediol, 1,2,3,4,4a,9,10,10a-octahydro-2-(3-methylbutyl)-4a-(phenylmethyl)-, [2R-(2α,4aα,10aβ)]-, MS: 361 (M−17)$^+$.

Examples 354–355

The title compounds of Examples 354–355 were prepared by procedures analogous to those described above in Example 74.

Example 354

2-Phenanthrenol, 1,2,3,4,4a,9,10,10a-octahydro-2-(3-methyl-1-butynyl)-4a-(phenylmethyl)-7-(3-pyridinylmethoxy)-,[2R-(2α,4aα,10aβ)]-, MS: 448 (M−17)$^+$.

Example 355

2-Phenanthrenol, 1,2,3,4,4a,9,10,10a-octahydro-4a-(phenylmethyl)-7-(3-pyridinylmethoxy)-2-(3,3,3-trifluoropropyl)-,[2S-(2α,4aα,10aβ)]-, MS: 496 (M+1)$^+$.

Example 356

4H-Benzo[a]quinolizin-4-one, 1,2,3,6,7,11 b-hexahydro-9-hydroxy-3-(hydroxymethyl)-11 b-(phenylmethyl)-3-propyl-, (3S-cis)-, $^1$H NMR (400 MHz, CD$_3$OD) δ 4.53 (dm, 1H, J=13).

The title compound of this example was prepared by procedures analogous to those described above in Example 42.

Examples 357–358

The title compounds of Examples 357–358 were prepared by procedures analogous to those described above in Example 9.

Example 357

2-Phenanthreneacetonitrile, 1,2,3,4,4a,9,10,10a-octahydro-2,7-dihydroxy-4a-(phenylmethyl)-, (4aS,10aR)-, MS: 346 (M−1)$^+$.

Example 358

2-Phenanthreneacetonitrile, 1,2,3,4,4a,9,10,10a-octahydro-2,7-dihydroxy-4a-(phenylmethyl)-, (4aS,10aR)-, MS: 346 (M−1)$^+$.

Examples 359–360

The title compounds of Examples 359–360 were prepared by procedures analogous to those described above in Example 136.

Example 359

2,7-Phenanthrenediol, 2-cyclopentyl-1,2,3,4,4a,9,10,10a-octahydro-4a-(phenylmethyl)-, (4aS,10aR)-, MS: 359 (M−17)$^+$.

Example 360

2,7-Phenanthrenediol, 2-cyclohexyl-1,2,3,4,4a,9,10,10a-octahydro-4a-(phenylmethyl)-, (4aS,10aR)-, MS: 389 (M−1)$^+$.

Examples 361–363

The title compounds of Examples 361–363 were prepared by procedures analogous to those described above in Example 332.

Example 361

2-Phenanthrenecarboxamide, 4b,5,6,7,8,8a,9,10-octahydro-7-hydroxy-4b-(phenylmethyl)-7-propyl-N4-pyridinyl-,[4bS-(4bα,7α,8aβ)]-, MS: 455 (M+1)$^+$.

Example 362

2-Phenanthrenecarboxamide, N-(2,6-dichloro-4-pyridinyl)-4b,5,6,7,8,8a,9,10-octahydro-7-hydroxy-4b-(phenylmethyl)-7-propyl-,[4bS-(4bα,7α,8aβ)]-, MS: 523 (M).

Example 363

2-Phenanthrenecarboxamide, 4b,5,6,7,8,8a,9,10-octahydro-7-hydroxy-4b-(phenylmethyl)-7-propyl-N-3-pyridinyl-,[4bS-(4bα,7α,8aβ)]-, MS: 455 (M+1)$^+$.

Examples 364–365

The title compounds of Examples 364–365 were prepared by procedures analogous to those described above in Example 76.

Example 364

2-Phenanthrenol, 1,2,3,4,4a,9,10,10a-octahydro-2-(2-methylpropyl)-4a-(phenylmethyl)-7-(3-pyridinylmethoxy)-,[2S-(2α,4aα,10aβ)]-, MS: 456 (M+1)$^+$.

Example 365

2-Phenanthrenol, 1,2,3,4,4a,9,10,10a-octahydro-2-(3-methylbutyl)-4a-(phenylmethyl)-7-(3-pyridinylmethoxy)-,[2R-(2α,4aα,10aβ)]-, MS: 370 (M+1)$^+$.

Examples 366–368

The title compounds of Examples 366–368 were prepared by procedures analogous to those described above in Example 10.

Example 366

2,7-Phenanthrenediol, 1,2,3,4,4a,9,10,10a-octahydro-2-(4-methylpentyl)-4a-(phenylmethyl)-, [2R-(2α,4aα,10aβ)]-, MS: 391 (M−1)$^+$.

Example 367

2,7-Phenanthrenediol, 1,2,3,4,4a,9,10,10a-octahydro-2-(4-methylpentyl)-4a-(phenylmethyl)-, [2S-(2α,4aα,10aβ)]-, MS: 391 (M−1)$^+$.

Example 368

2,7-Phenanthrenediol, 1,2,3,4,4a,9,10,10a-octahydro-2-(3-hydroxy-3-methylbutyl)-4a-(phenylmethyl)-,[2S-(2α,4aα,10aβ)]-, MS: 393 (M−1)$^+$.

Examples 369–370

The title compounds of Examples 369–370 were prepared by procedures analogous to those described above in Example 76.

Example 369

2-Phenanthrenepropanol, 1,2,3,4,4a,9,10,10a-octahydro-2-hydroxy-a,a-dimethyl-4a-(phenylmethyl)-7-(3-pyridinylmethoxy)-,[2S-(2α,4aα,10aβ)]-, MS: 486 (M+1)$^+$.

Example 370

2-Phenanthrenol, 1,2,3,4,4a,9,10,10a-octahydro-2-(4-methylpentyl)-4a-(phenylmethyl)-7-(3-pyridinylmethoxy)-,[2R-(2α,4aα,10aβ)]-, MS: 484 (M+1)$^+$.

Examples 371–372

The title compounds of Examples 371–372 were prepared by procedures analogous to those described above in Example 9.

Example 371

2,7-Phenanthrenediol, 2-(cyclopropylmethyl)-1,2,3,4,4a,9,10,10a-octahydro-4a-(phenylmethyl)-,[2S-(2α,4aα,10aβ)]-, MS: 363 (M+1)$^+$.

Example 372

2,7-Phenanthrenediol, 2-(cyclopropylmethyl)-1,2,3,4,4a,9,10,10a-octahydro-4a-(phenylmethyl)-,[2R-(2α,4aα,10aβ)]-, MS: 363 (M+1)$^+$.

Example 373

2,7-Phenanthrenediol, 1,2,3,4,4a,9,10,10a-octahydro-2-(3-hydroxypropyl)-4a-(phenylmethyl)-, (4aS,10aR)-

The title compound of this example was prepared by procedures analogous to those described above in Example 10. MS: 365 (M−1)$^+$.

Examples 374–375

The title compounds of Examples 374–375 were prepared by procedures analogous to those described above in Example 9.

Example 374

2,7-Phenanthrenediol, 2-(3,3-dimethyl-1-butynyl)-1,2,3,4,4a,9,10,10a-octahydro-4a-(phenylmethyl)-, [2R-(2α,4aα,10aβ)]-, MS: 387 (M−1)$^+$.

Example 375

2,7-Phenanthrenediol, 2-(3,3-dimethyl-1-butynyl)-1,2,3,4,4a,9,10,10a-octahydro-4a-(phenylmethyl)-,[2S-(2α,4aβ,10aα)]-, MS: 387 (M−1)$^+$.

Example 376

2-Phenanthrenol, 2-(cyclopropylethynyl)-1,2,3,4,4a,9,10,10a-octahydro-4a-(phenylmethyl)-7-(3-pyridinylmethoxy)-,[2R- (2α,4aα,10aβ)]-

The title compound of this example was prepared by procedures analogous to those described above in Example 76. MS: 464 (M+1)$^+$.

Example 377

2,7-Phenanthrenediol, 2-(2-cyclopropylethyl)-1,2,3,4,4a,9,10,10a-octahydro-4a-(phenylmethyl)-,[2R-(2α,4aα,10aβ)]-

The title compound of this example was prepared by procedures analogous to those described above in Example 10. MS: 361 (M−17)$^+$.

Examples 378–379

The title compounds of Examples 378–379 were prepared by procedures analogous to those described above in Example 76.

Example 378

2-Phenanthrenol, 2-(3,3-dimethyl-1-butynyl)-1,2,3,4,4a,9,10,10a-octahydro4a-(phenylmethyl)-7-(3-pyridinylmethoxy)-,[2R-(2α,4aα,10aβ)]-, $^1$H NMR (400 MHz, CD$_3$OD) δ 8.61 (s, 1H).

Example 379

2-Phenanthrenepropanol, 1,2,3,4,4a,9,10,10a-octahydro-2-hydroxy-4a-(phenylmethyl)-7-(3-pyridinylmethoxy)-,[2S-(2α,4aα,10aβ]-, MS: 458 (M+1)$^+$.

Examples 380–381

The title compounds of Examples 380–381 were prepared by procedures analogous to those described above in Example 9.

Example 380

2,7-Phenanthrenediol, 1,2,3,4,4a,9,10,10a-octahydro-2-(phenylethynyl)-4a-(phenylmethyl)-, [2R-(2α,4aα,10aβ)]-, MS: 407 (M−1)$^+$.

Example 381

2,7-Phenanthrenediol, 1,2,3,4,4a,9,10,10a-octahydro-2-(phenylethynyl)-4a-(phenylmethyl)-, [2S-(2α,4aα,10aα)]-, MS: 407 (M−1)$^+$.

Example 382

2,7-Phenanthrenediol, 2-(3,3-dimethylbutyl)-1,2,3,4,4a,9,10,10a-octahydro-4a-(phenylmethyl)-,[2R-(2α,4aα,10aβ)]-

The title compound of this example was prepared by procedures analogous to those described above in Example 10. MS: 391 (M−1)$^+$.

Example 383

2-Phenanthrenol, 2-(2-cyclopropylethyl)-1,2,3,4,4a, 9,10,10a-octahydro-4a-(phenylmethyl)-7-(3-pyridinylmethoxy)-,[2R- (2α,4aα,10aβ)]-

The title compound of this example was prepared by procedures analogous to those described above in Example 76. MS: 450 (M−17)$^+$.

Example 384

2(3H)-Phenanthrenone, 4,4a,9,10-tetrahydro-7-hydroxy-4a-[(4-hydroxyphenyl)methyl]-, (S)-

The title compound of this example was prepared by procedures analogous to those described above in Example 3. Mass: 321 (M+1)$^+$

Example 385

(3H)-Phenanthrenone, 4,4a,9,10-tetrahydro-4a-[(4-hydroxyphenyl)methyl]-7-methoxy-, (S)-

The title compound of this example was prepared by procedures analogous to those described above in Example 1. Mass: 335 (M+1)$^+$.

Examples 386–387

The title compounds of Examples 386–387 were prepared by procedures analogous to those described above in Example 6.

Example 386

2(1H)-Phenanthrenone, 3,4,4a,9,10,10a-hexahydro-7-hydroxy-4a-[(4-hydroxyphenyl)methyl]-, (4aS)-, Mass:321 (M−1)$^+$.

Example 387

2(1H)-Phenanthrenone, 3,4,4a,9,10,10a-hexahydro-4a-[(4-hydroxyphenyl)methyl]-7-methoxy-, (4aS)-, Mass:335 (M−1)$^+$.

Example 388

2,7-Phenanthrenediol, 2-(chloroethynyl)-2,3,4,4a,9, 10-hexahydro-4a-[(4-hydroxyphenyl)methyl]-, (2R-cis)-

The title compound of this example was prepared by procedures analogous to those described above in Example 8. Mass: 363 (M−17)$^+$.

Example 389

2,7-Phenanthrenediol, 1,2,3,4,4a,9, 10,10a-octahydro-4a-[(4-hydroxyphenyl)methyl]-, (4aS)-

The title compound of this example was prepared by procedures analogous to those described above in Example 6. Mass: 325 (M+1)$^+$.

Examples 390–391

The title compounds of Examples 390–391 were prepared by procedures analogous to those described above in Example 8.

Example 390

2-Phenanthrenol, 2-(chloroethynyl)-1,2,3,4,4a,9,10, 10a-octahydro-4a-[(4-hydroxyphenyl)methyl]-7-methoxy-, Mass: 397 (M+1)$^+$.

Example 391

2-Phenanthrenol, 2-(chloroethynyl)-1,2,3,4,4a,9,10, 10a-octahydro-4a-[(4-hydroxyphenyl)methyl]-7-methoxy-, Mass: 397 (M+1)$^+$.

Examples 392–393

The title compounds of Examples 392–393 were prepared by procedures analogous to those described above in Example 10.

Example 392

2,7-Phenanthrenediol, 1,2,3,4,4a ,9,10,10a-octahydro-4a-[(4-hydroxyphenyl)methyl]-2-propyl-, (4aS)-, Mass: 366 (M), 384 (M+18)$^+$.

Example 393

2,7-Phenanthrenediol, 1,2,3,4,4a,9,10,10a-octahydro-4a-[(4-hydroxyphenyl)methyl]-2-propyl-, (4aS)-, Mass: 366 (M), 384 (M+18)$^+$.

Examples 394–406

The title compounds of Examples 394–406 were prepared by procedures analogous to those described above in Example 77.

Example 394

2(1H)-Phenanthrenone, 3,4,4a,9,10,10a-hexahydro-7-hydroxy-4a-(phenylmethyl)-,oxime, (4aS)-, Mass: 322 (M+1)$^+$.

Example 395

2(1H)-Phenanthrenone, 3,4,4a,9,10,10a-hexahydro-7-hydroxy-4a-(phenylmethyl)-,O-(phenylmethyl) oxime, (4aS)-, Mass: 412 (M+1)$^+$.

Example 396

2(1)-Phenanthrenone, 3,4,4a,9,10,10a-hexahydro-7-hydroxy-4a-(phenylmethyl)-,O-[(4-nitrophenyl) methyl]oxime, (4aS)-, Mass: 457 (M+1)$^+$.

Example 397

2(3H)-Phenanthrenone, 4,4a,9,10-tetrahydro-7-hydroxy-4a-[(4-hydroxyphenyl)methyl]-,O-ethyloxime, (S)-, Mass: 364 (M+1)$^+$.

Example 398

2(1H)-Phenanthrenone, 3,4,4a,9,10,10a-hexahydro-1,7,10a-trihydroxy-4a-[(4-hydroxyphenyl)methyl]-, O-ethyloxime, Mass: 398 (M+1)$^+$.

Example 399

2(1H)-Phenanthrenone, 3,4,4a,9,10,10a-hexahydro-1,7,10a-trihydroxy-4a-[(4-hydroxyphenyl)methyl]-, O-ethyloxime, Mass: 398 (M+1)$^+$.

Example 400

Benzoic acid, [3,4,4a,9,10,10a-hexahydro-7-hydroxy-4a-[(4-hydroxyphenyl)methyl]-2(1H)-phenanthrenylidene]hydrazide, (4aS-trans)-, Mass: 441 (M+1)+.

Example 401

2(1H)-Phenanthrenone, 3,4,4a,9,10,10a-hexahydro-7-hydroxy-4a-[(4-hydroxyphenyl)methyl]-,O-2-propenyloxime, (4aS-trans)-, Mass: 378 (M+1)+.

Example 402

Acetic acid, [[[3,4,4a,9, 10,10a-hexahydro-7-hydroxy-4a-[(4-hydroxyphenyl)methyl]-2(1H)-phenanthrenylidene]amino]oxy]-, (4aS-trans)-, Mass: 396 (M+1)+.

Example 403

Hydrazinecarboxylic acid, [3,4,4a,9, 10,10a-hexahydro-7-hydroxy-4a-[(4-hydroxyphenyl)methyl]-2(1H)-phenanthrenylidene]-, ethyl ester, (4aS-trans)-, Mass: 409 (M+1)+.

Example 404

Acetic acid, [[[3,4,4a,9,10,10a-hexahydro-7-hydroxy-4a-[(4-hydroxyphenyl)methyl]-2(1H)-phenanthrenylidene]amino]oxy]-, methyl ester, (4aS-trans)-, Mass: 410 (M+1)+.

Example 405

2(3H)-Phenanthrenone, 4,4a,9,10-tetrahydro-7-hydroxy-4a-[(4-hydroxyphenyl)methyl]-, O-methyloxime, Mass: 350 (M+1)+.

Example 406

3-Pyridinecarboxylic acid, [3,4,4a,9, 10,10a-hexahydro-7-hydroxy-4a-[(4-hydroxyphenyl)methyl]-2(1H)-phenanthrenylidene]hydrazide,(4aS-trans)-, Mass: 442 (M+1)+.

Example 407

Acetic acid, [4,4a,9,10-tetrahydro-7-hydroxy-4a-[(4-hydroxyphenyl)methyl]-2(3H)-phenanthrenylidene]-, ethyl ester, [S-(E)]-

The title compound of this example was prepared by procedures analogous to those described above in Example 78. Mass: 391 (M+1)+.

Example 408

Acetic acid, cyano-, [3,4,4a,9,10,10a-hexahydro-7-hydroxy-4a-[(4-hydroxyphenyl)methyl]-2(1H)-phenanthrenylidene]hydrazide,(4aS-trans)-

The title compound of this example was prepared by procedures analogous to those described above in Example 77. Mass: 404 (M+1)+.

Example 409

2,7-Phenanthrenediol, 4a-[(4-aminophenyl)methyl]-1,2,3,4,4a,9,10,10a-octahydro-[2R-(2α,4aα,10aβ)]-

The title compound of this example was prepared by procedures analogous to those described above in Example 6. Mass: 322 (M−1)+.

Examples 410–411

The title compounds of Examples 410–411 were prepared by procedures analogous to those described above in Example 77.

Example 410

Hydrazinecarboxylic acid, [4,4a,9,10-tetrahydro-7-hydroxy-4a-[(4-hydroxyphenyl)methyl]-2(3H)-phenanthrenylidene]-, ethyl ester, (S)-, Mass: 407 (M+1)+.

Example 411

2(1H)-Phenanthrenone, 4a-[(4-aminophenyl)methyl]-3,4,4a,9,10,10a-hexahydro-7-hydroxy-, O-ethyloxime, Mass: 365 (M+1)+.

Examples 412–413

The title compounds of Examples 412–413 were prepared by procedures analogous to those described above in Example 10.

Example 412

2,7-Phenanthrenediol, 1,2,3,4,4a,9,10,10a-octahydro-4a-[[4-[(1-methylethyl)amino]phenyl]methyl]-2-propyl-, (4aS,10aR-, Mass: 408 (M+1)+.

Example 413

2,7-Phenanthrenediol, 1,2,3,4,4a,9,10,10a-octahydro-4a-[[4-[(1-methylethyl)amino]phenyl]methyl]-2-propyl-, (4aS,10aR)-, Mass: 408 (M+1)+.

Examples 414–415

The title compounds of Examples 414–415 were prepared by procedures analogous to those described above in Example 77.

Example 414

2(1H)-Phenanthrenone, 3,4,4a,9,10,10a-hexahydro-7-hydroxy-4a-[[4-[(1-methylethyl)amino]phenyl]methyl]-, O-ethyloxime, (4aS-trans)-, Mass: 407 (M+1)+.

Example 415

2(1H)-Phenanthrenone, 3,4,4a,9,10,10a-hexahydro-7-hydroxy-4a-[[4-[(1-methylethyl)amino]phenyl]methyl]-, O-methyloxime, (4aS-trans)-, Mass: 393 (M+1)+.

Examples 416–418

The title compounds of Examples 416–418 were prepared by procedures analogous to those described above in Example 78.

Example 416

2-Phenanthrenol, 4b,5,6,7,8,8a,9,10-octahydro-4b-[(4-hydroxyphenyl)methyl]-7-propylidene-, (4bS, 7Z)-, Mass: 349 (M+1)+.

Example 417

2-Phenanthrenol, 7-butylidene-4b,5,6,7,8,8a,9,10-octahydro-4b-[(4-hydroxyphenyl)methyl]-, (4bS, 7Z)-, Mass: 363 (M+1)+.

Example 418

Acetonitrile, [3,4,4a,9,10,10a-hexahydro-7-hydroxy-4a-[(4-hydroxyphenyl)methyl]-2(1H)-phenanthrenylidene]-,[4aS-(2Z,4aα,10aβ)]-, Mass: 363 (M+18)+.

Examples 419–421

The title compounds of Examples 419–421 were prepared by procedures analogous to those described above in Example 136.

Example 419

2,7-Phenanthrenediol, 1,2,3,4,4a,9,10,10a-octahydro-4a-[[4-[(tetrahydro-2H-pyran-4-yl)amino]phenyl]methyl]-2-propyl-,(4aS,10aR)-, Mass: 450 (M+1)+.

Example 420

2,7-Phenanthrenediol, 1,2,3,4,4a,9,10,10a-octahydro-4a-[[4-[(tetrahydro-2H-pyran-4-yl)amino]phenyl]methyl]-2-propyl-,(4aS,10aR)-, Mass: 450 (M+1)+.

Example 421

2,7-Phenanthrenediol, 1,2,3,4,4a,9,10,10a-octahydro-4a-[[4-[(1-methylethyl)amino]phenyl]methyl]-2-propyl-, (4aS,10aR)-, Mass: 409 (M+1)+.

Example 422

2,7-Phenanthrenediol, 1,2,3,4,4a,9,10,10a-octahydro-4a-[(4-hydroxyphenyl)methyl]-2-(1-hydroxypropyl)-, (4aS)-

The title compound of this example was prepared by procedures analogous to those described above in Example 30. Mass: 400 (M+18)+.

Examples 423–426

The title compounds of Examples 423–426 were prepared by procedures analogous to those described above in Example 136.

Example 423

2,7-Phenanthrenediol, 1,2,3,4,4a,9,10,10a-octahydro-4a-[(4-hydroxyphenyl)methyl]-2-propyl-, (4aS,10aR)-, Mass: 349 (M+17)+.

Example 424

2,7-Phenanthrenediol, 1,2,3,4,4a,9,10,10a-octahydro-4a-[(4-hydroxyphenyl)methyl]-2-propyl-, (4aS,10aR)-, Mass: 349 (M+17)+.

Example 425

2,7-Phenanthrenediol, 1,2,3,4,4a,9,10,10a-octahydro-4a-[[4-[[1-(1-methylethyl)-4-piperidinyl]amino]phenyl]methyl]-2-propyl-,(4aS,10aR)-, Mass: 491 (M+1)+.

Example 426

2,7-Phenanthrenediol, 1,2,3,4,4a,9,10,10a-octahydro-4a-[[3-[(1-methylethyl)amino]phenyl]methyl]-2-propyl-, (4aS,10aR)-, Mass: 408 (M+1)+.

Example 427

2,7-Phenanthrenediol, 1,2,3,4,4a,9,10,10a-octahydro-4a-[(4-hydroxyphenyl)methyl]-2-(1-hydroxypropyl)-, (4aS,10aS)-

The title compound of this example was prepared by procedures analogous to those described above in Example 30. Mass: 382 (M).

Examples 428–429

The title compounds of Examples 428–429 were prepared by procedures analogous to those described above in Example 78.

Example 428

2-Phenanthrenol, 7-butylidene-4b,5,6,7,8,8a,9,10-octahydro-4b-[(4-hydroxyphenyl)methyl]-,[4bS-(4bα,7Z,8aα)]-, Mass: 363 (M+1)+.

Example 429

2-Phenanthrenol, 4b,5,6,7,8,8a,9,10-octahydro-4b-[(4-hydroxyphenyl)methyl]-7-pentylidene-,[4bS-(4bα,7Z,8aα)]-, Mass: 377 (M+1)+.

Examples 430–432

The title compounds of Examples 430–432 were prepared by procedures analogous to those described above in Example 77.

Example 430

2(1H)-Phenanthrenone, 3,4,4a,9,10,10a-hexahydro-7-hydroxy-4a-[(4-hydroxyphenyl)methyl]-, O-(phenylmethyl)oxime, (4aS-cis)-, Mass: 428 (M+1)+.

Example 431

2(1H)-Phenanthrenone, 3,4,4a,9,10,10a-hexahydro-7-hydroxy-4a-[(4-hydroxyphenyl)methyl]-, O-2-propenyloxime, (4aS-cis)-, Mass: 378 (M+1)+.

Example 432

2(1H)-Phenanthrenone, 3,4,4a,9,10,10a-hexahydro-7-hydroxy-4a-[(4-hydroxyphenyl)methyl]-, O-ethyloxime, (4aS-cis)-, Mass: 366 (M+1)+.

Example 433

2,7-Phenanthrenediol, 4a-[(3-aminophenyl)methyl]-1,2,3,4,4a,9,10,10a-octahydro-2-propyl-, (4aS, 10aS)-

The title compound of this example was prepared by procedures analogous to those described above in Example 136. Mass: 366 (M+1)+.

Examples 434–435

The title compounds of Examples 434–435 were prepared by procedures analogous to those described above in Example 9.

Example 434

2,7-Phenanthrenediol, 1,2,3,4,4a,9,10,10a-octahydro-4a-[(4-hydroxyphenyl)methyl]-2-[3-[(tetrahydro-2H-pyran-2-yl)oxy]-1 -propynyl]-, (4aS, 10aS)-, Mass: 481 (M+18)$^+$.

Example 435

2,7-Phenanthrenediol, 1,2,3,4,4a,9,10,10a-octahydro-4a-[(4-hydroxyphenyl)methyl]- 2-[3-[(tetrahydro-2H-pyran-2-yl)oxy]-1-propynyl]-, (4aS, 10aS)-, Mass: 481 (M+18)$^+$.

Examples 436–438

The title compounds of Examples 436–438 were prepared by procedures analogous to those described above in Example 136.

Example 436

2,7-Phenanthrenediol, 2-butyl-1,2,3,4,4a,9,10,10a-octahydro-4a-[(4-hydroxyphenyl)methyl]-, (4aS, 10aS)-, Mass: 380 (M).

Example 437

2,7-Phenanthrenediol, 2-butyl-1,2,3,4,4a,9,10,10a-octahydro-4a-[(4-hydroxyphenyl)methyl]-, (4aS, 10aS)-, Mass: 381 (M+1)$^+$.

Example 438

2,7-Phenanthrenediol, 1,2,3,4,4a,9,10,10a-octahydro-4a-[[3-[(1-methyl-4-piperidinyl)amino]phenyl]methyl]-2-propyl-,(4aS,10aR)-, Mass: 463 (M+1)$^+$.

Example 439

2,7-Phenanthrenediol, 4a-[(3-aminophenyl)methyl]-1,2,3,4,4a,9,10,10a-octahydro-2-(1-propynyl)-, (4aS, 10aR)-

The title compound of this example was prepared by procedures analogous to those described above in Example 9. Mass: 362 (M+1)$^+$.

Examples 440–442

The title compounds of Examples 440–442 were prepared by procedures analogous to those described above in Example 136.

Example 440

2,7-Phenanthrenediol, 1,2,3,4,4a,9,10,10a-octahydro-4a-[[3-(methylamino)phenyl]methyl]-2-propyl-, (4aS,10aS)-, Mass: 380 (M+1)$^+$.

Example 441

2,7-Phenanthrenediol, 1,2,3,4,4a,9,10,10a-octahydro-4a-[[3-[(1-methylethyl)amino]phenyl]methyl]-2-propyl-, (4aS,10aR)-, Mass: 408 (M+1)$^+$.

Example 442

2,7-Phenanthrenediol, 1,2,3,4,4a,9,10,10a-octahydro-4a-[[3-[(1-methylethyl)amino]phenyl]methyl]-2-propyl-, (4aS,10aR)-, Mass: 408 (M+1)$^+$.

Examples 443–444

The title compounds of Examples 443–444 were prepared by procedures analogous to those described above in Example 9.

Example 443

2,7-Phenanthrenediol, 1,2,3,4,4a,9,10,10a-octahydro-4a-[[3-[(1-methylethyl)amino]phenyl]methyl]-2-(1-propynyl)-,(4aS,10aS)-, Mass: 404 (M+1)$^+$.

Example 444

2,7-Phenanthrenediol, 2-ethynyl-1,2,3,4,4a,9,10,10a-octahydro-4a-[[3-[(1-methylethyl)amino]phenyl]methyl]-, (4aS,10aS)-, Mass: 390 (M+1)$^+$.

Example 445

2,7-Phenanthrenediol, 1,2,3,4,4a,9,10,10a-octahydro-4a-[[4-[(methylsulfonyl)oxy]phenyl]methyl ]-2-propyl-, (4aS,10aS)-

The title compound of this example was prepared by procedures analogous to those described above in Example 136. Mass: 462 (M+14)$^+$.

Examples 446–447

The title compounds of Examples 446–447 were prepared by procedures analogous to those described above in Example 77.

Example 446

2(1H)- Phenanthrenone, 3,4,4a,9,10,10a-hexahydro-7-hydroxy-4a-(phenylmethyl)-,O-ethyloxime, (4aS-trans)-, Mass: 350 (M+1)$^+$.

Example 447

2(1H)-Phenanthrenone, 3,4,4a,9,10,10a-hexahydro-7-hydroxy-4a-(phenylmethyl)-,O-ethyloxime, (4aS-trans)-, Mass: 350 (M+1)$^+$.

Examples 448–449

The title compounds of Examples 448–449 were prepared by procedures analogous to those described above in Example 9.

Example 448

2,7-Phenanthrenediol, 1,2,3,4,4a,9,10,10a-octahydro-4a-(phenylmethyl)-2-(2-pyridinylethynyl)-, (4aS,10aR)-, Mass: 410 (M+1)$^+$.

Example 449

2,7-Phenanthrenediol, 4a-[[3-(dimethylamino)phenyl]methyl]-1,2,3,4,4a,9,10,10a-octahydro-2-(1-propynyl)-, (4aS,10aR)-, Mass: 390 (M+1)$^+$.

Example 450

2-Phenanthrenol, 4b-[[3-(dimethylamino)phenyl]methyl]-7,7-diethoxy-4b,5,6,7,8,8a,9,10-octahydro-, (4bS-trans)-

The title compound of this example was prepared by procedures analogous to those described above Preparation 5. Mass: 424 (M+1)$^+$.

Example 451

2-Phenanthrenol, 7,7-diethoxy-4b,5,6,7,8,8a,9,10-octahydro-4b-(phenylmethyl)-, (4bS-trans)-

The title compound of this example was prepared by procedures analogous to those described above in Example 77. Mass: 335 (M−45)$^+$.

Example 452

2,7-Phenanthrenediol, 2-[3-(dimethylamino)-1-propynyl]-1,2,3,4,4a,9, 10,10a-octahydro-4a-(phenylmethyl)-,(4aS,10aR)-

The title compound of this example was prepared by procedures analogous to those described above in Example 9. Mass: 390 (M+1)$^+$.

Example 453

2(1H)-Phenanthrenone, 4a-[[3-(dimethylamino) phenyl]methyl]-3,4,4a,9,10,10a-hexahydro-7-hydroxy-, O-ethyloxime, (4aS-trans)-

The title compound of this example was prepared by procedures analogous to those described above in Example 77. Mass: 393 (M+1)$^+$.

Examples 454–456

The title compounds of Examples 454–456 were prepared by procedures analogous to those described above in Example 136.

Example 454

2,7-Phenanthrenediol, 4a-[(4-aminophenyl)methyl]-1,2,3,4,4a,9,10,10a-octahydro-2-propyl-, (4aS, 10aS)-, Mass: 348 (M−17)$^+$.

Example 455

Acetamide, N-[4-[(1,3,4,9,10,10a-hexahydro-2,7-dihydroxy-2-propyl-4a(2H)-phenanthrenyl)methyl] phenyl]-, (4aS,10aS)-, Mass: 407 (M).

Example 456

Acetamide, N-[3-[[2-(acetyloxy)-1,3,4,9,10,10a-hexahydro-7-hydroxy-2-propyl-4a(2H)-phenanthrenyl)methyl]phenyl]-, (4aS,10aS)-, Mass: 450 (M+1)$^+$.

Example 457

2,7-Phenanthrenediol, 4a-[[4-(dimethylamino) phenyl]methyl]-1,2,3,4,4a,9,10,10a-octahydro-2-(1-propynyl)-, (4aS,10aR)-

The title compound of this example was prepared by procedures analogous to those described above Example 9. Mass: 390 (M+1)$^+$.

Example 458

2,7-Phenanthrenediol, 1,2,3,4,4a,9,10,10a-octahydro-4a-[[4-[(1-methylethyl)amino]phenyl] methyl]-2-propyl-, (4aS,10aS)-

The title compound of this example was prepared by procedures analogous to those described above in Example 136. Mass: 408 (M+1)$^+$.

Example 459

Carbamic acid, dimethyl-, 7-(chloroethynyl)-4b,5,6,7,8,8a,9,10-octahydro-7-hydroxy-4b-(phenylmethyl)-2-phenanthrenyl ester, (4bS,8aR)-

The title compound of this example was prepared by procedures analogous to those described above in Example 58. Mass: 438 (M+1)$^+$.

Example 460

Acetamide, N-[3-[[1,3,4,9,10,10a-hexahydro-2,7-dihydroxy-2-(1-propynyl)-4a(2H)-phenanthrenyl] methyl]phenyl]-,[2R-(2α,4aα,10aβ)]-

The title compound of this example was prepared by procedures analogous to those described above in Example 9. Mass: 386 (M−17)$^+$.

Example 461

1-Pyrrolidinecarboxylic acid, 7-(chloroethynyl)-4b,5,6,7,8,8a,9,10-octahydro-7-hydroxy-4b-(phenylmethyl)-2-phenanthrenyl ester, (4bS,8aR)-

The title compound of this example was prepared by procedures analogous to those described above in Example 58. Mass: 464 (M).

Examples 462–465

The title compounds of Examples 462–465 were prepared by procedures analogous to those described above in Example 136.

Example 462

Cyanamide, [3-[(1,3,4,9,10,10a-hexahydro-2,7-dihydroxy-2-propyl-4a(2H)-phenanthrenyl)methyl] phenyl]-, (4aS,10aS)-, Mass: 389 (M−1)$^+$

Example 463

Cyanamide, [3-[(1,3,4,9,10,10a-hexahydro-2,7-dihydroxy-2-propyl-4a(2H)-phenanthrenyl)methyl] phenyl]-, (4aS,10aS)-, Mass: 389 (M−1)$^+$

Example 464

2,7-Phenanthrenediol, 1,2,3,4,4a,9,10,10a-octahydro-2-propyl-4a-[[3-[(tetrahydro -2H-pyran-4-yl)amino]phenyl]methyl]-, (4aS,10aS)-, Mass: 450 (M+1)$^+$

Example 465

2,7-Phenanthrenediol, 1,2,3,4,4a,9,10,10a-octahydro-2-propyl-4a-[[3-[(tetrahydro -2H-pyran-4-yl)amino]phenyl]methyl]-, (4aS,10aS)-, Mass: 450 (M+1)$^+$

Example 466

Carbamic acid, dimethyl-, 4-[[7-[[(dimethylamino) carbonyl]oxy]-1,3,4,9,10,10a-hexahydro-2-hydroxy-2-propyl-4a(2H)-phenanthrenyl]methyl]phenyl ester,(4aS,10aS)-

The title compound of this example was prepared by procedures analogous to those described above in Example 58. Mass: 526 (M+18)$^+$.

Example 467

2,7-Phenanthrenediol, 1,2,3,4,4a,9,10,10a-octahydro-4a-[[4-[(1-methylethyl)amino]phenyl] methyl]-2-propyl-, (4aS,10aS)-

The title compound of this example was prepared by procedures analogous to those described above in Example 136. Mass: 408 (M+1)$^+$.

Example 468

2(1H)-Phenanthrenone, 4a-[(3-aminophenyl) methyl]-3,4,4a,9,10,10a-hexahydro-7-hydroxy-, O-ethyloxime, (4aS-trans)-

The title compound of this example was prepared by procedures analogous to those described above in Example 77. Mass: 365 (M+1)$^+$.

Example 469

Carbamic acid, dimethyl-, 4b,5,6,7,8,8a,9,10-octahydro-7-hydroxy-4b-[[4-[(1-methylethyl)amino] phenyl]methyl]-7-propyl-2-phenanthrenyl ester, (4bS,8aS)-

The title compound of this example was prepared by procedures analogous to those described above in Example 58. Mass: 479 (M+1)$^+$.

Example 470

2-Phenanthrenol, 4b-[(3-aminophenyl)methyl]-7-(ethoxyamino)-4b,5,6,7,8,8a,9,10-octahydro-, (4bS, 8aR)-

The title compound of this example was prepared by procedures analogous to those described above in Example 10. Mass: 367 (M+1)$^+$.

Examples 471–472

The title compounds of Examples 471–472 were prepared by procedures analogous to those described above in Examples 58.

Example 471

Carbamic acid, dimethyl-, 4b-[(3-aminophenyl) methyl]-7-(ethoxyimino)-4b,5,6,7,8,8a,9,10-octahydro-2-phenanthrenyl ester, (4aS-trans)-, Mass: 436 (M+1)$^+$.

Example 472

Carbamic acid, dimethyl-, 4b-[[3-[[(dimethylamino) carbonyl]amino]phenyl]methyl]-7-(ethoxyimino)-4b, 5,6,7,8,8a,9,10-octahydro-2-phenanthrenyl ester, (4aS-trans)-, Mass: 407 (M+1)$^+$.

Example 473

2,7-Phenanthrenediol, 4a-[[4-(dimethylamino) phenyl]methyl]-1,2,3,4,4a,9,10,10a-octahydro-2-(1-propynyl)-, (4aS,10aS)-

The title compound of this example was prepared by procedures analogous to those described above in Example 9. Mass: 390 (M+1)$^+$.

Example 474

Carbamic acid, dimethyl-, 4b-[[4-(dimethylamino) phenyl]methyl]-4b,5,6,7,8,8a,9,10-octahydro- 7-hydroxy-7-(1-propynyl)-2-phenanthrenyl ester, (4bS,8aR)-

The title compound of this example was prepared by procedures analogous to those described above in Example 58. Mass: 461 (M+1)$^+$.

Example 475

2-Phenanthrenol, 4b-[[3-(dimethylamino)phenyl] methyl]-7-(ethylamino)-4b,5,6,7,8,8a,9,10-octahydro-, (4bS,8aS)-

The title compound of this example was prepared by procedures analogous to those described above in Preparation 4. Mass: 379 (M+1)$^+$.

Example 476

Acetamide, N-[4a-[[3-(dimethylamino)phenyl] methyl]-1,2,3,4,4a,9, 10,10a-octahydro-7-hydroxy-3-phenanthrenyl]-N-ethyl-, (4aR,10aS)-

The title compound of this example was prepared by procedures analogous to those described above in Example 47. Mass: 421 (M+1)$^+$.

Example 477

Acetamide, N-[4-[[1,3,4,9,10,10a-hexahydro-2,7-dihydroxy-2- (1-propynyl)-4a(2H)-phenanthrenyl] methyl]phenyl]-,(4aS,10aR)-

The title compound of this example was prepared by procedures analogous to those described above in Example 9. Mass: 404 (M+1)$^+$.

Examples 478–479

The title compounds of Examples 478–479 were prepared by procedures analogous to those described above in Example 58.

Example 478

1-Piperazinecarboxylic acid, 4-methyl-, 4b-[[3-(dimethylamino)phenyl]methyl]-4b,5,6,7,8,8a,9,10-octahydro-7-hydroxy-7-(1-propynyl)-2-phenanthrenyl ester,(4bS,8aR)-, Mass: 516 (M+1)$^+$

Example 479

2,7-Phenanthrenediol, 4a-[[3-(dimethylamino) phenyl]methyl]-1,2,3,4,4a,9,10,10a-octahydro-2-(1-propynyl)-, 7-carbamate, (4aS,10aR)-, Mass: 433 (M+1)$^+$

Example 480

4-Morpholinecarboxamide, N-[4-[[1,3,4,9,10,10a-hexahydro-2,7-dihydroxy-2-(1-propynyl)-4a(2H)-phenanthrenyl]methyl]phenyl]-,[2R-(2α,4aα,10aβ)]-

The title compound of this example was prepared by procedures analogous to those described above in Example 9. Mass: 476 (M+2)$^+$.

Example 481

Carbamic acid, [3-(dimethylamino)propyl]-, 4b-[[3-(dimethylamino)phenyl]methyl]-4b,5,6,7,8,8a,9,10-octahydro-7-hydroxy-7-(1-propynyl)-2-phenanthrenyl ester,(4bS,8aR)-

The title compound of this example was prepared by procedures analogous to those described above in Example 59. Mass: 518 (M+1)$^+$.

Example 482

Acetamide, N-[4-[[7-[(aminocarbonyl)oxy]-1,3,4,9, 10,10a-hexahydro-2-hydroxy-2-(1-propynyl)-4a (2H)-phenanthrenyl]methyl]phenyl]-, (4aS,10aR)-

The title compound of this example was prepared by procedures analogous to those described above in Example 55. Mass: 447 (M+1)$^+$.

Example 483

Benzonitrile, 4-[[1,3,4,9,10,10a-hexahydro-2,7-dihydroxy-2-propyl-4a(2H)-phenanthrenyl]methyl]-, (4aS,10aS)-

The title compound of this example was prepared by procedures analogous to those described above or below in Example 136. Mass: 375 (M).

Examples 484–487

The title compounds of Examples 484–487 were prepared by procedures analogous to those described above in Example 59.

Example 484

Carbamic acid, (2-(1-pyrrolidinyl)ethyl]-,4b-[[3-(dimethylamino)phenyl]methyl]-4b,5,6,7,8,8a,9,10-octahydro-7-hydroxy-7-(1-propynyl)-2-phenanthrenyl ester,[4bS- (4bα,7α,8aβ)]-, Mass: 530 $(M+1)^+$.

Example 485

1-Piperidinecarboxylic acid, 4-(dimethylamino)-,4b-[[3-(dimethylamino)phenyl]methyl]-4b,5,6,7,8,8a,9,10-octahydro-7-hydroxy-7-(1-propynyl)-2-phenanthrenyl ester, [4bS-(4bα,7α,8aβ)]-, Mass: 544 $(M+1)^+$.

Example 486

1-Piperazinecarboxylic acid, 4-acetyl-, 4b-[[3-(dimethylamino)phenyl]methyl]-4b,5,6,7,8,8a,9,10-octahydro-7-hydroxy-7-(1-propynyl)-2-phenanthrenyl ester,[4bS- (4bα,7α,8aβ)]-, Mass: 544 $(M+1)^+$.

Example 487

2,7-Phenanthrenediol, 4a-[[3-(dimethylamino)phenyl]methyl]-1,2,3,4,4a,9,10,10a-octahydro-2-(1-propynyl)-,7-(methylcarbamate),[2R-(2α,4aα,10aβ)]-, Mass: 447 $(M+1)^+$.

Examples 488–489

The title compounds of Examples 488–489 were prepared by procedures analogous to those described above in Example 6.

Example 488

2(1H)-Phenanthrenone, 4a-[[3-(dimethylamino)phenyl]methyl]-3,4,4a,9,10,10a-hexahydro-7-hydroxy-, (4aS-trans)-, Mass: 350 $(M+1)^+$.

Example 489

Carbamic acid, [4-[(1,3,4,9, 10,10a-hexahydro-7-hydroxy-2-oxo-4a(2H)-phenanthrenyl)methyl]phenyl]-, 1,1-dimethylethyl ester, (4aS-trans)-, Mass: 423 $(M+2)^+$.

Example 490

Carbamic acid, 1H-1,2,4-triazol-3-yl-, 4b-[[3-(dimethylamino)phenyl]methyl]-4b,5,6,7,8,8a,9,10-octahydro-7-hydroxy-7-(1-propynyl)-2-phenanthrenyl ester,(4bS,8aR)-

The title compound of this example was prepared by procedures analogous to those described above in Example 59. Mass: 500 $(M+1)^+$.

Example 491

2,7-Phenanthrenediol, 4a-[[3-(dimethylamino)phenyl]methyl]-1,2,3,4,4a,9,10,10a-octahydro-2-propyl-, [2R-(2α,4aα,10aα)]-

The title compound of this example was prepared by procedures analogous to those described above in Example 136. Mass: 395 $(M+2)^+$.

Examples 492–495

The title compounds of Examples 492–495 were prepared by procedures analogous to those described above in Example 9.

Example 492

2,7-Phenanthrenediol, 1,2,3,4,4a,9,10,10a-octahydro-4a-[(4-hydroxyphenyl)methyl]-2-(1-propynyl)-,[2R-(2α,4aα,10aβ)]-, Mass: 362 (M).

Example 493

Glycine, N-[3-[[1,3,4,9,10,10a-hexahydro-2-hydroxy-7-(2-methoxy-2-oxoethoxy)-2-(1-propynyl)-4a(2H)-phenanthrenyl]methyl]phenyl]-N-methyl-, methyl ester, [2R-(2α,4aα,10aβ)]-, Mass: 521 $(M+2)^+$.

Example 494

Glycine, N-[3-[[1,3,4,9,10,10a-hexahydro-2-hydroxy-7-(2-methoxy-2-oxoethoxy)-2-(1-propynyl) 4a(2H)-phenanthrenyl]methyl]phenyl]-N-(2-methoxy-2-oxoethyl)-,methyl ester, [2R-(2α,4aα, 10aβ)]-, Mass: 579 $(M+2)^+$.

Example 495

Urea, N'-[4-[[1,3,4,9,10,10a-hexahydro-2,7-dihydroxy-2-(1-propynyl)-4a(2H)-phenanthrenyl]methyl]phenyl]-N,N-dimethyl-,[2R-(2α,4aα,10aβ)]-, Mass: 435 $(M+2)^+$.

Example 496

Acetamide, 2-[[3-[[7-(2-amino-2-oxoethoxy)-1,3,4, 9,10,10a-hexahydro-2-hydroxy-2-(1-propynyl)-4a (2H)-phenanthrenyl]methyl]phenyl]methylamino]-, [2R-(2α,4aα,10aβ)]-

The title compound of this example was prepared by procedures analogous to those described above in Example 55. Mass: 491 $(M+2)^+$.

Examples 497–499

The title compounds of Examples 497–499 were prepared by procedures analogous to those described above in Example 9.

Example 497

Methanesulfonamide, N-[4-[[1,3,4,9,10,10a-hexahydro-2,7-dihydroxy-2-(1-propynyl)-4a(2H)-phenanthrenyl]methyl]phenyl]-,[2R-(2α,4aα,10aβ)]-, Mass: 442 (M+3)$^+$.

Example 498

Acetamide, N-[4-[[1,3,4,9,10,10a-hexahydro-2,7-dihydroxy-2-(1-propynyl)-4a(2H)-phenanthrenyl]methyl]phenyl]-,[2R-(2α,4aα,10aβ)]-, Mass: 404 (M+1)$^+$.

Example 499

Acetamide, N-[4-[[1,3,4,9,10,10a-hexahydro-2,7-dihydroxy-2-(1-propynyl)-4a(2H)-phenanthrenyl]methyl]phenyl]-,[2R-(2α,4aα,10aβ)]-, Mass: 404 (M+1)$^+$.

Example 500

Carbamic acid, [2-(1-pyrrolidinyl)ethyl]-,4b,5,6,7,8,8a,9,10-octahydro-7-hydroxy-4b-(phenylmethyl)-7-(1-propynyl)-2-phenanthrenyl ester,[4bS-(4bα,7α,8aβ)]-

The title compound of this example was prepared by procedures analogous to those described above in Example 59. Mass: 470 (M−16)$^+$.

Example 501

2-Pyridinecarboxamide, N-[4-[[1,3,4,9,10,10a-hexahydro-2,7-dihydroxy-2-(1-propynyl)-4a(2H)-phenanthrenyl]methyl]phenyl]-,[2R-(2α,4aα,10aβ)]-

The title compound of this example was prepared by procedures analogous to those described above in Example 9. Mass: 434 (M−32)$^+$.

Example 502

Carbamic acid, [2-(1-pyrrolidinyl)ethyl]-, 4b,5,6,7,8,8a,9,10-octahydro-7-hydroxy-4b-(phenylmethyl)-7-(1-propynyl)-2-phenanthrenyl ester, monohydrochloride,[4bS-(4bα,7α,8aβ)]-

The title compound of this example was prepared by procedures analogous to those described above in Example 59. Mass: 506 (M−17)$^+$.

Example 503

5-Isoxazolecarboxamide, N-[4-[[1,3,4,9,10,10a-hexahydro-2,7-dihydroxy-2-(1-propynyl)-4a(2H)-phenanthrenyl]methyl]phenyl]-,[2R-(2α,4aα,10aβ)]-

The title compound of this example was prepared by procedures analogous to those described above in Example 9. Mass: 459 (M+3)$^+$.

Example 504

Acetamide, 2-[[4b,5,6,7,8,8a,9,10-octahydro-7-hydroxy-4b-(phenylmethyl)-7-(1-propynyl)-2-phenanthrenyl]oxy]-,[4bS-(4bα,7α,8aβ)]-

The title compound of this example was prepared by procedures analogous to those described above in Example 55. Mass: 404 (M+1)$^+$.

Example 505

1(2H)-Pyrimidineacetamide, N-[4-[[1,3,4,9,10,10a-hexahydro-2,7-dihydroxy-2-(1-propynyl)-4a(2H)-phenanthrenyl]methyl]phenyl]-3,4-dihydro-5-methyl-2,4-dioxo-,[2R-(2α,4aα,10aβ)]-

The title compound of this example was prepared by procedures analogous to those described above in Example 9. Mass: 546 (M+18)$^+$.

Example 506

Carbamic acid, dimethyl-, 2-[[7-[[(dimethylamino)carbonyl]oxy]-4b-[[3-(dimethylamino)phenyl]methyl]-4b,5,6,7,8,8a,9,10-octahydro-7-(1-propynyl)-2-phenanthrenyl]oxy]ethyl ester, [4bS-(4bα,7α,8aβ)]-

The title compound of this example was prepared by procedures analogous to those described above in Example 59. Mass: 576 (M+1)$^+$.

Example 507

Acetamide, N-[2-(dimethylamino)ethyl]-2-[[4b,5,6,7,8,8a,9,10-octahydro-7-hydroxy-4b-(phenylmethyl)-7-(1-propynyl)-2-phenanthrenyl]oxy]-,[4bS-(4bα,7α,8aβ)]-

The title compound of this example was prepared by procedures analogous to those described above in Example 244. Mass: 476 (M+2)$^+$.

Examples 508–511

The title compounds of Examples 508–511 were prepared by procedures analogous to those described above in Example 59.

Example 508

Carbamic acid, [3-(dimethylamino)propyl]-, 4b,5,6,7,8,8a,9,10-octahydro-7-hydroxy4b-(phenylmethyl)-7-(1-propynyl)-2-phenanthrenyl ester,[4bS-(4bα,7α,8aβ)]-, Mass: 457 (M−17)$^+$.

Example 509

Carbamic acid, dimethyl-, 1,2,3,4,4a,9, 10,10a-octahydro-4a-(phenylmethyl)-2-(1-propynyl)-2,7-phenanthrenediyl ester,[2R-(2α,4aα,10aβ)]-, Mass: 489 (M+1)$^+$.

Example 510

Carbamic acid, [2-(4-morpholinyl)ethyl]-, 4b,5,6,7,8,8a,9,10-octahydro-7-hydroxy-4b-(phenylmethyl)-7-(1-propynyl)-2-phenanthrenyl ester,[4bS-(4bα,7α,8aβ)]-, Mass: 485 (M−17)$^+$.

Example 511

Carbamic acid, [3-(1H-imidazol-1-yl)propyl]-,4b,5,6,7,8,8a,9,10-octahydro-7-hydroxy-4b-(phenylmethyl)-7-(1-propynyl)-2-phenanthrenyl ester,[4bS-(4bα,7α,8aβ)]-, Mass: 498 (M+1)$^+$.

Example 512

Acetic acid, [(4b,5,6,7,8,8a,9,10-octahydro-7-hydroxy-4b-(phenylmethyl)-7-(1-propynyl)-2-phenanthrenyl]oxy]-, methyl ester, [4bS-(4bα,7α,8aβ)]-

The title compound of this example was prepared by procedures analogous to those described above in Example 54. Mass: 418 (M).

Example 513

1H-Imidazole-4-sulfonamide, N-[4-[[1,3,4,9,10,10a-hexahydro-2,7-dihydroxy-2-(1-propynyl)-4a(2H)-phenanthrenyl]methyl]phenyl]-1-methyl-,[2R-(2α,4aα,10aβ)]-

The title compound of this example was prepared by procedures analogous to those described above in Example 9. Mass: 523 (M+18)$^+$.

Example 514

Acetamide, N-[2-(4-morpholinyl)ethyl]-2-[[4b,5,6,7,8a,9,10-octahydro-7-hydroxy-4b-(phenylmethyl)-7-(1-propynyl)-2-phenanthrenyl]oxy]-,[4bS-(4bα,7α,8a β)]-

The title compound of this example was prepared by procedures analogous to those described above in Example 244. Mass: 517 (M+1)$^+$.

Example 515

Acetamide, 2,2'-[[1,2,3,4,4a,9,10,10a-octahydro-4a-(phenylmethyl)-2-(1-propynyl)-2,7-phenanthrenediyl]bis(oxy)]bis-, [2R-(2α,4aα,10aβ)]-

The title compound of this example was prepared by procedures analogous to those described above in Example 55. Mass: 459 (M−1)$^+$.

Example 516

Acetamide, N-[3-(1H-imidazol-1-yl)propyl]-2-[[4b,5,6,7,8,8a,9,10-octahydro-7-hydroxy-4b-(phenylmethyl)-7-(1-propynyl)-2-phenanthrenyl]oxy]-,[4bS-(4bα,7α,8aβ)]-

The title compound of this example was prepared by procedures analogous to those described above in Example 244. Mass: 512 (M+1)$^+$.

Example 517

Carbamic acid, [2-(dimethylamino)ethyl]-, 4b,5,6,7,8,8a,9,10-octahydro-7-hydroxy-4b-(phenylmethyl)-7-(1-propynyl)-2-phenanthrenyl ester,[4bS-(4bα,7α,8aβ)]-

The title compound of this example was prepared by procedures analogous to those described above in Example 59. Mass: 461 (M+1)$^+$.

Example 518

Carbamic acid, [2-(dimethylamino)ethyl]-, 4b,5,6,7,8,8a,9,10-octahydro-7-hydroxy4b-(phenylmethyl)-7-(1-propynyl)-2-phenanthrenyl ester,[4bS-(4bα,7α,8aβ)]-HCl The title product of this example is the HCl salt of the title product of Example 517. Mass: 498 (M+1)$^+$.

Examples 519–523

The title compounds of Examples 519–523 were prepared by procedures analogous to those described above in Example 244.

Example 519

Acetamide, 2-[[4b,5,6,7,8,8a,9,10-octahydro-7-hydroxy-4b-(phenylmethyl)-7-(1-propynyl)-2-phenanthrenyl]oxy]-N-[2-(3-pyridinyl)ethyl]-,[4bS-(4bα,7α,8aβ)]-, Mass: 509 (M+1)$^+$.

Example 520

Piperazine, 1-methyl-4-[[[4b,5,6,7,8,8a,9,10-octahydro-7-hydroxy-4b-(phenylmethyl)-7-(1-propynyl)-2-phenanthrenyl]oxy]acetyl]-,[4bS-(4bα,7α,8aβ)]-, Mass: 487 (M+1)$^+$.

Example 521

Acetamide, N-[3-(4-methyl-1-piperazinyl)propyl]-2-[[4b,5,6,7,8,8a,9,10-octahydro-7-hydroxy-4b-(phenylmethyl)-7-(1-propynyl)-2-phenanthrenyl]oxy]-,[4bS-(4bα,7α,8aβ)]-, Mass: 544 (M+1)$^+$.

Example 522

Piperidine, 1-[[[4b,5,6,7,8,8a,9,10-octahydro-7-hydroxy-4b-(phenylmethyl)-7-(1-propynyl)-2-phenanthrenyl]oxy]acetyl]-4-(1-pyrrolidinyl)-,[4bS-(4bα,7α,8aβ)]-, Mass: 541 (M+1)$^+$.

Example 523

Acetamide, N-methoxy-2-[[4b,5,6,7,8,8a,9,10-octahydro-7-hydroxy-4b-(phenylmethyl)-7-(1-propynyl)-2-phenanthrenyl]oxy]-,[4bS-(4bα,7α,8aβ)]-, Mass: 432 (M−1)$^+$.

Example 524

2-Phenanthrenol, 7-[(4,5-dihydro-1H-imidazol-2-yl)methoxy]-1,2,3,4,4a,9,10,10a-octahydro-4a-(phenylmethyl)-2-(1-propynyl)-,[2R-(2α,4aα,10aβ)]-

The title compound of this example was prepared by procedures analogous to those described above in Example 74. Mass: 429 (M+1)$^+$.

Examples 525–526

The title compounds of Examples 525–526 were prepared by procedures analogous to those described above in Example 59.

Example 525

Carbamic acid, [3-(1-pyrrolidinyl)propyl]-, 4b,5,6,7,8,8a,9,10-octahydro-7-hydroxy-4b-(phenylmethyl)-7-(1-propynyl)-2-phenanthrenyl ester,[4bS-(4bα,7α,8aβ)]-, Mass: 501 (M+1)$^+$.

Example 526

Acetamide, N-hydroxy-2-[[4b,5,6,7,8,8a,9,10-octahydro-7-hydroxy-4b-(phenylmethyl)-7-(1-propynyl)-2-phenanthrenyl]oxy]-,[4bS-(4bα,7α,8aβ)]-, Mass: 418 (M−1)$^+$.

Examples 527–528

The title compounds of Examples 527–528 were prepared by procedures analogous to those described above in Example 67.

Example 527

2-Phenanthrenol, 1,2,3,4,4a,9,10,10a-octahydro-4a-(phenylmethyl)-2-(1-propynyl)-7-[2-(1-pyrrolidinyl)ethoxy]-, Mass: 444 (M+1)$^+$; isomer of title compound of Example 528.

Example 528

2-Phenanthrenol, 1,2,3,4,4a,9,10,10a-octahydro-4a-(phenylmethyl)-2-(1-propynyl)-7-[2-(1-pyrrolidinyl)ethoxy]-, Mass: 444 (M+1)$^+$; isomer of title compound of Example 527.

Examples 529–535

The title compounds of Examples 529–535- were prepared by procedures analogous to those described above in Example 244.

Example 529

Acetamide, N-(methylsulfonyl)-2-[[4b,5,6,7,8,8a,9,10-octahydro-7-hydroxy-4b-(phenylmethyl)-7-(1-propynyl)-2-phenanthrenyl]oxy]-,[4bS-(4bα,7α,8aβ)]-, Mass: 480 (M−1)$^+$.

Example 530

Acetamide, 2-[[4b,5,6,7,8,8a,9,10-octahydro-7-hydroxy-4b-(phenylmethyl)-7-(1-propynyl)-2-phenanthrenyl]oxy]-N-(2-pyridinylmethyl)-,[4bS-(4bα,7α,8aβ)]-, Mass: 495 (M+1)$^+$.

Example 531

Acetamide, 2-[[4b,5,6,7,8,8a,9,10-octahydro-7-hydroxy-4b-(phenylmethyl)-7-(1-propynyl)-2-phenanthrenyl]oxy]-N-(3-pyridinylmethyl)-,[4bS-(4bα,7α,8aβ)]-, Mass: 495 (M+1)$^+$.

Example 532

Acetamide, 2-[[4b,5,6,7,8,8a,9,10-octahydro-7-hydroxy-4b-(phenylmethyl)-7-(1-propynyl)-2-phenanthrenyl]oxy]-N-3-pyridinyl-,[4bS-(4bα,7α,8aβ)]-, Mass: 481 (M+1)$^+$.

Example 533

Acetamide, 2-[[4b,5,6,7,8,8a,9,10-octahydro-7-hydroxy-4b-(phenylmethyl)-7-(1-propynyl)-2-phenanthrenyl]oxy]-N-pyrazinyl-, [4bS-(4bα,7α,8aβ)]-, Mass: 482 (M+1)$^+$.

Example 534

Ethanimidamide, 2-[[4b,5,6,7,8,8a,9,10-octahydro-7-hydroxy-4b-(phenylmethyl)-7-(1-propynyl)-2-phenanthrenyl]oxy]-,[4bS-(4bα,7α,8aβ)]-, Mass: 403 (M+1)$^+$.

Example 535

Carbamic acid, [2-(1-pyrrolidinyl)ethyl]-, 4b-[[4-(acetylamino)phenyl]methyl]-4b,5,6,7,8,8a,9,10-octahydro-7-hydroxy-7-(1-propynyl)-2-phenanthrenyl ester,[4bS-(4bα,7α,8aβ)]-, Mass: 544 (M+1)$^+$.

Example 536

Carbamothioic acid, dimethyl-, O-[4b,5,6,7,8,8a,9,10-octahydro-7-hydroxy-4b-(phenylmethyl)-7-(1-propynyl)-2-phenanthrenyl] ester, [4bS-(4bα,7α,8aβ)]-

The title compound of this example was prepared by procedures analogous to those described above in Example 59. Mass: 434 (M+1)$^+$.

Examples 537–538

The title compounds of Examples 537–538 were prepared by procedures analogous to those described in Example 74.

Example 537

2-Phenanthrenol, 1,2,3,4,4a,9,10,10a-octahydro-4a-(phenylmethyl)-2-(1-propynyl)-7-(2-pyrimidinyloxy)-,[2R-(2α,4aα,10aβ)]-, Mass: 425 (M+1)$^+$.

Example 538

2-Phenanthrenol, 7-[(2-amino-6-methyl-4-pyrimidinyl)oxy]-1,2,3,4,4a,9,10,10a-octahydro-4a-(phenylmethyl)-2-(1-propynyl)-,[2R-(2α,4aα,10aβ)]-, Mass: 454 (M+1)$^+$.

Example 539

Acetamide, N-[2-(1-methyl-2-pyrrolidinyl)ethyl]-2-[[4b,5,6,7,8,8a,9,10-octahydro-7-hydroxy-4b-(phenylmethyl)-7-(1-propynyl)-2-phenanthrenyl]oxy]-,[4bS-(4bα,7α,8aβ)]-

The title compound of this example was prepared by procedures analogous to those described above in Example 244. Mass: 515 (M+1)$^+$.

Example 540

Carbamic acid, [2-(1-methyl-2-pyrrolidinyl)ethyl]-, 4b,5,6,7,8,8a,9,10-octahydro-7-hydroxy4b-(phenylmethyl)-7-(1-propynyl)-2-phenanthrenyl ester,[4bS-(4bα,7α,8aβ)]-

The title compound of this example was prepared by procedures analogous to those described above in Example 59. Mass: 501 (M+1)$^+$.

Example 541

3-Pyridinecarboxamide, 6-[[4b,5,6,7,8,8a,9,10-octahydro-7-hydroxy-4b-(phenylmethyl)-7-(1-propynyl)-2-phenanthrenyl]oxy]-,[4bS-(4bα,7α,8aβ)]-

The title compound of this example was prepared by procedures analogous to those described above in Example 74. Mass: 467 (M+1)$^+$.

Example 542

Carbamic acid, [2-(1-pyrrolidinyl)ethyl]-, 4b,5,6,7,8,8a,9,10-octahydro-7-hydroxy-4b-(2-propenyl)-7-(1-propynyl)-2-phenanthrenyl ester, [4bS-(4bα,7α,8aβ)]-

The title compound of this example was prepared by procedures analogous to those described above in Example 59. Mass: 437 (M+1)$^+$.

Examples 543–544

The title compounds of Examples 543–544 were prepared by procedures analogous to those described above in Example 69.

Example 543

2-Phenanthrenol, 7-[[5-[2-(dimethylamino)ethyl]-1,2,4-oxadiazol-3-yl]methoxy]-1,2,3,4,4a,9,10,10a-octahydro-4a-(phenylmethyl)-2-(1-propynyl)-,[2R-(2α,4aα,10aβ)]-, Mass: 500 (M+1)$^+$.

Example 544

2-Phenanthrenol, 1,2,3,4,4a,9,10,10a-octahydro-4a-(phenylmethyl)-7-[[5-(1-piperidinylmethyl)-1,2,4-oxadiazol-3-yl]methoxy]-2-(1-propynyl)-,[2R-(2α,4aα,10aβ)]-, Mass: 526 (M+1)$^+$.

Example 545

2-Phenanthrenol, 7-[(4,6-dimethoxy-1,3,5-triazin-2-yl)oxy]-1,2,3,4,4a,9,10,10a-octahydro-4a-(phenylmethyl)-2-(1-propynyl)-,[2R-(2α,4aα,10aβ)]-

The title compound of this example was prepared by procedures analogous to those described above in Example 74. Mass: 486 (M+1)$^+$.

Examples 546–547

The title compounds of Examples 546–547 were prepared by procedures analogous to those described above in Example 72.

Example 546

2-Phenanthrenol, 1,2,3,4,4a,9,10,10a-octahydro-4a-(phenylmethyl)-7-[[3-(1-piperidinylmethyl)-1,2,4-oxadiazol-5-yl]methoxy]-2-(1-propynyl)-,[2R-(2α,4aα,10aβ)]-, Mass: 526 (M+1)$^+$.

Example 547

2-Phenanthrenol, 1,2,3,4,4a,9,10,10a-octahydro-4a-(phenylmethyl)-2-(1-propynyl)-7-[[3-(2-pyridinyl)-1,2,4-oxadiazol-5-yl]methoxy]-,[2R-(2α,4aα,10aβ)]-, Mass: 506 (M+1)$^+$.

Examples 548–550

The title compounds of Examples 548–550 were prepared by procedures analogous to those described above in Example 59.

Example 548

Carbamic acid, [2-(3-pyridinyl)ethyl]-, 4b,5,6,7,8,8a,9,10-octahydro-7-hydroxy-4b-(phenylmethyl)-7-(1-propynyl)-2-phenanthrenyl ester,[4bS-(4bα,7α,8aβ)]-, Mass: 495 (M+1)$^+$.

Example 549

Carbamic acid, (2-pyridinylmethyl)-, 4b,5,6,7,8,8a,9,10-octahydro-7-hydroxy-4b-(phenylmethyl)-7-(1-propynyl)-2-phenanthrenyl ester, [4bS-(4bα,7α,8aβ)]-, Mass: 481 (M+1)$^+$.

Example 550

Carbamic acid, [2-(2-pyridinyl)ethyl]-, 4b,5,6,7,8,8a,9,10-octahydro-7-hydroxy-4b-(phenylmethyl)-7-(1-propynyl)-2-phenanthrenyl ester,[4bS-(4bα,7α,8aβ)]-, Mass: 495 (M+1)$^+$.

Example 551

2-Phenanthrenol, 4b,5,6,7,8,8a,9,10-octahydro-4b-pentyl-7-propyl-,(4bR,8aR)-

The title compound of this example was prepared by procedures analogous to those described above in Example 10. Mass: 313 (M−1)$^+$.

Examples 552–553

The title compounds of Examples 552–553 were prepared by procedures analogous to those described above in Example 59.

Example 552

Carbamic acid, [2-(1-pyrrolidinyl)ethyl]-, 4b,5,6,7,8,8a,9,10-octahydro-7-hydroxy-4b-propyl-7-(1-propynyl)-2-phenanthrenyl ester,[4bR-(4bα,7α,8aβ)]-, Mass: 439 (M+1)$^+$.

Example 553

Carbamic acid, [2-(dimethylamino)ethyl]-, 4b,5,6,7,8,8a,9,10-octahydro-7-hydroxy-4b-propyl-7-(1-propynyl)-2-phenanthrenyl ester,[4bR-(4bα,7α,8aβ)]-, Mass: 413 (M+1)$^+$.

Example 554

2-Phenanthrenol, 1,2,3,4,4a,9,10,10a-octahydro-4a-propyl-2-(1-propynyl)-7-(pyrazinyloxy)-,[2R-(2α,4aα,10aβ)]-

The title compound of this example was prepared by procedures analogous to those described above in Example 74. Mass: 377 (M+1)$^+$.

Example 555

Carbamic acid, (1H-tetrazol-5-ylmethyl)-, 4b,5,6,7,8,8a,9,10-octahydro-7-hydroxy-4b-(phenylmethyl)-7-(1-propynyl)-2-phenanthrenyl ester,[4bS-(4bα,7α,8aβ)]-

The title compound of this example was prepared by procedures analogous to those described above in Example 59. Mass: 470 (M−1)$^+$.

Example 556

2-Phenanthrenol, 7-[(4-chloro-2-pyrimidinyl)oxy]-1,2,3,4,4a,9,10,10a-octahydro-4a-(phenylmethyl)-2-(1-propynyl)-,[2R-(2α,4aα,10aβ)]-

The title compound of this example was prepared by procedures analogous to those described above in Example 74. Mass: 460 (M+1)$^+$.

Examples 557–558

The title compounds of Examples 557–558 were prepared by procedures analogous to those described above in Example 72.

Example 557

2-Phenanthrenol, 1,2,3,4,4a,9,10,10a-octahydro-7-[[3-(1-piperidinylmethyl)-1,2,4-oxadiazol-5-yl]methoxy]-4a-propyl-2-(1-propynyl)-,[2R-(2α,4aα,10aβ)]-, Mass: 478 (M+1)$^+$.

Example 558

2-Phenanthrenol, 1,2,3,4,4a,9,10,10a-octahydro-4a-propyl-2-(1-propynyl)-7-[[3-(2-pyridinyl)-1,2,4-oxadiazol-5-yl]methoxy]-,[2R-(2α,4aα,10aβ)]-, Mass: 458 (M+1)$^+$.

Examples 559–561

The title compounds of Examples 559–561 were prepared by procedures analogous to those described above in Example 59.

Example 559

Carbamic acid, (4-pyridinylmethyl)-, 4b,5,6,7,8,8a,9,10-octahydro-7-hydroxy-4b-(phenylmethyl)-7-(1-propynyl)-2-phenanthrenyl ester,[4bS-(4bα,7α,8aβ)]-, Mass: 481 (M+1)$^+$.

Example 560

Carbamic acid, (3-pyridinylmethyl)-, 4b,5,6,7,8,8a,9,10-octahydro-7-hydroxy-4b-(phenylmethyl)-7-(1-propynyl)-2-phenanthrenyl ester,[4bS-(4bα,7α,8aβ)]-, Mass: 481 (M+1)$^+$.

Example 561

Carbamic acid, (3-pyridinylmethyl)-, 4b,5,6,7,8,8a,9,10-octahydro-7-hydroxy-4b-propyl-7-(1-propynyl)-2-phenanthrenyl ester,[4bR-(4bα,7α,8aβ)]-, Mass: 433 (M+1)$^+$.

Example 562

2-Phenanthrenol, 1,2,3,4,4a,9,10,10a-octahydro-7-[(5-methoxy-2-pyrimidinyl)oxy]-4a-(phenylmethyl)-2-(1-propynyl)-,[2R-(2α,4aα,10aβ)]-

The title compound of this example was prepared by procedures analogous to those described above in Example 74. Mass: 455 (M+1)$^+$.

Example 563

Morpholine, 4-[[6-[[4b,5,6,7,8,8a,9,10-octahydro-7-hydroxy-4b-(phenylmethyl)-7-(1-propynyl)-2-phenanthrenyl]oxy]-3-pyridinyl]carbonyl]-,[4bS-(4bα,7α,8aβ)]-

The title compound of this example was prepared by procedures analogous to those described above in Example 244. Mass: 537 (M+1)$^+$.

Examples 564–565

The title compounds of Examples 564–565 were prepared by procedures analogous to those described above in Example 59.

Example 564

Carbamic acid, (2-pyridinylmethyl)-, 4b,5,6,7,8,8a,9,10-octahydro-7-hydroxy-4b-propyl-7-(1-propynyl)-2-phenanthrenyl ester, [4bR-(4bα,7α,8aβ)]-, Mass: 433 (M+1)$^+$.

Example 565

Carbamic acid, (4-pyridinylmethyl)-, 4b,5,6,7,8,8a,9,10-octahydro-7-hydroxy-4b-propyl-7-(1-propynyl)-2-phenanthrenyl ester,[4bR-(4bα,7α,8aβ)]-, Mass: 433 (M+1)$^+$.

Example 566

2-Phenanthrenol, 7-[(5-amino-1H-1,2,4-triazol-3-yl)methoxy]-1,2,3,4,4a,9,10,10a-octahydro-4a-propyl-2-(1-propynyl)-,[2R-(2α,4aα,10aβ)]-

The title compound of this example was prepared by procedures analogous to those described above in Example 62.

Examples 567–568

The title compounds of Examples 567–568 were prepared by procedures analogous to those described above in Example 76. Mass: 395 (M+1)$^+$.

Example 567

Pyridine, 3,3'-[[1,2,3,4,4a,9,10,10a-octahydro-4a-(phenylmethyl)-2-(1-propynyl)-2,7-phenanthrenediyl]bis(oxymethylene)]bis-,[2R-(2α,4aα,10aβ)]-, Mass: 529 (M+1)$^+$.

Example 568

Pyridine, 4,4'-[[1,2,3,4,4a,9,10,10a-octahydro-4a-(phenylmethyl)-2-(1-propynyl)-2,7-phenanthrenediyl]bis(oxymethylene)]bis-,[2R-(2α,4aα,10aβ)]-, Mass: 529 (M+1)$^+$.

Example 569

2-Phenanthrenol, 1,2,3,4,4a,9,10,10a-octahydro-4a-(phenylmethyl)-2-(1-propynyl)-7-(4-pyridinylmethoxy)-,[2R-(2α,4aα,10aβ)]

The title compound was obtained as described in Example 76, except 4-picolyl chloride hydrochloride was used instead of 3-picolyl chloride hydrochloride. MS m/z438 (M+H)$^+$.

Example 570

2,7-Phenanthrenediol, 1,2,3,4,4a,9,10,10a-octahydro-4a-pentyl-2-propyl-,[2R-(2α,4aα,10aβ)]-

The title compound of this example was prepared by procedures analogous to those described above in Example 10. Mass: 313 (M–17)$^+$.

Example 571

2-Phenanthrenol, 1,2,3,4,4a,9,10,10a-octahydro-4a-pentyl-2-(1-propynyl)-7-(pyrazinyloxy)-,[2R-(2α,4aα,10aβ)]-

The title compound of this example was prepared by procedures analogous to those described above in Example 74. Mass: 405 (M+1)$^+$.

Example 572

Carbamic acid, [2-(1-pyrrolidinyl)ethyl]-, 4b,5,6,7,8,8a,9,10-octahydro-7-hydroxy-4b-pentyl-7-(1-propynyl)-2-phenanthrenyl ester, [4bR-(4bα,7α,8aβ)]-

The title compound of this example was prepared by procedures analogous to those described above in Example 59. Mass: 467 (M+1)$^+$.

Example 573

2-Phenanthrenol, 1,2,3,4,4a,9,10,10a-octahydro-4a-propyl-2-(1-propynyl)-7-(4-pyridinylmethoxy)-,[2R-(2α,4aα,10aβ)]-

The title compound of this example was prepared by procedures analogous to those described above in Example 76. Mass: 390 (M+1)$^+$.

Example 574

Carbamic acid, [2-(4-pyridinyl)ethyl]-, 4b,5,6,7,8,8a,9,10-octahydro-7-hydroxy-4b-(phenylmethyl)-7-(1-propynyl)-2-phenanthrenyl ester, [4bS-(4bα,7α,8aβ)]-

The title compound of this example was prepared by procedures analogous to those described above in Example 59. Mass: 495 (M+1)$^+$.

Example 575

2-Phenanthrenol, 1,2,3,4,4a,9,10,10a-octahydro-4a-pentyl-2-(1-propynyl)-7-(2-pyridinylmethoxy)-,[2R-(2α,4aα,10aβ)]-

To a solution of 50 mg of the title compound of Example 252 and 9.2 mg of 60% NaH in 2 mL of anhydrous DMF was added 30 mg of 2-picolyl chloride hydrochloride at RT under $N_2$ atmosphere overnight. The reaction was quenched with $NH_4Cl$ (sat.), extracted with EtOAc (X3), washed with brine, dried over $Na_2SO_4$, filtered and concentrated to dryness. Purification by preparative TLC $SiO_2$ using 4% MeOH in $CH_2Cl_2$ as the elutant afforded 40 mg (65%) of the title product of this example as white fluffy powder. Mass: 419 $(M+2)^+$.

Examples 576–577

The title compounds of Examples 576–577 were prepared by procedures analogous to those described above in Example 244.

Example 576

Acetamide, 2-[[4b,5,6,7,8,8a,9,10-octahydro-7-hydroxy-4b-(phenylmethyl)-7-(1-propynyl)-2-phenanthrenyl]oxy]-N-[2-(4-pyridinyl)ethyl]-,[4bS-(4bα,7α,8aβ)]-, Mass: 509 $(M+1)^+$.

Example 577

Acetamide, 2-[[4b,5,6,7,8,8a,9,10-octahydro-7-hydroxy-4b-(phenylmethyl)-7-(1-propynyl)-2-phenanthrenyl]oxy]-N-[2-(2-pyridinyl)ethyl]-,[4bS-(4bα,7α,8aβ)]-, Mass: 509 $(M+1)^+$.

Example 578

2-Phenanthrenol, 1,2,3,4,4a,9,10,10a-octahydro-4a-(phenylmethyl)-2-(1-propynyl)-7-(2-pyridinylmethoxy)-,[2R-(2α,4aα,10aβ)]

The title compound was obtained as described in Example 76, except 2-picolyl chloride hydrochloride was used instead of 3-picolyl chloride hydrochloride. MS m/z 438 $(M+H)^+$.

Examples 579–580

The title compounds of Examples 579–580 were prepared by procedures analogous to those described above in Example 59.

Example 579

Carbamic acid, [2-(2-pyridinyl)ethyl]-, 4b,5,6,7,8,8a,9,10-octahydro-7-hydroxy-4b-pentyl-7-(1-propynyl)-2-phenanthrenyl ester, [4bR-(4bα,7α,8aβ)]-, Mass: 476 $(M+2)^+$.

Example 580

Carbamic acid, [2-(4-morpholinyl)ethyl]-, 4b,5,6,7,8,8a,9,10-octahydro-7-hydroxy-4b-pentyl-7-(1-propynyl)-2-phenanthrenyl ester, [4bR-(4bα,7α,8aβ)]-, Mass: 483 $(M+1)^+$.

Example 581

2-Phenanthrenol, 1,2,3,4,4a,9,10,10a-octahydro-7-[2-(4-morpholinyl)ethoxy]-4a-(phenylmethyl)-2-(1-propynyl)-,[2R-(2α,4aα,10aβ)]-

The title compound of this example was prepared by procedures analogous to those described above in Example 67. Mass: 460 $(M+1)^+$.

Example 582

2-Phenanthrenol, 7-[(2,6-dimethoxy-4-pyrimidinyl)oxy]-1,2,3,4,4a,9,10,10a-octahydro-4a-(phenylmethyl)-2-(1-propynyl)-,[2R-(2α,4aα,10aβ)]-

The title compound of this example was prepared by procedures analogous to those described above in Example 74. Mass: 485 $(M+1)^+$.

Examples 583–584

The title compounds of Examples 583–584 were prepared by procedures analogous to those described above in Example 59.

Example 583

Carbamic acid, (4-pyridinylmethyl)-, 4b,5,6,7,8,8a,9,10-octahydro-7-hydroxy-4b-pentyl-7-(1-propynyl)-2-phenanthrenyl ester, [4bR-(4bα,7α,8aβ)]-, Mass: 461 $(M+1)^+$.

Example 584

Carbamic acid, (3-pyridinylmethyl)-, 4b,5,6,7,8,8a,9,10-octahydro-7-hydroxy-4b-pentyl-7-(1-propynyl)-2-phenanthrenyl ester, [4bR-(4bα,7α,8aβ)]-, Mass: 461 $(M+1)^+$.

Examples 585–588

The title compounds of Examples 585–586 were prepared by procedures analogous to those described above in Example 75.

Example 585

2-Phenanthrenol, 1,2,3,4,4a,9,10,10a-octahydro-4a-(phenylmethyl)-2-(1-propynyl)-7-[[3-(1-pyrrolidinyl)pyrazinyl]oxy]-,[2R-(2α,4aα,10aβ)]-, Mass: 494 $(M+1)^+$.

Example 586

2-Phenanthrenol, 1,2,3,4,4a,9,10,10a-octahydro-4a-(phenylmethyl)-2-(1-propynyl)-7-[[6-(1-pyrrolidinyl)-4-pyrimidinyl]oxy]-,[2R-(2α,4aα,10aβ)]-, Mass: 494 $(M+1)^+$.

Example 587

2-Phenanthrenol, 1,2,3,4,4a,9,10,10a-octahydro-4a-(phenylmethyl)-2-(1-propynyl)-7-[[6-(1-pyrrolidinyl)-2-pyridinyl]oxy]-,[2R-(2α,4aα,10aβ)]-, Mass: 493 $(M+1)^+$.

Example 588

2-Phenanthrenol, 1,2,3,4,4a,9,10,10a-octahydro-4a-(phenylmethyl)-2-(1-propynyl)-7-[[6-(1-pyrrolidinyl)pyrazinyl]oxy]-,[2R-(2α,4aα,10aβ)]-, Mass: 494 $(M+1)^+$.

Example 589

2-Phenanthrenol, 1,2,3,4,4a,9,10,10a-octahydro-4a-(phenylmethyl)-2-(1-propynyl)-7-(pyrazinylmethoxy)-,[2R-(2α,4aα,10aβ)]-

The title compound of this example was prepared by procedures analogous to those described above in Example 74. Mass: 439 $(M+1)^+$.

Examples 590–591

The title compounds of Examples 590–591 were prepared by procedures analogous to those described above in Example 67.

Example 590

2-Phenanthrenol, 1,2,3,4,4a,9,10,10a-octahydro-4a-(phenylmethyl)-7-[2-(1-piperazinyl)ethoxy]-2-(1-propynyl)-,[2R-(2α,4aα,10aβ)]-, Mass: 459 (M+1)$^+$.

Example 591

Piperazine, 1-acetyl-4-[2-[[4b,5,6,7,8,8a,9,10-octahydro-7-hydroxy-4b-(phenylmethyl)-7-(1-propynyl)-2-phenanthrenyl]oxy]ethyl]-,[4bS-(4bα,7α,8aβ)]-, Mass: 501 (M+1)$^+$.

Example 592

2-Phenanthrenol, 1,2,3,4,4a,9,10,10a-octahydro-4a-pentyl-2-(1-propynyl)-7-(2-pyrimidinyloxy)-,[2R-(2α,4aα,10aβ)]-

The title compound of this example was prepared by procedures analogous to those described above in Example 74. Mass: 405 (M+1)$^+$.

Example 593

2-Phenanthrenol, 1,2,3,4,4a,9,10,10a-octahydro-4a-pentyl-2-(1-propynyl)-7-(pyrazinylmethoxy)-,[2R-(2α,4aα,10aβ)]-

The title compound of this example was prepared by procedures analogous to those described above in Example 76. Mass: 419 (M+1)$^+$.

Example 594

2-Phenanthrenol, 1,2,3,4,4a,9,10,10a-octahydro-4a-pentyl-2-(1-propynyl)-7-(3-pyridinylmethoxy)-,[2R-(2α,4aα,10aβ)]-

The title compound was obtained as described in Example 575, except 3-picolyl chloride hydrochloride was used instead of 2-picolyl chloride hydrochloride. Mass: 418 (M+1)$^+$

Example 595

2-Phenanthrenol, 1,2,3,4,4a,9,10,10a-octahydro-4a-pentyl-2-(1-propynyl)-7-(4-pyridinylmethoxy)-,[2R-(2α,4aα,10aβ)]

The title compound was obtained as described in Example 575, except 4-picolyl chloride hydrochloride was used instead of 2-picolyl chloride hydrochloride. Mass: 418 (M+1)$^+$.

Examples 596–599

The title compounds of Examples 596–599 were prepared by procedures analogous to those described above in Example 67.

Example 596

2-Phenanthrenol, 1,2,3,4,4a,9,10,10a-octahydro-4a-(phenylmethyl)-2-(1-propynyl)-7-[2-[4-(2-pyrimidinyl)-1-piperazinyl]ethoxy]-,[2R-(2α,4aα10aβ)]-, Mass: 537 (M+1)$^+$.

Example 597

2-Phenanthrenol, 1,2,3,4,4a,9,10,10a-octahydro-4a-(phenylmethyl)-2-(1-propynyl)-7-[2-(4-pyridinylamino)ethoxy]-, Mass: 467 (M+1)$^+$; isomer of title compound of Example 598.

Example 598

2-Phenanthrenol, 1,2,3,4,4a,9,10,10a-octahydro-4a-(phenylmethyl)-2-(1-propynyl)-7-[2-(4-pyridinylamino)ethoxy]-, Mass: 467 (M+1)$^+$; isomer of title compound of Example 597.

Example 599

2-Phenanthrenol, 1,2,3,4,4a,9,10,10a-octahydro-7-[2-(4-morpholinyl)ethoxy]-4a-pentyl-2-(1-propynyl)-,[2R-(2α,4aα,10aβ)]-, Mass: 441 (M+2)$^+$.

Examples 600–601

The title compounds of Examples 600–601 were prepared by procedures analogous to those described above in Example 76.

Example 600

2-Phenanthrenol, 1,2,3,4,4a,9,10,10a-octahydro-4a-pentyl-2-(1-propynyl)-7-(5-pyrimidinylmethoxy)-, [2R-(2α,4aα,10aβ)]-, Mass: 419 (M+1)$^+$.

Example 601

2-Phenanthrenol, 1,2,3,4,4a,9,10,10a-octahydro-4a-(phenylmethyl)-2-(1-propynyl)-7-(4-pyrimidinylmethoxy)-,[2R-(2α,4aα,10aβ)]-, Mass: 439 (M+1)$^+$.

Examples 602–603

The title compounds of Examples 602–603 were prepared by procedures analogous to those described above in Example 75.

Example 602

2-Phenanthrenol, 1,2,3,4,4a,9,10,10a-octahydro-4a-(phenylmethyl)-2-(1-propynyl)-7-[[2-(1-pyrrolidinyl)-4-pyridinyl]methoxy]-,[2R-(2α,4aα,10aβ)]-, Mass: 507 (M+1)$^+$.

Example 603

2-Phenanthrenol, 1,2,3,4,4a,9,10,10a-octahydro-4a-pentyl-2-(1-propynyl)-7-[[6-(1-pyrrolidinyl)-3-pyridinyl]methoxy]-,[2R-(2α,4aα,10aβ)]-, Mass: 487 (M+1)$^+$.

Example 604

2-Phenanthrenecarbonitrile, 4b,5,6,7,8,8a,9,10-octahydro-7-hydroxy-4b-pentyl-7-(1-propynyl)-, [4bR-(4bα,7α,8aβ)]-

The title compound of this example was prepared by procedures analogous to those described above in Example 15. Mass: 335 (M).

Example 605

2-Phenanthrenol, 1,2,3,4,4a,9,10,10a-octahydro-7-[2-(4-morpholinyl)ethoxy]-4a-(phenylmethyl)-2-propyl-,[2R-(2α,4aα,10aβ)]-

The title compound of this example was prepared by procedures analogous to those described above in Example 67. Mass: 464 (M+1)$^+$.

Example 606

2-Phenanthrenol, 1,2,3,4,4a,9,10,10a-octahydro-7-[2-(4-morpholinyl)ethoxy]-4a-(phenylmethyl)-2-propyl-,[2R-(2α,4aα,10aβ)]-HCl The title product of this example is the HCl salt of the title product of Example 605. Mass: 464 (M+1-HCl)$^+$.

Example 607

2-Phenanthrenol, 1,2,3,4,4a,9,10,10a-octahydro-7-[2-(4-morpholinyl)ethoxy]-2,4a-dipropyl-,[2R-(2α,4aα,10aβ)]-

The title compound of this example was prepared by procedures analogous to those described above in Example 67. Mass: 416 (M+1)$^+$.

Examples 608–609

The title compounds of Examples 608–609 were prepared by procedures analogous to those described above in Example 76.

Example 608

2-Phenanthrenol, 1,2,3,4,4a,9,10,10a-octahydro-4a-pentyl-7-(2-piperidinylmethoxy)-2-propyl-,[2R-(2α,4aα,10aβ)]-, Mass: 428 (M+1)$^+$.

Example 609

2-Phenanthrenol, 1,2,3,4,4a,9,10,10a-octahydro-4a-(phenylmethyl)-2-propyl-7-[1-(4-pyridinyl)ethoxy]-,[2R-(2α,4aα,10aβ)]-, Mass: 456 (M+1)$^+$.

Example 610

2-Phenanthrenol, 1,2,3,4,4a,9,10,10a-octahydro-7-[2-(4-morpholinyl)ethoxy]-4a-pentyl-2-propyl-,[2R-(2α,4aα,10aβ)]-

The title compound of this example was prepared by procedures analogous to those described above in Example 67. Mass: 444 (M+1)$^+$.

Example 611

Acetamide, N-[2-(4-morpholinyl)ethyl]-2-[[4b,5,6,7,8,8a,9,10-octahydro-7-hydroxy-4b-(phenylmethyl)-7-propyl-2-phenanthrenyl]oxy]-,[4bS-(4bα,7α,8aβ)]-

The title compound of this example was prepared by procedures analogous to those described above in Example 244. Mass: 521 (M+1)$^+$.

Example 612

2-Phenanthrenol, 1,2,3,4,4a,9,10,10a-octahydro-4a-pentyl-2-propyl-7-(4-pyridinylmethoxy)-,[2R-(2α,4aα,10aβ)]-

The title compound of this example was prepared by procedures analogous to those described above in Example 76. Mass: 422 (M+1)$^+$.

Examples 613–614

The title compounds of Examples 613–614 were prepared by procedures analogous to those described above in Example 15.

Example 613

2-Phenanthrenecarbonitrile, 4b,5,6,7,8,8a,9,10-octahydro-7-methoxy-4b-pentyl-7-(1-propynyl)-,[4bR-(4bα,7α,8aβ)]-, Mass: 367 (M+18)$^+$.

Example 614

2-Phenanthrenecarbonitrile, 4b,5,6,7,8,8a,9,10-octahydro-7-methoxy-4b-pentyl-7-propyl-,[4bR-(4bα,7α,8aβ)]-, Mass: 371 (M+18)$^+$.

Examples 615–619

The title compounds of Examples 615–619 were prepared by procedures analogous to those described above in Example 74.

Example 615

2-Phenanthrenol, 1,2,3,4,4a,9,10,10a-octahydro-4a-(phenylmethyl)-2-propyl-7-(pyrazinyloxy)-,[2R-(2α,4aα,10aβ)]-,Mass: 429 (M+1)$^+$.

Example 616

2-Phenanthrenol, 1,2,3,4,4a,9,10,10a-octahydro-4a-(phenylmethyl)-2-propyl-7-(2-pyrimidinyloxy)-,[2R,-(2α,4aα,10aβ)]-, Mass: 429 (M+1)$^+$.

Example 617

2-Phenanthrenol, 1,2,3,4,4a,9,10,10a-octahydro-7-[(3-methylpyrazinyl)oxy]-4a-(phenylmethyl)-2-(1-propynyl)-,[2R-(2α,4aα,10aβ)]-, Mass: 439 (M+1)$^+$.

Example 618

2-Phenanthrenol, 1,2,3,4,4a,9,10,10a-octahydro-7-[(3-methyl-2-quinoxalinyl)oxy]-4a-(phenylmethyl)-2-(1-propynyl)-,[2R-(2α,4aα,10aβ)]-, Mass: 489 (M+1)$^+$.

Example 619

2-Phenanthrenol, 7-[(3,6-dimethylpyrazinyl)oxy]-1,2,3,4,4a,9,10,10a-octahydro-4a-(phenylmethyl)-2-(1-propynyl)-,[2R-(2α,4aα,10aβ)]-, Mass: 453 (M+1)$^+$.

Example 620

2-Phenanthrenol, 1,2,3,4,4a,9,10,10a-octahydro-7-[(2-methyl-3-pyridinyl)methoxy]-4a-(phenylmethyl)-2-(1-propynyl)-,[2R-(2α,4aα,10aβ)]-

The title compound of this example was prepared by procedures analogous to those described above in Example 76. Mass: 452 (M+1)$^+$.

Example 621

2-Phenanthrenol, 1,2,3,4,4a,9,10,10a-octahydro-7-[(2-methyl-3-pyridinyl)methoxy]4a-(phenylmethyl)-2-propyl-,[2R-(2α,4aα,10aβ)]

The title compound was obtained as described in Example 627, below, except 2-methyl-3-picolyl chloride hydrochloride was used instead of 2-picolyl chloride hydrochloride. Mass: 456 (M+1)$^+$.

Example 622

2-Phenanthrenol, 7-[(2-amino-6-methyl-4-pyrimidinyl)oxy]-1,2,3,4,4a,9,10,10a-octahydro-4a-(phenylmethyl)-2-propyl-,[2R-(2α,4aα,10aβ)]-

The title compound of this example was prepared by procedures analogous to those described above in Example 74. Mass: 458 (M+1)$^+$.

Example 623

2-Phenanthrenol, 1,2,3,4,4a,9,10,10a-octahydro-7-[(6-methyl-2-pyridinyl)methoxy]-4a-(phenylmethyl)-2-propyl-,[2R-(2α,4aα,10aβ)]-

The title compound of this example was prepared by procedures analogous to those described above in Example 76. Mass: 456 (M+1)$^+$.

Example 624

2-Phenanthrenol, 1,2,3,4,4a,9,10,10a-octahydro-7-[(6-methyl-2-pyridinyl)methoxy]-4a-(phenylmethyl)-2-(1-propynyl)-,[2R-(2α,4aα,10aβ)]

The title compound was obtained as described in Example 76, except 3-methyl-2-picolyl chloride hydrochloride was used instead of 3-picolyl chloride hydrochloride, yield 90%. MS m/z452 (M+H)$^+$.

Examples 625–626

The title compounds of Examples 625–626 were prepared by procedures analogous to those described above in Example 74.

Example 625

2-Phenanthrenol, 1,2,3,4,4a,9,10,10a-octahydro-4a-(phenylmethyl)-2-propyl-7-[[4-(trifluoromethyl)-2-pyrimidinyl]oxy]-,[2R-(2α,4aα,10aβ)]-, Mass: 479 (M−17)$^+$.

Example 626

2-Phenanthrenol, 1,2,3,4,4a,9,10,10a-octahydro-4a-(phenylmethyl)-2-(1-propynyl)-7-[[4-(trifluoromethyl)-2-pyrimidinyl]oxy]-,[2R-(2α,4aα,10aβ)]-, Mass: 493 (M+1)$^+$.

Example 627

2-Phenanthrenol, 1,2,3,4,4a,9,10,10a-octahydro-4a-(phenylmethyl)-2-propyl-7-(2-pyridinylmethoxy)-,[2R-(2α,4aα,10aβ)]

To a solution of 30 mg of the title compound of Example 10 and 8 mg of 60% NaH in 2 mL of anhydrous DMF was added 17 mg of 2-picolyl chloride hydrochloride at RT under N$_2$ atmosphere overnight. The reaction was quenched with NH$_4$Cl (sat.), extracted with EtOAc (X3), washed with brine, dried over Na$_2$SO$_4$, filtered and concentrated to dryness. Purification by preparative TLC SiO$_2$ using 30% EtOAc in hexanes as the eluant afforded 32 mg (84%) of the title product of this example as white fluffy powder. Mass: 442 (M+1)$^+$.

Example 628

2-Phenanthrenol, 1,2,3,4,4a,9,10,10a-octahydro-4a-(phenylmethyl)-2-propyl-7-(3-pyridinylmethoxy)-,[2R-(2α,4aα,10a β)]

The title compound was obtained as described in Example 627, except the 3-picolyl chloride hydrochloride was used instead of 2-picolyl chloride hydrochloride. Mass: 442 (M+1)$^+$.

Examples 629–633

The title compounds of Examples 629–633 were prepared by procedures analogous to those described above in Example 76.

Example 629

2-Phenanthrenol, 1,2,3,4,4a,9,10,10a-octahydro-7-[(6-methyl-3-pyridinyl)methoxy]-4a-(phenylmethyl)-2-propyl-,[2R-(2α,4aα,10aβ)]-, Mass: 456 (M+1)$^+$.

Example 630

2-Phenanthrenol, 1,2,3,4,4a,9,10,10a-octahydro-7-[(6-methyl-3-pyridinyl)methoxy]-4a-(phenylmethyl)-2-(1-propynyl)-,[2R-(2α,4aα,10aβ)]-, Mass: 452 (M+1)$^+$.

Example 631

Pyridine, 3,3'-[[1,2,3,4,4a,9,10,10a-octahydro-4a-(phenylmethyl)-2-(1-propynyl)-2,7-phenanthrenediyl]bis(oxymethylene)]bis[6-methyl-,[2R-(2α,4aα,10aβ)]-, Mass: 557 (M+1)$^+$.

Example 632

2-Pyridinecarbonitrile, 6-[[[4b,5,6,7,8,8a,9,10-octahydro-7-hydroxy-4b-(phenylmethyl)-7-propyl-2-phenanthrenyl]oxy]methyl]-,[4bS-(4bα,7α,8aβ)]-, Mass: 467 (M+1)$^+$.

Example 633

2-Pyridinecarbonitrile, 6-[[[4b,5,6,7,8,8a,9,10-octahydro-7-hydroxy-4b-(phenylmethyl)-7-(1-propynyl)-2-phenanthrenyl]oxy]methyl]-,[4bS-(4bα,7α,8aα)]-, Mass: 481 (M+18)$^+$.

Examples 634–646

The title compounds of Examples 634–646 were prepared by procedures analogous to those described above in Example 74.

Example 634

2-Phenanthrenol, 7-[(3-amino-4-methyl-2-pyridinyl)oxy]-1,2,3,4,4a,9,10,10a-octahydro-4a-(phenylmethyl)-2-propyl-,[2R-(2α,4aα,10aβ)]-, Mass: 457 (M+1)$^+$.

Example 635

2-Phenanthrenol, 7-[(3-amino-2-pyridinyl)oxy]-1,2,3,4,4a,9,10,10a-octahydro-4a-(phenylmethyl)-2-propyl-,[2R-(2α,4aα,10aβ)]-, Mass: 443 (M+1)$^+$.

Example 636

3-Pyridinecarbonitrile, 6-methyl-2-[[4b,5,6,7,8,8a,9,10-octahydro-7-hydroxy-4b-(phenylmethyl)-7-(1-propynyl)-2-phenanthrenyl]oxy]-,[4bS-(4bα,7α,8aβ)]-, Mass: 463 (M+1)$^+$.

Example 637

3-Pyridinecarbonitrile, 6-methyl-2-[[4b,5,6,7,8,8a,9,10-octahydro-7-hydroxy-4b-(phenylmethyl)-7-propyl-2-phenanthrenyl]oxy]-,[4bS-(4bα,7α,8aβ)]-, Mass: 467 (M+1)$^+$.

Example 638

3-Pyridinecarbonitrile, 2-[[4b,5,6,7,8,8a,9,10-octahydro-7-hydroxy-4b-(phenylmethyl)-7-propyl-2-phenanthrenyl]oxy]-,[4bS-(4bα,7α,8aβ)]-, Mass: 453 (M+1)$^+$.

Example 639

2-Phenanthrenol, 1,2,3,4,4a,9,10,10a-octahydro-4a-(phenylmethyl)-2-propyl-7-[2-(trifluoromethyl)phenoxy]-,[2R-(2α,4aα,10aβ)]-, Mass: 496 (M+1)⁺

Example 640

2-Pyridinecarbonitrile, 6-[[4b,5,6,7,8,8a,9,10-octahydro-7-hydroxy-4b-(phenylmethyl)-7-(1-propynyl)-2-phenanthrenyl]oxy]-, Mass: 449 (M+1)⁺.

Example 641

2-Phenanthrenol, 1,2,3,4,4a,9,10,10a-octahydro-4a-(phenylmethyl)-2-(1-propynyl)-7-[[6-(trifluoromethyl)-2-pyridinyl]oxy]-, Mass: 492 (M+1)⁺.

Example 642

2-Pyridinecarbonitrile, 6-[[4b,5,6,7,8,8a,9,10-octahydro-7-hydroxy-4b-(phenylmethyl)-7-propyl-2-phenanthrenyl]oxy]-,[4bS-(4bα,7α,8aβ)]-, Mass: 471 (M+18)⁺.

Example 643

3-Pyridinecarbonitrile, 4,6-dimethyl-2-[[4b,5,6,7,8,8a,9,10-octahydro-7-hydroxy-4b-(phenylmethyl)-7-(1-propynyl)-2-phenanthrenyl]oxy]-,[4bS-(4bα,7α,8aβ)]-, Mass: 477 (M+1)⁺.

Example 644

3-Pyridinecarbonitrile, 6-[[4b,5,6,7,8,8a,9,10-octahydro-7-hydroxy-4b-(phenylmethyl)-7-(1-propynyl)-2-phenanthrenyl]oxy]-,[4bS-(4bα,7α,8aβ)]-, Mass: 449 (M+1)⁺.

Example 645

3-Pyridinecarbonitrile, 6-[[4b,5,6,7,8,8a,9,10-octahydro-7-hydroxy-4b-(phenylmethyl)-7-propyl-2-phenanthrenyl]oxy]-,[4bS-(4bα,7α,8aβ)]-, Mass: 453 (M+1)⁺.

Example 646

3-Pyridinecarbonitrile, 4,6-dimethyl-2-[[4b,5,6,7,8,8a,9,10-octahydro-7-hydroxy-4b-(phenylmethyl)-7-propyl-2-phenanthrenyl]oxy]-,[4bS-(4bα,7α,8aβ)]-, Mass: 481 (M+1)⁺.

Examples 647–649

The title compounds of Examples 647–649 were prepared by procedures analogous to those described above in Example 76.

Example 647

2-Phenanthrenol, 7-[(2,6-dichloro-4-pyrimidinyl)methoxy]-1,2,3,4,4a,9,10,10a-octahydro4a-(phenylmethyl)-2-propyl-,[2R-(2α,4aα,10aβ)]-, Mass: 511 (M).

Example 648

2-Phenanthrenol, 7-[(2,6-dimethoxy-4-pyrimidinyl)methoxy]-1,2,3,4,4a,9,10,10a-octahydro4a-(phenylmethyl)-2-propyl-,[2R-(2α,4aα,10aβ)]-, Mass: 503 (M+1)⁺.

Example 649

2-Phenanthrenol, 7-[(2-chloro-6-methyl-4-pyridinyl)methoxy]-1,2,3,4,4a,9,10,10a-octahydro-4a-(phenylmethyl)-2-propyl-,[2R-(2α,4aα,10aβ)]-, Mass: 490 (M).

Example 650

2-Phenanthrenol, 7-[(6-chloro-2-pyridinyl)oxy]-1,2,3,4,4a,9,10,10a-octahydro-4a-(phenylmethyl)-2-propyl-,[2R-(2α,4aα,10a β)]-

The title compound of this example was prepared by procedures analogous to those described above in Example 74. Mass: 444 (M–18)⁺.

Example 651

2-Pyridinecarbonitrile, 3-[[[4b,5,6,7,8,8a,9,10-octahydro-7-hydroxy-4b-(phenylmethyl)-7-(1-propynyl)-2-phenanthrenyl]oxy]methyl]-,[4bS-(4bα,7α,8aβ)]

The title compound was obtained as described in Example 76, except 2-cyano-3-picolyl chloride hydrochloride was used instead of 3-picolyl chloride hydrochloride, yield 90%. MS m/z 463 (M+H)⁺.

Example 652

2-Pyridinecarbonitrile, 3-[[[4b,5,6,7,8,8a,9,10-octahydro-7- hydroxy4b-(phenylmethyl)-7-propyl-2-phenanthrenyl]oxy]methyl]-,[4bS-(4bα,7α,8aβ)]

The title compound was obtained as described in Example 627, except 2-cyano-3-picolyl chloride hydrochloride was used instead of 2-picolyl chloride hydrochloride. Mass: 449 (M–17)⁺.

Examples 653–660

The title compounds of Examples 653–660 were prepared by procedures analogous to those described above in Example 76.

Example 653

2-Phenanthrenol, 1,2,3,4,4a,9,10,10a-octahydro-7-[(2-methoxy-6-methyl4-pyridinyl)methoxy]-4a-(phenylmethyl)-2-propyl-,[2R-(2α,4aα,10aβ)]-, Mass: 486 (M+1)⁺.

Example 654

2-Phenanthrenol, 1,2,3,4,4a,9,10,10a-octahydro-7-[(2-methyl-4-pyridinyl)methoxy]-4a-(phenylmethyl)-2-propyl-,[2R-(2α,4aα,10aβ)]-, Mass: 456 (M+1)⁺.

Example 655

2-Phenanthrenol, 1,2,3,4,4a,9,10,10a-octahydro-4a-(phenylmethyl)-2-(1-propynyl)-7-(2-quinolinylmethoxy)-,[2R-(2α,4aα,10aβ)]-, Mass: 488 (M+1)⁺.

Example 656

2-Phenanthrenol, 1,2,3,4,4a,9,10,10a-octahydro-4a-(phenylmethyl)-2-propyl-7-(2-quinolinylmethoxy)-,[2R-(2α,4aα,10aβ)]-, Mass: 492 (M+1)⁺.

Example 657

2-Phenanthrenol, 1,2,3,4,4a,9,10,10a-octahydro-7-[(2-methoxy-3-pyridinyl)methoxy]-4a-(phenylmethyl)-2-propyl-,[2R-(2α,4aα,10aβ)]-, Mass: 472 (M+1)$^+$.

Example 658

2-Phenanthrenol, 1,2,3,4,4a,9,10,10a-octahydro-4a-(phenylmethyl)-2-propyl-7-(pyrazinylmethoxy)-, [2R-(2α,4aα,10aβ)]-, Mass: 443 (M+1)$^+$.

Example 659

2(1H)-Pyridinone, 3-[[[4b,5,6,7,8,8a,9,10-octahydro-7-hydroxy-4b-(phenylmethyl)-7-propyl-2-phenanthrenyl]oxy]methyl]-,[4bS-(4bα,7α,8aβ)]-, Mass: 458 (M+1)$^+$.

Example 660

2-Phenanthrenol, 1,2,3,4,4a,9,10,10a-octahydro-4a-(phenylmethyl)-2-propyl-7-(4-pyrimidinylmethoxy)-,[2R-(2α,4aα,10aβ)]-, Mass: 443 (M+1)$^+$.

Example 661

2,7-Phenanthrenediol, 1,2,3,4,4a,9,10,10a-octahydro-2-(3-methoxy-1-propynyl)-4a-(phenylmethyl)-,[2R-(2α,4aα,10aβ)]-

The title compound of this example was prepared by procedures analogous to those described above in Example 9. Mass: 359 (M–17)$^+$.

Example 662

3-Pyridinecarboxamide, 6-methyl-2-[[4b,5,6,7,8,8a,9,10-octahydro-7-hydroxy-4b-(phenylmethyl)-7-propyl-2-phenanthrenyl]oxy]-,[4bS-(4bα,7α,8aβ)]-

The title compound of this example was prepared by procedures analogous to those described above in Example 74. Mass: 485 (M+1)$^+$.

Examples 663–665

The title compounds of Examples 663–665 were prepared by procedures analogous to those described above in Example 76.

Example 663

2-Phenanthrenol, 7-[(4,6-dimethyl-2-pyrimidinyl)methoxyl-1,2,3,4,4a,9,10,10a-octahydro-4a-(phenylmethyl)-2-propyl-,[2R-(2α,4aα,10aβ)]-, Mass: 471 (M+1)$^+$.

Example 664

2-Phenanthrenol, 1,2,3,4,4a,9,10,10a-octahydro-4a-(phenylmethyl)-2-propyl-7-(3-quinolinylmethoxy)-, [2R-(2α,4aα,10aβ)]-, Mass: 492 (M+1)$^+$.

Example 665

2-Phenanthrenol, 1,2,3,4,4a,9,10,10a-octahydro4a-(phenylmethyl)-2-propyl-7-(4-quinolinylmethoxy)-, [2R-(2α,4aα,10aβ)]-, Mass: 492 (M+1)$^+$.

Example 666

2-Phenanthrenol, 1,2,3,4,4a,9,10,10a-octahydro-7-[(3-methyl-2-quinoxalinyl)oxy]-4a-(phenylmethyl)-2-propyl-,[2R-(2α,4aα,10aβ)]-

The title compound of this example was prepared by procedures analogous to those described above in Example 74. Mass: 493 (M+1)$^+$.

Example 667

2-Phenanthrenol, 1,2,3,4,4a,9,10,10a-octahydro-7-[(5-methyl-3-isoxazolyl)methoxy]-4a-(phenylmethyl)-2-propyl-,[2R-(2α,4aα,10aβ)]-

The title compound of this example was prepared by procedures analogous to those described above in Example 76. Mass: 428 (M–17)$^+$.

Example 668

2,7-Phenanthrenediol, 1,2,3,4,4a,9,10,10a-octahydro-2-(3-methoxypropyl)-4a-(phenylmethyl)-, [2S-(2α,4aα,10aβ)]-

The title compound of this example was prepared by procedures analogous to those described above in Example 10. Mass: 363 (M–17)$^+$.

Example 669

2,7-Phenanthrenediol, 2-(ethoxyethynyl)-1,2,3,4,4a,9,10,10a-octahydro-4a-(phenylmethyl)-,[2R-(2α,4aα,10aβ)]-

The title compound of this example was prepared by procedures analogous to those described above in Example 9. Mass: 359 (M–17)$^+$.

Examples 670–671

The title compounds of Examples 670–671 were prepared by procedures analogous to those described above in Example 10.

Example 670

2,7-Phenanthrenediol, 1,2,3,4,4a,9,10,10a-octahydro-4a-(phenylmethyl)-2-(3-phenyl-2-propynyl)-,[2R-(2α,4aα,10aβ)]-, Mass: 405 (M–17)$^+$.

Example 671

2,7-Phenanthrenediol, 2-(2-ethoxyethyl)-1,2,3,4,4a,9,10,10a-octahydro-4a-(phenylmethyl)-,[2R-(2α,4aα,10aβ)]-, Mass: 363 (M–17)$^+$.

Example 672

3-Pyridinecarbonitrile, 6-[[[4b,5,6,7,8,8a,9,10-octahydro-7-hydroxy-4b-(phenylmethyl)-7-propyl-2-phenanthrenyl]oxy]methyl]-,[4bS-(4bα,7α,8aβ)]-

The title compound of this example was prepared by procedures analogous to those described above in Example 76. Mass: 467 (M+1)$^+$.

Example 673

2-Phenanthrenol, 1,2,3,4,4a,9,10,10a-octahydro-2-(3-methoxypropyl)-4a-(phenylmethyl)-7-(3-pyridinylmethoxy)-,[2S-(2α,4aα,10aβ)]

To a solution of 28 mg of the title compound of Example 668 and 7 mg of 60% NaH in 2 mL of anhydrous DMF was added 15 mg of 3-picolyl chloride hydrochloride at RT under $N_2$ atmosphere overnight. The reaction was quenched with $NH_4Cl$ (sat.), extracted with EtOAc (X3), washed with brine, dried over $Na_2SO_4$, filtered and concentrated to dryness. Purification by preparative TLC SiO$_2$ using 35% EtOAc in hexanes as the eluant afforded 30 mg (87%) of the title product of this example as white fluffy powder. Mass: 472 (M+1)$^+$.

Example 674

2-Phenanthrenol, 1,2,3,4,4a,9,10,10a-octahydro-7-[(6-methoxy-2-pyridinyl)methoxy]-4a-(phenylmethyl)-2-propyl-,[2R-(2α,4aα,10aβ)]-

The title compound of this example was prepared by procedures analogous to those described above in Example 76. Mass: 472 (M+1)$^+$.

Examples 675–677

The title compounds of Examples 675–677 were prepared by procedures analogous to those described above in Example 81.

Example 675

2,7-Phenanthrenediol, 2-[(cyclopropylmethoxy)methyl]-1,2,3,4,4a,9,10,10a-octahydro-4a-(phenylmethyl)-,[2R-(2α,4aα,10aβ)]-, Mass: 375 (M−17)$^+$.

Example 676

2,7-Phenanthrenediol, 2-(ethoxymethyl)-1,2,3,4,4a,9,10,10a-octahydro-4a-(phenylmethyl)-,[2R-(2α,4aα,10aβ)]-, Mass: 349 (M−17)$^+$.

Example 677

2,7-Phenanthrenediol, 1,2,3,4,4a,9,10,10a-octahydro-4a-(phenylmethyl)-2-[(2,2,2-trifluoroethoxy)methyl]-,[2R-(2α,4aα,10aβ)]-, Mass: 403 (M−17)$^+$.

Example 678

2,7-Phenanthrenediol, 1,2,3,4,4a,9,10,10a-octahydro-2-(1-piperidinylmethyl)-4a-(phenylmethyl)-,[2R-(2α,4aα,10aβ)]-

The title compound of this example was prepared by procedures analogous to those described above in Example 83. Mass: 406 (M+1)$^+$.

Examples 679–682

The title compounds of Examples 679–682 were prepared by procedures analogous to those described above in Example 81.

Example 679

2,7-Phenanthrenediol, 1,2,3,4,4a,9,10,10a-octahydro-2-[[2-(1-methylethoxy)ethoxy]methyl]-4a-(phenylmethyl)-,[2R-(2α,4aα,10aβ)]-, Mass: 423 (M+1)$^+$.

Example 680

2-Phenanthrenol, 1,2,3,4,4a,9,10,10a-octahydro-2-(methoxymethyl)-4a-(phenylmethyl)-7-(3-pyridinylmethoxy)-,[2R-(2α,4aα,10aβ)]-, Mass: 444 (M+1)$^+$.

Example 681

2-Phenanthrenol, 2-(ethoxymethyl)-1,2,3,4,4a,9,10,10a-octahydro-4a-(phenylmethyl)-7-(3-pyridinylmethoxy)-,[2R-(2α,4aα,10aβ)]-, Mass: 458 (M+1)$^+$.

Example 682

2,7-Phenanthrenediol, 1,2,3,4,4a,9,10,10a-octahydro-2-[(2-methoxyethoxy)methyl]-4a-(phenylmethyl)-, (4aS,10aR)-, Mass: 397 (M+1)$^+$.

Example 683

2-Phenanthrenol, 1,2,3,4,4a,9,10,10a-octahydro-7-[(2-methyl-5-thiazolyl)methoxy]-4a-(phenylmethyl)-2-propyl-,[2R-(2α,4aα,10aβ)]-

The title compound of this example was prepared by procedures analogous to those described above in Example 76. Mass: 462 (M+1)$^+$.

Examples 684–685

The title compounds of Examples 684–685 were prepared by procedures analogous to those described above in Example 72.

Example 684

2-Phenanthrenol, 7-[[5-(1,1-dimethylethyl)-1,2,4-oxadiazol-3-yl]methoxy]-1,2,3,4,4a,9,10,10a-octahydro-4a-(phenylmethyl)-2-propyl-,[2R-(2α,4aα,10aβ)]-, Mass: 489 (M+1)$^+$.

Example 685

2-Phenanthrenol, 7-[[5-(3,5-dimethyl-4-isoxazolyl)-1,2,4-oxadiazol-3-yl]methoxy]-1,2,3,4,4a,9,10,10a-octahydro-4a-(phenylmethyl)-2-propyl-,[2R-(2α,4aα,10aβ)]-, Mass: 510 (M−17)$^+$.

Example 686

2-Phenanthrenol, 1,2,3,4,4a,9,10,10a-octahydro-2-(3-methoxy-1-propynyl)-4a-(phenylmethyl)-7-(2-pyridinylmethoxy)-,[2R-(2α,4aα,10a β)]-

The title compound of this example was prepared by procedures analogous to those described above for the preparation of the title compound of Example 76. Mass: 468 (M+1)$^+$.

Example 687

2-Phenanthrenol, 4b,5,6,10-tetrahydro-7-phenyl-4b-(phenylmethyl)-, (S)-

The title compound of this example was prepared by procedures analogous to those described above in Example 136. MS: 364 (M+1)$^+$.

Examples 688–691

The title compounds of Examples 688–691 were prepared by procedures analogous to those described above in Example 51.

Example 688

2(1H)-Phenanthrenone, 4b-(2-butenyl)-3,4,4b,5,6,7,8,8a,9,10-decahydro-7-hydroxy-7-(1-propynyl)-, [4bS-[4bα(E),7α,8aβ]]-; See also Example 51.

Example 689

2(3H)-Phenanthrenone, 4b-(2-butenyl)-4,4a,4b,5,6,7,8,8a,9,10-decahydro-7-hydroxy-7-(1-propynyl)-, [4bS(E),7S,8aR]-, MS: 312 (M+1)$^+$.

Example 690

2(3H)-Phenanthrenone, 4b-(2-butenyl)-4,4a,4b,5,6,7,8,8a,9,10-decahydro-7-hydroxy-7-(1-propynyl)-, [4aR-[4aα,4bα(E),7β,8aα]]-; See also Example 51.

Example 691

2(1H)-Phenanthrenone, 4b-(2-butenyl)-3,4,4b,5,6,7,8,8a,9,10-decahydro-7-hydroxy-7-(1-propynyl)-, [4bS-[4bα(E),7β,8aβ]]-, MS: 313 (M+1)$^+$.

Example 692

2(3H)-Phenanthrenone, 4b-(2-butenyl)-4,4a,4b,5,6,7,8,8a,9,10-decahydro-7-hydroxy-7-(1-propynyl)-, oxime, [4bS(E),7R,8aR]-

The title compound of this example was prepared by procedures analogous to those described above in Example 77. MS: 328 (M+1)$^+$.

Examples 693–695

The title compounds of Examples 693–695 were prepared by procedures analogous to those described above in Example 136.

Example 693

2-Phenanthrenol, 4b,5,6,8a,9,10-hexahydro-4b-[(4-hydroxyphenyl)methyl]-7-propyl-, (4bS-cis), MS: 349 (M+1)$^+$.

Example 694

2,7-Phenanthrenediol, 4a-[[4-(dimethylamino)phenyl]methyl]-1,2,3,4,4a,9, 10,10a-octahydro-2-propyl-, (4aS,10aS)-, MS: 370 (M+1)$^+$; isomer of the title product of Example 695.

Example 695

2,7-Phenanthrenediol, 4a-[[4-(dimethylamino)phenyl]methyl]-1,2,3,4,4a,9,10,10a-octahydro-2-propyl-, (4aS,10aS)-, MS: 370 (M+1)$^+$; isomer of the title product of Example 694.

Example 696

2-Phenanthrenol, 4a-[[3-(dimethylamino)phenyl]methyl]-1,2,3,4,4a,9,10,10a-octahydro-7-(2-hydroxyethoxy)-2-(1-propynyl)-,[2R-(2α,4aα,10aβ)]-; See also Example 60.

Examples 697–699

The title compounds of Examples 697–699 were prepared by procedures analogous to those described above in Example 9.

Example 697

2,7-Phenanthrenediol, 1,2,3,4,4a,9,10,10a-octahydro-1,1,4a-trimethyl-2-(1-propynyl)-, MS: 299 (M+1)$^+$.

Example 698

2,7-Phenanthrenediol, 2-(3-fluoro-3-methyl-1-butynyl)-1,2,3,4,4a,9,10,10a-octahydro-4a-(phenylmethyl)-,[2R-(2α,4aα,10aβ)]-, MS: 394 (M+1)$^+$.

Example 699

2,7-Phenanthrenediol, 2-(3-fluoro-3-methyl-1-butynyl)-1,2,3,4,4a,9,10,10a-octahydro-4a-(phenylmethyl)-,[2S-(2α,4aβ,10aα)]-, MS: 394 (M+1)$^+$.

Example 700

2-Phenanthrenol, 2-(3,3-dimethylbutyl)-1,2,3,4,4a,9,10,10a-octahydro-4a-(phenylmethyl)-7-(3-pyridinylmethoxy)-,[2R-(2α,4aα,10aβ)]-

The title compound of this example was prepared by procedures analogous to those described above in Example 76. MS: 485 (M+1)$^+$.

Example 701

2,7-Phenanthrenediol, 1,2,3,4,4a,9,10,10a-octahydro-2-(2-phenylethyl)-4a-(phenylmethyl)-, [2R-(2α,4aα,10aβ)]-

The title compound of this example was prepared by procedures analogous to those described above in Example 10. MS: 414 (M+1)$^+$

Example 702

2,7-Phenanthrenediol, 1,2,3,4,4a,9,10,10a-octahydro-2-[(methylthio)methyl]-4a-(phenylmethyl)-,[2R-(2α,4aα,10aβ)]-

The title compound of this example was prepared by procedures analogous to those described above in Example 81. MS: 370 (M+1)$^+$.

Examples 703–705

The title compounds of Examples 703–705 were prepared by procedures analogous to those described above in Example 76.

Example 703

2-Phenanthrenol, 1,2,3,4,4a,9,10,10a-octahydro-2-(2-phenylethyl)-4a-(phenylmethyl)-7-(3-pyridinylmethoxy)-,[2R-(2α,4aα,10aβ)]-, MS: 505 (M+1)$^+$.

Example 704

2-Phenanthrenol, 1,2,3,4,4a,9,10,10a-octahydro-7-[(2-methyl-5-thiazolyl)methoxy]-4a-(phenylmethyl)-2-propyl-,[2R-(2α,4aα,10aβ)]-, MS: 463 (M+1)$^+$.

Example 705

2-Phenanthrenol, 7-[[5-(1,1-dimethylethyl)-1,2,4-oxadiazol-3-yl]methoxy]-1,2,3,4,4a,9, 10,10a-octahydro4a-(phenylmethyl)-2-propyl-,[2R-(2α,4aα,10aβ)]-, MS: 490 (M+1)$^+$.

Example 706

2-Phenanthrenol, 7-[[5-(3,5-dimethyl-4-isoxazolyl)-1,2,4-oxadiazol-3-yl]methoxy]-1,2,3,4,4a,9,10,10a-octahydro-4a-(phenylmethyl)-2-propyl-,[2R-(2α,4aα,10aβ)]-

The title compound of this example was prepared by procedures analogous to those described above in Example 69. MS: 529 (M+1)$^+$.

Example 707

2-Phenanthrenol, 1,2,3,4,4a,9,10,10a-octahydro-2-(3-methoxy-1-propynyl)-4a-(phenylmethyl)-7-(2-pyridinylmethoxy)-,[2R-(2α,4aα,10aβ)]-

The title compound of this example was prepared by procedures analogous to those described above in Example 76. MS: 469 (M+1)$^+$.

Examples 708–710

The title compounds of Examples 708–710 were prepared by procedures analogous to those described above in Example 81.

Example 708

2-Phenanthrenol, 2-[(cyclopropylmethoxy)methyl]-1,2,3,4,4a,9,10,10a-octahydro-4a-(phenylmethyl)-7-(3-pyridinylmethoxy)-,[2R-(2α,4aα,10aβ)]-, MS: 485 (M+1)$^+$.

Example 709

2-Phenanthrenol, 1,2,3,4,4a,9,10,10a-octahydro-4a-(phenylmethyl)-7-(3-pyridinylmethoxy)-2-[(2,2,2-trifluoroethoxy)methyl]-,[2R-(2α,4aα,10aβ)]-, MS: 513 (M+1)$^+$.

Example 710

2-Phenanthrenol, 1,2,3,4,4a,9,10,10a-octahydro-2-[(1-methylethoxy)methyl]-4a-(phenylmethyl)-7-(2-pyridinylmethoxy)-,[2R-(2α,4aα,10aβ)]-, MS: 458 (M+1)$^+$.

Example 711

2- Phenanthrenol, 2-(azidomethyl)-1,2,3,4,4a,9,10,10a-octahydro-4a-(phenylmethyl)-7-(2-pyridinylmethoxy)-,[2R-(2α,4aα,10aβ)]-

The title compound of this example was prepared by procedures analogous to those described above in Example 82. MS: 473 (M+1)$^+$.

Examples 712–717

The title compounds of Examples 712–717 were prepared by procedures analogous to those described above in Example 81.

Example 712

2-Phenanthrenol, 1,2,3,4,4a,9,10,10a-octahydro-4a-(phenylmethyl)-7-(3-pyridinylmethoxy)-2-[(2-pyridinylmethoxy)methyl]-,[2R-(2α,4aα,10aβ)]-, MS: 522 (M+1)$^+$.

Example 713

Propanenitrile, 3-[[1,2,3,4,4a,9,10,10a-octahydro-2-hydroxy-4a-(phenylmethyl)-7-(3-pyridinylmethoxy)-2-phenanthrenyl]methoxy]-,[2R-(2α,4aα,10aβ)]-, MS: 484 (M+1)$^+$.

Example 714

2-Phenanthrenol, 2-[(cyclopentyloxy)methyl]-1,2,3,4,4a,9,10,10a-octahydro-4a-(phenylmethyl)-7-(3-pyridinylmethoxy)-,[2R-(2α,4aα,10aβ)]-, MS: 499 (M+1)$^+$.

Example 715

2-Phenanthrenol, 1,2,3,4,4a,9,10,10a-octahydro-2-[[(3-methyl-3-oxetanyl)methoxy]methyl]-4a-(phenylmethyl)-7-(3-pyridinylmethoxy)-,[2R-(2α,4aα,10aβ)]-, MS: 515 (M+1)$^+$.

Example 716

2-Phenanthrenol, 2-[(1,1-dimethylethoxy)methyl]-1,2,3,4,4a,9,10,10a-octahydro-4a-(phenylmethyl)-7-(3-pyridinylmethoxy)-,[2R-(2α,4aα,10aβ)]-, MS: 487 (M+1)$^+$.

Example 717

2-Phenanthrenol, 1,2,3,4,4a,9,10,10a-octahydro-2-(phenoxymethyl)-4a-(phenylmethyl)-7-(3-pyridinylmethoxy)-,[2R-(2α,4aα,10aβ)]-, MS: 507 (M+1)$^+$.

Example 718

1H-Benz[e]indene-2-carboxylic acid, 2,3,3a,4,5,9b-hexahydro-9b-(phenylmethyl)-7-(3-pyridinylmethoxy)-, methyl ester, [2R-(2α,3aα,9bβ)]-

The title compound of this example was prepared by procedures analogous to those described above in Example 76. MS: 429 (M+1)$^+$.

Example 719

Spiro[1,3-dioxolane-2,2'(1'H)-phenanthren]-7'-ol, 3', 4',4═a,9',10',10'a-hexahydro-4'a-(phenylmethyl)-, (4'aS-trans)-

The title compound of this example was prepared by procedures analogous to those described above in Example 7. MS: 351 (M+1)$^+$.

Example 720

2,7-Phenanthrenediol, 1,2,3,4,4a,9,10,10a-octahydro-2-(1H-imidazol-1-ylmethyl)-4a-(phenylmethyl)-,[2R-(2α,4aα,10aβ)]-

The title compound of this example was prepared by procedures analogous to those described above in Example 48. MS: 390 (M+1)$^+$.

Example 721

2,7-Phenanthrenediol, 1,2,3,4,4a,9,10,10a-octahydro-4a-(phenylmethyl)-2-(1H-1,2,4-triazol-1-ylmethyl)-,[2R-(2α,4aα,10aβ)]-; See also Example 48.

Example 722

2,7-Phenanthrenediol, 1,2,3,4,4a,9,10,10a-octahydro-4a-(phenylmethyl)-2-[2-(2-pyridinyl)ethyl]-,[2S-(2α,4aα,10aβ)]-

The title compound of this example was prepared by procedures analogous to those described above in Example 10. MS: 415 (M+1)$^+$.

Examples 723–724

The title compounds of Examples 723–724 were prepared by procedures analogous to those described above in Example 76. MS: 506 (M+1)$^+$.

Example 723

2-Phenanthrenol, 1,2,3,4,4a,9,10,10a-octahydro-4a-(phenylmethyl)-2-[2-(2-pyridinyl)ethyl]-7-(3-pyridinylmethoxy)-,[2S-(2α,4aα,10aβ)]-

Example 724

2-Phenanthrenol, 1,2,3,4,4a,9,10,10a-octahydro-2-[(methylthio)methyl]-4a-(phenylmethyl)-7-(3-pyridinylmethoxy)-,[2R-(2α,4aα,10aβ)]-, MS: 461 (M+1)$^+$.

Example 725

2-Phenanthrenol, 2-[(cyclobutyloxy)methyl]-1,2,3,4,4a,9,10,10a-octahydro-4a-(phenylmethyl)-7-(3-pyridinylmethoxy)-,[2R-(2α,4aα,10aβ)]-

To a solution of 20 mg of the title compound of Preparation 20 and 6 mg of Na in 1 mL of anhydrous DMF was added 0.019 mL of cyclobutanol at 85° C. under $N_2$ atmosphere overnight. The reaction was quenched with $NH_4Cl$ (sat.), extracted with EtOAc (X3), washed with brine, dried over $Na_2SO_4$, filtered and concentrated to dryness. Purification by preparative TLC $SiO_2$ using 8% acetone in methylene chloride as the eluant afforded 18 mg (76%) of the title product of this example as white fluffy powder. Mass: 484 (M+1)$^+$.

Examples 726–734

The title compounds of Examples 726–734 were prepared by procedures analogous to those described above in Example 725.

Example 726

2-Phenanthrenol, 2-[(2-fluoroethoxy)methyl]-1,2,3,4,4a,9,10,10a-octahydro-4a-(phenylmethyl)-7-(3-pyridinylmethoxy)-,[2R-(2α,4aα,10aβ)]-, MS: 477 (M+1)$^+$.

Example 727

2-Phenanthrenol, 1,2,3,4,4a,9,10,10a-octahydro-2-[[2-(methylthio)ethoxy]methyl]-4a-(phenylmethyl)-7-(3-pyridinylmethoxy)-,[2R-(2α,4aα,10aβ)]-, MS: 505 (M+1)$^+$.

Example 728

2-Phenanthrenol, 2-[(2,2-dimethylpropoxy)methyl]-1,2,3,4,4a,9,10,10a-octahydro-4a-(phenylmethyl)-7-(3-pyridinylmethoxy)-,[2R-(2α,4aα,10aβ)]-, MS: 501 (M+1)$^+$.

Example 729

2-Phenanthrenol, 2-[(2-ethylbutoxy)methyl]-1,2,3,4,4a,9,10,10a-octahydro-4a-(phenylmethyl)-7-(3-pyridinylmethoxy)-,[2R-(2α,4aα,10aβ)]-, MS: 515 (M+1)$^+$

Example 730

2-Phenanthrenol, 2-[(2-butynyloxy)methyl]-1,2,3,4,4a,9,10,10a-octahydro-4a-(phenylmethyl)-7-(3-pyridinylmethoxy)-,[2R-(2α,4aα,10aβ)]-, MS: 483 (M+1)$^+$.

Example 731

2-Phenanthrenol, 2-[(cyclohexylmethoxy)methyl]-1,2,3,4,4a,9,10,10a-octahydro-4a-(phenylmethyl)-7-(3-pyridinylmethoxy)-,[2R-(2α,4aα,10aβ)]-, MS: 527 (M+1)$^+$.

Example 732

2-Phenanthrenol, 2-[(cyclopentylmethoxy)methyl]-1,2,3,4,4a,9,10,10a-octahydro-4a-(phenylmethyl)-7-(3-pyridinylmethoxy)-,[2R-(2α,4aα,10aβ)]-, MS: 513 (M+1)$^+$.

Example 733

2-Phenanthrenol, 2-[(cyclobutylmethoxy)methyl]-1,2,3,4,4a,9,10,10a-octahydro-4a-(phenylmethyl)-7-(3-pyridinylmethoxy)-,[2R-(2α,4aα,10aβ)]-, MS: 499 (M+1)$^+$.

Example 734

2-Phenanthrenol, 1,2,3,4,4a,9,10,10a-octahydro-4a-(phenylmethyl)-2-[[(3-phenyl-1-propynyl)oxy]methyl]-7-(3-pyridinylmethoxy)-,[2R-(2α,4aα,10aβ)]-, MS: 545 (M+1)$^+$.

Example 735

2-Phenanthrenol, 2-(3-fluoro-3-methyl-1-butynyl)-1,2,3,4,4a,9,10,10a-octahydro-4a-(phenylmethyl)-7-(3-pyridinylmethoxy)-,[2R-(2α,4aα,10aβ)]-

The title compound of this example was prepared by procedures analogous to those described above in Example 9. MS: 485 (M+1)$^+$.

Examples 736–738

The title compounds of Examples 736–738 were prepared by procedures analogous to those described above in Example 76.

Example 736

2-Phenanthrenol, 1,2,3,4,4a,9,10,10a-octahydro-2-(1H-imidazol-1-ylmethyl)-4a-(phenylmethyl)-7-(3-pyridinylmethoxy)-,[2R-(2α,4aα,10aβ)]-, MS: 481 (M+1)$^+$.

Example 737

2-Phenanthrenol, 1,2,3,4,4a,9,10,10a-octahydro-4a-(phenylmethyl)-7-(3-pyridinylmethoxy)-2-(1H-1,2,4-triazol-1-ylmethyl)-,[2R-(2α,4aα,10aβ)]-, MS: 482 (M+1)$^+$.

Example 738

Pyridine, 3-[[[3',4',4'a,9',10',10'a-hexahydro-4'a-(phenylmethyl)spiro[1,3-dioxolane-2,2'(1'H)-phenanthren]-7'-yl]oxy]methyl]-, (4'aS-trans)-, MS: 443 (M+1)$^+$.

Example 739

2-Phenanthrenol, 2-(ethoxymethyl)-1,2,3,4,4a,9,10,10a-octahydro-4a-(phenylmethyl)-7-(2-pyridinylmethoxy)-,[2R-(2α,4aα,10aβ)]-

To a solution of 20 mg of the title compound of Example 676 and 5 mg of 60% NaH in 2 mL of anhydrous DMF was added 11 mg of 2-picolyl chloride hydrochloride at RT under N$_2$ atmosphere overnight. The reaction was quenched with NH$_4$Cl (sat.), extracted with EtOAc (X3), washed with brine, dried over Na$_2$SO$_4$, filtered and concentrated to dryness. Purification by preparative TLC (SiO$_2$) using 45% EtOAc in hexanes as the eluant afforded 24 mg (96%) of the title product of this example as white fluffy powder. Mass: 458 (M+1)$^+$.

Example 740

2-Phenanthrenol, 2-(ethoxymethyl)-1,2,3,4,4a,9,10,10a-octahydro-7-[(5-methyl-3-isoxazolyl)methoxy]-4a-(phenylmethyl)-,[2R-(2α,4aα,10aβ)]-

The title compound of this example was prepared by procedures analogous to those described above in Example 81. MS: 463 (M+1)$^+$.

Example 741

2-Phenanthrenol, 2-(ethoxymethyl)-1,2,3,4,4a,9,10,10a-octahydro-7-[2-(4-morpholinyl)ethoxy]-4a-(phenylmethyl)-,[2R-(2α,4aα,10aβ)]-

The title compound of this example was prepared by procedures analogous to those described above in Example 67. MS: 481 (M+1)$^+$.

Examples 742–744

The title compounds of Examples 742–744 were prepared by procedures analogous to those described above in Example 74.

Example 742

2-Phenanthrenol, 2-(ethoxymethyl)-1,2,3,4,4a,9,10,
10a-octahydro-4a-(phenylmethyl)-7-(pyrazinyloxy)-,
[2R-(2α,4aα,10aβ)]-, MS: 446 (M+1)+.

Example 743

2-Phenanthrenol, 7-[(2-amino-6-methyl-4-
pyrimidinyl)oxy]-1,2,3,4,4a,9,10,10a-octahydro-4a-
(phenylmethyl)-,[2R-(2α,4aα,10aβ)]-, MS: 475
(M+1)+.

Example 744

3-Pyridinecarboxamide, 6-[[7-(ethoxymethyl)-4b,5,
6,7,8,8a,9,10-octahydro-7-hydroxy-4b-
(phenylmethyl)-2-phenanthrenyl]oxy]-,[4bS-(4bα,
7α,8aβ)]-, MS: 488 (M+1)+.

Example 745

2,7-Phenanthrenediol, 1,2,3,4,4a,9,10,10a-
octahydro-2-[(methylsulfonyl)methyl]-4a-
(phenylmethyl)-,[2R-(2α,4aα,10aβ)]-

At room temperature, under nitrogen, meta-chloroperoxybenzoic acid (58 mg) was added to the title product of Example 702 (20 mg) in CH$_2$Cl$_2$ and monitored by TLC. When no starting material remained, the reaction was quenched with 10% sodium bissulfite solution and extracted with CH$_2$Cl$_2$ (3×). The organics were combined and dried with Na$_2$SO$_4$, filtered and concentrated. Purification by flash chromatography with 10% MeOH in CH$_2$Cl$_2$ yielded 15 mg of white solid. Mass: 402 (M+1)+.

Example 746

2-Phenanthrenol, 2-(cyclopropylethynyl)-1,2,3,4,4a,
9, 10,10a-octahydro-7-[(2-methyl-3-pyridinyl)
methoxy]-4a-(phenylmethyl)-,[2R-(2α,4aα,10aβ)]-

The title compound was obtained as described in Example 764 except the title compound of Example 150 was used as starting material. Mass: 478 (M+1)+.

Examples 747–748

The title compounds of Examples 747–748 were prepared by procedures analogous to those described above in Example 76.

Example 747

2-Phenanthrenol, 2-(cyclopropylethynyl)-1,2,3,4,4a,
9,10,10a-octahydro-4a-(phenylmethyl)-7-(2-
pyridinylmethoxy)-,[2R-(2α,4aα,10aβ)]-, MS: 465
(M+1)+.

Example 748

2-Phenanthrenol, 2-(2-cyclopropylethyl)-1,2,3,4,4a,
9,10,10a-octahydro-4a-(phenylmethyl)-7-(2-
pyridinylmethoxy)-,[2R-(2α,4aα,10aβ)]-, MS: 469
(M+1)+.

Example 749

2-Phenanthrenol, 2-(2-cyclopropylethyl)-1,2,3,4,4a,
9,10,10a-octahydro-7-[(2-methyl-3-pyridinyl)
methoxy]4a-(phenylmethyl)-,[2R-(2α,4aα,10aβ)]-

The title compound was obtained as described in Example 764 except the title product of Example 377 was used as starting material. MS: 482 (M+1)+.

Example 749a

2-Phenanthrenol, 1,2,3,4,4a,9,10,10a-octahydro-7-
[(2-methyl-3-pyridinyl)methoxy]-4a-
(phenylmethyl)-2-(trifluoromethyl)-,(2R,4aS,10aR)-

The title compound was obtained as described in Example 764 except the title product of Example 799 was used as starting material. MS: 482 (M+1)+.

Example 749b

2-Pyridinecarbonitrile, 3-[[[(4bS,7R,8aR)-4b,5,6,7,8,
8a,9,10-octahydro-7-hydroxy-7-methyl-4b-
(phenylmethyl)-2-phenanthrenyl]oxy]methyl]-

To a solution of 222 mg of the title compound of Example 750 and 55 mg of 60% NaH in 5 mL of anhydrous DMF was added 400 mg of 2-cyanol-3-picolyl chloride hydrochloride at RT under N$_2$ atmosphere overnight. The reaction was quenched with NH$_4$Cl (sat.), extracted with EtOAc (X3), washed with brine, dried over Na$_2$SO$_4$, filtered and concentrated to dryness. Purification by column chromatography using 35% EtOAc in hexanes as the eluant afforded 220 mg (74%) of the title product of this example as white fluffy powder. MS: 439 (M+1)+.

Example 750

2,7-Phenanthrenediol, 1,2,3,4,4a,9,10,10a-
octahydro-2-methyl-4a-(phenylmethyl)-,[2R-(2α,
4aα,10aβ)]-

The title compound of this example was prepared by procedures analogous to those described above in Example 9. MS: 323 (M+1)+.

Example 751

2-Phenanthrenol, 2-[(cyclobutyloxy)methyl]-1,2,3,4,
4a,9,10,10a-octahydro-7-[(1-oxido-3-pyridinyl)
methoxy]-4a-(phenylmethyl)-,[2R-(2α,4aα,10aβ)]-

The title compound of this example was prepared by procedures analogous to those described above in Example 76. MS: 503 (M+1)+.

Example 752

Carbamic acid, dimethyl-, 7-(ethoxymethyl)-4b,5,6,
7,8,8a,9,10-octahydro-7-hydroxy-4b-
(phenylmethyl)-2-phenanthrenyl ester, [4bS-(4bα,
7α,8aβ)]-

The title compound of this example was prepared by procedures analogous to those described above in Example 58. MS: 439 (M+1)+.

Example 753

2-Phenanthrenol, 1,2,3,4,4a,9,10,10a-octahydro-7-
(1-methylethoxy)-4a-(phenylmethyl)-2-[(2-
pyridinylmethoxy)methyl]-,[2R-(2α,4aα,10aβ)]-

The title compound of this example was prepared by procedures analogous to those described above in Example 81. MS: 473 (M+1)+.

Example 754

2-Phenanthrenol, 1,2,3,4,4a,9,10,10a-octahydro4a-
(phenylmethyl)-2-[[2-(1H-pyrazol-1-yl)ethoxy]
methyl]-7-(3-pyridinylmethoxy)-,[2R-(2α,4aα,
10aβ)]-

The title compound of this example was prepared by procedures analogous to those described above in Example 725. MS: 525 (M+1)+.

Example 755

2-Phenanthrenecarboxylic acid, 7-(cyclopropylethynyl)-4b,5,6,7,8,8a,9,10-octahydro-7-hydroxy-4b-(phenylmethyl)-, methyl ester, [4bS-(4bα,7α,8aβ)]-

The title compound of this example was prepared by procedures analogous to those described above in Example 14. MS: 416 (M+1)$^+$.

Example 756

2-Phenanthrenol, 1,2,3,4,4a,9,10,10a-octahydro-7-[(2-methyl-3-pyridinyl)methoxy]-4a-(phenylmethyl)-2-(3,3,3-trifluoropropyl)-,[2S-(2α,4aα,10aβ)]-

The title compound was obtained as described in Example 764 except the title product of Example 348 was used as starting material. MS: 510 (M+1)$^+$.

Example 757

2-Phenanthrenol, 1,2,3,4,4a,9,10,10a-octahydro-4a-(phenylmethyl)-7-(2-pyridinylmethoxy)-2-(3,3,3-trifluoropropyl)-,[2S-(2α,4aα,10a β)]-

The title compound of this example was prepared by procedures analogous to those described above in Example 76. MS: 497 (M+1)$^-$.

Example 758

2-Phenanthrenemethanol, 7-(cyclopropylethynyl)-4b,5,6,7,8,8a,9,10-octahydro-7-hydroxy-a,a-dimethyl-4b-(phenylmethyl)-,[4bS-(4bα,7α,8aβ)]-

The title compound of this example was prepared by procedures analogous to those described above in Example 19. MS: 415 (M+1)$^+$.

Examples 759–760

The title compounds of Examples 759–760 were prepared by procedures analogous to those described above in Example 725.

Example 759

2-Phenanthrenol, 2-[(cyclopropylmethoxy)methyl]-1,2,3,4,4a,9,10,10a-octahydro-7-[(2-methyl-4-thiazolyl)methoxy]-4a-(phenylmethyl)-,[2R-(2α,4aα,10aβ)]-, MS: 505 (M+1)$^+$.

Example 760

2-Phenanthrenol, 2-[(cyclopropylmethoxy)methyl]-1,2,3,4,4a,9,10,10a-octahydro-7-[(5-methyl-3-isoxazolyl)methoxy]-4a-(phenylmethyl)-,[2R-(2α,4aα,10aβ)]-, MS: 489 (M+1)$^+$.

Example 761

2-Phenanthrenol, 2-(ethoxymethyl)-1,2,3,4,4a,9,10,10a-octahydro-7-[(2-methyl-4-thiazolyl)methoxy]-4a-(phenylmethyl)-,[2R-(2α,4aα,10aβ)]-

The title compound of this example was prepared by procedures analogous to those described above in Example 81. MS: 479 (M+1)$^+$.

Example 762

2-Phenanthrenol, 2-[(cyclopropylmethoxy)methyl]-1,2,3,4,4a,9,10,10a-octahydro-4a-(phenylmethyl)-7-(2-pyridinylmethoxy)-,[2R-(2α,4aα,10aβ)]-

The title compound of this example was prepared by procedures analogous to those described above in Example 725. MS: 485 (M+1)$^+$.

Example 763

2- Phenanthrenol, 2-[(cyclopropylmethoxy)methyl]-1,2,3,4,4a,9,10,10a-octahydro-7-[(2-methyl-3-pyridinyl)methoxy]-4a-(phenylmethyl)-,[2R-(2α,4aα,10aβ)]-

The title compound was obtained as described in Example 764 except the title product of Example 675 was used as starting material. MS: 498 (M+1)$^+$

Example 764

2-Phenanthrenol, 2-(ethoxymethyl)-1,2,3,4,4a,9,10,10a-octahydro-7-[(2-methyl-3-pyridinyl)methoxy]-4a-(phenylmethyl)-,[2R-(2α,4aα,10aβ)]-

To a solution of 20 mg of the title compound of Example 676 and 3 mg of 60% NaH in 2 mL of anhydrous DMF was added 9 mg of 2-methyl-3-picolyl chloride hydrochloride at RT under N$_2$ atmosphere with stirring overnight. The reaction was quenched with NH$_4$Cl(sat.), extracted with EtOAc (X3), washed with brine, dried over Na$_2$SO$_4$, filtered and concentrated to dryness. Purification by preparative TLC (SiO$_2$) using 55% EtOAc in hexanes as the eluant afforded 21 mg (81%) of the title product of this example as white fluffy powder. MS: 472 (M+1)$^+$.

Example 765

2-Phenanthrenecarboxamide, 7-(ethoxymethyl)-4b,5,6,7,8,8a,9,10-octahydro-7-hydroxy-4b-(phenylmethyl)-N-3-pyridinyl-,[4bS-(4bα,7α,8aβ)]-

The title compound of this example was prepared by procedures analogous to those described above in Example 244. MS: 472 (M+1)$^+$.

Example 766

2-Phenanthrenol, 2-(2-cyclopropylethyl)-1,2,3,4,4a,9,10,10a-octahydro-7-[(2-methylphenyl)methoxy]-4a-(phenylmethyl)-,[2R-(2α,4aα,10aβ)]-

The title compound of this example was prepared by procedures analogous to those described above in Example 76. MS: 482 (M+1)$^+$.

Example 767

2-Phenanthrenol, 2-(2-cyclopropylethyl)-1,2,3,4,4a,9,10,10a-octahydro-7-(phenylmethoxy)-4a-(phenylmethyl)-,[2R-(2α,4aα,10aβ)]-

The title compound of this example was prepared by procedures analogous to those described above in Example 10. MS: 468 (M+1)$^+$.

Example 768

2-Phenanthrenecarbonitrile, 7-(ethoxymethyl)-4b,5,6,7,8,8a,9,10-octahydro-7-hydroxy-4b-(phenylmethyl)-,[4bS-(4bα,7α,8aβ)]-

The title compound of this example was prepared by procedures analogous to those described above in Example 81. MS: 377 (M+1)$^+$.

Examples 769–770

The title compounds of Examples 769–770 were prepared by procedures analogous to those described above in Example 725.

Example 769

2-Phenanthrenecarbonitrile, 4b,5,6,7,8,8a,9,10-octahydro-7-hydroxy-4b-(phenylmethyl)-7-[(2,2,2-trifluoroethoxy)methyl]-,[4bS-(4bα,7α,8aβ)]-, MS: 430 (M+1)$^+$.

Example 770

2-Phenanthrenecarbonitrile, 7-[(cyclopropylmethoxy)methyl]-4b,5,6,7,8,8a,9,10-octahydro-7-hydroxy-4b-(phenylmethyl)-,[4bS-(4bα,7α,8aβ)]-, MS: 403 (M+1)$^+$.

Example 771

2-Phenanthrenecarboxamide, 7-(2-pentyl)-4b,5,6,7,8,8a,9,10-octahydro-7-hydroxy-N-[(2-methyl-3-pyridinyl)methyl]-4b-(phenylmethyl)-,[4bS-(4bα,7α,8aβ)]-

To a stirring solution of 150 mg of 2-phenanthrenecarboxylic acid, 4b,5,6,7,8,8a,9,10-octahydro-7-hydroxy-4b-(phenylmethyl)-7-(pentyl)-, methyl ester, [4bS-(4bα,7α,8aβ)]- in 7 mL of dichloromethane was added 2 mL of 0.5 M 2-methyl-3-aminomethylpyridine aluminum amide solution prepared as in Example 772. The mixture was heated to reflux for 3 h. An additional 1 mL of 0.5 M 2-methyl-3-aminomethylpyridine aluminum amide solution was added and the mixture was heated to reflux for an additional 2 h. The mixture was cooled to 0° C. To the reaction mixture was added 1 N HCl dropwise until the aqueous layer was approximately pH 4. The resultant mixture was extracted with EtOAc, dried over Na$_2$SO$_4$, filtered, and concentrated to dryness. Purification by flash chromatography over SiO2 using 10% MeOH in dichloromethane as the eluant afforded 172 mg (94%) of the title product of this example as a white solid. MS: 511 (M+1)$^+$.

Example 771A-1

2 (2-Phenanthrenecarboxylic acid, 4b,5,6,7,8,8a,9,10-octahydro-7-hydroxy4b-(phenylmethyl)-7-(butyl)-, methyl ester, [4bS-(4bα,7α,8aβ)]-

The title compound of this example was prepared by procedures analogous to those described above in Example 14. MS: 421 (M+1)$^+$.

Example 771 A-2

2-Phenanthrenecarboxamide, 7-butyl-4b,5,6,7,8,8a,9,10-octahydro-7-hydroxy-N-[(2-methyl-3-pyridinyl)methyl]-4b-(phenylmethyl)-, (4bS,7R,8aR)-

To a stirring solution of 210 mg of the title compound of Example 771A-1 in 10 mL of dichloromethane was added 3 mL of 0.5 M 2-methyl-3-aminomethylpyridine aluminum amide solution prepared as in Example 772. The mixture was heated to reflux overnight. The mixture was cooled to 0° C. To the reaction mixture was added 1 N HCl dropwise until the aqueous layer was approximately pH 4. The resultant mixture was extracted with EtOAc, dried over Na$_2$SO$_4$, filtered, and concentrated to dryness. Purification by flash chromatography over SiO$_2$ using 40% acetone in hexanes to 50% acetone in hexanes as the gradient eluant afforded 163 mg (63%) of the title product of this example as a white solid. MS: 497 (M+1)$^+$.

Example 771 B

2- Phenanthrenecarboxamide, 7-(cyclopropylethynyl)-4b,5,6,7,8,8a,9,10-octahydro-7-hydroxy-N-[(2-methyl-3-pyridinyl)methyl]-4b-(phenylmethyl)-, (4bS,7R,8aR)- (Refer to Scheme C: C-5→C-8)

To a stirring solution of 200 mg of 2-phenanthrenecarboxylic acid, 4b,5,6,7,8,8a,9,10-octahydro-7-hydroxy-4b-(phenylmethyl)-7-(cyclopropylethynyl)-,methyl ester, [4bS-(4bα,7α,8aβ)]-) in 10 mL of dichloromethane was added 3 mL of 0.5 M 2-methyl-3-aminomethylpyridine aluminum amide solution prepared as in Example 772. The mixture was heated to reflux overnight The mixture was cooled to 0° C. To the reaction mixture was added 1 N HCl dropwise until the aqueous layer was approximately pH 4. The resultant mixture was extracted with EtOAc, dried over Na$_2$SO$_4$, filtered, and concentrated to dryness. Purification by flash chromatography over SiO$_2$ using 40% acetone in hexanes to 50% acetone in hexanes as the gradient eluant afforded 196 mg (81%) of the title product of this example as a white solid. MS: 505 (M+1)$^+$.

Example 771 C-1

Methanesulfonic acid, trifluoro, 4b,5,6,7,8,8a,9,10-octahydro-7-hydroxy4b-(phenylmethyl)-7-(3,3,3-trifluoropropyl)-2-phenanthrenylester, [4bS,7S,8aR]-

The title compound of this example was prepared by procedures analogous to those described above for the preparation of the title compound of Example 13. MS: 537 (M+1)$^+$;$^1$H NMR (400MHz, d$_6$-acetone) δ 7.18 (d, 1H, J=2.9) 6.83 (dd, 1H, J=2.9, 8.7), 6.43 (d, 1H, J=8.7).

Example 771 C-2

2-Phenanthrenecarboxylic acid, 4b,5,6,7,8,8a,9,10-octahydro-7-hydroxy-4b-(phenylmethyl)-7-(3,3,3-trifluoropropyl)-, methyl ester, [4bS,7S,8aR]-

The title compound of this example was prepared by procedures analogous to those described above for the preparation of the title compound of Example 14. MS: 447 ((M+1)$^+$;$^1$H NMR (400 Mhz, CDOD$_3$) δ 7.75 (d, 1H, J=1.7), 7.40 (dd, 1H, J=1.7, 8.2), 6.39 (d, 1H, J=8.2).

Example 771 C-3

2-Phenanthrenecarboxamide, 4b,5,6,7,8a,9,10-octahydro-7-hydroxy-N-[(2-methyl-3-pyridinyl) methyl]-4b-(phenylmethyl)-7-(3,3,3-trifluoropropyl)-, (4bS,7S,8aR)-

To a stirring solution of 286 mg of the title compound of Example 771 C-2 in 12 mL of dichloromethane was added 4 mL of 0.5 M 2-methyl-3-aminomethylpyridine aluminum amide solution prepared as in Example 772. The mixture was heated to reflux overnight. The mixture was cooled to 0° C. To the reaction mixture was added 1 N HCl dropwise until the aqueous layer was approximately pH 4. The resultant mixture was extracted with EtOAc, dried over Na$_2$SO$_4$, filtered, and concentrated to dryness. Purification by flash chromatography over SiO$_2$ using 40% acetone in hexanes to 50% acetone in hexanes as the gradient eluant afforded 272 mg (79%) of the title product of this example as a white solid. MS: 537 (M+1)$^+$.

Example 771 D

2-Phenanthrenecarboxamide, 4b,5,6,7,8,8a,9,10-octahydro-7-hydroxy-4b-(phenylmethyl)-7-(propoxymethyl)-N-3-pyridinyl-, (4bS,7R,8aR)-

To a stirring solution of 50 mg of 2-phenanthrenecarboxylic acid, 4b,5,6,7,8,8a,9,10-octahydro-7-hydroxy-4b-(phenylmethyl)-7-(propoxymethyl)-, methyl ester, [4bS-(4bα,7α,8aβ)]- in 5 mL of dichloromethane was added 4 mL of 0.5 M 3-aminopyridine aluminum amide solution prepared as in Example 772. The mixture was heated to reflux overnight. The mixture was cooled to 0° C. To the reaction mixture was added 1 N HCl dropwise until the aqueous layer was approximately pH 4. The resultant mixture was extracted with EtOAc, dried over Na$_2$SO$_4$, filtered, and concentrated to dryness. Purification by preparative TLC (SiO$_2$) with 3% MeOH in dichloromethane afforded 9 mg (16%) of the title product of this example as a white solid. MS: 485 (M+1)$^+$.

Example 771 E-1

(2-Phenanthrenecarboxylic acid, 4b,5,6,7,8,8a,9,10-octahydro-7-hydroxy-4b-(phenylmethyl)-7-(methyl)-, methyl ester, [4bS-(4bα,7α,8aβ)]-)

The title compound of this example was prepared by procedures analogous to those described above in Example 14. $^1$HNMR (400 MHz, CD$_3$OD) δ 7.81 (s,1H), 3.90 (s, 1H), 1.29 (s, 1H); MS: 365 (M+1)$^+$.

Example 771 E-2

2-Phenanthrenecarboxamide, 4b,5,6,7,8,8a,9,10-octahydro-7-hydroxy-7-methyl-N-[(2-methyl-3-pyridinyl)methyl]-4b-(phenylmethyl)-, (4bS,7R,8aR)-

To a stirring solution of 300 mg of the title compound of Example 771 E-1 in 16 mL of dichloromethane was added 8.2 mL of 0.5 M 2-methyl-3-aminomethylpyridine aluminum amide solution prepared as in Example 772. The mixture was heated to reflux overnight. The mixture was cooled to 0° C. To the reaction mixture was added 1 N HCl dropwise until the aqueous layer was approximately pH 4. The resultant mixture was extracted with EtOAc, dried over Na$_2$SO$_4$, filtered, and concentrated to dryness. Purification by flash chromatography over SiO$_2$ using 40% acetone in hexanes to 50% acetone in hexanes as the gradient eluant afforded 344 mg (92%) of the title product of this example as a white solid. MS: 455 (M+1)$^+$.

Example 772

2-Phenanthrenecarboxamide, 7-(ethoxymethyl)-4b,5,6,7,8,8a,9,10-octahydro-7-hydroxy-8a-methyl-N-[(2-methyl-3-pyridinyl)methyl]-4b-(phenylmethyl)-, [4bS-(4bα,7α,8aβ)]-

To a stirring solution of 31 mL of of 2.0 M trimethylaluminum in toluene and 24 mL of dichloromethane was added 8.25 g of 2-methyl-3-aminomethylpyridine in 80 mL of dichloromethane at 0° C. under N$_2$. The mixture was stirred at 0° C. for 20 min. then at RT for 1 h to give 2-methyl-3-aminomethylpyridine aluminum amide solution. A separate flask was charged with 1.68 g of 2-phenanthrenecarboxylic acid, 4b,5,6,7,8,8a,9,10-octahydro-7-hydroxy4b-(phenylmethyl)-7-(ethoxymethyl)-, methyl ester, [4bS-(4bα,7α,8aβ)]- in 80 mL of dichloromethane. To this solution was added 32 mL of 2-methyl-3-aminomethylpyridine aluminum amide solution, prepared as described above. The mixture was heated to reflux overnight. The mixture was cooled to 0° C. To the reaction mixture was added 1 N HCl dropwise until the aqueous layer was approximately pH 4. The resultant mixture was extracted with dichloromethane, dried over Na$_2$SO$_4$, filtered, and concentrated to dryness. Purification by flash chromatography over SiO$_2$ using 40% acetone in hexanes to 50% acetone in hexanes as the gradient eluant afforded 1.9 g (96%) of the title product of this example as a white solid. MS: 499 (M+1)$^+$.

Example 773

2-Phenanthrenol, 1,2,3,4,4a,9,10,10a-octahydro-2-[(1-methylethoxy)methyl]-7-[(2-methyl-3-pyridinyl)methoxy]-4a-(phenylmethyl)-,[2R-(2α,4aα,10aβ)]-

To a solution of 500 mg of the title product of Preparation 21 and 135 mg of Na in 5 mL of anhydrous DMF was added 10 ml of isopropanol at 85° C. under N$_2$ atmosphere overnight. The reaction was quenched with NH$_4$Cl (sat.), extracted with EtOAc (X3), washed with brine, dried over Na$_2$SO$_4$, filtered and concentrated to dryness. Purification by column chromatography using 1.5% methanol in methylene chloride as the eluant afforded 528 mg (93%) of the title product of this example as white fluffy powder. MS: 486 (M+1)$^+$ Example 774

2-Phenanthrenol, 1,2,3,4,4a,9,10,10a-octahydro-7-[(2-methyl-3-pyridinyl)methoxy]-4a-(phenylmethyl)-2-[(2,2,2-trifluoroethoxy)methyl]-, [2R-(2α,4aα,10aβ)]-

The title compound of this example was prepared by procedures analogous to those described above in Example 773. MS: 525.6 (M+1)$^+$.

Example 775

2(3H)-Phenanthrenone, 4a-[(4-isopropylaminophenyl)methyl]-4,4a,9,10-tetrahydro-7-hydroxy-, (S)-; MS: 362 (M+H)$^+$; see also Preparation 4.

Example 776

2,7-Phenanthrenediol, 4a-[(4-aminophenyl)methyl]-1,2,3,4,4a,9,10,10a-octahydro-2-(1-propynyl)-,[2R-(2α,4aα,10aβ)]-;

The title compound of this example was prepared by procedures analogous to those described above in Example 9. MS: 462 (M+1)$^+$.

Example 777

2-Phenanthrenol, 7-[(2-chloro-4-pyrimidinyl)oxy]-1,2,3,4,4a,9,10,10a-octahydro-4a-(phenylmethyl)-2-(1-propynyl)-,[2R-(2α,4aα,10aβ)]-

The title compound of this example was prepared by procedures analogous to those described above in Example 74. MS: 460 (M+1)$^+$.

Example 778

3H-Naphtho[2,1-b]pyran-3-one, 1,2,4a,5,6,10b-hexahydro-8-hydroxy-10b-(phenylmethyl)-

The title compound of this example was prepared by procedures analogous to those described above in Example 3. MS: 309 (M+1)$^+$.

Example 779

1H-Naphtho[2,1-b]pyran-3,8-diol, 2,3,4a,5,6,10b-hexahydro-10b-(phenylmethyl)-3-(1-propynyl)-

The title compound of this example was prepared by procedures analogous to those described above in Example 9. MS: 349 (M+1)$^+$.

Example 780

1H-Naphtho[2,1-b]pyran-8-ol, 2,3,4a,5,6,10b-hexahydro-10b-(phenylmethyl)-3-[(phenylmethyl)imino]-, (4aS,10bR)-

The title compound of this example was prepared by procedures analogous to those described above in Example 77. MS: 397 (M+1)$^+$.

Example 781

2,7-Phenanthrenediol, 1,2,3,4,4a,9,10,10a-octahydro-2-(methoxymethyl)-4a-(phenylmethyl)-, (2S,4aS,10aR)-

The title compound of this example was prepared by procedures analogous to those described above in Example 81. MS: 353 (M+1)$^+$.

Example 782

Benzonitrile, 4-[[(2R,4aS)-3,4,9,10-tetrahydro-2,7-dihydroxy-2-(1-propynyl)-4a(2H)-phenanthrenyl]methyl]-

The title compound of this example was prepared by procedures analogous to those described above in Example 5. MS: 370 (M+1)$^+$.

Example 783

2-Phenanthrenecarbonitrile, 4b-[(4-cyanophenyl)methyl]-4b,5,6,7,8,8a,9,10-octahydro-7-hydroxy-7-(1-propynyl)-, (4bS,7R,8aR)-

The title compound of this example was prepared by procedures analogous to those described above in Example 9. MS: 381 (M+1)$^+$.

Example 784

2-Phenanthrenecarboxamide, 4b,5,6,7,8,8a,9,10-octahydro-7-hydroxy-N-[(2-methyl-3-pyridinyl)methyl]-4b-(phenylmethyl)-7-(propoxymethyl)-, (4bS,7R,8aR)-

The title compound of this example was prepared by procedures analogous to those described above in Example 244. MS: 514 (M+1)$^+$.

Example 785

2-Phenanthrenol, 1,2,3,4,4a,9,10,10a-octahydro-7-[(2-methyl-3-pyridinyl)methoxy]-2-(1-pentynyl)-4a-(phenylmethyl)-, (2R,4aS,10aR)-

The title compound of this example was prepared by procedures analogous to those described above in Example 76. MS: 481 (M+1)$^+$.

Examples 786–793

The title compounds of Examples 786–793 were prepared by procedures analogous to those described above in Example 244.

Example 786

2-Phenanthrenecarboxamide, 7-(1-butynyl)-4b,5,6,7,8,8a,9,10-octahydro-7-hydroxy-N-[(2-methyl-3-pyridinyl)methyl]-4b-(phenylmethyl)-, (4bS,7R,8aR)-; MS: 494 (M+1)$^+$.

Example 787

2-Phenanthrenecarboxamide, 4b,5,6,7,8,8a,9,10-octahydro-7-hydroxy-N-[(2-methyl-3-pyridinyl)methyl]-4b-(phenylmethyl)-7-[(2,2,2trifluoroethoxy)methyl]-,(4bS,7R,8aR)-; MS: 554 (M+1)$^+$.

Example 788

2-Phenanthrenecarboxamide, 7-[(cyclopropylmethoxy)methyl]-4b,5,6,7,8,8a,9,10-octahydro-7-hydroxy-N-[(2-methyl-3-pyridinyl)methyl]-4b-(phenylmethyl)-,(4bS,7R,8aR)-; MS: 526 (M+1)$^+$.

Example 789

2-Phenanthrenecarboxamide, 7-[(cyclopropylmethoxy)methyl]-4b,5,6,7,8,8a,9,10-octahydro-7-hydroxy-4b-(phenylmethyl)-N-3-pyridinyl-, (4bS,7R,8aR)-; MS: 498 (M+1)$^+$.

Example 790

2-Phenanthrenecarboxamide, 4b,5,6,7,8,8a,9,10-octahydro-7-hydroxy-7-[(1-methylethoxy)methyl]-N-[(2-methyl-3-pyridinyl)methyl]-4b-(phenylmethyl)-,(4bS,7R,8aR)-; MS: 514 (M+1)$^+$.

Example 791

2-Phenanthrenecarboxamide, 4b,5,6,7,8,8a,9,10-octahydro-7-hydroxy-7-methyl-4b-(phenylmethyl)-N-3-pyridinyl-, (4bS,7R,8aR)- MS: 428 (M+1)$^+$.

Example 792

2-Phenanthrenecarboxamide, 4b,5,6,7,8,8a,9,10-octahydro-7-hydroxy-7-(3-methylbutyl)-N-[(2-methyl-3-pyridinyl)methyl]-4b-(phenylmethyl)-, (4bS,7R,8aR)-; MS: 512 (M+1)$^+$.

Example 793

2-Phenanthrenecarboxamide, 4b,5,6,7,8,8a,9,10-octahydro-7-hydroxy-7-(3-methyl -1-butynyl)-N-[(2-methyl-3-pyridinyl)methyl]-4b-(phenylmethyl)-, (4bS,7R,8aR)-; MS: 508 (M+1)$^+$.

Example 794

2-Phenanthrenol, 2-(1-butynyl)-1,2,3,4,4a,9,10,10a-octahydro-7-[(2-methyl -3-pyridinyl)methoxy]-4a-(phenylmethyl)-, (2R,4aS,10aR)-

The title compound of this example was prepared by procedures analogous to those described above in Example 76. MS: 467 (M+1)$^+$.

Example 795

2-Phenanthrenecarboxamide, 4b,5,6,7,8,8a,9,10-octahydro-7-hydroxy-7-[(2-methylpropoxy)methyl]-N-[(2-methyl-3-pyridinyl)methyl]-4b-(phenylmethyl)-,(4bS,7R,8aS)-

The title compound of this example was prepared by procedures analogous to those described above in Example 81. MS: 528 (M+1)$^+$.

Examples 796–798

The title compounds of Examples 796–798 were prepared by procedures analogous to those described above in Example 9.

Example 796

2,7-Phenanthrenediol, 1,2,3,4,4a,9,10,10a-octahydro-2-methyl-4a-(phenylmethyl)-,(2R,4aS,10aS)-; MS: 323 (M+1)$^+$.

Example 797

2,7-Phenanthrenediol, 1,2,3,4,4a,9,10,10a-octahydro-2-methyl-4a-(phenylmethyl)-,(2S,4aS,10aS)-; MS: 323 (M+1)$^+$.

Example 798

2,7-Phenanthrenediol, 1,2,3,4,4a,9,10,10a-octahydro-2-methyl-4a-propyl-,(2R,4aR,10aS)-; MS: 275 (M+1)$^+$.

Example 799

2,7-Phenanthrenediol, 1,2,3,4,4a,9,10,10a-octahydro-4a-(phenylmethyl)-2-(trifluoromethyl)-, (2R,4aS,10aR)-;

To a solution of 455 mg of the title product of Example 6 in 20 mL of anhydrous THF and 15 mL of 1 M trifluoromethyl trimethylsilane was added 194 mg of TBAF at 0° C. under nitrogen atmosphere for 10 min. The mixture was then stirred at RT for 3 hr. Two equivalents of TBAF were added and stirred for 1 hr at RT. The mixture was concentrated and purification by flash chromatography SiO$_2$ using 100% hexanes to 20% ethyl acetate in hexanes as the gradient eluant afforded 518 mg (93%) of the title product as white fluffy powder. MS m/z 375 (M−1)$^+$.

Example 800

2,7-Phenanthrenediol, 1,2,3,4,4a,9,10,10a-octahydro-4a-(phenylmethyl)-2-(trifluoromethyl)-, (4aS,10aS)-

The title compound of this example was prepared by procedures analogous to those described above in Example 799. MS: 377 (M+1)$^+$.

Example 801

2-Phenanthrenol, 1,2,3,4,4a,9,10,10a-octahydro-2-methyl-7-[(2-methyl-3-pyridinyl)methoxy]-4a-(phenylmethyl)-, (2R,4aS,10aS)-

The title compound of this example was prepared by procedures analogous to those described above in Example 76. MS: 429 (M+1)$^+$.

Example 802

2-Phenanthrenecarboxamide, 7-(ethoxyimino)-4b,5,6,7,8,8a,9,10-octahydro-N-[(2-methyl-3-pyridinyl)methyl]-4b-(phenylmethyl)-, (4bS,7Z,8aR)-

The title compound of this example was prepared by procedures analogous to those described above in Example 244. MS: 483 (M+1)$^+$.

Example 803A

Methanesulfonic acid, trifluoro, 4b,5,6,7,8,8a,9,10-octahydro-7-hydroxy-4b (phenylmethyl)-7-(trifluoromethyl)-2-phenathrenyl ester [(4bα,7α,8aβ)]

A solution of 50 mg of the title compound of Example 799, 55 mg of K$_2$CO$_3$, 43 mg of 4-nitrophenyltriflate in 5 mL of anhydrous DMF was stirred under N$_2$ at room temperature overnight. The reaction mixture was quenched with NaHCO$_3$ (sat.), extracted with EtOAc, dried over MgSO$_4$, filtered and concentrated to dryness. Purification by preparative TLC using 25% EtOAc in hexanes as the eluant yielded 45 mg (66%) of the title product of this example as a white solid. MS: 509 (M+1)$^+$

Example 803B

2- Phenanthrene carboxylic acid, 4b,5,6,7,8,8a,9,10-octahydro-7-hydroxy-4b(phenylmethyl)-7-(trifluoromethyl)-, methyl ester, [4bS-(4bα,7α,8aβ)]

Starting with the title product of Example 803A and utilizing procedures analogous to those described in Example 14, the title product of this example was obtained. MS: 419 ((M+1).$^+$

Example 803C

2-Phenanthrenecarboxamide, 4b,5,6,7,8,8a,9,10-octahydro-7-hydroxy-N-[(2-methyl-3-pyridinyl)methyl]-4b-(phenylmethyl)-7-(trifluoromethyl)-, (4bS, 7R, 8aR)-

To a stirring solution of 300 mg of the title compound of Example 803B in 12 mL of dichloromethane was added 4 mL of 0.5 M 2-methyl-3-aminomethylpyridine aluminum amide solution prepared as in Example 772. The mixture was heated to reflux overnight. The mixture was cooled to 0° C. To the reaction mixture was added 1 N HCl dropwise until the aqueous layer was approximately pH 4. The resultant mixture was extracted with EtOAc, dried over Na$_2$SO$_4$, filtered, and concentrated to dryness. Purification by flash chromatography over SiO$_2$ using 40% acetone in hexanes to 50% acetone in hexanes as the gradient eluant afforded 290 mg (80%) of the title product of this example as a white solid. MS: 509 (M+1)$^+$.

Example 804

2-Phenanthrenecarboxamide, 4b,5,6,7,8,8a,9,10-octahydro-7-hydroxy-7-methyl-N-[(2-methyl-3-pyridinyl)methyl]-4b-propyl-, (4bR,7R,8aS)-

The title compound of this example was prepared by procedures analogous to those described above in Example 244. MS: 408 (M+1)$^+$.

Example 805

2(3H)-Phenanthrenone, 4a-(2-butenyl)-4,4a,9,10-tetrahydro-7-methoxy-, [S-(E)]-

The title compound of this example was prepared by procedures analogous to those described above in Example 1. MS: 283 (M+1)$^+$.

Example 806

Carbamic acid, [4-[[1,3,4,9,10,10a-hexahydro-2,7-dihydroxy-2-(1-propynyl)-4a(2H)-phenanthrenyl]methyl]phenyl]-, 1,1-dimethylethyl ester, [2R-(2α, 4aα,10aβ)]-

The title compound of this example was prepared by procedures analogous to those described above in Example 9. MS: 463 (M+1)$^+$ The compounds of this invention either alone or in combination with each other or other compounds generally will be administered in a convenient formulation.

The following formulation examples only are illustrative and are not intended to limit the scope of the present invention.

In the formulations which follow, "active ingredient" means a compound of this invention.

Formulation 1: Gelatin Capsules

Hard gelatin capsules are prepared using the following:

| Ingredient | Quantity (mg/capsule) |
| --- | --- |
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:
Formulation 2: Tablets

| Ingredient | Quantity (mg/tablet) |
| --- | --- |
| Active ingredient | 0.25–100 |
| Cellulose, microcrystalline | 200–650 |
| Silicon dioxide, fumed | 10–650 |
| Stearic acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
| --- | --- |
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
| --- | --- |
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container. Suppositories are prepared as follows:

Formulation 6: Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimum necessary heat. The mixture is then poured into a suppository mold of nominal 2 g capacity and allowed to cool.

An intravenous formulation is prepared as follows:

Formulation 7: Intravenous Solution

| Ingredient | Quantity |
| --- | --- |
| Active ingredient | 20 mg |
| Isotonic saline | 1,000 mL |

The solution of the above ingredients is intravenously administered to a patient at a rate of about 1 mL per minute.

The active ingredient in any of the formulations above may also be a combination of agents.

What is claimed is:
1. A compound of formula I

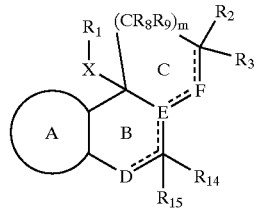

an isomer thereof, a prodrug of said compound or isomer, or a pharmaceutically acceptable salt of said compound, isomer or prodrug;
wherein m is 1 or 2;
— represents an optional bond;
A is

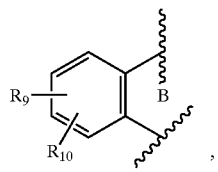

D is $CR_7$, or $CR_7R_{16}$,
E is C, or $CR_6$;
F is $CR_4$, or $CR_4R_5$;

G, H and I together with 2 carbon atoms from the A-ring or 2 carbon atoms from the B-ring form a 5-membered heterocyclic ring comprising one or more N, O or S atoms; provided that there is at most one of O and S per ring;

J, K, L and M together with 2 carbon atoms from the B-ring forms a 6-membered heterocyclic ring comprising 1 or more N atoms;

X is a) absent, b) —$CH_2$—, c) —CH(OH)— or d) —C(O)—;

$R_1$ is a) —H, b) —Z—$CF_3$, c) —($C_1$–$C_6$)alkyl, d) —($C_2$–$C_6$)alkenyl, e) —($C_2$–$C_6$)alkynyl, f) —CHO, g) —CH=N—$OR_{12}$, h) —Z—C(O)$OR_{12}$, i) —Z—C(O)—$NR_{12}R_{13}$, j) —Z—C(O)—$R_{12}$—Z-het, k) —Z—$NR_{12}R_{13}$, l) —Z—$NR_{12}$het, m) —Z-het, n) —Z—O-het, o) —Z-aryl', p) —Z—O-aryl', q) —CHOH-aryl' or r) —C(O)-aryl' wherein aryl' in substituents o) to r) is substituted independently with 0, 1 or 2 of the following: —Z—OH, —Z—$NR_{12}R_{13}$, —Z—$NR_{12}$-het, —C(O)$NR_{12}R_{13}$, —C(O)O($C_1$–$C_6$) alkyl, —C(O)OH, —C(O)-het, —$NR_{12}$—C(O)—($C_1$–$C_6$)alkyl, —$NR_{12}$—C(O)—($C_2$–$C_6$)alkenyl, —$NR_{12}$—C(O)—($C_2$–$C_6$)alkynyl, —$NR_{12}$—C(O)—Z-het, —CN, —Z-het, —O—($C_1$–$C_3$)alkyl- C(O)—$NR_{12}R_{13}$, —$NR_{12}$—Z—C(O)—$NR_{12}R_{13}$, —Z—N $R_{12}$—$SO_2$—$R_{13}$, —$NR_{12}$—$SO_2$-het, —C(O)H, —Z—N 12—Z—C($C_1$–$C_6$)alkyl, —Z—N $R_{12}$—Z—N $R_{12}R_{13}$, —Z—$NR_{12}$—($C_3$–$C_6$)cycloalkyl, —Z—N (Z—O($C_1$–$C_6$)alkyl)$_2$, —$O_2R_{12}$, —$SOR_{12}$, —$SR_{12}$, —$SO_2N$ $R_{12}R_{13}$, —O—C(O)—($C_1$–$C_4$)alkyl, —O—$SO_2$—($C_1$–$C_4$)alkyl, -halo or —$CF_3$;

Z for each occurrence is independently a) —($C_1$–$C_6$) alkyl, b) —($C_2C_6$)alkenyl or c) —($C_2$–$C_6$)alkynyl;

$R_2$ is —OH;

$R_3$ is a) —H, b) —($C_1$–$C_{10}$)alkyl wherein 1 or 2 carbon atoms, other than the connecting carbon atom, may optionally be replaced with 1 or 2 heteroatoms independently selected from S, O and N and wherein each carbon atom is substituted with 0, 1 or 2 $R_y$, c) —($C_2$–$C_{10}$)alkenyl substituted with 0, 1 or 2 $R_y$, d) —($C_2$–$C_{10}$)alkynyl wherein 1 carbon atom, other than the connecting carbon atom, may optionally be replaced with 1 oxygen atom and wherein each carbon atom is substituted with 0, 1 or 2 $R_y$, e) —CH=C=$C_2$, f) —CN, g) —($C_3$–$C_6$)cycloalkyl, h) —Z-aryl, i) —Z-het, j) —C(O)O($C_1C_6$)alkyl, k) —O($C_1$–$C_6$)alkyl, l) —Z—S—$R_{12}$, m) —Z—S(O)—$R_{12}$, n) —Z—S(O)$_2$—$R_{12}$, o) —$CF_3$ p) —$NR_{12}$O—($C_1$–$C_6$) alkyl or q) —$CH_2OR_y$;

provided that one of $R_2$ and $R_3$ is absent when there is a double bond between $CR_2R_3$ (the 7 position) and the F moiety (the 8 position) of the C-ring;

$R_y$ for each occurrence is independently a) —OH, b) -halo, c) —Z—$CF_3$, d) —Z—CF($C_1$–$C_3$ alkyl)$_2$, e) —CN, f) —$NR_{12}R_{13}$, g) —($C_{3-C6}$)cycloalkyl, h) —($C_3$–$C_6$)cycloalkenyl, i) —($C_0$–$C_3$)alkyl-aryl, j) -het or k) —$N_3$;

$R_4$ and $R_5$ for each occurrence are independently a) —H, b) —CN, —($C_1$–$C_6$)alkyl substituted with 0 to 3 halo, d) —($C_2$–$C_6$)alkenyl substituted with 0 to 3 halo, e) —($C_2$–$C_6$)alkynyl substituted with 0 to 3 halo, f) —O—($C_1$–$C_6$)alkyl substituted with 0 to 3 halo, g) —O—($C_2$–$C_6$)alkenyl substituted with 0 to 3 halo, h) —O—($C_2$–$C_6$)alkynyl substituted with 0 to 3 halo, i) halo, j) —OH, k) ($C_3$–$C_6$)cycloalkyl or l) ($C_3$–$C_6$) cycloalkenyl;

or $R_4$ and $R_5$ are taken together to form =O;

$R_6$ is a) —H, b) —CN, c) —($C_1$–$C_6$)alkyl substituted with 0 to 3 halo, d) —($C_2$–$C_6$)alkenyl substituted with 0 to 3 halo, e) —($C_{2-06}$)alkynyl substituted with 0 to 3 hal or f) —OH;

$R_7$ and $R_{16}$ for each occurrence are independently a) —H, b) -halo, c) —CN, d) —($C_1$–$C_6$)alkyl substituted with 0 to 3 halo, e) —($C_2$–$C_6$)alkenyl substituted with 0 to 3 halo or f) —($C_2$–$C_6$)alkynyl substituted with 0 to 3 halo; provided that $R_7$ is other than —CN or -halo when D is $NR_7$;

or $R_7$ and $R_{16}$ are taken together to form =O;

$R_8$, $R_9$, $R_{14}$ and $R_{15}$ for each occurrence are independently a) —H b) -halo, c) ($C_1$–$C_6$)alkyl substituted with 0 to 3 halo, d) —($C_2$–$C_6$)alkenyl substituted with 0 to 3 halo, e) —($C_2$–$C_6$)alkynyl substituted with 0 to 3 halo, f) —CN, g) —($C_3$–$C_6$)cycloalkyl, h) —($C_3$–$C_6$) cycloalkenyl, i) —OH, j) —O—($C_1$–$C_6$)alkyl, k) —O—($C_1$–$C_6$)alkenyl, l) —O—($C_1$–$C_6$)alkynyl, m) —$NR_{12}R_{13}$, n) —C(O)$OR_{12}$ or o) —C(O)$NR_{12}R_{13}$;

or $R_8$ and $R_9$ are taken together on the C-ring to form =O; provided that when m is 2, only one set of $R_8$ and $R_9$ are taken together to form =O;

or $R_{14}$ and $R_{15}$ are taken together to form =O; provided that when $R_{14}$ and $R_{15}$ are taken together to form =O, D is other than $CR_7$ and E is other than C;

$R_{10}$ is a) —($C_1$–$C_{10}$)alkyl substituted with 0 to 3 substituents independently selected from -halo, —OH and —$N_3$, b) —($C_2$–$C_{10}$)alkenyl substituted with 0 to 3 substituents independently selected from -halo, —OH and —$N_3$, c) —($C_2$–$C_{10}$)alkynyl substituted with 0 to 3 substituents independently selected from -halo, —OH and —$N_3$, d) -halo, e) —Z—CN, f) —OH, g) —Z-het, h) —Z—NR$_{12}$R$_{13}$, i) —Z—C(O)-het, j) —Z—C(O)—(C$_1$–C$_6$)alkyl, k) —Z—C(O)—R$_{12}$R$_{13}$, l) —Z—C(O)—NR$_{12}$—Z—CN, m) —Z—C(O)—NR$_{12}$—Z-het, n) —Z—C(O)—NR$_{12}$—Z-aryl, o) —Z—C(O)—NR$_{12}$—Z—NR$_{12}$R$_{13}$, p) —Z—C(O)—NR$_{12}$—Z—O(C$_1$–C$_6$)alkyl, q) —(C$_0$–C$_6$)alkyl- O(O)OH, r) —Z—C(O)O(C$_1$–C$_6$)alkyl, s) —Z—O—(C$_0$–C$_6$)alkyl-het, t) —Z—O—(C$_0$C$_6$)alkyl-aryl, u) —Z—O—(C$_1$–C$_6$) alkyl substituted with 0 to 2 R$_x$, v) —Z—O—(C$_1$–C$_6$) alkyl- OH(O), w) —Z—O—(C$_1$–C$_6$)alkyl- NR$_{12}$-het, x) —Z—O—Z-het-Z-het, y) —Z—O—Z-het-Z—NR$_{12}$R$_{13}$, z) —Z—O—Z-het-O(O)-het, a1) Z—O—Z—C(O)-het, b1) —Z—O—Z—C(O)-het-het, c1) —Z—O—Z—C(O)—(C$_1$–C$_6$)alkyl, d1) —Z—O—Z—O(S)—NR 2R$_{13}$, e1) —Z—O—Z—C(O)—NR$_{12}$R$_{13}$, f1) —Z—O—Z-(C$_1$–C$_3$)alkyl-O(O)—NR$_{12}$R$_{13}$, g 1) —Z—O—Z—CO(O)—O(C$_1$–C$_6$)alkyl, h1) —Z—O—Z—C(O)—OH, ii) —Z—O—Z—C(O)—NR$_{12}$—O(C$_1$–C$_6$)alkyl, j1) —Z—O—Z—C(O)—NR$_{12}$—OH, k1) —Z—O—Z—C(O)—NR$_{12}$—Z—NR$_{12}$R$_{13}$, 11) —Z—O—Z—C(O)—NR$_{12}$—Z-het, m1) —Z—O—Z—C(O)—NR$_{12}$—SO$_2$—(C$_1$–C$_6$) alkyl, n1) —Z—O—Z—C(=N R$_{12}$)(NR$_{12}$R$_{13}$), o1) —Z—O—Z—C(=NOR$_{12}$)(NR$_{12}$R$_{13}$), p1) —Z—NR$_{12}$—C(O)—O—Z—NR$_{12}$R$_{13}$, q1) —Z—S—C(O)—NR$_{12}$R$_{13}$, r1) —Z—O—SO$_2$—(C$_1$–C$_6$)alkyl, s1) —Z—O—SO$_2$-aryl, t1) —Z—O—SO$_2$—NR$_{12}$R$_{13}$, u1) —Z—SO$_2$—CF$_3$, v1) —Z—NR$_{12}$C(O)OR$_{13}$ or w1) —Z—NR$_{12}$C(O)R$_{13}$;

or R$_9$ and R$_{10}$ are taken together on the moiety of formula A-5 to form a)=O or b)=NOR$_{12}$, R$_{11}$ is a) —H, b) —(C$_1$–C$_5$)alkyl, c) —(C$_3$–C$_6$)cycloalkyl or d) —(C$_0$–C$_3$)alkyl-aryl;

R$_{12}$ and R$_{13}$ for each occurrence are each independently a) —H, b) —(C$_1$–C$_6$)alkyl wherein 1 or 2 carbon atoms, other than the connecting carbon atom, may optionally be replaced with 1 or 2 heteroatoms independently selected from S, O and N and wherein each carbon atom is substituted with 0 to 6 halo, c) —(C$_2$–C$_6$)alkenyl substitute with 0 to 6 halo or d) —(C$_1$–C$_6$)alkynyl wherein 1 carbon atom, other than the connecting carbon atom, may optionally be replaced with 1 oxygen atom and wherein each carbon atom is substituted with 0 to 6 halo;

or R$_{12}$ and R$_{13}$ are taken together with N to form het;

or R$_6$ and R$_{14}$ or R$_{15}$ are taken together to form 1,3-dioxolanyl;

aryl is a) phenyl substituted with 0 to 3 R$_x$, b) naphthyl substitute with 0 to 3 R$_x$ or c) biphenyl substituted with 0 to 3 R$_x$;

het is a 5-,6- or 7-membered saturated, partially saturated or unsaturated ring containing from one (1) to three (3) heteroatoms independently selected from the group consisting of nitrogen, oxygen and sulfur; and including any bicyclic group in which any of the above heterocyclic rings is fused to a benzene ring or another heterocycle; and the nitrogen may be in the oxidized state giving the N-oxide form; and substituted with 0 to 3 R$_x$;

R$_x$ for each occurrence is independently a) -halo, b) —OH, c) —(C$_1$–C$_6$)alkyl, d) —(C$_2$–C$_6$)alkenyl, e) —(C$_2$–C$_6$)alkynyl, f) —O(C$_1$–C$_6$)alkyl, g) —O(C$_2$–C$_6$)alkenyl h) —O(C$_2$–C$_6$)alkynyl, i) —(C$_0$–C$_6$)alkyl-NR$_{12}$R$_{13}$, j) —C(O)—NR$_{12}$R$_{13}$, k) —Z—SO$_2$R$_{12}$, l)—Z—SO$_2$R$_{12}$, m) Z—SR$_{12}$, n) —NR$_{12}$—SO$_2$R$_{13}$, o) —NR$_{12}$—C(O)—R$_{13}$, p) —NR$_{12}$—OR$_{13}$, q) —SO$_2$—NR$_{12}$R$_{13}$, r) —CN, s) —CF$_3$, t) —C(O)(C$_1$–C$_6$)alkyl, u) =O, v) —Z—SO$_2$-phenyl or w) —Z—SO$_2$-het';

aryl' is phenyl, naphthyl or biphenyl;

het' is a 5-, 6- or 7-membered saturated, partially saturated or unsaturated ring containing from one (1) to three (3) heteroatoms independently selected from the group consisting of nitrogen, oxygen and sulfur; and including any bicyclic group in which any of the above heterocyclic rings is fused to a benzene ring or another heterocycle;

provided that:

1) X—R$_1$ is other than hydrogen or methyl;
2) when R$_9$ and R$_{10}$ are substituents on the A-ring, they are other than mono- or di-methoxy;
5) when X—R$_1$ is (C$_1$–C$_4$)alkyl, (C$_2$–C$_4$)alkenyl or (C$_2$–C$_4$)alkynyl, R$_9$ and R$_{10}$ are other than mono-hydroxy or =O, including the diol form thereof, when taken together; and
6) when X is absent, R$_1$ is other than a moiety containing a heteroatom independently selected from N, O or S directly attached to the juncture of the B-ring and the C-ring.

2. A compound of claim 1, an isomer thereof, a prodrug of said compound or isomer, or a pharmaceutically acceptable salt of said compound, isomer or prodrug; wherein D is CH$_2$; E is CH; F is CH$_2$; R$_8$ is —H; R$_9$ is —H; m is 2; R$_{14}$ is —H; R$_{15}$ is —H; and the A-ring is the moiety of formula A-1a.

3. A compound of claim 2 of formula II

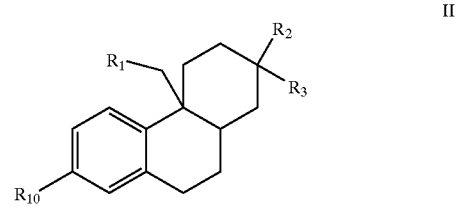

II an isomer thereof, a prodrug of said compound or isomer, or a pharmaceutically acceptable salt of said compound, isomer or prodrug;

wherein R$_2$ is a) —OH;

R$_3$ is a) —(C$_1$–C$_6$)alkyl substituted with 0 or 1 of the following: —CF —CN, —(C$_3$–C$_6$)cycloalkyl, -phenyl or —N$_3$, b) —C≡C— substituted with 1 of the following: —(C$_1$–C$_5$)alkyl, —Cl, —CF$_3$—(C$_3$–C$_6$) cycloalkyl, -phenyl or -benzyl; c) —CH$_2$OH, d) —CH$_2$O(C$_1$–C$_5$)alkyl wherein 1 carbon atom may optionally be replaced with 1 oxygen atom, e) —CH$_2$O (C$_2$–C$_5$)alkenyl, f) —CH$_2$O(C$_2$–C$_5$)alkynyl wherein 1 carbon atom may optionally be replace with 1 oxygen atom, g) —CH$_2$OR$_y$, h) —CN or i) —CF$_3$;

R$_y$ is a) —(C$_1$–C$_3$)alkyl-CF$_3$, b) —(C$_3$–C$_6$)cycloalkyl, c) -phenyl or d) -benzyl;

or R$_2$ and R$_3$ are taken together to form a) -1,3-dioxolan-4-yl or b) =NOR$_{11}$;

R$_{11}$ is a) —H, b) —(C$_1$–C$_5$)alkyl, c) —(C$_3$–C$_6$) cycloalkyl, d) -phenyl or e) -benzyl.

4. A compound of claim 3 of formula II

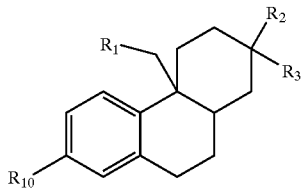
II an isomer thereof, a prodrug of said compound or isomer, or a pharmaceutically acceptable salt of said compound, isomer or prodrug;

wherein $R_1$ is a) —$(C_1-C_4)$alkyl, b) —$(C_2-C_4)$alkenyl, c) -phenyl substituted with zero or one of the following: —OH, —$NR_{12}R_{13}$, —$NR_{12}$—C(O)—$(C_1-C_4)$alkyl, —CN, —Z-het, —O—$(C_1-C_3)$alkyl-C(O)—$NR_{12}R_{13}$, —$NR_{12}$—Z—C(O)—$NR_{12}R_{13}$, —Z—$NR_{12}$—$SO_2$—$R_{13}$, $NR_{12}$—$SO_2$-het, —O—C(O)—$(C_1-C_4)$alkyl or —O—$SO_2$—$(C_1-C_4)$alkyl; d) —O-phenyl substituted with 0 or 1 of the following: —Z—$NR_{12}R_{13}$ or —C(O)$NR_{12}R_{13}$, or e) —OH=CH-phenyl wherein phenyl is substituted with 0 or 1 of the following: —Z—$NR_{12}R_{13}$ or —C(O)$NR_{12}R_{13}$;

Z for each occurrence is independently —$(C_0-C_2)$alkyl;

$R_{10}$ is a) —OH(OH)$(C_1-C_5)$alkyl, b) —CN, c) —OH, d) -het, e) —C(O)—$(C_1-C_4)$alkyl, f) —C(O)—$NR_{12}R_{13}$, g) —C(O)—NH—Z-het, h) —O—$(C_0-C_2)$alkyl-het, i) —O—Z—C(O)—$R_{12}R_{13}$, j) —O—Z—C(O)—NH—$(C_0-C_3)$alkyl-het or k) —O—Z—C(O)—NH—$(C_0-C_3)$alkyl-N $R_{12}R_{13}$;

$R_{12}$ and $R_{13}$ are independently a) —H or b) —$(C_1-C_4)$alkyl;

or $R_{12}$ and $R_{13}$ are taken together with N to form het.

5. A compound of claim 4 of formula II

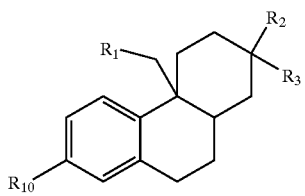
II an isomer thereof, a prodrug of said compound or isomer, or a pharmaceutically acceptable salt of said compound, isomer or prodrug;

wherein $R_1$ is a) —$(C_2-C_4)$alkyl, b) —$CH_2$—OH=$CH_2$ or c) -phenyl;

$R_2$ is —OH;

$R_3$ is a) —$(C_1-C_6)$alkyl substituted with 0 or 1 $CF_3$, b) —C≡C—$CH_3$, c) —C≡C—Cl, d) —C≡C—$CF_3$, e) —$CH_2O(C_1-C_3)$alkyl substituted with 0 or 1 $CF_3$, or f) —$CF_3$;

$R_{10}$ is —OH.

6. A compound of claim 5 of formula III

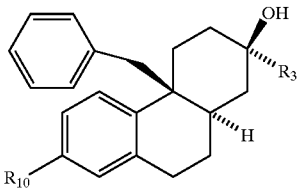
III a prodrug thereof, or a pharmaceutically acceptable salt of said compound or prodrug; wherein $R_3$ and $R_{10}$ are as defined in claim 5.

7. A compound of claim 6 selected from the group consisting of:

2,7-phenanthrenediol ,2-(chloroethynyl)-1,2,3,4,4a,9,10, 10a-octahydro-4a-(phenylmethyl)-, [2R-(2α,4aα, 10aβ)]-;

2,7-phenanthrenediol,1,2,3,4,4a,9,10,10a-octahydro-4a-(phenylmethyl)-2-propyl-[2R-(2α,4aα,10aβ)]-;

2,7-phenanthrenediol,1,2,3,4,4a,9,10,10a-octahydro-4a-(phenylmethyl)-2-(1-propynyl)-, [2R-(2α,4aα,10aβ)]-;

2,7-phenanthrenediol,1,2,3,4,4a ,9,10,10a-octahydro-4a-(phenylmethyl)-2-(3,3,3-trifluoro-1-propynyl)-, [2R-(2α,4aα,10aβ)]-;

2,7-phenanthrenediol, 1,2,3,4,4a ,9,10,10a-octahydro-4a-(phenylmethyl)-2-(3,3,3-trifluoropropyl)-,[2S-(2α,4aα,10aβ)]-;

2,7-phenanthrenediol, 1,2,3,4,4a,9,10,10a-octahydro-2-methyl-4a-(phenylmethyl)-,[2R-(2□,4a□,10a□)]-; and 2,7-phenanthrenediol,1,2,3,4,4a,9,10,10a-octahydro-4a-(phenylmethyl)-2-(trifluoromethyl)-, (2R,4aS,10aR)-;

a prodrug thereof, or a pharmaceutically acceptable salt of said compound or prodrug.

8. A compound of claim 4 of formula II

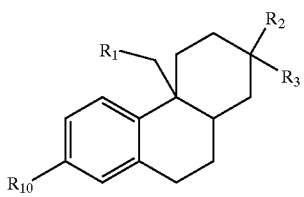
II an isomer thereof, a prodrug of said compound or isomer, or a pharmaceutically acceptable salt of said compound, isomer or prodrug;

wherein $R_1$ is a) —$(C_2-C_4)$alkyl, b) —$CH_2$—CH=$CH_2$ or c) -phenyl;

$R_2$ is —OH;

$R_3$ is a) —$(C_1-C_5)$alkyl substituted with 0 or 1 $CF_3$, b) —C≡C—$CH_3$, c) —C≡C—Cl, d) —C≡C—$CF_3$, e) —$CH_2O(C_1-C_3)$alkyl substituted with 0 or 1 $CF_3$, or f) —$CF_3$; $R_{10}$ is —CN.

9. A compound of claim 8 of formula III

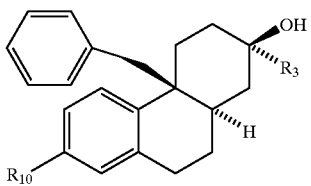

a prodrug thereof, or a pharmaceutically acceptable salt of said compound or prodrug; wherein $R_3$ and $R_{10}$ are as defined in claim 8.

10. A compound of claim 9 selected from the group consisting of:

2-phenanthrenecarbonitrile, 4b,5,6,7,8,8a,9,10-octahydro-7-hydroxy-4b-(phenylmethyl)-7-(1-propynyl)-, [4bS-(4bα,7α,8aβ)]; and 2-phenanthrenecarbonitrile, 4b,5,6,7,8,8a,9,10-octahydro-7-hydroxy-4b-(phenylmethyl)-7-propyl-, [4bS-(4bα,7α,8aβ)]-;

or a prodrug thereof, or a pharmaceutically acceptable salt of said compound or prodrug.

11. The compound of claim 9 wherein $R_3$ is —C≡C—$CH_3$ and $R_{10}$ is —CN; or a pharmaceutically acceptable salt thereof.

12. The compound of claim 9 wherein $R_3$ is —$(CH_2)_2$—$CH_3$ and $R_{10}$ is —CN; or a pharmaceutically acceptable salt thereof.

13. The compound of claim 9 wherein $R_3$ is —$CF_3$ an $R_{10}$ is —CN; or a pharmaceutically acceptable salt thereof.

14. The compound of claim 9 wherein $R_3$ is —$CH_2CH_2CF_3$ and $R_{10}$ is —CN; or a pharmaceutically acceptable salt thereof.

15. The compound of claim 4 of formula II

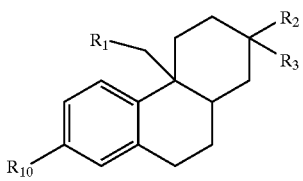

an isomer thereof, a prodrug of said compound or isomer, or a pharmaceutically acceptable salt of said compound, isomer or prodrug;

wherein $R_1$ is a) —$(C_2-C_4)$alkyl, b) —$CH_2$—CH=$CH_2$ or c) -phenyl;

$R_2$ is —OH;

$R_3$ is a) —$(C_1-C_6)$alkyl substituted with 0 or 1 $CF_3$, b) —C≡C—$CH_3$, c) —C≡C—Cl, d) —C≡C—$CF_3$, e) —$CH_2O(C_1-C_3)$alkyl substituted with 0 or 1 $CF_3$, or f) —$CF_3$;

$R_{10}$ is —C(O)—NH—Z-het wherein het is selected from the group consisting of a) pyridinyl substituted with 0 or 1 methyl, b) pyrimidinyl, c) pyrazinyl, d) morpholinyl and e) oxadiazolyl;

Z is —$(C_0-C_2)$ alkyl.

16. A compound of claim 15 of formula III

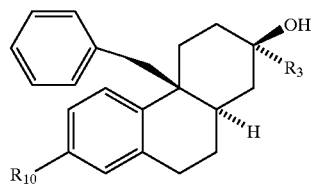

a prodrug thereof, or a pharmaceutically acceptable salt of said compound or prodrug;

wherein $R_3$ is a) —$(CH_2)_2$—$CF_3$, b) —$(CH_2)_2$—$CH_3$, c) —$CH_3$, d) —C≡C—$CH_3$, e) —C≡C—Cl or f) —$CF_3$;

$R_{10}$ is as defined in claim 15.

17. A compound of claim 4 of formula II

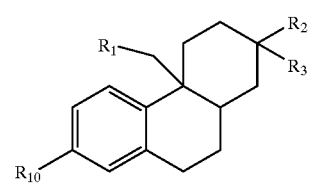

an isomer thereof, a prodrug of said compound or isomer, or a pharmaceutically acceptable salt of said compound, isomer or prodrug;

wherein $R_1$ is a) —$(C_2-C_4)$alkyl, b) —$CH_2$—CH=$CH_2$ or c) -phenyl;

$R_2$ is —OH;

$R_3$ is a) —$(C_1-C_4)$alkyl substituted with 0 or 1 $CF_3$, b) —C≡C—$CH_3$, c) —C≡C—Cl, d) —C≡C—$CF_3$, e) —$CH_2O(C_1-C_3)$alkyl substituted with 0 or 1 $CF_3$, or f) —$CF_3$;

$R_{10}$ is —O—$(C_1-C_2)$alkyl-het wherein het is selected from the group consisting of a) pyridinyl substituted with 0 or 1 methyl, b) pyrimidinyl, c) pyrazinyl, d) morpholinyl and f) oxadiazolyl.

18. A compound of claim 17 of formula III

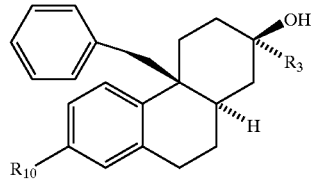

a prodrug thereof, or a pharmaceutically acceptable salt of said compound or prodrug;

wherein $R_3$ is a) —$(CH_2)_2$—$CF_3$, b) —$(CH_2)_2$—$CH_3$, c) —$CH_3$, d) —C≡C—$CH_3$, e) —C≡C—Cl or f) —$CF_3$;

$R_{10}$ is —O—$(C_1-C_2)$alkyl-het wherein het is selected from the group consisting of a) 2-pyridinyl, b) 3-pyridinyl, c) 4-pyridinyl, d) 2-methyl-3-pyridinyl and e) pyrazinyl.

19. A compound of claim 18 selected from the group consisting of:

2-phenanthrenol, 1,2,3,4,4a,9,10,10a-octahydro-4a-(phenylmethyl)-2-(1-propynyl)-7-(3-pyridinylmethoxy)-, [2R-(2α,4aα, 10aβ)]-;

2-phenanthrenol, 1,2,3,4,4a,9,10,10a-octahydro-4a-(phenylmethyl)-2-(1-propynyl)-7-(4-pyridinylmethoxy)-, [2R-(2a,4aα,10aβ)];

2-phenanthrenol, 1,2,3,4,4a,9,10,10a-octahydro-4a-(phenylmethyl)-2-(1-propynyl)-7-(2-pyridinylmethoxy)-, [2R-(2α,4aα,10aβ)];

2-phenanthrenol, 1,2,3,4,4a,9,10,10a-octahydro-7-[(2-methyl-3-pyridinyl)methoxy]-4a-(phenylmethyl)-2-(1-propynyl)-, [2R-(2α,4aα,10β)]-;

2-phenanthrenol, 1,2,3,4,4a,9,10,10a-octahydro-7-[(2-methyl-3-pyridinyl)methoxy]-4a-(phenylmethyl)-2-propyl-, [2R-(2α,4aα,10aβ)];

2-phenanthrenol, 1,2,3,4,4a,9,10,10a-octahydro-4a-(phenylmethyl)-2-propyl-7-(2-pyridinylmethoxy)-, [2R-(2α,4aα,10a β)];

2-phenanthrenol, 1,2,3,4,4a,9,10,10a-octahydro-4a-(phenylmethyl)-2-propyl-7-(3-pyridinylmethoxy)-, [2R-(2α,4aα,10aβ)];

2-phenanthrenol, 1,2,3,4,4a,9,10,10a-octahydro-7-[(2-methyl-4-pyridinyl)methoxy]-4a-(phenylmethyl)-2-propyl-, [2R-(2α,4aα,10aβ)]-;

2-phenanthrenol, 1,2,3,4,4a,9,10,10a-octahydro-4a-(phenylmethyl)-2-propyl-7-(pyrazinylmethoxy)-, [2R-(2α,4aα,10aβ)]-;

2-phenanthrenol, 1,2,3,4,4a,9,10,10a-octahydro-4a-(phenylmethyl)-7-(3-pyridinylmethoxy)-2-(3,3,3-trifluoropropyl)-, [2S-(2α,4aα, 1aβ)]-;

2-phenanthrenol, 1,2,3,4,4a,9,10,10a-octahydro-7-[(2-methyl-3-pyridinyl)methoxy]-4a-(phenylmethyl)-2-(3,3,3-trifluoropropyl)-, [2S-(2α,4aα,10aβ)]-;

2-phenanthrenol, 1,2,3,4,4a,9,10,10a-octahydro-4a-(phenylmethyl)-7-(2-pyridinylmethoxy)-2-(3,3,3-trifluoropropyl)-, [2S-(2□,4a □, 10a□)]-; and 2-phenanthrenol, 1,2,3,4,4a,9,10,10a-octahydro-7-[(2-methyl-3-pyridinyl)methoxy]-4a-(phenylmethyl)-2-(trifluoromethyl)-, (2R,4aS,10 R)-;

or a prodrug thereof, or a pharmaceutically acceptable salt of said compound or prodrug.

20. A compound of claim 19 selected from the group consisting of:

2-phenanthrenol, 1,2,3,4,4a,9,10,10a-octahydro-4a-(phenylmethyl)-2-(1-propynyl)-7-(4-pyridinylmethoxy)-, [2R-(2α,4aα,10aβ)];

2-phenanthrenol, 1,2,3,4,4a,9,10,10a-octahydro-4a-(phenylmethyl)-2-(1-propynyl)-7-(2-pyridinylmethoxy)-, [2R-(2α,4aα,10aβ)];

2-phenanthrenol, 1,2,3,4,4a,9,10,10a-octahydro-4a-(phenylmethyl)-7-(3-pyridinylmethoxy)-2-(3,3,3-trifluoropropyl)-, [2S-(2α,4aα,10β)]-;

2-phenanthrenol, 1,2,3,4,4a,9,10,10a-octahydro-7-[(2-methyl-3-pyridinyl)methoxy]-4a-(phenylmethyl)-2-(3,3,3-trifluoropropyl)-, [2S-(2α,4aα,10aβ)]-

2-phenanthrenol, 1,2,3,4,4a,9,10,10a-octahydro-4a-(phenylmethyl)-7-(2-pyridinylmethoxy)-2-(3,3,3-trifluoropropyl)-, [2S-(2□,4□,10a□)]-; and 2-phenanthrenol, 1,2,3,4,4a,9,10,10a-octahydro-7-[(2-methyl-3-pyridinyl)methoxy]-4a-(phenylmethyl)-2-(trifluoromethyl)-, (2R,4aS,10R)-;

or a prodrug thereof, or a pharmaceutically acceptable salt of said compound or prodrug.

21. The compound of claim 18 wherein $R_3$ is —C≡C—$CH_3$ and $R_{10}$ is —O—$CH_2$-(4-pyridinyl); or a pharmaceutically acceptable salt thereof.

22. The compound of claim 18 wherein $R_3$ is —C≡C—$C_3$ and $R_{10}$ is —O—$CH_2$-(2-pyridinyl); or a pharmaceutically acceptable salt thereof.

23. The compound of claim 18 wherein $R_3$ is —$(CH_2)_2$—$CF_3$ and $R_{10}$ is —O—$CH_2$—(3-pyridinyl); or a pharmaceutically acceptable salt thereof.

24. The compound of claim 18 wherein $R_3$ is —$(CH_2)_2$—$CF_3$ and $R_{10}$ is —O—$CH_2$—(2-methyl-3-pyridinyl); or a pharmaceutically acceptable salt thereof.

25. The compound of claim 18 wherein $R_3$ is —$(CH_2)_2$—$CF_3$ and $R_{10}$ is —O—$CH_2$—(2-pyridinyl); or a pharmaceutically acceptable salt thereof.

26. The compound of claim 18 wherein $R_3$ is —$CF_3$ an $R_{10}$ is —O—$CH_2$—(2-methyl-3-pyridinyl); or a pharmaceutically acceptable salt thereof.

27. A compound of claim 4 of formula II

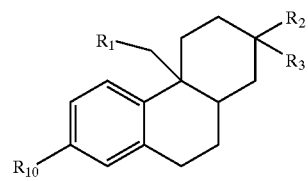

II an isomer thereof, a prodrug of said compound or isomer, or a pharmaceutically acceptable salt of said compound, isomer or prodrug, wherein $R_1$ is a) —$(C_2-C_4)$alkyl, b) —$CH_2$—CH=$CH_2$ or c) -phenyl;

$R_2$ is —OH;

$R_3$ is a) —$(C_1-C_4)$alkyl substituted with 0 or 1 $CF_3$, b) —C≡C—$CH_3$, c) —C≡C—Cl, d) —C≡C—$CF_3$, e) —$CH_2O(C_1-C_3)$alkyl substituted with 0 or 1 $CF_3$, or f) —$CF_3$;

$R_{10}$ is a) —O—Z—C(O)—NH—$(C_0-C_3)$alkyl-N$((C_1-C_2)$alkyl$)_2$, b) —O—Z—C(O)—N$R_{12}R_{13}$, or c) —O—Z—C(O)—NH—$(C_0-C_3)$alkyl-het wherein het is selected from the group consisting of 1) pyridinyl substituted with 0 or 1 methyl, 2) pyrimidinyl, 3) pyrazinyl, 4) morpholinyl, 5) pyrrolidinyl, 6) imidazolyl and 7) oxadiazolyl;

$R_{12}$ and $R_{13}$ are independently a) —H or b) —$(C_1-C_2)$ alkyl; or $R_{12}$ an $R_{13}$ taken together with N to form pyrrolidinyl;

Z is $(C_0-C_1)$ alkyl.

28. A compound of claim 27 of formula III

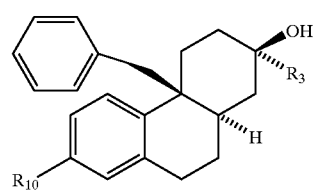

III a prodrug thereof, or a pharmaceutically acceptable salt of said compound or prodrug;

wherein $R_3$ is a) —$(CH_2)_2$—$CF_3$, b) —$(CH_2)_2$—$CH_3$, c) —$CH_3$, d) —C≡C—$CH_3$, e) —C≡C—Cl or f) —$CF_3$;

$R_{10}$ is a) —O—C(O)—NH—$(C_0-C_3)$alkyl-N$((C_1-C_2)$ alkyl$)_2$, b) —O—C(O)—N$(CH_3)_2$, c) —O—C(O)—(1-pyrrolidinyl) or d) —O—C(O)—NH—$(C_0-C_3)$alkyl-het wherein het is selected from the group consisting of 1) 2-pyridinyl, 2) 3-pyridinyl, 3) 4-pyridinyl, 4) 2-methyl -3-pyridinyl, 5) pyrazinyl, 6) morpholinyl, 7) pyrrolidinyl and 8) imidazolyl.

29. A compound of claim 28 selected from the group consisting of:

carbamic acid, dimethyl-, 7-(chloroethynyl)-4b,5,6,7,8, 8a,9,10-octahydro-7-hydroxy-4b-(phenylmethyl)-2-phenanthrenyl ester, (4bS,8aR)-;

1-pyrrolidinecarboxylic acid, 7-(chloroethynyl)-4b,5,6,7,
8,8a,9,10 octahydro-7-hydroxy-4b-(phenylmethyl)-2-
phenanthrenyl ester, (4bS,8aR)-;

carbamic acid, [2-(1-pyrrolidinyl)ethyl]-,
4b,5,6,7,8,8a ,9,10-octahydro-7-hydroxy-4b-(phenyl-
methyl)-7-(1-propynyl)-2-phenanthrenyl ester,
monohydrochloride, [4bS-(4bα,7α,8aβ)]-;

carbamic acid, [2-(4-morpholinyl)ethyl]-,
4b,5,6,7,8,8a ,9,10-octahydro-7-hydroxy-4b-(phenyl-
methyl)-7-(1-propynyl)-2-phenanthrenyl ester,[4bS-
(4bα,7α,8aβ)]-;

carbamic acid, [3-(1H-imidazol-1-yl)propyl]-, 4b,5,6,7,8,
8a,9,10-octahydro-7-hydroxy-4b-(phenylmethyl)-7-(1-
propynyl)-2-phenanthrenyl ester,[4bS-(4bα,7α,8β)]-;

carbamic acid, [2-(dimethylamino)ethyl]-, 4b,5,6,7,8,8a
,9,10-octahydro-7-hydroxy-4b-(phenylmethyl)-7-(1-
propynyl)-2-phenanthrenyl ester,[4bS-(4bα,7α,8β)]-;

carbamic acid, [3-(1-pyrrolidinyl)propyl]-, 4b,5,6,7,8,8a,
9,10-octahydro-7-hydroxy-4b-(phenylmethyl)-7-(1-
propynyl)-2-phenanthrenyl ester, [4bS-(4bα,7α,8β)]-;

carbamic acid, [2-(3-pyridinyl)ethyl]-, 4b,5,6,7,8,8a
,9,10-octahydro-7-hydroxy-4b-(phenylmethyl)-7-(1-
propynyl)-2-phenanthrenyl ester, [4bS-(4α,7α,8β)]-;

carbamic acid, (2-pyridinylmethyl)-, 4b,5,6,7,8,8a,9,10-
octahydro-7-hydroxy-4b-(phenylmethyl)-7-(1-
propynyl)-2-phenanthrenyl ester, [4bS-(4bα,7α,8aβ)]-;

carbamic acid, [2-(2-pyridinyl)ethyl]-, 4b,5,6,7,8,8a,9,10-
octahydro-7-hydroxy-4b-(phenylmethyl)-7-(1-
propynyl)-2-phenanthrenyl ester, [4bS-(4bα,7α,8aβ)]-;

carbamic acid, (4-pyridinylmethyl)-, 4b,5,6,7,8,8a,9,10-
octahydro-7-hydroxy-4b-(phenylmethyl)-7-(1-
propynyl)-2-phenanthrenyl ester, [4bS-(4α,7α,8aβ)]-;

carbamic acid, (3-pyridinylmethyl)-, 4b,5,6,7,8,8a,9,10-
octahydro-7-hydroxy-4b-(phenylmethyl)-7-(1-
propynyl)-2-phenanthrenyl ester, [4bS-(4α,7α,8aβ)]-;
and carbamic acid, [2-(4-pyridinyl)ethyl]-, 4b,5,6,7,8,8a,9,10-
octahydro-7-hydroxy-4b-(phenylmethyl)-7-(1-
propynyl)-2-phenanthrenyl ester, [4bS-(4α,7α,8aβ)]-;

or a prodrug thereof, or a pharmaceutically acceptable salt
of said compound or prodrug.

30. A compound of claim 29 selected from the group
consisting of:

carbamic acid, [2-(1-pyrrolidinyl)ethyl]-, 4b,5,6,7,8,8a
,9,10-octahydro-7-hydroxy-4b-(phenylmethyl)-7-(1-
propynyl)-2-phenanthrenyl ester, monohydrochloride,
[4bS-(4bα,7α,8aβ)]-;

carbamic acid, [2-(dimethylamino)ethyl]-, 4b,5,6,7,8,8a
,9,10-octahydro-7-hydroxy-4b-(phenylmethyl)-7-(1-
propynyl)-2-phenanthrenyl ester,[4bS-(4α,7α,8aβ)]-;

carbamic acid, (2-pyridinylmethyl)-, 4b,5,6,7,8,8a,9,10-
octahydro-7-hydroxy-4b-(phenylmethyl)-7-(1-
propynyl)-2-phenanthrenyl ester, [4bS-(4α,7α,8aβ)]-;

carbamic acid, (4-pyridinylmethyl)-, 4b,5,6,7,8,8a,9,10-
octahydro-7-hydroxy-4b-(phenylmethyl)-7-(1-
propynyl)-2-phenanthrenyl ester, [4bS-(4α,7α,8aβ)]-;
and carbamic acid, (3-pyridinylmethyl)-, 4b,5,6,7,8,8a,9,10-
octahydro-7-hydroxy-4b-(phenylmethyl)-7-(1-
propynyl)-2-phenanthrenyl ester, [4bS-(4α,7α,8aβ)]-;

a prodrug thereof, or a pharmaceutically acceptable salt of
said compound or prodrug.

31. The compound of claim 28 wherein $R_3$ is —C≡C—
$CH_3$ and $R_{10}$ is —O—C(O)—NH—$(CH_2)_2$—(1-
pyrrolidinyl); or a pharmaceutically acceptable salt thereof.

32. The compound of claim 28 wherein $R_3$ is —C≡C—
$CH_3$ and $R_{10}$ is —O—C(O)—NH—$(CH_2)_2$—$(CH_3)_2$; or a
pharmaceutically acceptable salt thereof.

33. The compound of claim 28 wherein $R_3$ is —C≡C—
$CH_3$ and $R_{10}$ is —O—C(O)—NH—$CH_2$-2-pyridyl; or a
pharmaceutically acceptable salt thereof.

34. The compound of claim 28 wherein $R_3$ is —C≡C—
$CH_3$ and $R_{10}$ is —O—C(O)—NH—$CH_2$-4-pyridyl; or a
pharmaceutically acceptable salt thereof.

35. The compound of claim 28, wherein $R_3$ is —C≡C—
$CH_3$ and $R_{10}$ is —O—C(O)—NH—$CH_2$-3-pyridyl; or a
pharmaceutically acceptable salt thereof.

36. A compound of formula VII or an isomer thereof;
wherein — is an optional bond;

$X'$ is —$CH_2$—;

$R'_1$ is phenyl substituted with 0, 1 or 2 $R'_x$;

$R'_2$ is —OH;

$R'_3$ is a) —$(C_1-C_6)$alkyl substituted with 0 or 1 $R'_y$, or b)
—$(C_2-C_6)$alkynyl substituted with 0 or 1 $R'_y$;

$R'_y$ is —$CF_3$;

or $R'_2$ and $R'_3$ are taken together to form =O;

$R'_9$ is —H;

$R'_{10}$ is a) -halo, b) —C(O)OH, c) —C(O)O$(C_1-C_6)$alkyl,
d) —C(O)—$NR'_{12}R'_{13}$, e) —CN, f) —OH or g) —O—
$(C_1C_3)$alkyl;

$R'_x$ is a) -halo, b) —OH, c) —$(C_1-C_6)$alkyl, d) —CN, e)
—$CF_3$, f) —$(C_0-C_6$ alkyl-$NR_2R'_{13}$, g) —C(O)—
$NR'_{12}R'_{13}$, h) —$NR'_{12}$—$SO_2R'_{13}$, i) —$NR'_{12}$—C(O)—
$R'_{13}$, j) —$SO_2R'_{12}$ or k) $SO_2$—$NR'_{12}R'_{13}$;

$R'_{12}$ and $R'_{13}$ for each occurrence are each independently
a) —H or b) —$(C_1-C_6)$alkyl.

37. A compound of claim 36, wherein said compound is
2(3H)-Phenanthrenone, 4, 4a, 9, 10-tetrahydro-7-bromo-4a-
phenylmethyl)-,(S)—.

38. A compound of claim 2 of formula II an isomer thereof, a prodrug of said compound or isomer, or
a pharmaceutically acceptable salt of said compound, isomer
or prodrug;
wherein $R_1$ is -phenyl;

$R_2$ is —OH;

$R_3$ is a) —$(C_1-C_6)$alkyl substituted with 0 or 1 $CF_3$, b)
—C≡C—$CH_3$, c) —C≡C—Cl d) —C≡C—$CF_3$, e)
—$CH_2O(C_1-C_3)$alkyl substituted with 0 or 1 $CF_3$, or f)
—$CF_3$;

R$_{10}$ is —OH, —CN, —C(O)OH or —C(O)O(C$_1$–C$_6$) alkyl.

39. A compound of claim 38 of formula III

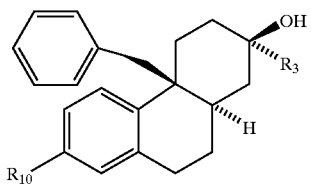

III a prodrug thereof, or a pharmaceutically acceptable salt of said compound or prodrug;
wherein R$_3$ is a) —(CH$_2$)$_2$—CF$_3$, b) —(CH$_2$)$_2$—CH$_3$, c) —CH$_3$, d) —C≡C—CH$_3$, e) —C≡C—Cl or f) —CF$_3$;
R$_{10}$ is as defined in claim 38.

40. A compound of claim 39 selected from the group consisting of:
a compound of formula III wherein R$_3$ is —C≡C—CH$_3$ and R$_{10}$ is —OH; or a pharmaceutically acceptable salt thereof;
a compound of formula III wherein R$_3$ is —C≡C—CH$_3$ and R$_{10}$ is —CN; or a pharmaceutically acceptable salt thereof;
a compound of formula III wherein R$_3$ is —C≡C—CH$_3$ and R$_{10}$ is —COOH; or a pharmaceutically acceptable salt thereof;
a compound of formula III wherein R$_3$ is —(CH$_2$)$_2$—CH$_3$ and R$_{10}$ is OH; or a pharmaceutically acceptable salt thereof;
a compound of formula III wherein R$_3$ is —(CH$_2$)$_2$—CH$_3$ and R$_{10}$ is —CN; or a pharmaceutically acceptable salt thereof;
a compound of formula III wherein R$_3$ is —(CH$_2$)$_2$—CH$_3$ and R$_{10}$ is COOH; or a pharmaceutically acceptable salt thereof;
a compound of formula III wherein R$_3$ is —(CH$_2$)$_2$—CF$_3$ and R$_{10}$ is —OH; or a pharmaceutically acceptable salt thereof;
a compound of formula III wherein R$_3$ is —(CH$_2$)$_2$—CF$_3$ and R$_{10}$ is —CN; or a pharmaceutically acceptable salt thereof;
a compound of formula III wherein R$_3$ is —(CH$_2$)$_2$—CF$_3$ and R$_{10}$ is —COOH; or a pharmaceutically acceptable salt thereof;
a compound of formula III wherein R$_3$ is —CH$_3$ and R$_{10}$ is —OH; or a pharmaceutically acceptable salt thereof;
a compound of formula III wherein R$_3$ is —CH$_3$ and R$_{10}$ is —CN; or a pharmaceutically acceptable salt thereof;
a compound of formula III wherein R$_3$ is —CH$_3$ and R$_{10}$ is —COOH; or a pharmaceutically acceptable salt thereof;
a compound of formula III wherein R$_3$ is —CF$_3$ and R$_{10}$ is —OH; or a pharmaceutically acceptable salt thereof;
a compound of formula III wherein R$_3$ is —CF$_3$ and R$_{10}$ is —CN; or a pharmaceutically acceptable salt thereof; and
a compound of formula III wherein R$_3$ is —CF$_3$ and R$_{10}$ is —COOH; or a pharmaceutically acceptable salt thereof.

41. A method of treating obesity in a mammal comprising administering to said mammal a therapeutically effective amount of a compound of claim 1, an isomer thereof, a prodrug of said compound or isomer, or a pharmaceutically acceptable salt of said compound, isomer or prodrug.

42. The method of claim 41 wherein the mammal is a female or male human.

43. A pharmaceutical composition comprising a therapeutically effective amount of a compound of claim 1, an isomer thereof, a prodrug of said compound or isomer, or a pharmaceutically acceptable salt of said compound, isomer or prodrug; and a pharmaceutically acceptable carrier, vehicle or diluent.

44. A pharmaceutical composition for the treatment of obesity comprising an obesity treating amount of a compound of claim 1, an isomer thereof, a prodrug of said compound or isomer, or a pharmaceutically acceptable salt of said compound, isomer or prodrug; and a pharmaceutically acceptable carrier, vehicle or diluent.

45. A pharmaceutical combination composition comprising: a therapeutically effective amount of a composition comprising:
a first compound, said first compound being a compound of claim 1, an isomer thereof, a prodrug of said compound or isomer, or a pharmaceutically acceptable salt of said compound, isomer or prodrug;
a second compound, said second compound being a β$_3$ agonist a thyromimetic agent, an eating behavior modifying agent or a NPY antagonist; and
a pharmaceutical carrier, vehicle or diluent.

46. The composition of claim 45 wherein the second compound is orlistat or sibutramine.

47. A method of treating obesity comprising administering to a mammal in need of such treatment
an amount of a first compound, said first compound being a compound of claim 1, an isomer thereof, a prodrug of said compound or isomer, or a pharmaceutically acceptable salt of said compound, isomer or prodrug;
a second compound, said second compound being a β$_3$ agonist, a thyromimetic agent, an eating behavior modifying agent or a NPY antagonist; and
wherein the amounts of the first and second compounds result in a therapeutic effect.

48. The method of claim 47 wherein the second compound is orlistat or sibutramine.

49. A kit comprising:
a) a first compound, said first compound being a compound of claim 1, an isomer thereof, a prodrug of said compound or isomer, or a pharmaceutically acceptable salt of said compound, isomer or prodrug and a pharmaceutically acceptable carrier, vehicle or diluent in a first unit dosage form;
b) a second compound, said second compound being a β$_3$ agonist, a thyromimetic agent, an eating behavior modifying agent or a NPY antagonist; and
a pharmaceutically acceptable carrier, vehicle or diluent in a second unit dosage form; and
c) a container for containing said first and second dosage forms; wherein the amounts of said first and second compounds result in a therapeutic effect.

50. A method of inducing weight loss in a mammal comprising administering to said mammal a therapeutically effective amount of a compound of claim 1, an isomer thereof, a prodrug of said compound or isomer, or a pharmaceutically acceptable salt of said compound, isomer or prodrug.

51. A pharmaceutical composition for inducing weigh loss comprising a weight loss-treating amount of a compound of claim 1, an isomer thereof, a prodrug of said compound or isomer, or a pharmaceutically acceptable salt of said compound, isomer or prodrug; and a pharmaceutically acceptable carrier, vehicle or diluent.

52. A method of treating diabetes in a mammal comprising administering to said mammal a therapeutically effective amount of a compound of claim 1, an isomer thereof, a prodrug of said compound or isomer, or a pharmaceutically acceptable salt of said compound, isomer or prodrug.

53. A pharmaceutical composition for the treatment of diabetes comprising a diabetes-treating amount of a compound of claim 1, an isomer thereof, a prodrug of said compound or isomer, or a pharmaceutically acceptable salt of said compound, isomer or prodrug; and a pharmaceutically acceptable carrier, vehicle or diluent.

54. A pharmaceutical combination composition comprising: a therapeutically effective amount of a composition comprising:
   a first compound, said first compound being a compound of claim 1, an isomer thereof, a prodrug of said compound or isomer, or a pharmaceutically acceptable salt of said compound, isomer or prodrug;
   a second compound, said second compound being an aldose reductase inhibitor, a glycogen phosphorylase inhibitor, a sorbitol dehydrogenase inhibitor, insulin, troglitazone, sulfonylurea, glipazide, glyburide, or chlorpropamide; and
   a pharmaceutical carrier, vehicle or diluent.

55. A pharmaceutical composition as recited in claim 54 wherein the aldose reductase inhibitor is 1-phthalazineacetic acid, 3,4-dihydro-4-ox -3-[[5-trifluoromethyl)-2-benzothiazolyl]methyl]- or a pharmaceutically acceptable salt thereof.

56. A method of treating diabetes comprising administering to a mammal in need of such treatment
   an amount of a first compound, said first compound being a compound of claim 1, an isomer thereof, a prodrug of said compound or isomer, or a pharmaceutically acceptable salt of said compound, isomer or prodrug;
   a second compound, said second compound being an aldose reductase inhibitor, a glycogen phosphorylase inhibitor, a sorbitol dehydrogenase inhibitor, insulin, troglitazone sulfonylurea, glipazide, glyburide, or chlorpropamide; and
   wherein the amounts of the first and second compounds result in a therapeutic effect.

57. A pharmaceutical combination composition comprising:
   therapeutically effective amounts of a compound of claim 1, an isomer thereof, a prodrug of said compound or isomer, or a pharmaceutically acceptable salt of said compound, isomer or prodrug; and
   a compound selected from the group consisting of a glucocorticoid receptor agonist, a cholinomimetic drug, an anti-Parkinson's drug, an antianxiolytic drug, an antidepressant drug and an antipsychotic drug; and
   a pharmaceutical carrier, vehicle or diluent.

58. The composition of claim 57 wherein the anti-Parkinson's drug is selected from the group consisting of L-dopa, bromocriptine and selegiline.

59. The composition of claim 57 wherein the antianxiolytic drug is selected from the group consisting of benzodiazepine, valium and librium.

60. The composition of claim 57 wherein the antidepressant drug is selected from the group consisting of desipramine, sertraline hydrochloride and fluoxetine hydrochloride.

61. The composition of claim 57 wherein the antipsychotic drug is selected from the group consisting of haloperidol and clozapine.

62. A kit comprising:
   a) a first compound, said first compound being a compound of claim 1, an isomer thereof, a prodrug said compound or isomer, or a pharmaceutically acceptable salt of said compound, isomer or prodrug; and a pharmaceutically acceptable carrier, vehicle or diluent in a first unit dosage form;
   b) a second compound, said second compound being selected from the group consisting of a glucocorticoid receptor agonist, a cholinomimetic drug, a anti-Parkinson's drug, an antianxiolytic drug, an antidepressant drug, and an antipsychotic drug; and a pharmaceutically acceptable carrier, vehicle or diluent in a second unit dosage form; and
   c) a container for containing said first and second dosage forms wherein the amounts of said first and second compounds result in a therapeutic effect.

63. The kit of claim 62 wherein the anti-Parkinson's drug is selected from the group consisting of L-dopa, bromocriptine and selegiline.

64. The kit of claim 62 wherein the antianxiolytic drug is selected from the group consisting of benzodiazepine, valium and librium.

65. The kit of claim 62 wherein the antidepressant drug is selected from the group consisting of desipramine, sertraline hydrochloride and fluoxetine hydrochloride.

66. The kit of claim 62 wherein the antipsychotic drug is selected from the group consisting of haloperidol and clozapine.

67. A method of treating anxiety in a mammal comprising administering to said mammal a therapeutically effective amount of a compound of claim 1, an isomer thereof, a prodrug of said compound or isomer, or a pharmaceutically acceptable salt of said compound, isomer or prodrug.

68. A pharmaceutical composition for the treatment of anxiety comprising an anxiety-treating amount of a compound of claim 1, an isomer thereof, a prodrug of said compound or isomer, or a pharmaceutically acceptable salt of said compound, isomer or prodrug; and a pharmaceutically acceptable carrier, vehicle or diluent.

69. A method of treating depression in a mammal comprising administering to said mammal a therapeutically effective amount of a compound of claim 1, an isomer thereof, a prodrug of said compound or isomer, or a pharmaceutically acceptable salt of said compound, isomer or prodrug.

70. A pharmaceutical composition for the treatment of depression comprising a depression-treating amount of a compound of claim 1, an isomer thereof, a prodrug of said compound or isomer, or a pharmaceutically acceptable salt of said compound, isomer or prodrug; and a pharmaceutically acceptable carrier, vehicle or diluent.

71. A method of treating neurodegeneration in a mammal comprising administering to said mammal a therapeutically effective amount of a compound of claim 1, an isomer thereof, a prodrug of said compound or isomer, or a pharmaceutically acceptable salt of said compound, isomer or prodrug.

72. A pharmaceutical composition for the treatment of neurodegeneration comprising a neurodegeneration-treating amount of a compound of claim 1, an isomer thereof, a prodrug of said compound or isomer, or a pharmaceutically acceptable salt of said compound, isomer or prod rug; and a pharmaceutically acceptable carrier, vehicle or diluent.

73. A method of affecting glucocorticoid receptor activity comprising administering to a mammal in need thereof a therapeutically effective amount of a compound of claim 1, an isomer thereof, a prodrug of said compound or isomer, or a pharmaceutically acceptable salt of said compound, isomer or prodrug.

74. A method of modulating a process mediated by glucocorticoid receptor comprising administering to a mammal in need thereof a therapeutically effective amount of a compound of claim 1, an isomer thereof, a prodrug of said compound or isomer, or a pharmaceutically acceptable salt of said compound, isomer or prodrug.

75. A method of treating a mammal requiring glucocorticoid receptor therapy comprising administering to said mammal a therapeutically effective amount of a glucocorticoid receptor modulator compound of claim 1, an isomer thereof, a prodrug of said compound or isomer, or a pharmaceutically acceptable salt of said compound, isomer or prodrug.

76. A method of treating an inflammatory disease in mammal comprising administering to said mammal a therapeutically effective amount of a compound of claim 1, an isomer thereof, a prodrug of said compound or isomer, or a pharmaceutically acceptable salt of said compound, isomer or prodrug.

77. The method of claim 76 wherein the mammal is a female or male human.

78. A pharmaceutical composition for the treatment of an inflammatory disease comprising an inflammatory-treating amount of a compound of claim 1, an isomer thereof, a prodrug of said compound or isomer, or a pharmaceutically acceptable salt of said compound, isomer or prodrug; and a pharmaceutically acceptable carrier.

79. A method for the treatment of an inflammatory disease in a mammal and for reducing the undesirable side effects of said treatment which comprises: administering to said mammal therapeutically effective amounts of a glucocorticoid receptor modulator and a glucocorticoid receptor agonist.

80. A method of claim 79 wherein the inflammatory disease is selected from the group consisting of arthritis, asthma, rhinitis and immunomodulation.

81. The method of claim 79 wherein the glucocorticoid receptor modulator is a compound of claim 1, an isomer thereof, a prodrug of said compound or isomer, or a pharmaceutically acceptable salt of said compound, isomer or prodrug.

82. The method of claim 79 wherein the glucocorticoid receptor agonist is a compound selected from the group consisting of prednisone, prednylidene, prednisolone, cortisone, dexamethasone and hydrocortisone.

* * * * *